United States Patent
Xi et al.

(10) Patent No.: US 9,938,257 B2
(45) Date of Patent: *Apr. 10, 2018

(54) SUBSTITUTED HETEROARYL COMPOUNDS AND METHODS OF USE

(71) Applicants: Sunshine Lake Pharma Co., Ltd., Dongguan, Guangdong (CN); Calitor Sciences, LLC, Newbury Park, CA (US)

(72) Inventors: Ning Xi, Newbury Park, CA (US); Minxiong Li, Guangdong (CN); Xiaobo Li, Guangdong (CN); Wuhong Chen, Guangdong (CN); Tao Zhang, Guangdong (CN); Haiyang Hu, Guangdong (CN); Weilong Dai, Guangdong (CN); Yanjun Wu, Guangdong (CN)

(73) Assignees: CALITOR SCIENCES, LLC, Newbury Park, CA (US); SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/257,926

(22) Filed: Sep. 7, 2016

(65) Prior Publication Data

US 2017/0073334 A1    Mar. 16, 2017

Related U.S. Application Data

(60) Provisional application No. 62/217,676, filed on Sep. 11, 2015.

(51) Int. Cl.
| | |
|---|---|
| *C07D 401/14* | (2006.01) |
| *A61K 31/4155* | (2006.01) |
| *A61P 9/10* | (2006.01) |
| *C07D 403/14* | (2006.01) |
| *A61K 31/506* | (2006.01) |
| *A61K 31/5377* | (2006.01) |
| *A61K 45/06* | (2006.01) |

(52) U.S. Cl.
CPC .......... *C07D 403/14* (2013.01); *A61K 31/506* (2013.01); *A61K 31/5377* (2013.01); *A61K 45/06* (2013.01); *C07D 401/14* (2013.01)

(58) Field of Classification Search
CPC combination set(s) only.
See application file for complete search history.

(56) References Cited

U.S. PATENT DOCUMENTS

| | | | |
|---|---|---|---|
| 7,427,681 B2 | 9/2008 | Bebbington et al. | |
| 7,557,210 B2 | 7/2009 | Singh et al. | |
| 7,582,648 B2 | 9/2009 | Singh et al. | |
| 7,754,714 B2 | 7/2010 | Li et al. | |
| 7,863,286 B2 | 1/2011 | Argade et al. | |
| 7,868,013 B2 | 1/2011 | Li et al. | |
| 7,947,698 B2 | 5/2011 | Atuegbu et al. | |
| 8,063,058 B2 | 11/2011 | Jia et al. | |
| 8,097,630 B2 | 1/2012 | Singh et al. | |
| 8,101,621 B2 | 1/2012 | Kato et al. | |
| 8,138,339 B2 | 3/2012 | Bauer et al. | |
| 8,211,929 B2 | 7/2012 | Chen et al. | |
| 8,263,632 B2 | 9/2012 | Iwama et al. | |
| 8,304,422 B2 | 11/2012 | Atuegbu et al. | |
| 8,334,297 B2 | 12/2012 | Li et al. | |
| 8,377,924 B2 | 2/2013 | Singh et al. | |
| 8,426,408 B2 | 4/2013 | Curtin et al. | |
| 8,450,335 B2 | 5/2013 | Singh et al. | |
| 8,476,434 B2 | 7/2013 | Geuns-Meyer et al. | |
| 8,563,559 B2 | 10/2013 | Singh et al. | |
| 8,697,694 B2 | 4/2014 | Arasappan et al. | |
| 8,710,223 B2 | 4/2014 | Holland et al. | |
| 8,962,609 B2 | 2/2015 | Perrior et al. | |
| 9,145,387 B2 | 9/2015 | Haq et al. | |
| 9,321,763 B2 | 4/2016 | Singh et al. | |
| 9,394,281 B2* | 7/2016 | Xi | C07D 493/04 |
| 9,399,637 B2 | 7/2016 | Xi et al. | |
| 9,403,801 B2* | 8/2016 | Xi | C07D 493/04 |
| 9,670,194 B2* | 6/2017 | Xi | C07D 401/14 |
| 2003/0022885 A1 | 1/2003 | Bebbington et al. | |
| 2007/0293522 A1 | 12/2007 | Singh et al. | |
| 2009/0281073 A1 | 11/2009 | Bhattacharya et al. | |

(Continued)

FOREIGN PATENT DOCUMENTS

| | | |
|---|---|---|
| CN | 104262328 A | 1/2015 |
| CN | 104974163 A | 10/2015 |
| CN | 105367555 A | 3/2016 |
| WO | 2003030909 A1 | 4/2003 |
| WO | 2014040555 A1 | 3/2014 |
| WO | 2014058685 A1 | 4/2014 |
| WO | 2014081718 A1 | 5/2014 |
| WO | 2015039613 A1 | 3/2015 |
| WO | 2015094803 A1 | 6/2015 |
| WO | WO2015094803 A1 | 6/2015 |

OTHER PUBLICATIONS

Curtin et al., Pyrazole diaminopyrimidines as dual inhibitors of KDR and Aurora B kinases, Bioorganic & Medicinal Chemistry Letters, 2012, vol. 22, Issue 14, p. 4750-4755

(Continued)

*Primary Examiner* — Amanda L Aguirre
(74) *Attorney, Agent, or Firm* — Kam W. Law; Squire Patton Boggs (US) LLP

(57) ABSTRACT

The present invention provides novel heteroaryl compounds, pharmaceutical acceptable salts and formulations thereof. They are useful in preventing, managing, treating or lessening the severity of a protein kinase-mediated disease. The invention also provides pharmaceutically acceptable compositions comprising such compounds and methods of using the compositions in the treatment of protein kinase-mediated disease.

24 Claims, No Drawings

(56) References Cited

U.S. PATENT DOCUMENTS

| | | |
|---|---|---|
| 2010/0130486 A1 | 5/2010 | Singh et al. |
| 2011/0130415 A1 | 6/2011 | Singh et al. |
| 2012/0094999 A1 | 4/2012 | Gray et al. |
| 2013/0210810 A1 | 8/2013 | Singh et al. |
| 2013/0267491 A1* | 10/2013 | Perrior .................. C07D 239/42 514/210.2 |
| 2014/0228322 A1 | 8/2014 | Haq et al. |
| 2014/0275055 A1 | 9/2014 | Singh et al. |
| 2014/0329842 A1 | 11/2014 | Holland et al. |
| 2015/0005281 A1 | 1/2015 | Hobson et al. |
| 2015/0087663 A1* | 3/2015 | Xi ......................... C07D 401/14 514/266.21 |
| 2015/0274704 A1* | 10/2015 | Xi ......................... C07D 493/04 514/171 |
| 2016/0052930 A1 | 2/2016 | Fensome et al. |
| 2016/0058760 A1 | 3/2016 | Singh et al. |
| 2016/0102076 A1 | 4/2016 | Suh et al. |
| 2016/0159774 A1 | 6/2016 | Schwartz et al. |
| 2016/0229837 A1 | 8/2016 | Xi et al. |

OTHER PUBLICATIONS

ISR of PCT/US16/50454, dated Jan. 19, 2017.

\* cited by examiner

SUBSTITUTED HETEROARYL COMPOUNDS AND METHODS OF USE

CROSS-REFERENCE TO RELATED APPLICATION

The application claims the benefit of U.S. Provisional Application Ser. No. 62/217,676, filed on Sep. 11, 2015, which is hereby incorporated by reference in its entirety.

FIELD OF THE INVENTION

The present invention provides novel substituted aminopyrimidine compounds, and salts thereof, which are useful in the treatment of proliferative disease, autoimmune disease, allergic disease, inflammatory disease, transplantation rejection, and other diseases, in mammals. In particular, this invention relates to compounds that modulate the activity of JAK kinases, FLT3 kinase, and Aurora kinases resulting in the modulation of inter- and/or intra-cellular signaling. This invention also relates to a method of using such compounds in the treatment of proliferative disease, autoimmune disease, allergic disease, inflammatory disease, transplantation rejection, and other diseases in mammals, especially humans, and to pharmaceutical compositions containing such compounds.

BACKGROUND OF THE INVENTION

Protein kinases constitute a large family of structurally related enzymes that are responsible for the control of a variety of signal transduction processes within the cell. Protein kinases, containing a similar 250-300 amino acid catalytic domain, catalyze the phosphorylation of target protein substrates. It is reported that many diseases are associated with abnormal cellular responses triggered by protein kinase-mediated events. These diseases include benign and malignant proliferation disorders, diseases resulting from inappropriate activation of the immune system, allograft rejection, graft vs host disease, autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

The kinases may be categorized into families by the substrates in the phosphorylate (e.g., protein-tyrosine, protein-serine/threonine, lipids, etc.). Tyrosine phosphorylation is a central event in the regulation of a variety of biological processes such as cell proliferation, migration, differentiation and survival. Several families of receptor and non-receptor tyrosine kinases control these events by catalyzing the transfer of phosphate from ATP to a tyrosine residue of specific cell protein targets. Sequence motifs have been identified that generally correspond to each of these kinase families (Hanks et al., *FASEB J.*, 1995, 9, 576-596; Knighton et al., *Science*, 1991, 253, 407-414; Garcia-Bustos et al., *EMBO J.*, 1994, 13:2352-2361). Some non-limiting examples of the protein kinase include abl, Aurora, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRafl, CSF1 R, CSK, EGFR, ErbB2, ErbB3, ErbB4, Erk, Fak, fes, Flt-3, FGFR1, FGFR2, FGFR3, FGFR4, FGFR5, Fgr, Flt-1, Fps, Frk, Fyn, Hck, IGF-1 R, INS-R, JAK, KDR, Lck, Lyn, MEK, p38, PDGFR, PIK, PKC, PYK2, ros, Tie, Tie-2, TRK, Yes, and Zap70.

Aurora kinase family is a collection of highly related serine/threonine kinase that are key regulators of mitosis, essential for accurate and equal segtion of genomic material from parent to daught cells. Members of the Aurora kinase family include three related kinases known as Aurora-A, Aurora-B, and Aurora-C (also known as Aurora-1, Aurora-2, and Aurora-3). Despite significant sequence homology, the localization and functions of these kinases are largely distinct from one another (Richard D. Carvajal, et al. *Clin. Cancer Res.*, 2006, 12(23): 6869-6875; Daruka Mahadevan, et al., *Expert Opin. Drug Discov.*, 2007 2(7): 1011-1026).

Aurora-A is ubiquitously expressed and regulates cell cycle events occurring from late S phase through M phase, including centrosome maturation, mitotic entry, centrosome separation, bipolar-spindle assembly, chromosome alignment on the metaphase plate, cytokinesis and mitotic exit. Aurora-A protein levels and kinase activity both increase from late G2 through M phase, with peak activity in prometaphase. Once activated, Aurora-A mediates its multiple functions by interacting with various substrates including centrosome, transforming acidic coiled-coil protein, cdc25b, Eg5, and centromere protein A.

Aurora-B is a chromosomal passenger protein critical for accurate chromosomal segregation, cytokinesis, protein localization to the centromere and kinetochore, correct microtubule-kinetochore attachments and regulation of the mitotic checkpoint. Aurora-B localizes first to the chromosomes during prophase and then to the inner centromere region between sister chromatids during prometaphase and metaphase (Zeitlin S G, et al. *J. Cell. Biol.*, 2001, 155:1147-1157). Aurora-B participates in the establishment of chromosomal biorientation, a condition where sister kinetochores are linked to opposite poles of the bipolar spindle via amphitelic attachments. The primary role of Aurora-B at this point of mitosis is to repair incorrect microtubule-kinetochore attachments (Hauf S, et al., *J. Cell Biol.*, 2003, 161: 281-294; Ditchfield C, et al., *J. Cell Biol.*, 2003, 161:267-280; Lan W, et al. *Curr. Biol.*, 2004, 14:273-286). Without Aurora-B activity, the mitotic checkpoint is compromised, resulting in increased numbers of aneuploid cells, genetic instability, and tumorigenesis (Weaver B A, et al., *Cancer Cell.*, 2005, 8:7-12).

Aurora-A overexpression is a necessary feature of Aurora-A induced tumorigenesis. In cells with Aurora-A overexpression, mitosis is characterized by the presence of multiple centrosomes and multipolar spindles (Meraldi P et al., *EMBO J.*, 2002, 21:483-492). These cells fail to undergo cytokinesis, and, with additional cell cycles, polyploidy and progressive chromosomal instability develop (Anand S, et al., *Cancer Cell*, 2003, 3:51-62).

The evidence linking Aurora overexpression and malignancy proliferation disorders, such as colon, breast, lung, pancrease, prostate, bladder, head, neck, cervix, and ovarian cancers, liver, gastric and pancreatic tumors, has stimulated interest in developing Aurora inhibitors for cancer therapy. In normal cells, Aurora-A inhibition results in delayed, but not blocked, mitotic entry, centrosome separation defects resulting in unipolar mitotic spindles, and failure of cytokinesis (Marumoto T, et al., *J. Biol. Chem.*, 2003, 278:51786-51795). Encouraging antitumor effects with Aurora-A inhibition were shown in three human pancreatic cancer cell lines (Panc-1, MIA PaCa-2, and SU.86.86), with growth suppression in cell culture and near-total abrogation of tumorigenicity in mouse xenografts (Hata T, et al., *Cancer Res.*, 2005, 65:2899-2905).

Aurora-B inhibition results in abnormal kinetochore-microtubule attachments, failure to achieve chromosomal biorientation, and failure of cytokinesis (Goto H, et al., *J. Biol. Chem.*, 2003, 278:8526-30; Severson $AF_1$ et al., *Curr. Biol.*, 2000, 10:1162-1171). Recurrent cycles of aberrant mitosis without cytokinesis result in massive polyploidy and, ultimately, to apoptosis (Hauf S, et al., *J. Cell Biol.*, 2003, 161:281-294; Ditchfield C, et al., *J. Cell Biol.*, 2003, 161:267-80; Giet R, et al., *J. Cell Biol.*, 2001, 152:669-682; Murata-Hori M, *Curr. Biol.*, 2002, 12:894-899; Kallio M J, et al., *Curr. Biol.*, 2002, 12:900-905).

Inhibition of Aurora-A or Aurora-B activity in tumor cells results in impaired chromosome alignment, abrogation of the mitotic checkpoint, polyploidy, and subsequent cell death. These in vitro effects are greater in transformed cells than in either non-transformed or non-dividing cells (Ditchfield C, et al., *J. Cell Biol.*, 2003, 161:267-280). Thus, targeting Aurora may achieve in vivo selectivity for cancer. Although toxicity to rapidly dividing cell of the hematopoietic and gastrointestinal system is expected, the activity and clinical tolerability shown in xenograft models indicates the presence of a reasonable therapeutic index. Given the preclinical antitumor activity and potential for tumor selectivity, several Aurora kinase inhibitors have been developed.

FLT3 (Flt3, FMS-related tyrosine kinase 3), also known as FLK-2 (fetal liver kinase 2) and STK-1 (human stem cell kinase 1), belongs to a member of the class III receptor tyrosine kinase (RTK-III) family that include KIT, PDGFR, FMS and FLT1 (Stirewalt D L, et al., *Nat. Rev. Cancer,* 2003, 3:650-665; Rosnet O, et al., *Genomics* 1991, 9:380-385; Yarden Y, et al., *Nature*, 1986, 323: 226-232; Stanley E R, et. al., *J. Cell. Biochem.*, 1983, 21:151-159; Yarden Y, et al., *EMBO J.*, 1987, 6:3341-3351). FLT3 is a membrane-spanning protein and composed of four domains; an extracellular ligand-binding domains consisting of five immunoglobin-like structures, a transmembrane (TM) domain, a juxtamembrane (JM) domain and a cytoplasmic C-Terminal tyrosine kinase (TK) domain (Agnes F, et al., *Gene*, 1994, 145:283-288, Scheijen B, et al., *Oncogene*, 2002, 21: 3314-3333).

The ligand for FLT3 (FLT3 or FL) was cloned in 1993 and shown to be a Type I transmembrane protein expressed in cells of the hematopoietic bone marrow microenvironment, including bone marrow fibroblasts and other cells (Lyman S D, et al., *Cell* 1993, 75:1157-1167). Both the membrane-bound and soluable forms can activate the tyrosine kinase activity of the receptor and stimulate growth of progenitor cells in the marrow and blood. Binding of ligand to receptor induces dimerisation of the receptor and activation of the kinase domains; which then autophosphorylate and catalyse phosphorylation of substrate proteins of various signal transduction pathways such as signal transducer and activator of STATS, RAS/MAPK, PI3K, SHC, SHIP, and SHP2, which play important roles in cellular proliferation, differentiation, and survival (Dosil M, et al., *Mol. Cell Biol.*, 1993, 13:6572-6585. Zhang S, *Biochem. Biophys. Res. Commun.*, 1999, 254:440-445). In addition to hemotopoietic cells, FLT3 gene is also expressed in placenta, gonads and brain (Maroc N, et al., *Oncogene*, 1993, 8: 909-918) and also plays an import and role in the immune response (deLapeyriere O, et al., *Leukemia*, 1995, 9:1212-1218).

FLT3 has also been implicated in hematopoietic disorders which are pre-malignant disorders including myeloproliferative disorders, such as thrombocythemia, essential thrombocytosis (ET), myelofibrosis (MF), chronic idiopathic myelofibrosis (IMF), and polycythemia vera (PV), pre-malignant myelodysplastic syndromes. Hematological malignancies include leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL). FLT3 is overexpressed at the levels in 70-100% of cases of acute myeloid leukemias (AML), and in a high percentage of T-acute lymphocytic leukemia (ALL) cases (Griffin J D, et al., *Haematol J.* 2004, 5: 188-190). It is also overexpressed in a smaller subset of chronic myeloid leukemia (CML) in blast crisis. Studies have shown that the leukemic cells of B lineage ALL and AML frequently co-express FLT3, setting up autocrine or paracrine signaling loops that result in the constitutive activation of FLT3 (Zheng R, et. al., *Blood.*, 2004, 103: 267-274). A high level of the FLT3 ligand is found in the serum of patients with Langerhans cell histocytosis and systemic lupus erythematosus, which further implicates FLT3 signaling in the dysregulation of dendritic cell progenitors in those autoimmune diseases (Rolland et al., *J. Immunol.*, 2005, 174:3067-3071).

Evidence is rapidly accumulating that many types of leukemias and myeloproliferative syndromes have mutation in tyrosine kinases. FLT3 mutations are one of the most frequent somatic alterations in AML, occurring in approximately ⅓ of patients. There are two types of activating mutations in FLT3 described in patients with leukemia. These include a spectrum of internal tandem duplications (ITD) occurring within the auto-inhibitory juxtamembrane domain (Nakao M, et al., *Leukemia*, 1996, 10:1911-1918; Thiede C, et al., *Blood,* 2002, 99:4326-4335), and activation loop mutations that include Asp835Tyr (D835Y), Asp835Val (D835V), Asp835His (D835H), Asp835Glu (D835E), Asp835Ala (D835A), Asp835Asn (D835N), Asp835 deletion and Ile836 deletion (Yamamoto $Y_1$ et al., *Blood* 2001, 97:2434-2439; Abu-Duhier F M, et al., *Br. J. Haematol.*, 2001, 113:983-988). Internal tandem duplication (ITD) mutations within the JM domain contribute to about 17-34% of FLT3 activating mutations in AML. FLT3-ITD has also been detected at low frequency in myelodysplastic syndrome (MDS) (Yokota S, et al., *Leukemia,* 1997, 11:1605-1609; Horiike S, et al., *Leukemia,* 1997, 11:1442-1446). Both FLT3-ITD and FLT3-Asp835 mutations are associated with FLT3 autophosphorylation and phosphorylation of downstream targets (Mizuki M, et al., *Blood,* 2000, 96:3907-3914; Mizuki M, et al., *Blood,* 2003, 101:3164-3173; Hayakawa F, et al., *Oncogene,* 2000, 19: 624-631).

Inhibitors of FLT3 are presently being studied and have reached clinical trials as monotherapy in relapsed or refractory AML patients, some or all of whom had FLT3 mutations. Collectively, these data suggest that FLT3 is an attractive therapeutic target for the development of kinase inhibitors for AML and other associated diseases.

Janus kinase (JAK) is a family of intracellular, non-receptor tyrosine kinases that transduce cytokine-mediated signals via the JAK-STAT pathway. The JAK family plays a role in the cytokine-dependent regulation of proliferation and function of cells involved in immune response. Cytokines bind to their receptors, causing receptor dimerization, and this enables JAKs to phosphorylate each other as well as specific tyrosine motifs within the cytokine receptors. STATs that recognize these phosphotyrosine motifs are recruited to the receptor, and are then themselves activated by a JAK-dependent tyrosine phosphorylation event. Upon activation, STATs dissociate from the receptors, dimerize, and translocate to the nucleus to bind to specific DNA sites and alter transcription.

Currently, there are four known mammalian JAK family members: JAK1 (Janus kinase-1), JAK2 (Janus kinase-2), JAK3 (Janus kinase, leukocyte; JAKL; L-JAK and Janus kinase-3) and TYK2 (protein-tyrosine kinase 2). While JAK1, JAK2 and TYK2 are ubiquitously expressed, JAK3 is reported to be preferentially expressed in natural killer (NK) cells and not resting T cells ("Biology and significance of the JAK/STAT signaling pathways." Growth Factors, April 2012; 30(2): 88).

JAK1 is essential for signaling for certain type I and type II cytokines. It interacts with the common gamma chain (γc) of type I cytokine receptors to elicit signals from the IL-2 receptor family, the IL-4 receptor family, the gp130 receptor family. It is also important for transducing a signal by type I (IFN-α/β) and type II (IFN-γ) interferons, and members of the IL-10 family via type II cytokine receptors. Genetic and biochemical studies have shown that JAK1 is functionally and physically associated with the type I interferon (e g., IFNalpha), type II interferon (e.g., IFNgamma), IL-2 and IL-6 cytokine receptor complexes. Furthermore, characterization of tissues derived from JAK1 knockout mice demonstrated critical roles for this kinase in the IFN, IL-IO, IL-2/IL-4, and IL-6 pathways.

Expression of JAK1 in cancer cells enables individual cells to contract, potentially allowing them to escape their tumor and metastasize to other parts of the body. Elevated levels of cytokines which signal through JAK1 have been implicated in a number of immune and inflammatory diseases. JAK1 or JAK family kinase inhibitors may be useful for modulating or treating in such diseases. (Kisseleva et al., *Gene*, 2002, 285:1-24; Levy et al., *Nat. Rev. Mol. Cell Biol.*, 2005, 3:651-662). A humanized monoclonal antibody targeting the IL-6 pathway (Tocilizumab) was approved by the European Commission for the treatment of moderate-to-severe rheumatoid arthritis (Scheinecker et al., *Nat. Rev. Drug Discov.*, 2009, 8:273-274).

JAK2 is implicated in signaling by members of the type II cytokine receptor family (e.g. interferon receptors), the GM-CSF receptor family, the gp130 receptor family. JAK2 signaling is activated downstream from the prolactin receptor. Studies have identified a high prevalence of an acquired activating JAK2 mutation (JAK2V617F) in myleoproliferative disorders such as polycythemia vera, essential thrombocythemia and idiopathic myelofibrosis, etc. The mutant JAK2 protein is able to activate downstream signaling in the absence of cytokine stimulation, resulting in autonomous growth and/or hypersensitivity to cytokines and is believed to play a role in driving these diseases. Additional mutations or translocations resulting dysregulated JAK2 function have been described in other malignancies (Ihle J. N. and Gilliland D. G., *Curr. Opin. Genet. Dev.*, 2007, 17:8; Sayyah J. and Sayeski P. P., *Curr. Oncol. Rep.*, 2009, 11: 117). Inhibitors of JAK2 have been described to be useful in myeloproliferative diseases (Santos et al, *Blood*, 2010, 115: 1131; Barosi G. and Rosti V., *Curr. Opin. Hematol*, 2009, 16:129, Atallah E. and Versotvsek S., *Exp. Rev. Anticancer Ther.*, 2009, 9:663).

JAK3 associates exclusively with the gamma common cytokine receptor chain, which is present in the IL-2, IL-4, IL-7, IL-9, IL-15 and IL-21 cytokine receptor complexes. JAK3 is predominantly expressed in immune cells and transduces a signal in response to its activation via tyrosine phosphorylation by interleukin receptors. Since JAK3 expression is restricted mostly to hematopoietic cells, its role in cytokine signaling is thought to be more restricted than other JAKs. Mutations of JAK3 result in severe combined immunodeficiency (SCID). (O'Shea et al., 2002, *Cell*, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., *Arthritis & Rheumatism*, 2005, 52:2686-2692; Changelian et al., *Science* 2003, 302: 875-878).

TYK2 is implicated in IFN-α, IL-6, IL-10 and IL-12 signaling. Biochemical studies and gene-targeted mice uncovered the crucial role of TYK2 in immunity. Tyk2-deficient mice are viable and fertile but display multiple immunological defects, most prominently high sensitivity to infections and defective tumor surveillance. In contrast, inhibition of TYK2 results in increased resistance against allergic, autoimmune and inflammatory diseases. Particularly, targeting Tyk2 appears to be a promising strategy for the treatment of IL-12-, IL-23- or Type 1 IFN-mediated diseases. These include but are not limited to rheumatoid arthritis, multiple sclerosis, lupus, psoriasis, psoriatic arthritis, inflammatory bowel disease, uveitis, sarcoidosis, and tumors (Shaw, M. et al., *Proc. Natl. Acad. Sci. USA*, 2003, 100, 11594-11599; Ortmann, R. A., and Shevach, E. M. *Clin. Immunol*, 2001, 98, 109-118; Watford et al, *Immunol. Rev.*, 2004, 202: 139). ["Janus Kinase (JAK) Inhibitors in Rheumatoid Arthritis." Current Rheumatology Reviews, 2011, 7, 306-312].

A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., *N. Engl. J. Med.*, 2007, 356:580-92; Reich et al., *Nat. Rev. Drug Discov.*, 2009, 8:355-356). In addition, an antibody targeting the IL-12 and IL-23 pathways underwent clinical trials for treating Crohn's Disease (Mannon et al., *N. Engl. J. Med.*, 2004, 351: 2069-79).

When dysregulated, JAK-mediated responses can positively or negatively affect cells leading to over-activation and malignancy or immune and hematopoietic deficiencies, respectively, and suggests the utility for use of inhibitors of JAK kinases. The JAK/STAT signaling pathway is involved in a variety of hyperproliferative and cancer-related processes including cell-cycle progression, apoptosis, angiogenesis, invasion, metastasis and evasion of the immune system (Haura et al., *Nature Clinical Practice Oncology*, 2005, 2(6), 315-324; Verna et al., *Cancer and Metastasis Reviews*, 2003, 22, 423-434). In addition, the JAK/STAT signaling pathway is important in the genesis and differentiation of hematopoietic cells and regulating both pro- and anti-inflammatory and immune responses (O'Sullivan et al., *Molecular Immunology* 2007, 44:2497).

Therefore, the JAK/STAT pathway, and in particular all four members of the JAK family, are believed to play a role in the pathogenesis of the asthmatic response, chronic obstructive pulmonary disease, bronchitis, and other related inflammatory diseases of the lower respiratory tract. The JAK/STAT pathway has also been implicated to play a role in inflammatory diseases/conditions of the eye including, but not limited to, iritis, uveitis, scleritis, conjunctivitis, as well as chronic allergic responses. Since cytokines utilize different patterns of JAK kinases (O'Sullivan et al., *Mol. Immunol*, 2007, 44:2497; Murray J., *Immunol*, 2007, 178: 2623), there may be utility for antagonists of JAK kinases with differing intra-family selectivity profiles in diseases associated with particular cytokines or in diseases associated with mutations or polymorphisms in the JAK/STAT pathways.

Rheumatoid arthritis (RA) is an autoimmune disease characterized by chronic joint inflammation. Patients with rheumatoid arthritis treated with JAK inhibitor showed that inhibition of JAK1 and JAK3 blocks signalling by multiple cytokines that are important for lymphocyte function, including interleukin-2 (IL-2), IL-4, IL-7, IL-9, IL-15 and IL-21. (Fleischmann, R. et al., "Placebo-controlled trial of tofacitinib monotherapy in rheumatoid arthritis." *N. Engl. J. Med.*, 2012, 367, 495-507). It was conjectured that small-molecule inhibitors that directly inactivate specific JAK isoforms would also reduce not only the clinical symptoms of RA, but also suppress the upregulation of many of the proinflammatory cytokines that are critical in driving RA disease progression. ("Inhibitors of JAK for the treatment of rheumatoid arthritis: rationale and clinical data." *Clin. Invest.*, 2012, 2(1), 39-47)

Persistent activation of STAT3 or STAT5 has been demonstrated in a wide spectrum of solid human tumors including breast, pancreatic, prostate, ovarian and hepatic carcinomas, as well as in the majority of hematopoietic tumors including lymphomas and leukemias. In this context, inactivation of JAK/STAT signaling in many hematopoietic tumors resulted in inhibition of cell proliferation and/or induction of apoptosis. Although STAT3 in tumor cells can be activated by various kinases, JAK2 has been shown to be the most important upstream activator mediating STAT3 activation in human tumor cell lines derived from various solid tumors (Mohamad Bassam Sonbol, Belal Firwana, Ahmad Zarzour, Mohammad Morad, Vishal Rana and Ramon V. Tiu, Therapeutic Advances in Hematology, 2013, 4(1), 15-35; Hedvat M, Huszar D, Herrmann A, Gozgit J M, Schroeder A, Sheehy A, et al., *Cancer Cell* 2009; 16(6): 487-97). Therefore, inhibition of JAK kinases may have a beneficial role in the therapeutic treatment of these diseases.

Clearly, protein kinase inhibitors have gathered attention as a new drug category for both immunosuppresion and antiinflammatory drug, and for cancer drug. Thus, new or improved agents which inhibit protein kinases such as Aurora inhibitors, FLT3 inhibitors and Janus kinases inhibitors are continually needed that act as immunosuppressive agents for organ transplants, and antitumor agents, as well as agents for the prevention and treatment of autoimmune diseases (e.g., multiple sclerosis, psoriasis, rheumatoid arthritis, asthma, type I diabetes, inflammatory bowel disease, Crohn's disease, polycythemia vera, essential thrombocythemia, myelofibrosis, autoimmune thyroid disorders, Alzheimer's disease), diseases involving a hyperactive inflammatory response (e.g., eczema), allergies, chronic obstructive pulmonary disease, bronchitis, cancer (e.g., prostate, acute myelogenous leukemia, chronic myelogenous leukemia, acute lymphocytic leukemia, leukemia, multiple myeloma), and some immune reactions (e.g., skin rash or contact dermatitis or diarrhea) caused by other therapeutics, to name a few. The compounds, compositions and methods described herein are directed toward these needs and other ends.

SUMMARY OF THE INVENTION

The invention provides compounds that inhibit, regulate, and/or modulate one or more protein kinases such as JAK, FLT3 and Aurora kinases activities, and are useful for treating proliferative diseases, autoimmune diseases, allergic diseases, inflammatory diseases, transplantation rejections, and their co-morbidities. This invention also provides methods of making the compound, methods of using such compounds in the treatment of said diseases in mammals, especially in humans, and pharmaceutical compositions containing these compounds. The compounds or the pharmaceutical composition disclosed herein have better prospects for clinical application. Compared with the similar compounds, the compounds disclosed herein have a better pharmacological activity, pharmacokinetic properties, physical and chemical properties and/or lesser toxicity. In particular, the compounds of the present invention display potent inhibitory activities against target kinases, and optimized selectivity. In addition, the compounds or the pharmaceutical composition disclosed herein have good membrane permeability and solubility, and are suitable for topical administration.

Specifically, in one aspect, provided herein is a compound having Formula (I):

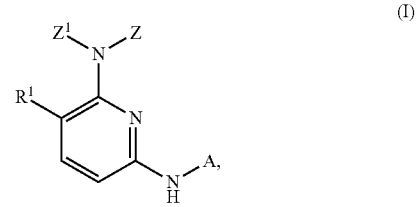

or a stereoisomer, a tautomer, an N-oxide, a solvate, a metabolite, a pharmaceutically acceptable salt or a prodrug thereof, wherein each of Z, $Z^1$, A and $R^1$ is as defined herein.

In one embodiment, Z is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein Z is substituted by 1, 2, 3, 4 or 5 $R^2$ groups;

$Z^1$ is H, $C_1$-$C_{12}$ alkyl, $C_3$-$C_{12}$ cycloalkyl or 3-12 membered heterocyclyl, wherein each of the $C_1$-$C_{12}$ alkyl, $C_3$-$C_{12}$ cycloalkyl and 3-12 membered heterocyclyl is optionally independently substituted by 1, 2, 3, 4 or 5 $R^{2a}$ groups;

A is

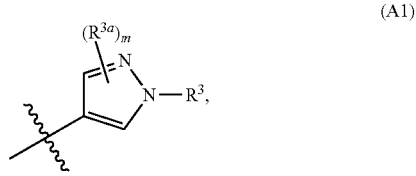

(A1)

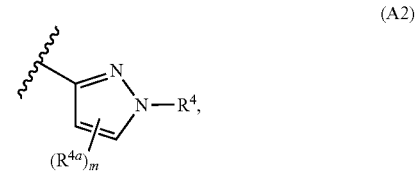

(A2)

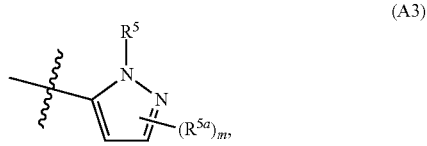

(A3)

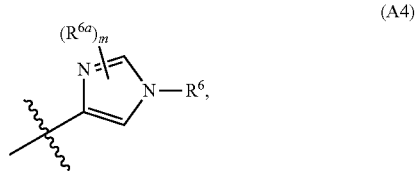

(A4)

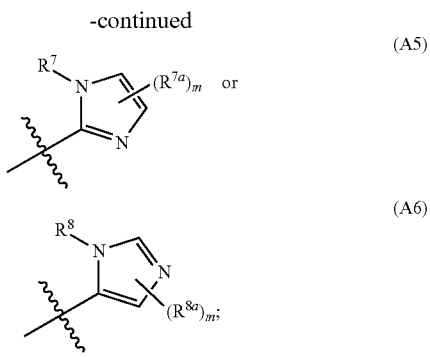

(A5)

(A6)

R¹ is H, F, Cl, Br, I, N₃, CN, —NO₂, C₁-C₁₂ alkyl, C₁-C₁₂ alkoxyl, C₂-C₁₂ alkenyl, C₂-C₁₂ alkynyl, C₃-C₁₂ cycloalkyl, 3-12 membered heterocyclyl, C₆-C₁₂ aryl, 5-12 membered heteroaryl, —NR$^{9a}$R$^{9b}$, —OR$^{9c}$, —C(=O)OR$^{9c}$, —C(=O)NR$^{9a}$R$^{9b}$ or —S(=O)₂NR$^{9a}$R$^{9b}$, wherein each of the C₁-C₁₂ alkyl, C₁-C₁₂ alkoxyl, C₂-C₁₂ alkenyl, C₂-C₁₂ alkynyl, C₃-C₁₂ cycloalkyl, 3-12 membered heterocyclyl, C₆-C₁₂ aryl and 5-12 membered heteroaryl is optionally independently substituted by 1, 2, 3, 4 or 5 R¹¹ groups;

each R² is independently F, Cl, Br, I, —NO₂, N₃, CN, —OH, —NH₂, —C(=O)CH₂CN, —NHC(=O)CH₂CN, —N(CH₃)C(=O)CH₂CN, C₁-C₁₂ alkyl, C₂-C₁₂ alkenyl, C₂-C₁₂ alkynyl, C₁-C₁₂ alkoxyl, C₃-C₁₂ cycloalkyl, 3-12 membered heterocyclyl, C₆-C₁₂ aryl, 5-12 membered heteroaryl, —NR$^{10a}$R$^{10b}$, —O—(C₀-C₄ alkylene)-R$^{10c}$, —O—(C₁-C₄ alkylene)-OR$^{10c}$, —C(=O)R$^{10d}$, —OC(=O)R$^{10d}$, —N(R$^{10e}$)C(=O)R$^{10d}$, —C(=O)NR$^{10a}$R$^{10b}$, —N(R$^{10e}$)C(=O)NR$^{10a}$R$^{10b}$, —C(=O)N(R$^{10e}$)C(=O)R$^{10d}$, —S(=O)₂R$^{10f}$, —N(R$^{10e}$)S(=O)₂R$^{10f}$ or —S(=O)₂NR$^{10a}$R$^{10b}$, or two adjacent R² taken together with the atoms to which they are attached form a C₃-C₁₂ cycloalkyl or 3-12 membered heterocycloalkyl group, wherein each of the C₁-C₁₂ alkyl, C₂-C₁₂ alkenyl, C₂-C₁₂ alkynyl, C₁-C₁₂ alkoxyl, C₃-C₁₂ cycloalkyl, 3-12 membered heterocyclyl, C₆-C₁₂ aryl, 5-12 membered heteroaryl, and 3-12 membered heterocycloalkyl group is optionally independently substituted by 1, 2, 3, 4 or 5 R¹¹ groups;

each R$^{2a}$ is independently H, F, Cl, Br, I, —NO₂, N₃, CN, —OH, —NH₂, C₁-C₁₂ alkyl, C₂-C₁₂ alkenyl, C₂-C₁₂ alkynyl, C₁-C₁₂ alkoxyl, C₃-C₁₂ cycloalkyl, 3-12 membered heterocyclyl, C₆-C₁₂ aryl or 5-12 membered heteroaryl, wherein each of the C₁-C₁₂ alkyl, C₂-C₁₂ alkenyl, C₂-C₁₂ alkynyl, C₁-C₁₂ alkoxyl, C₃-C₁₂ cycloalkyl, 3-12 membered heterocyclyl, C₆-C₁₂ aryl, 5-12 membered heteroaryl, and 3-12 membered heterocycloalkyl group is optionally independently substituted by 1, 2, 3, 4 or 5 R¹¹ groups;

R³ is H, C₃-C₁₂ hydroxyalkyl, C₃-C₁₂ alkyl, C₁-C₁₂ haloalkyl, C₁-C₁₂ aminoalkyl, C₂-C₁₂ alkenyl, C₂-C₁₂ alkynyl, C₃-C₁₂ cycloalkyl, C₆-C₁₂ aryl, 3-12 membered heterocyclyl or 5-12 membered heteroaryl, wherein each of the C₃-C₁₂ hydroxyalkyl, C₃-C₁₂ alkyl, C₁-C₁₂ haloalkyl, C₁-C₁₂ aminoalkyl, C₂-C₁₂ alkenyl, C₂-C₁₂ alkynyl, C₃-C₁₂ cycloalkyl, C₆-C₁₂ aryl, 3-12 membered heterocyclyl and 5-12 membered heteroaryl is optionally independently substituted by 1, 2, 3, 4 or 5 R¹¹ groups;

R⁴ is C₁-C₁₂ hydroxyalkyl, C₃-C₁₂ alkyl, C₁-C₁₂ haloalkyl, C₁-C₁₂ aminoalkyl, C₂-C₁₂ alkenyl, C₂-C₁₂ alkynyl, C₃-C₁₂ cycloalkyl, C₆-C₁₂ aryl, 3-12 membered heterocyclyl or 5-12 membered heteroaryl, wherein R⁴ is optionally substituted by 1, 2, 3, 4 or 5 R¹¹ groups;

each of R⁵, R⁶, R⁷ and R⁸ is independently H, C₁-C₁₂ hydroxyalkyl, C₃-C₁₂ alkyl, C₁-C₁₂ haloalkyl, C₁-C₁₂ aminoalkyl, C₂-C₁₂ alkenyl, C₂-C₁₂ alkynyl, C₃-C₁₂ cycloalkyl, 3-12 membered heterocyclyl, C₆-C₁₂ aryl or 5-12 membered heteroaryl, wherein each of the C₁-C₁₂ hydroxyalkyl, C₃-C₁₂ alkyl, C₁-C₁₂ haloalkyl, C₁-C₁₂ aminoalkyl, C₂-C₁₂ alkenyl, C₂-C₁₂ alkynyl, C₃-C₁₂ cycloalkyl, 3-12 membered heterocyclyl, C₆-C₁₂ aryl and 5-12 membered heteroaryl is optionally independently substituted by 1, 2, 3, 4 or 5 R¹¹ groups;

each R$^{3a}$, R$^{4a}$, R$^{5a}$, R$^{6a}$, R$^{7a}$ and R$^{8a}$ is independently H, F, Cl, CN, C₁-C₁₂ alkyl, C₂-C₁₂ alkenyl, C₂-C₁₂ alkynyl, C₁-C₁₂ alkoxyl, C₁-C₁₂ alkylamino, —(C₀-C₄ alkylene)-(C₃-C₁₂ cycloalkyl), —(C₀-C₄ alkylene)-(3-12 membered heterocyclyl), C₆-C₁₂ aryl or 5-12 membered heteroaryl, wherein each of the C₁-C₁₂ alkyl, C₂-C₁₂ alkenyl, C₂-C₁₂ alkynyl, C₁-C₁₂ alkoxyl, C₁-C₁₂ alkylamino, —(C₀-C₄ alkylene)-(C₃-C₁₂ cycloalkyl), —(C₀-C₄ alkylene)-(3-12 membered heterocyclyl), C₆-C₁₂ aryl and 5-12 membered heteroaryl is optionally independently substituted by 1, 2, 3, 4 or 5 R¹¹ groups;

each R$^{9a}$, R$^{9b}$, R$^{9c}$, R$^{10a}$, R$^{10b}$, R$^{10c}$ and R$^{10e}$ is independently H, C₁-C₁₂ alkyl, C₂-C₁₂ alkenyl, C₂-C₁₂ alkynyl, C₁-C₁₂ alkoxyl, C₃-C₁₂ cycloalkyl, —(C₀-C₄ alkylene)-(C₃-C₁₂ cycloalkyl), —(C₀-C₄ alkylene)-(3-12 membered heterocyclyl), —(C₀-C₄ alkylene)-(C₆-C₁₀ aryl) or —(C₀-C₄ alkylene)-(5-12 membered heteroaryl), or R$^{9a}$ and R$^{9b}$, R$^{10a}$ and R$^{10b}$ taken together with the nitrogen atom to which they are attached form a 3-12 membered heterocyclyl group, wherein each of the C₁-C₁₂ alkyl, C₂-C₁₂ alkenyl, C₂-C₁₂ alkynyl, C₁-C₁₂ alkoxyl, C₃-C₁₂ cycloalkyl, —(C₀-C₄ alkylene)-(C₃-C₁₂ cycloalkyl), —(C₀-C₄ alkylene)-(3-12 membered heterocyclyl), —(C₀-C₄ alkylene)-(C₆-C₁₀ aryl), —(C₀-C₄ alkylene)-(5-12 membered heteroaryl) and 3-12 membered heterocyclyl group is optionally substituted by 1, 2, 3 or 4 substituents independently selected from F, Cl, Br, CN, N₃, —NO₂, —OH, —NH₂, C₁-C₆ alkyl, C₁-C₆ haloalkyl, C₁-C₆ alkoxy, C₁-C₆ hydroxyalkyl, C₁-C₆ aminoalkyl and C₁-C₆ alkylamino;

each R$^{10d}$ and R$^{10f}$ is independently C₁-C₁₂ alkyl, C₂-C₁₂ alkenyl, C₂-C₁₂ alkynyl, C₁-C₁₂ alkoxyl, C₃-C₁₂ cycloalkyl, 3-12 membered heterocyclyl, C₆-C₁₂ aryl, 5-12 membered heteroaryl, —(C₁-C₄ alkylene)-(C₃-C₁₂ cycloalkyl), —(C₁-C₄ alkylene)-(3-12 membered heterocyclyl), —(C₁-C₄ alkylene)-(C₆-C₁₂ aryl) or —(C₁-C₄ alkylene)-(5-12 membered heteroaryl), wherein each of the above substituents is optionally substituted by 1, 2, 3 or 4 substituents independently selected from F, Cl, Br, CN, N₃, —OH, —NH₂, C₁-C₆ alkyl, C₁-C₆ haloalkyl, C₁-C₆ alkoxy, C₁-C₆ hydroxyalkyl, C₁-C₆ aminoalkyl and C₁-C₆ alkylamino;

each R¹¹ is independently F, Cl, Br, I, CN, —NO₂, N₃, —OH, —NH₂, C₁-C₁₂ alkyl, C₂-C₁₂ alkenyl, C₂-C₁₂ alkynyl, C₁-C₁₂ haloalkyl, C₃-C₁₂ cycloalkyl, C₆-C₁₂ aryl, 3-12 membered heterocyclyl, 5-12 membered heteroaryl, C₁-C₁₂ aminoalkyl, C₁-C₁₂ alkylamino, C₁-C₁₂ alkoxyl, C₁-C₁₂ hydroxyalkyl, —NH(C₀-C₄ alkylene)-(C₃-C₁₂ cycloalkyl), —NH(C₀-C₄ alkylene)-(C₆-C₁₂ aryl), —NH(C₀-C₄ alkylene)-(3-12 membered heterocyclyl), —NH(C₀-C₄ alkylene)-(5-12 membered heteroaryl), —N[(C₀-C₄ alkylene)-(C₃-C₁₂ cycloalkyl)]₂, —N[(C₀-C₄ alkylene)-(C₆-C₁₂ aryl)]₂, —N[(C₀-C₄ alkylene)-(3-12 membered heterocyclyl)]₂, —N[(C₀-C₄ alkylene)-(5-12 membered heteroaryl)]₂, —O—(C₀-C₄ alkylene)-(C₃-C₁₂ cycloalkyl), —O—(C₀-C₄ alkylene)-(C₆-C₁₂ aryl), —O—(C₀-C₄ alkylene)-(3-12 membered heterocyclyl) or —O—(C₀-C₄ alkylene)-(5-12 membered heteroaryl); and each m is independently 0, 1 or 2.

In another embodiment, Z is 8-11 membered spiro heterobicyclyl or 8-10 membered fused heterobicycloalkyl, wherein Z is substituted by 1, 2, 3 or 4 R² groups.
In one embodiment, Z is:
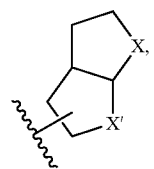
(Z-1)
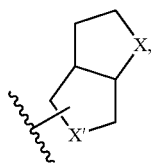
(Z-2)
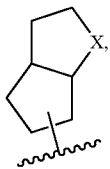
(Z-3)
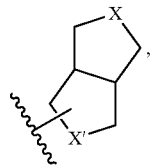
(Z-4)
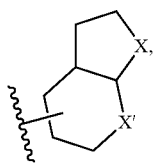
(Z-5)
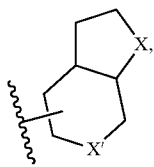
(Z-6)
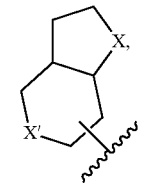
(Z-7)
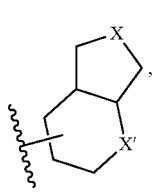
(Z-8)
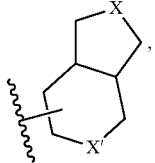
(Z-9)
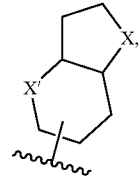
(Z-10)
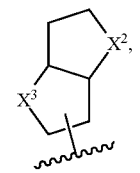
(Z-11)
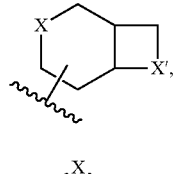
(Z-12)
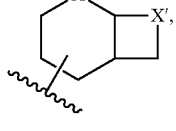
(Z-13)
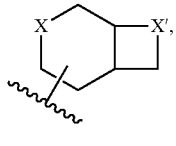
(Z-14)
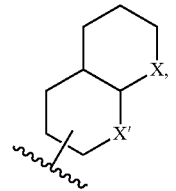
(Z-15)
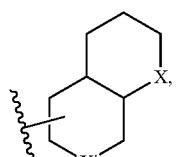
(Z-16)
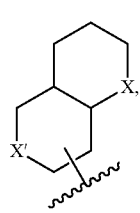
(Z-17)

-continued
(Z-18)
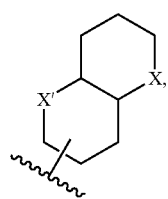
(Z-19)
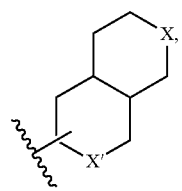
(Z-20)
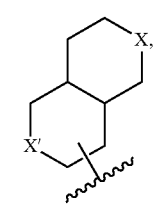
(Z-21)
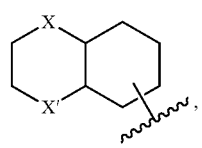
(Z-22)
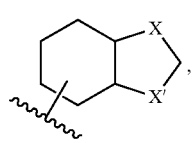
(Z-23)
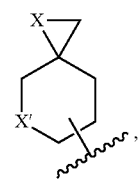
(Z-24)
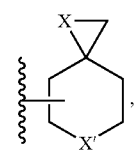
(Z-25)
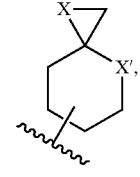
(Z-26)
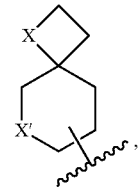
-continued
(Z-27)
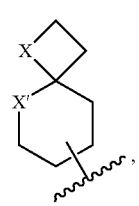
(Z-28)
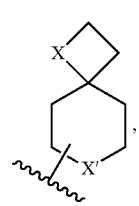
(Z-29)
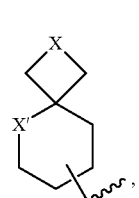
(Z-30)
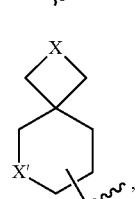
(Z-31)
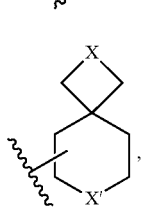
(Z-32)
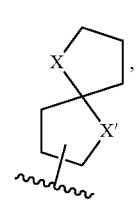
(Z-33)
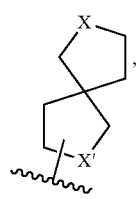
(Z-34)
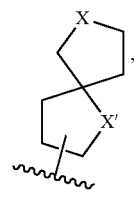

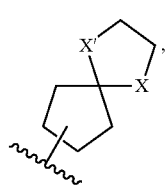 (Z-35)
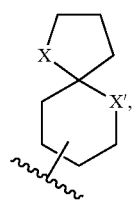 (Z-36)
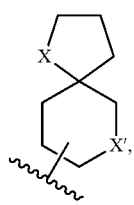 (Z-37)
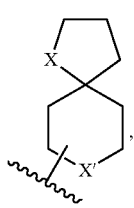 (Z-38)
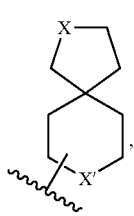 (Z-39)
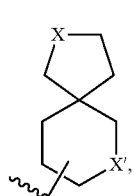 (Z-40)
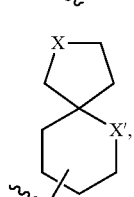 (Z-41)
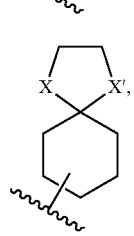 (Z-42)
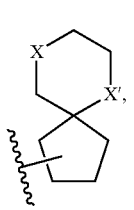 (Z-43)
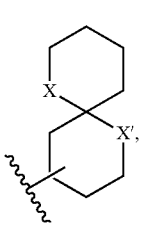 (Z-44)
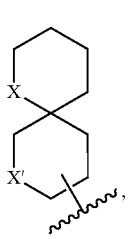 (Z-45)
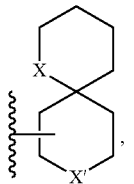 (Z-46)
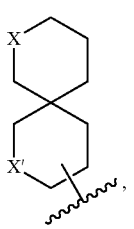 (Z-47)
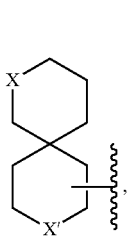 (Z-48)
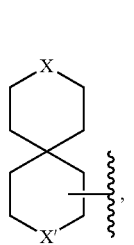 (Z-49)

-continued
(Z-50) 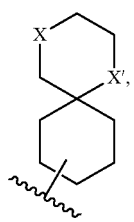
(Z-51) 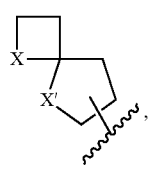
(Z-52) 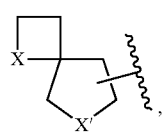
(Z-53) 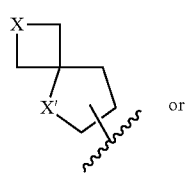 or
(Z-54) 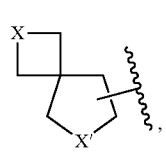
or a stereoisomer thereof, wherein each X, X¹, X², and X³ is independently —CH$_2$—, —NH— or —O—, with the proviso that X² and X³ are not —O— simultaneously; and wherein Z is substituted by 1, 2 or 3 R² groups.
In another embodiment, Z is:
(Z-55) 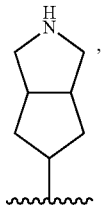
(Z-56) 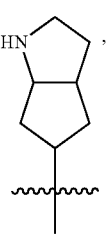
(Z-57) 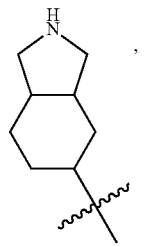
(Z-58) 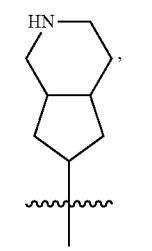
(Z-59) 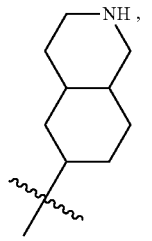
(Z-60) 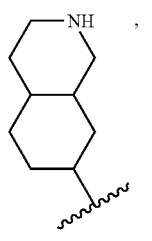
(Z-61) 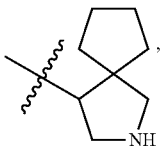
(Z-62) 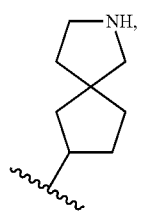
(Z-63) 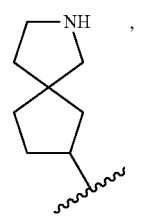

(Z-64) 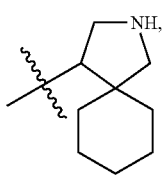

(Z-65) 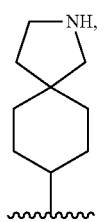

(Z-66) 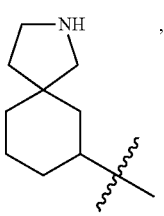

(Z-67) 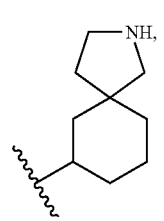

(Z-68) 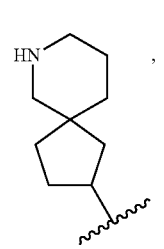

(Z-69) 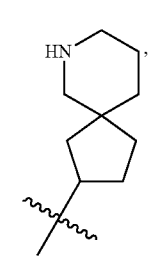

(Z-70) 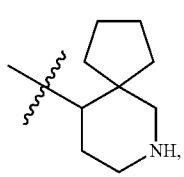

(Z-71) 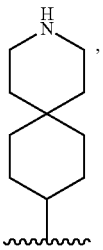

(Z-72) 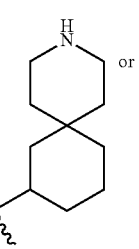  or (Z-73) 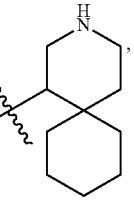

or a stereoisomer thereof, and wherein Z is substituted by 1, 2 or 3 $R^2$ groups.

In one embodiment, $Z^1$ is H, $C_1$-$C_6$ alkyl, $C_3$-$C_6$ cycloalkyl or 4-7 membered heterocyclyl, wherein each of the $C_1$-$C_6$ alkyl, $C_3$-$C_6$ cycloalkyl and 4-7 membered heterocyclyl is optionally independently substituted by 1, 2 or 3 $R^{2a}$ groups.

In one embodiment, $R^1$ is H, F, Cl, Br, I, $N_3$, CN, —$NO_2$, $C_1$-$C_6$ alkyl, $C_1$-$C_6$ alkoxyl, $C_2$-$C_6$ alkenyl, $C_2$-$C_6$ alkynyl, $C_3$-$C_6$ cycloalkyl, 4-7 membered heterocyclyl, —$NR^{9a}R^{9b}$, —$OR^{9c}$, —C(=O)$OR^{9c}$, —C(=O)$NR^{9a}R^{9b}$, or —S(=O)$_2NR^{9a}R^{9b}$, wherein each of the $C_1$-$C_6$ alkyl, $C_1$-$C_6$ alkoxyl, $C_2$-$C_6$ alkenyl, $C_2$-$C_6$ alkynyl, $C_3$-$C_6$ cycloalkyl and 4-7 membered heterocyclyl is optionally independently substituted by 1, 2 or 3 $R^{11}$ groups.

In another embodiment, each $R^2$ is independently F, Cl, Br, I, —$NO_2$, $N_3$, CN, —OH, —$NH_2$, —C(=O)$CH_2CN$, —NHC(=O)$CH_2CN$, —N($CH_3$)C(=O)$CH_2CN$, $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl, —$NR^{10a}R^{10b}$, —O—($C_0$-$C_3$ alkylene)-$R^{10c}$, —O—($C_1$-$C_3$ alkylene)-$OR^{10c}$, —C(=O)$R^{10d}$, —OC(=O)$R^{10d}$, —N($R^{10e}$)C(=O)$R^{10d}$, —C(=O)$NR^{10a}R^{10b}$, —N($R^{10e}$)C(=O)$NR^{10a}R^{10b}$, —C(=O)N($R^{10e}$)C(=O)$R^{10d}$, —S(=O)$_2R^{10f}$, —N($R^{10e}$)S(=O)$_2R^{10f}$ or —S(=O)$_2NR^{10a}R^{10b}$, or two adjacent $R^2$ taken together with the atoms to which they are attached form a $C_3$-$C_6$ cycloalkyl or 4-7 membered heterocycloalkyl group, wherein each of the $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl and 4-7 membered heterocycloalkyl group is optionally independently substituted by 1, 2 or 3 $R^{11}$ groups;

In another embodiment, each $R^{2a}$ is independently H, F, Cl, Br, I, —$NO_2$, $N_3$, CN, —OH, —$NH_2$, $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl or 5-6 membered heteroaryl.

In one embodiment, $R^3$ is H, $C_3$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_3$-$C_6$ cycloalkyl, phenyl, 4-7 membered heterocyclyl or 5-6 membered heteroaryl, wherein each of the $C_3$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_3$-$C_6$ cycloalkyl, phenyl, 4-7 membered heterocyclyl and 5-6 membered heteroaryl is optionally independently substituted by 1, 2 or 3 $R^{11}$ groups.

In another embodiment, $R^3$ is H, —$CH_2C(CH_3)_2OH$, —$(CH_2)_2CH_2OOH$, —$CH_2CH(OH)CH_3$, piperidinyl, pyrrolidinyl, morpholinyl, piperazinyl, pyridyl, pyrimidinyl, pyridazinyl, pyrazinyl, thiazolyl, pyrrolyl or oxazolyl, wherein each of the piperidinyl, pyrrolidinyl, morpholinyl, piperazinyl, pyridyl, pyrimidinyl, pyridazinyl, thiazolyl, pyrrolyl or oxazolyl is optionally independently substituted by 1, 2 or 3 $R^{11}$ groups.

In one embodiment, $R^4$ is $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, phenyl, 4-7 membered heterocyclyl or 5-6 membered heteroaryl, wherein $R^4$ is optionally substituted by 1, 2, or 3 $R^{11}$ groups.

In another embodiment, each of $R^5$, $R^6$, $R^7$ and $R^8$ is independently H, $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, 4-7 membered heterocyclyl, phenyl or 5-6 membered heteroaryl, wherein each of the $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, 4-7 membered heterocyclyl, phenyl and 5-6 membered heteroaryl is optionally independently substituted by 1, 2 or 3 $R^{11}$ groups.

In one embodiment, each $R^{3a}$, $R^{4a}$, $R^{5a}$, $R^{6a}$, $R^{7a}$ and $R^{8a}$ is independently H, F, Cl, CN, $C_1$-$C_6$ alkyl, $C_2$-$C_6$ alkenyl, $C_1$-$C_6$ alkoxyl, $C_1$-$C_6$ alkylamino, —$(C_0$-$C_3$ alkylene)-($C_3$-$C_6$ cycloalkyl), —$(C_0$-$C_3$ alkylene)-(4-7 membered heterocyclyl), phenyl or 5-6 membered heteroaryl, wherein each of the $C_1$-$C_6$ alkyl, $C_2$-$C_6$ alkenyl, $C_1$-$C_6$ alkoxyl, $C_1$-$C_6$ alkylamino, —$(C_0$-$C_3$ alkylene)-($C_3$-$C_6$ cycloalkyl), —$(C_0$-$C_3$ alkylene)-(4-7 membered heterocyclyl), phenyl and 5-6 membered heteroaryl is optionally independently substituted by 1, 2 or 3 $R^{11}$ groups.

In another embodiment, each $R^{9a}$, $R^{9b}$, $R^{9c}$, $R^{10a}$, $R^{10b}$, $R^{10c}$ and $R^{10e}$ is independently H, $C_1$-$C_6$ alkyl, $C_2$-$C_6$ alkenyl, $C_2$-$C_6$ alkynyl, $C_1$-$C_6$ alkoxyl, $C_3$-$C_6$ cycloalkyl, —$(C_0$-$C_3$ alkylene)-($C_3$-$C_6$ cycloalkyl), —$(C_0$-$C_3$ alkylene)-(4-7 membered heterocyclyl), —$(C_0$-$C_3$ alkylene)-phenyl, —$(C_0$-$C_3$ alkylene)-(5-6 membered heteroaryl), or $R^{9a}$ and $R^{9b}$, $R^{10a}$ and $R^{10b}$ taken together with the nitrogen atom to which they are attached form a 4-7 membered heterocyclyl group, wherein each of the $C_1$-$C_6$ alkyl, $C_2$-$C_6$ alkenyl, $C_2$-$C_6$ alkynyl, $C_1$-$C_6$ alkoxyl, $C_3$-$C_6$ cycloalkyl, —$(C_0$-$C_3$ alkylene)-($C_3$-$C_6$ cycloalkyl), —$(C_0$-$C_3$ alkylene)-(4-7 membered heterocyclyl), —$(C_0$-$C_3$ alkylene)-phenyl, —$(C_0$-$C_3$ alkylene)-(5-6 membered heteroaryl), and 4-7 membered heterocyclyl group is optionally substituted by 1, 2 or 3 substitutents independently selected from F, Cl, Br, CN, $N_3$, —$NO_2$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In one embodiment, each $R^{9a}$, $R^{9b}$, $R^{9c}$, $R^{10a}$, Rib, $R^{10c}$ and $R^{10e}$ is independently H, methyl, ethyl, n-propyl, isopropyl, n-butyl, isobutyl, sec-butyl, tert-butyl, allyl, vinyl, propenyl, $C_1$-$C_4$ alkoxyl, cyclopropyl, cyclobutyl, cyclopentyl, cyclohexyl, piperidinyl, pyrrolidinyl, morpholinyl, piperazinyl, -methylene-cyclopropy, -ethylidene-cyclopropyl, -methylene-cyclobutyl, -ethylidene-cyclobutyl, -methylene-cyclopentyl, -ethylidene-cyclopentyl, -methylene-cyclohexyl, -ethylidene-cyclohexyl, —$(C_1$-$C_3$ alkylene)-(4-7 membered heterocyclyl), phenyl, pyridyl, pyridazinyl, pyrimidinyl, —$(C_1$-$C_3$ alkylene)-phenyl or —$(C_1$-$C_3$ alkylene)-(5-6 membered heteroaryl), wherein each of the methyl, ethyl, n-propyl, isopropyl, n-butyl, isobutyl, sec-butyl, tert-butyl, allyl, vinyl, propenyl, $C_1$-$C_4$ alkoxyl, cyclopropyl, cyclobutyl, cyclopentyl, cyclohexyl, piperidinyl, pyrrolidinyl, morpholinyl, piperazinyl, -methylene-cyclopropyl, -ethylidene-cyclopropyl, -methylene-cyclobutyl, -ethylidene-cyclobutyl, -methylene-cyclopentyl, -ethylidene-cyclopentyl, -methylene-cyclohexyl, -ethylidene-cyclohexyl, —$(C_1$-$C_3$ alkylene)-(4-7 membered heterocyclyl), phenyl, pyridyl, pyridazinyl, pyrimidinyl, —$(C_1$-$C_3$ alkylene)-phenyl and —$(C_1$-$C_3$ alkylene)-(5-6 membered heteroaryl) is optionally substituted by 1, 2 or 3 substitutents independently selected from F, Cl, Br, CN, $N_3$, —$NO_2$, —OH, —$NH_2$, —$CF_3$, —$OCH_3$, —$CH_2OH$, —$CH_2CH_2OH$, —$NHCH_3$, —$N(CH_3)_2$ and —$CH_2NH_2$.

In another embodiment, each $R^{10d}$ and $R^{10f}$ is independently $C_1$-$C_4$ alkyl, $C_2$-$C_4$ alkenyl, $C_2$-$C_4$ alkynyl, $C_1$-$C_4$ alkoxyl, $C_3$-$C_6$ cycloalkyl, 4-7 membered heterocyclyl, phenyl, 5-6 membered heteroaryl, —$(C_1$-$C_3$ alkylene)-($C_3$-$C_6$ cycloalkyl), —$(C_1$-$C_3$ alkylene)-(4-7 membered heterocyclyl), —$(C_1$-$C_3$ alkylene)-phenyl or —$(C_1$-$C_3$ alkylene)-(5-6 membered heteroaryl), wherein each of the above substituents is optionally substituted by 1, 2 or 3 substitutents independently selected from F, Cl, Br, CN, $N_3$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In one embodiment, each $R^{10d}$ and $R^{10f}$ is independently methyl, ethyl, n-propyl, isopropyl, n-butyl, isobutyl, sec-butyl, tert-butyl, cyclopropyl, cyclobutyl, cyclopentyl, cyclohexyl, allyl, vinyl, propenyl, phenyl, piperidinyl, pyrrolidinyl, morpholinyl, piperazinyl, $C_1$-$C_4$ alkoxyl, -methylene-cyclopropy, -ethylidene-cyclopropyl, -methylene-cyclobutyl, -ethylidene-cyclobutyl, -methylene-cyclopentyl, -ethylidene-cyclopentyl, -methylene-cyclohexyl or -ethylidene-cyclohexyl, wherein each of the above substituents is optionally substituted by 1, 2 or 3 substitutents independently selected from F, Cl, Br, CN, $N_3$, —OH, —$NH_2$, —$CF_3$, —$OCH_3$, —$CH_2OH$, —$CH_2CH_2OH$, —$NHCH_3$, —$N(CH_3)_2$ and —$CH_2NH_2$.

In one embodiment, each $R^{11}$ is independently F, Cl, Br, I, CN, —$NO_2$, $N_3$, —OH, —$NH_2$, methyl, ethyl, n-propyl, isopropyl, cyclopropyl, methoxy, ethyoxyl, n-propoxy, isopropoxy, hydroxymethyl, hydroxyethyl, methylamino, dimethylamino or aminomethyl.

In another aspect, provided herein is a compound having Formula (II):

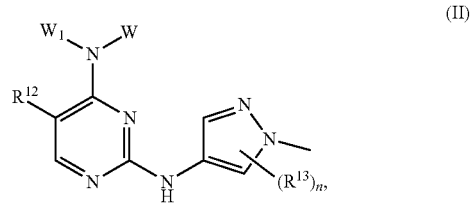

or a stereoisomer, a tautomer, an N-oxide, a solvate, a metabolite, a pharmaceutically acceptable salt or a prodrug thereof, wherein each of W, $W_1$, $R^{12}$, $R^{13}$ and n is as defined herein.

In one embodiment, W is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein W is substituted by 1, 2, 3, 4 or 5 $R^{14}$ groups;

$W_1$ is H, $C_1$-$C_6$ alkyl, $C_1$-$C_6$ haloalkyl, $C_1$-$C_6$ alkoxyl, $C_1$-$C_6$ aminoalkyl, $C_1$-$C_6$ hydroxyalkyl, $C_3$-$C_6$ cycloalkyl or 4-7 membered heterocyclyl;

$R^{12}$ is H, F, Cl, Br, I, $N_3$, CN, $-NO_2$, $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, $-NR^{15a}R^{15b}$, $-OR^{15c}$, $-C(=O)OR^{15c}$, $-C(=O)NR^{15a}R^{15b}$ or $-S(=O)_2NR^{15a}R^{15b}$, wherein each of the $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl and 5-12 membered heteroaryl is optionally independently substituted by 1, 2, 3, 4 or 5 $R^{17}$ groups;

each $R^{13}$ is independently H, F, Cl, CN, $C_1$-$C_{12}$ alkyl, $C_2$-$C_{12}$ alkenyl, $C_1$-$C_{12}$ alkoxyl, $-(C_0$-$C_4$ alkylene)-($C_3$-$C_{12}$ cycloalkyl), $-(C_0$-$C_4$ alkylene)-(3-12 membered heterocyclyl), $C_6$-$C_{12}$ aryl or 5-12 membered heteroaryl, wherein each of the $C_1$-$C_{12}$ alkyl, $C_2$-$C_{12}$ alkenyl, $C_1$-$C_{12}$ alkoxyl, $-(C_0$-$C_4$ alkylene)-($C_3$-$C_{12}$ cycloalkyl), $-(C_0$-$C_4$ alkylene)-(3-12 membered heterocyclyl), $C_6$-$C_{12}$ aryl and 5-12 membered heteroaryl is optionally independently substituted by 1, 2, 3, 4 or 5 $R^{17}$ groups;

each $R^{14}$ is independently F, Cl, Br, I, $NO_2$, $N_3$, CN, $C_3$-$C_{12}$ alkyl, $C_2$-$C_{12}$ alkenyl, $C_2$-$C_{12}$ alkynyl, $C_1$-$C_{12}$ hydroxyalkyl, $C_3$-$C_{12}$ alkoxyl, $C_1$-$C_{12}$ alkylamino, $C_1$-$C_{12}$ aminoalkyl, $C_3$-$C_{12}$ cycloalkyl, 4-7 membered heterocyclyl, $C_6$-$C_{12}$ aryl, 6-cyanopyridazine-3-yl, $-CH_2CN$, $-CH_2CH_2CN$, $-C(=O)R^{16d}$, $-S(=O)_2R^{16e}$, $-C(=O)NR^{16a}R^{16b}$, $-S(=O)_2NR^{16a}R^{16b}$, $-C(=O)O-R^{16c}$, $-N(R^{16a})C(=O)R^{16f}$, $-N(R^{16a})S(=O)_2R^{16g}$ or $-OC(=O)R^{16f}$, wherein each of the $-CH_2CN$, $-CH_2CH_2CN$, $C_3$-$C_{12}$ alkyl, $C_2$-$C_{12}$ alkenyl, $C_2$-$C_{12}$ alkynyl, $C_1$-$C_{12}$ hydroxyalkyl, $C_3$-$C_{12}$ alkoxyl, $C_1$-$C_{12}$ alkylamino, $C_1$-$C_{12}$ aminoalkyl, $C_3$-$C_{12}$ cycloalkyl, 4-7 membered heterocyclyl, $C_6$-$C_{12}$ aryl and 6-cyanopyridazine-3-yl is optionally independently substituted by 1, 2, 3, 4 or 5 $R^{17}$ groups;

each $R^{15a}$, $R^{15b}$, $R^{15c}$, $R^{16a}$ and $R^{16b}$ is independently H, $C_1$-$C_{12}$ alkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, $-(C_1$-$C_4$ alkylene)-($C_3$-$C_{12}$ cycloalkyl), $-(C_1$-$C_4$ alkylene)-(3-12 membered heterocyclyl), $-(C_1$-$C_4$ alkylene)-($C_6$-$C_{12}$ aryl), or $-(C_1$-$C_4$ alkylene)-(5-12 membered heteroaryl), or $R^{15a}$ and $R^{15b}$, taken together with the nitrogen atom to which they are attached form a 3-12 membered heterocyclyl group, wherein each of the $C_1$-$C_{12}$ alkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, $-(C_1$-$C_4$ alkylene)-($C_3$-$C_{12}$ cycloalkyl), $-(C_1$-$C_4$ alkylene)-(3-12 membered heterocyclyl), $-(C_1$-$C_4$ alkylene)-($C_6$-$C_{12}$ aryl), and $-(C_1$-$C_4$ alkylene)-(5-12 membered heteroaryl) is optionally substituted by 1, 2 or 3 substitutents independently selected from F, Cl, Br, CN, $N_3$, $-NO_2$, $-OH$, $-NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino; each $R^{16d}$, $R^{16e}$ and $R^{16g}$ is independently $C_2$-$C_{12}$ alkyl, $C_3$-$C_{12}$ cycloalkyl, 3-12 membered heterocyclyl, $C_6$-$C_{12}$ aryl, 5-12 membered heteroaryl, $-(C_1$-$C_4$ alkylene)-($C_3$-$C_{12}$ cycloalkyl), $-(C_1$-$C_4$ alkylene)-(3-12 membered heterocyclyl), $-(C_1$-$C_4$ alkylene)-($C_6$-$C_{12}$ aryl) or $-(C_1$-$C_4$ alkylene)-(5-12 membered heteroaryl), wherein each of the above substituents is optionally substituted by 1, 2, 3 or 4 substitutents independently selected from F, Cl, Br, CN, $N_3$, $-OH$, $-NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino;

each $R^{16c}$ and $R^{16f}$ is independently $C_1$-$C_3$ alkyl, $C_3$-$C_{12}$ cycloalkyl, 3-12 membered heterocyclyl, $C_6$-$C_{12}$ aryl, 5-12 membered heteroaryl, $-(C_1$-$C_4$ alkylene)-($C_3$-$C_{12}$ cycloalkyl), $-(C_1$-$C_4$ alkylene)-(3-12 membered heterocyclyl), $-(C_1$-$C_4$ alkylene)-($C_6$-$C_{12}$ aryl), or $-(C_1$-$C_4$ alkylene)-(5-12 membered heteroaryl), wherein each of the above substituents is optionally substituted by 1, 2, 3 or 4 substitutents independently selected from F, Cl, Br, CN, $N_3$, $-OH$, $-NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino;

each $R^{17}$ is independently F, Cl, Br, I, CN, $NO_2$, $N_3$, $-OH$, $-NH_2$, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, $C_6$-$C_{12}$ aryl, 4-7 membered heterocyclyl, 5-12 membered heteroaryl, $C_1$-$C_6$ aminoalkyl, $C_1$-$C_6$ alkylamino, $C_1$-$C_6$ alkoxyl, $C_1$-$C_6$ hydroxyalkyl, $-NH(C_0$-$C_4$ alkylene)-($C_3$-$C_6$ cycloalkyl), $-NH(C_0$-$C_4$ alkylene)-(4-7 membered heterocyclyl), $-N[(C_0$-$C_4$ alkylene)-($C_3$-$C_6$ cycloalkyl)]$_2$, $-N[(C_0$-$C_4$ alkylene)-(4-7 membered heterocyclyl)]$_2$, $-O(C_0$-$C_4$ alkylene)-($C_3$-$C_6$ cycloalkyl) or $-O(C_0$-$C_4$ alkylene)-(4-7 membered heterocyclyl); and n is 0, 1 or 2.

In another embodiment, W is 8-11 membered spiro heterobicyclyl or 8-10 membered fused heterobicycloalkyl, wherein W is substituted by 1, 2, 3 or 4 $R^{14}$ groups.

In one embodiment, W is:

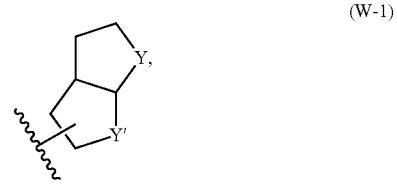

(W-1)

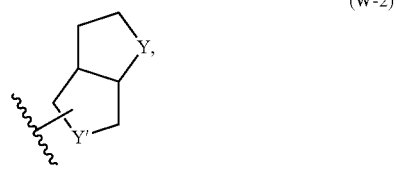

(W-2)

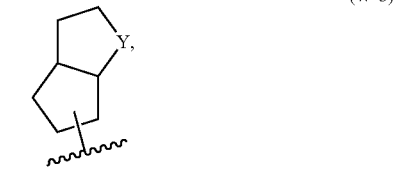

(W-3)

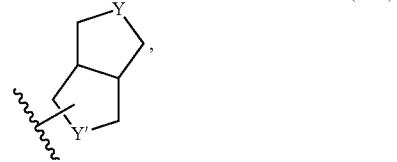

(W-4)

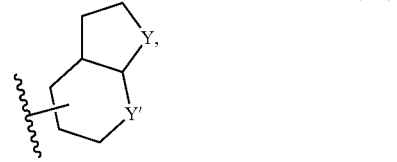

(Z-5)

-continued
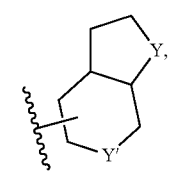 (W-6)
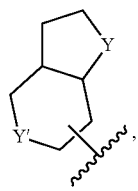 (W-7)
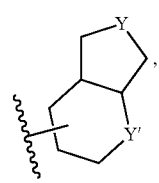 (W-8)
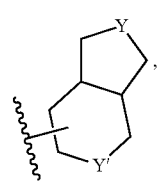 (W-9)
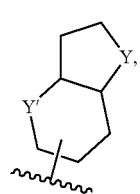 (W-10)
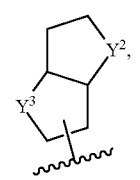 (W-11)
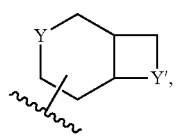 (W-12)
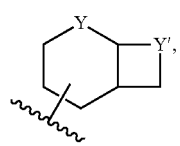 (W-13)
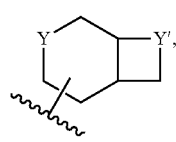 (W-14)
-continued
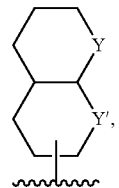 (W-15)
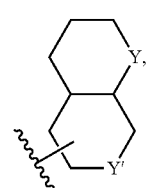 (W-16)
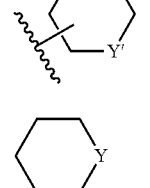 (W-17)
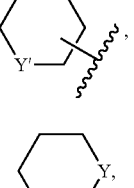 (W-18)
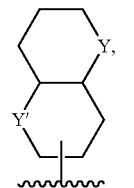 (W-19)
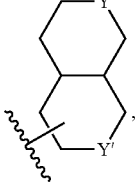 (W-20)
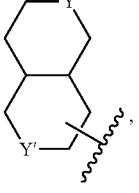 (W-21)
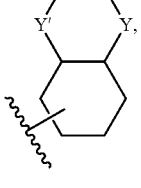 (W-22)
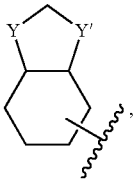

-continued
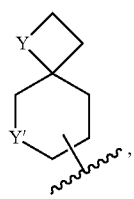 (W-23)
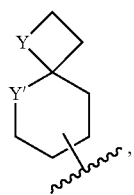 (W-24)
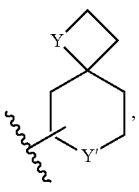 (W-25)
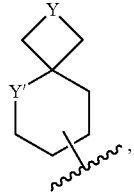 (W-26)
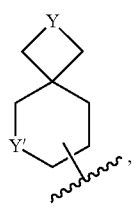 (W-27)
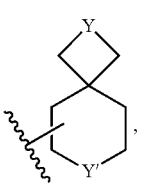 (W-28)
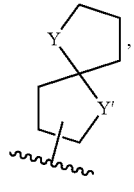 (W-29)
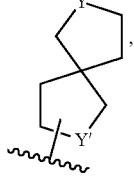 (W-30)
-continued
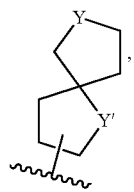 (W-31)
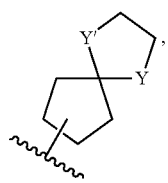 (W-32)
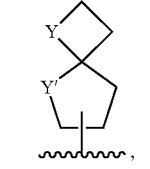 (W-33)
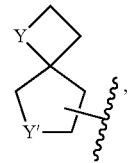 (W-34)
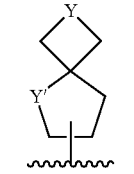 (W-35)
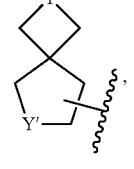 (W-36)
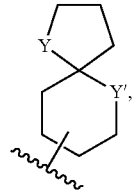 (W-37)
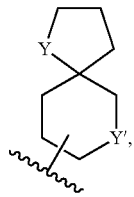 (W-38)

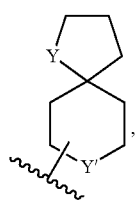 (W-39)
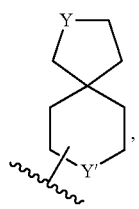 (W-40)
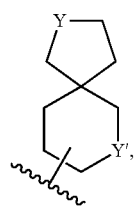 (W-41)
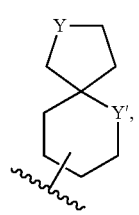 (W-42)
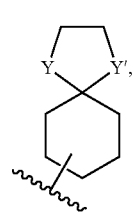 (W-43)
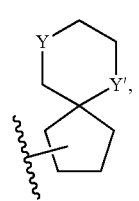 (W-44)
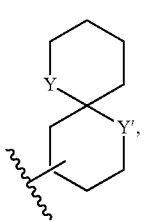 (W-45)
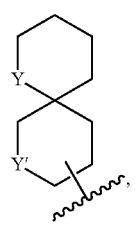 (W-46)
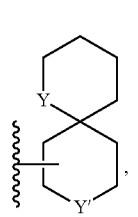 (W-47)
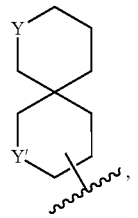 (W-48)
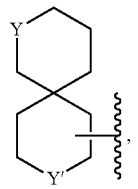 (W-49)
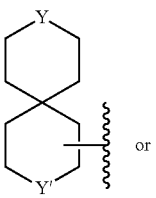 or (W-50)
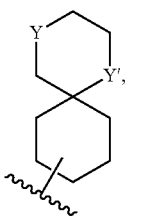
or a stereoisomer thereof, wherein each Y, $Y^1$, $Y^2$ and $Y^3$ is independently —$CH_2$—, —NH— or —O—, with the proviso that $Y^2$ and $Y^3$ are not —O— simultaneously; and wherein W is substituted by 1, 2 or 3 $R^{14}$ groups.

In another embodiment, W is:
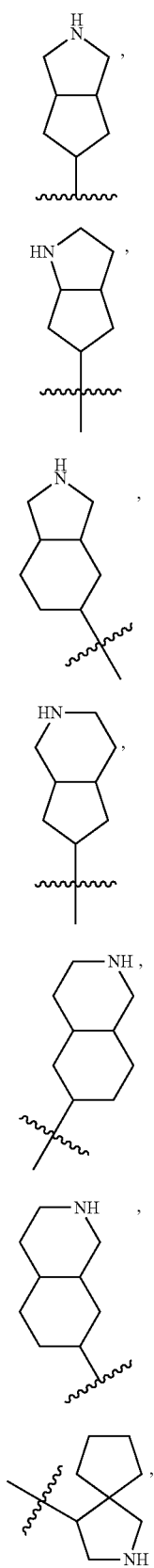
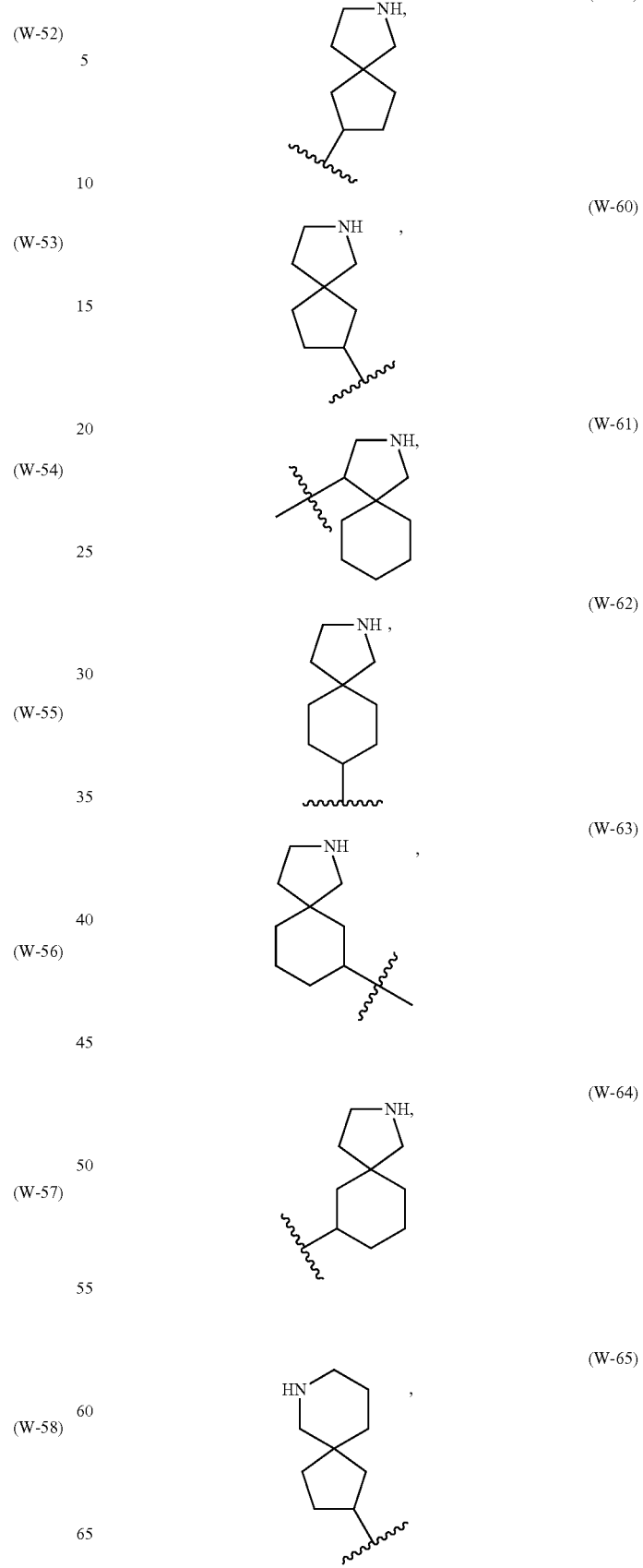

-continued

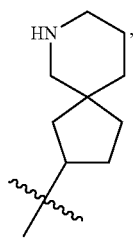 (W-66)

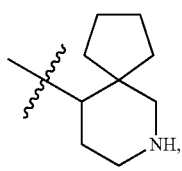 (W-67)

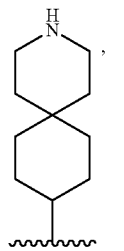 (W-68)

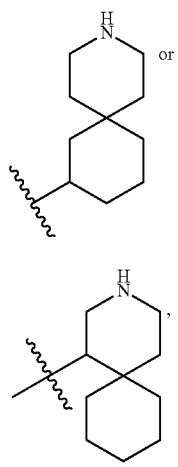 (W-69)

(W-70)

or a stereoisomer thereof, and wherein W is substituted by 1, 2 or 3 $R^{14}$ groups.

In one embodiment, $W_1$ is H, methyl, ethyl, n-propyl, isopropyl or cyclopropyl.

In another embodiment, $R^{12}$ is H, F, Cl, Br, I, $N_3$, CN, —$NO_2$, $C_1$-$C_4$ alkyl, $C_1$-$C_4$ alkoxyl, $C_2$-$C_4$ alkenyl, $C_2$-$C_4$ alkynyl, $C_3$-$C_6$ cycloalkyl, 4-7 membered heterocyclyl, —$NR^{15a}R^{15b}$, —$OR^{5c}$, —C(=O)$OR^{15c}$, —C(=O)$NR^{15a}R^{15b}$ or —S(=O)$_2NR^{15a}R^{15b}$, wherein each of the $C_1$-$C_4$ alkyl, $C_1$-$C_4$ alkoxyl, $C_2$-$C_4$ alkenyl, $C_2$-$C_4$ alkynyl, $C_3$-$C_6$ cycloalkyl and 4-7 membered heterocyclyl is optionally independently substituted by 1, 2 or 3 $R^{17}$ groups.

In one embodiment, each $R^{13}$ is independently H, F, Cl, CN, $C_1$-$C_4$ alkyl, $C_2$-$C_4$ alkenyl, $C_1$-$C_4$ alkoxyl, —($C_0$-$C_3$ alkylene)-($C_3$-$C_6$ cycloalkyl) or —($C_0$-$C_3$ alkylene)-(4-7 membered heterocyclyl), wherein each of the $C_1$-$C_4$ alkyl, $C_2$-$C_4$ alkenyl, $C_1$-$C_4$ alkoxyl, —($C_0$-$C_3$ alkylene)-($C_3$-$C_6$ cycloalkyl) and —($C_0$-$C_3$ alkylene)-(4-7 membered heterocyclyl) is optionally independently substituted by 1, 2 or 3 $R^{17}$ groups.

In another embodiment, each $R^{14}$ is independently F, Cl, Br, I, —$NO_2$, $N_3$, CN, $C_3$-$C_6$ alkyl, $C_2$-$C_6$ alkenyl, $C_2$-$C_6$ alkynyl, $C_1$-$C_6$ hydroxyalkyl, $C_3$-$C_6$ alkoxyl, $C_1$-$C_6$ alkylamino, $C_1$-$C_6$ aminoalkyl, $C_3$-$C_6$ cycloalkyl, 4-7 membered heterocyclyl, phenyl, 6-cyanopyridazine-3-yl, —$CH_2CN$, —$CH_2CH_2CN$, —C(=O)$R^{16d}$, —S(=O)$_2R^{16e}$, —C(=O)$NR^{16a}R^{16b}$, —S(=O)$_2NR^{16a}R^{16b}$, —C(=O)O—$R^{16c}$, —N($R^{16a}$)C(=O)$R^{16f}$, —N($R^{16a}$)S(=O)$_2R^{16g}$ or —OC(=O)$R^{16f}$, wherein each of the —$CH_2CN$, —$CH_2CH_2CN$, $C_3$-$C_6$ alkyl, $C_2$-$C_6$ alkenyl, $C_2$-$C_6$ alkynyl, $C_1$-$C_6$ hydroxyalkyl, $C_3$-$C_6$ alkoxyl, $C_1$-$C_6$ alkylamino, $C_1$-$C_6$ aminoalkyl, $C_3$-$C_6$ cycloalkyl, 4-7 membered heterocyclyl, phenyl and 6-cyanopyridazine-3-yl is optionally independently substituted by 1, 2 or 3 $R^{17}$ groups.

In one embodiment, each $R^{14}$ is independently F, Cl, Br, —$NO_2$, CN,

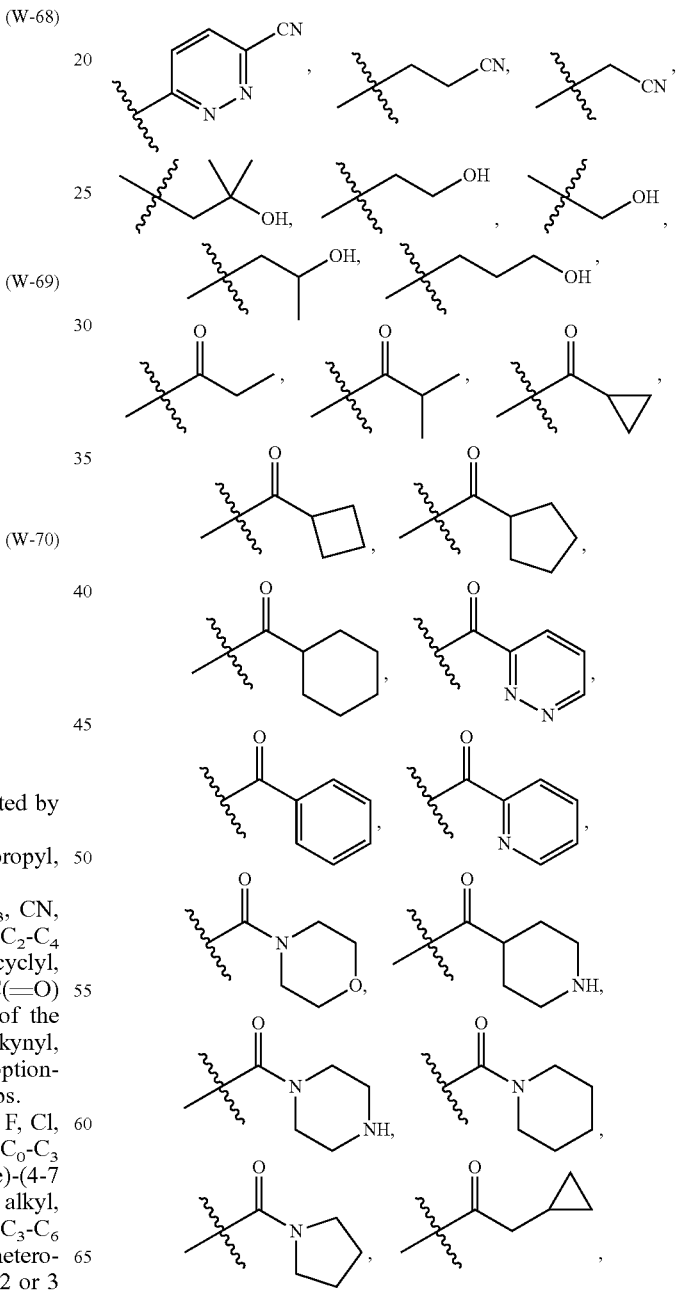

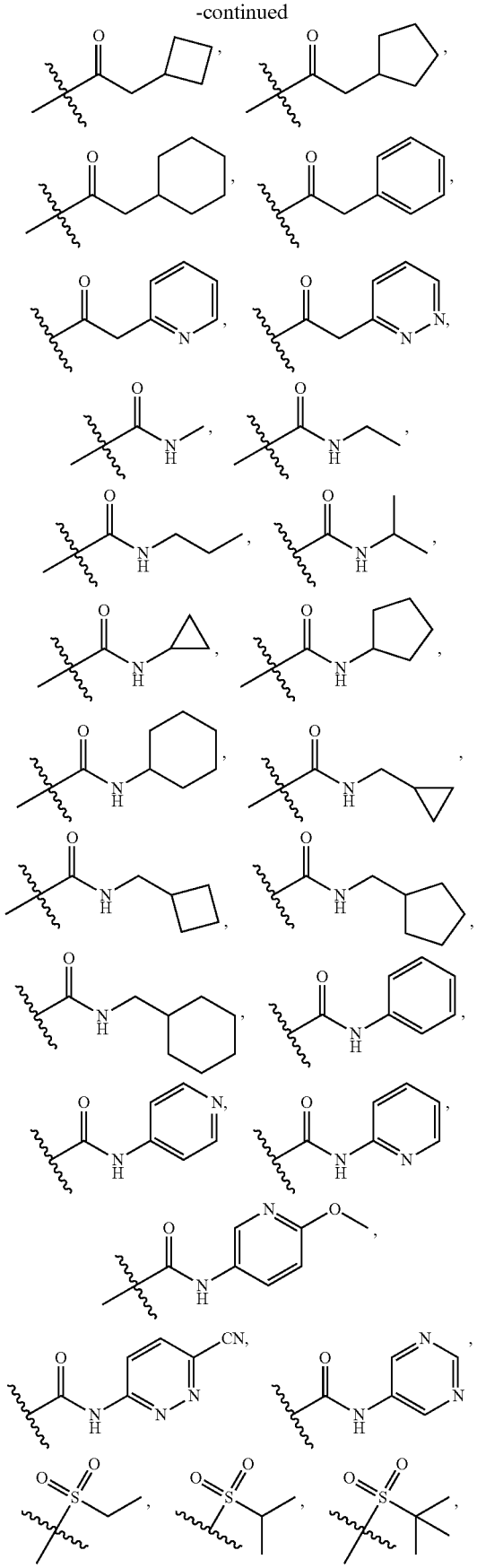
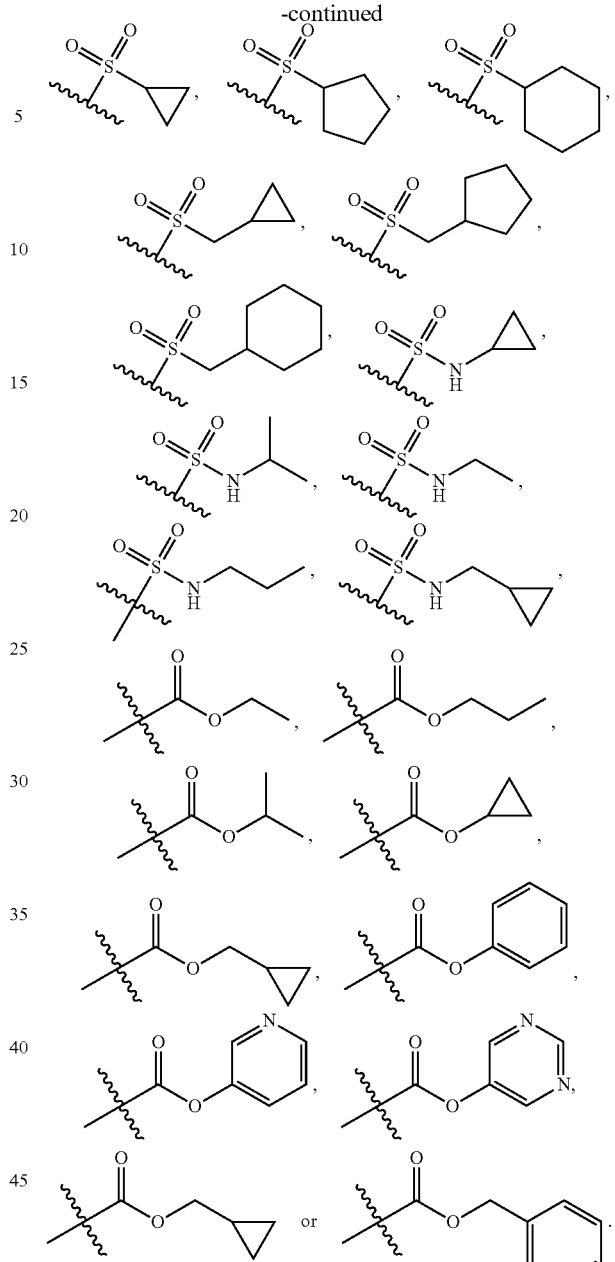

In another embodiment, each $R^{15a}$, $R^{15b}$, $R^{15c}$, $R^{16a}$ and $R^{16b}$ is independently H, $C_1$-$C_4$ alkyl, $C_2$-$C_4$ alkenyl, $C_2$-$C_4$ alkynyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl or —($C_1$-$C_3$ alkylene)-(5-6 membered heteroaryl), or $R^{15a}$ and $R^{15b}$, taken together with the nitrogen atom to which they are attached form a 4-7 membered heterocyclyl group, wherein each of the $C_1$-$C_4$ alkyl, $C_2$-$C_4$ alkenyl, $C_2$-$C_4$ alkynyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl and —($C_1$-$C_3$ alkylene)-(5-6 membered heteroaryl) is optionally substituted by 1, 2 or 3 substitutents independently selected from F, Cl, Br, CN, $N_3$, —$NO_2$, —OH, —NH$_2$, C$_1$-C$_3$ alkyl, C$_1$-C$_3$ haloalkyl, C$_1$-C$_3$ alkoxy, C$_1$-C$_3$ hydroxyalkyl, C$_1$-C$_3$ aminoalkyl and C$_1$-C$_3$ alkylamino.

In another embodiment, each R$^{16d}$, R$^{16e}$ and R$^{16g}$ is independently C$_2$-C$_6$ alkyl, C$_3$-C$_6$ cycloalkyl, 4-7 membered heterocyclyl, phenyl, 5-6 membered heteroaryl, —(C$_1$-C$_3$ alkylene)-(C$_3$-C$_6$ cycloalkyl), —(C$_1$-C$_3$ alkylene)-(4-7 membered heterocyclyl), —(C$_1$-C$_3$ alkylene)-phenyl, or —(C$_1$-C$_3$ alkylene)-(5-6 membered heteroaryl), wherein each of the above substituents is optionally substituted by 1, 2, 3 or 4 substituents independently selected from F, Cl, Br, CN, N$_3$, —OH, —NH$_2$, C$_1$-C$_3$ alkyl, C$_1$-C$_3$ haloalkyl, C$_1$-C$_3$ alkoxy, C$_1$-C$_3$ hydroxyalkyl, C$_1$-C$_3$ aminoalkyl and C$_1$-C$_3$ alkylamino.

In one embodiment, each R$^{16c}$ and R$^{16f}$ is independently C$_1$-C$_3$ alkyl, C$_3$-C$_6$ cycloalkyl, 4-7 membered heterocyclyl, phenyl, 5-6 membered heteroaryl, —(C$_1$-C$_3$ alkylene)-(C$_3$-C$_6$ cycloalkyl), —(C$_1$-C$_3$ alkylene)-(4-7 membered heterocyclyl), —(C$_1$-C$_3$ alkylene)-phenyl, or —(C$_1$-C$_3$ alkylene)-(5-6 membered heteroaryl), wherein each of the above substituents is optionally substituted by 1, 2, 3 or 4 substitutents independently selected from F, Cl, Br, CN, N$_3$, —OH, —NH$_2$, C$_1$-C$_3$ alkyl, C$_1$-C$_3$ haloalkyl, C$_1$-C$_3$ alkoxy, C$_1$-C$_3$ hydroxyalkyl, C$_1$-C$_3$ aminoalkyl and C$_1$-C$_3$ alkylamino.

In another aspect, provided herein is a pharmaceutical composition comprising the compound disclosed herein, and a pharmaceutically acceptable excipient, carrier, adjuvant, vehicle or a combination thereof.

In one embodiment, the pharmaceutical composition disclosed herein further comprising a therapeutic agent selected from the group consisting of chemotherapeutic agents, antiproliferative agents, phosphodiesterase 4 (PDE4) inhibitors, β$_2$-adrenoreceptor agonists, corticosteroids, non-steroidal GR agonists, anticholinergic agents, antihistamine, antiinflammatory agents, immunosuppressants, immunomodulators, agents for treating atherosclerosis, agents for treating pulmonary fibrosis and combinations thereof.

In another aspect, provided herein is a method of preventing, managing, treating or lessening the severity of a protein kinase-mediated disease in a patient by administering to the patient with the compound disclosed herein or the pharmaceutical composition disclosed herein. In one embodiment, the protein kinase-mediated disease is JAK-mediated disease, a FLT3-mediated disease, an Aurora-mediated disease.

In another embodiment, the protein kinase-mediated disease is a proliferative disease, an autoimmune disease, an allergic disease, an inflammatory disease or a transplantation rejection.

In another embodiment, the protein kinase-mediated disease is a cancer, polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic lupus erythematosis, cutaneous lupus erythematosis, lupus nephritis, dermatomyositis, Sjogren's syndrome, psoriasis, type I diabetes mellitus, an allergic airway disease, sinusitis, eczema, hives, a food allergy, an allergies to insect venom, inflammatory bowel syndrome, Chron's disease, rheumatoid arthritis, juvenile arthritis, psoriatic arthritis, an organ transplant rejection, a tissue transplant rejection or a cell transplant rejection.

In another aspect, provided herein is the compound or the pharmaceutical composition disclosed herein for use in preventing, managing, treating or lessening the severity of a protein kinase-mediated disease in a patient.

In another aspect, provided herein is the use of the compound or the pharmaceutical composition disclosed herein in the manufacture of a medicament for preventing, treating, or lessening a protein kinase-mediated disease.

In another aspect, provided herein is a method of modulating the activity of a protein kinase with the compound or the pharmaceutical composition disclosed herein.

In one embodiment, the protein kinase is JAK kinases, FLT3 kinase, Aurora kinases or a combination thereof. In one embodiment, JAK kinases are JAK1, JAK2, JAK3 or TYK2. In one embodiment, Aurora kinases are Aurora-A, Aurora-B, or Aurora-C.

In another aspect, provided herein is the compound or the pharmaceutical composition disclosed herein for use in modulating the activity of a protein kinase.

In still another aspect, provided herein is use of the compound or the pharmaceutical composition disclosed herein in the manufacture of a medicament for modulating the activity of a protein kinase.

In another aspect, provided herein are methods for preparation, separation and purification of the compounds represented by Formula (I) and Formula (II).

Biological test results indicate that the compounds provided herein can be used as preferable inhibitors of protein kinases.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiment as long as they are not contradictory to one another, even though the embodiments are described under different aspects of the invention.

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* (2$^{nd}$ Ed. Robert et al., Elsevier, Oxford, U K, 2012); Eliel et al., Stereochemistry of Carbon Compounds (McGraw-Hill, N Y, 1962); and Wilen et al., Tables of Resolving Agents and Optical Resolutions p. 268 (E. L. Eliel, Ed., Univ. of Notre Dame Press, Notre Dame, Ind., 1972). Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

As described herein, compounds disclosed herein may optionally be substituted with one or more substituents, such as those illustrated below, or as exemplified by particular classes, subclasses, and species of the invention. It will be appreciated that the phrase "optionally substituted" is used interchangeably with the phrase "substituted or unsubstituted". The term "optional" or "optionally" means that the subsequently described event or circumstance may but need not occur, and that the description includes instances where the event or circumstance occurs and instances in which it does not. In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

Some non-limiting examples of the substituents include D, F, Cl, Br, I, CN, $N_3$, —CN, —$NO_2$, —OH, —SH, —$NH_2$, —C(=O)$CH_2$CN, —NHC(=O)$CH_2$CN, —N($CH_3$)C(=O)$CH_2$CN, —$NR^{10a}R^{10b}$, C(=O)Rod, —OC(=O)Rod, —C(=O)$OR^{10c}$, —N($R^{10e}$)C(=O)$R^{10d}$, —C(=O)$NR^{10a}R^{10b}$, —N($R^{10e}$)C(=O)$NR^{10a}R^{10b}$, —C(=O)N($R^{10e}$)C(=O)$R^{1d}$, —S(=O)$_2R^{10f}$, —N($R^{10e}$)S(=O)$_2R^{10f}$, S(=O)$_2NR^{10a}R^{10b}$, alkyl, haloalkyl, alkenyl, alkynyl, alkoxyl, hydroxyalkyl, alkylthiolyl, alkylamino, aminoalkyl, cycloalkyl, heterocyclyl, aryl and heteroaryl, and the like, wherein each $R^{10a}$, $R^{10b}$, $R^{10c}$, $R^{10d}$, $R^{10e}$ and $R^{10f}$ carry the definitions described herein.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted independently with one or more substituents described below. Unless otherwise specified, the alkyl group contains 1-20 carbon atoms. In one embodiment, the alkyl group contains 1-12 carbon atoms. In another embodiment, the alkyl group contains 1-6 carbon atoms. In another embodiment, the alkyl group contains 3-6 carbon atoms. In still another embodiment, the alkyl group contains 1-4 carbon atoms. In yet another embodiment, the alkyl group contains 1-3 carbon atoms. The alkyl radical may be optionally substituted independently with one or more substituents described herein.

Some non-limiting examples of the alkyl group include methyl (Me, —$CH_3$), ethyl (Et, —$CH_2CH_3$), 1-propyl (n-Pr, n-propyl, —$CH_2CH_2CH_3$), 2-propyl (i-Pr, isopropyl, —CH($CH_3$)$_2$), 1-butyl (n-Bu, n-butyl, —$CH_2CH_2CH_2CH_3$), 2-methyl-1-propyl (i-Bu, i-butyl, —$CH_2$CH($CH_3$)$_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2$CH($CH_3$)$_2$), 2-methyl-1-butyl (—$CH_2$CH($CH_3$)$CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, 1-heptyl, 1-octyl, and the like.

The term "alkylene" refers to a saturated divalent or multivalent hydrocarbon group derived from a straight or branched chain saturated hydrocarbon by the removal of two or more hydrogen atoms. Unless otherwise specified, the alkylene group contains 1-12 carbon atoms. In one embodiment, the alkylene group contains 1-6 carbon atoms. In another embodiment, the alkylene group contains 1-4 carbon atoms. In another embodiment, the alkylene group contains 0-4 carbon atoms. In another embodiment, the alkylene group contains 0-3 carbon atoms. In still another embodiment, the alkylene group contains 1-3 carbon atoms. The alkylene group contains 0 carbon atom refers to a single bond. The alkylene group is exemplified by methylene (—$CH_2$—), ethylidene (—$CH_2CH_2$—), isopropylidene (—CH($CH_3$)$CH_2$—), and the like.

The term "alkenyl" refers to a linear or branched-chain monovalent hydrocarbon radical of 2 to 12 carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. In one embodiment, the alkenyl group contains 2-8 carbon atoms. In another embodiment, the alkenyl group contains 2-6 carbon atoms. In still another embodiment, the alkenyl group contains 2-4 carbon atoms. Some non-limiting examples of the alkenyl group include ethylenyl or vinyl (—CH=$CH_2$), allyl (—$CH_2$CH=$CH_2$), and the like. The alkenyl radical may be optionally substituted independently with one or more substituents described herein.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. In one embodiment, the alkynyl group contains 2-8 carbon atoms. In another embodiment, the alkynyl group contains 2-6 carbon atoms. In still another embodiment, the alkynyl group contains 2-4 carbon atoms. Some non-limiting examples of the alkynyl group include ethynyl (—C≡CH), propargyl (—$CH_2$C≡CH), propynyl (—C≡C—$CH_3$), and the like.

The term "alkoxy" refers to an alkyl group, as previously defined, attached to the principal carbon atom through an oxygen atom. Unless otherwise specified, the alkoxy group contains 1-12 carbon atoms. In one embodiment, the alkoxy group contains 1-6 carbon atoms. In another embodiment, the alkoxy group contains 1-4 carbon atoms. In still another embodiment, the alkoxy group contains 1-3 carbon atoms. The alkoxy radical may be optionally substituted independently with one or more substituents described herein.

Some non-limiting examples of alkoxy groups include methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, isopropoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "haloalkyl", "haloalkenyl" or "haloalkoxy" refers to alkyl, alkenyl, or alkoxy, as the case may be, substituted with one or more halogen atoms. Some non-limiting examples of haloalkyl and haloalkoxy are include trifluoromethyl (—CF$_3$), trifluoromethoxy (—OCF$_3$), difluoroethyl (—CH$_2$CHF$_2$, —CF$_2$CH$_3$, —CHFCH$_2$F), trifluoroethyl (—CH$_2$CF$_3$, —CF$_2$CH$_2$F, —CFHCHF$_2$) and the like.

The term "hydroxyalkyl" and "hydroxyalkoxy" refers to alkyl or alkoxy, as the case may be, substituted with one or more hydroxy. Some non-limiting examples of hydroxyalkyl and hydroxyalkoxy include hydroxymethyl (—CH$_2$OH), hydroxyethyl (—CH$_2$CH$_2$OH, —CH(OH)CH$_3$), hydroxymethoxy (—OCH$_2$OH) and the like.

The term "carbocycle", "carbocyclyl" or "carbocyclic ring" refers to a monovalent or multivalent non-aromatic, saturated or partially unsaturated ring having 3 to 12 carbon atoms as a monocyclic, bicyclic or tricyclic ring system. The carbobicyclyl refers to a spiro carbobicyclyl, a fused carbobicyclyl or a bridged carbobicyclyl. Some non-limiting examples of carbocyclyl groups include cycloalkyl, cycloalkenyl, and cycloalkynyl. Further non-limiting examples of carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like.

The term "cycloalkyl" refers to a monovalent or multivalent saturated ring having 3 to 12 carbon atoms as a monocyclic, bicyclic, or tricyclic ring system. The bicycloalkyl refers to spiro bicycloalkyl, fused bicycloalkyl or bridged bicycloalkyl. In one embodiment, the cycloalkyl contains 3-12 carbon atoms. In another embodiment, the cycloalkyl contains 3-8 carbon atoms. In another embodiment, the cycloalkyl contains 3-6 carbon atoms. In another embodiment, the cycloalkyl refers to a C$_7$-C$_{12}$ bicycloalkyl which contains 7-12 carbon atoms. The C$_7$-C$_{12}$ bicycloalkyl includes C$_7$-C$_{12}$ spiro, C$_7$-C$_{12}$ fused bicycloalkyl and C$_7$-C$_{12}$ bridged bicycloalkyl. In yet another embodiment, cycloalkyl may be a C$_8$-C$_{11}$ bicycloalkyl which refers to C$_8$-C$_{11}$ spiro, C$_8$-C$_{11}$ fused bicycloalkyl and C$_8$-C$_{11}$ bridged bicycloalkyl. Some non-limiting examples of cycloalkyl, include the C$_3$-C$_6$ cycloalkyl which refers to cyclopropyl, cyclobutyl, cyclopentyl and cyclohexyl. The cycloalkyl radical may be optionally substituted independently with one or more substituents described herein.

The term "heterocycle", "heterocyclyl", or "heterocyclic ring" as used interchangeably herein refers to a monovalent or multivalent, saturated or partially unsaturated, non-aromatic monocyclic, bicyclic or tricyclic ring containing 3-12 ring atoms of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. The heterocyclyl contains saturated heterocyclyl (i.e. heterocycloalkyl) and partially unsaturated heterocyclyl. Some non-limiting examples of heterocyclyl include oxiranyl, azetidinyl, oxetanyl, thietanyl, pyrrolidinyl, 1-pyrrolinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl (e.g. 1,4-oxazepinyl, 1,2-oxazepinyl), diazepinyl (e.g. 1,4-diazepinyl, 1,2-diazepinyl), dioxpinyl (e.g. 1,4-dioxpinyl, 1,2-dioxpinyl), thiazepinyl (e.g. 1,4-thiazepinyl, 1,2-thiazepinyl), 2-oxa-5-azabicyclo[2.2.1]hept-5-yl, 2-azaspiro[4.4]nonanyl, 1,6-dioxaspiro[4.4]nonanyl, 2-azaspiro[4.5]decanyl, 8-azaspiro[4.5]decanyl, 7-azaspiro[4.5]decanyl, 3-azaspiro[5.5]undecanyl, 2-azaspiro[5.5]undecanyl, octahydro-1H-isoindolyl, octahydrocyclopenta[c]pyrrolyl, indolinyl, 1,2,3,4-tetrahydroisoquinolinyl, 1,3-benzodioxolyl, hexahydrofuro[3,2-b]furanyl, decahydroisoquinolinyl, and the like. Some non-limiting examples of heterocyclyl wherein —CH$_2$— group is replaced by —C(=O)— moiety are 2-oxopyrrolidinyl, oxo-1,3-thiazolidinyl, 2-piperidinonyl and 3,5-dioxopiperidinyl. Some non-limiting examples of heterocyclyl wherein the ring sulfur atom is oxidized are sulfolanyl, 1,1-dioxotetrahydrothiophenyl, 1,1-dioxothiomorpholinyl, 1,1-dioxotetrahydro-2H-thiopyranyl. The heterocyclyl group may be optionally substituted with one or more substituents described herein.

In one embodiment, heterocyclyl may be a 3-8 membered heterocyclyl, which refers to a monovalent or multivalent, saturated or partially unsaturated, monocyclic ring containing 3-8 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 3-8 membered heterocyclyl include azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl, thiazepinyl, and the like. Some non-limiting examples of heterocyclyl wherein —CH$_2$— group is replaced by —C(=O)— moiety are 2-oxopyrrolidinyl, oxo-1,3-thiazolidinyl, 2-piperidinonyl and 3,5-dioxopiperidinyl. Some non-limiting examples of heterocyclyl wherein the ring sulfur atom is oxidized are sulfolanyl, 1,1-dioxo-thiomorpholinyl, and the like. The 3-8 membered heterocyclyl group may be optionally substituted with one or more substituents described herein.

In another embodiment, heterocyclyl may be a 4-7 membered heterocyclyl, which refers to a monovalent or multivalent, saturated or partially unsaturated, non-aromatic monocyclic ring containing 4-7 ring atoms, of which at least one ring atom is selected from nitrogen, sulfur and oxygen, and of which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 4-7 membered heterocyclyl include azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl and thiazepinyl. The 4-7 membered heterocyclyl group may be optionally substituted with one or more substituents described herein.

In another embodiment, heterocyclyl refers to a 7-12 membered heterocyclyl, which refers to a monovalent or multivalent, saturated or partially unsaturated spiro, fused or bridged heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 7-12 membered heterocyclyl include indolinyl, 1,2,3,4-tetrahydroisoquinolinyl, 1,3-benzodioxolyl, 2-oxa-5-azabicyclo[2.2.1]hept-5-yl, 2-azaspiro[4.4]nonanyl (e.g. 2-azaspiro[4.4]nonane-4-yl, 2-azaspiro[4.4]nonane-2-yl), 1,6-dioxaspiro[4.4]nonanyl (e.g. 1,6-dioxaspiro[4.4]nonan-9-yl, 1,6-dioxaspiro[4.4]nonane-4-yl), 2-azaspiro[4.5]decanyl (e.g. 2-azaspiro[4.5]decane-8-yl, 2-azaspiro[4.5]decane-2-yl), 7-azaspiro[4.5]decanyl (e.g. 7-azaspiro[4.5]decane-8-yl, 7-azaspiro[4.5]decane-2-yl), 3-azaspiro[5.5]undecanyl (e.g. 3-azaspiro[5.5]undecane-3-yl, 3-azaspiro[5.5]undecane-9-yl), 2-azaspiro[5.5]undecanyl, 8-azaspiro[4.5]decanyl, decahydroisoquinolinyl, octahydro-1H-isoindolyl (e.g. octahydro-1H-isoindole-5-yl, octahydro-1H-isoindole-7-yl), octahydrocyclopenta[c]pyrrolyl (e.g. octahydrocyclopenta[c]pyrrole-5-yl, octahydrocyclopenta[c]pyrrole-2-yl), hexahydrofuro[3,2-b]furanyl (e.g. hexahydrofuro[3,2-b]furan-2-yl, hexahydrofuro[3,2-b]furan-3-yl), and the like. The 7-12 membered heterocyclyl group may be optionally substituted with one or more substituents described herein.

In still one embodiment, heterocyclyl refers to a 7-12 membered spiro heterobicyclyl, which refers to a monovalent or multivalent, saturated or partially unsaturated, non-aromatic, spiro heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. The 7-12 membered spiro heterobicyclyl contains 7-12 membered saturated spiro heterobicyclyl (i.e. 7-12 membered spiro heterobicycloalkyl) and 7-12 membered partially unsaturated spiro heterobicyclyl. Some non-limiting examples of 7-12 membered spiro heterobicyclyl include 2-azaspiro[4.4]nonanyl (e.g. 2-azaspiro[4.4]nonane-4-yl, 2-azaspiro[4.4]nonane-2-yl), 1,6-dioxaspiro[4.4]nonanyl (e.g. 1,6-dioxaspiro[4.4]nonan-9-yl, 1,6-dioxaspiro[4.4]nonane-4-yl), 2-azaspiro[4.5]decanyl (e.g. 2-azaspiro[4.5]decane-8-yl, 2-azaspiro[4.5]decane-2-yl), 7-azaspiro[4.5]decanyl (e.g. 7-azaspiro[4.5]decane-8-yl, 7-azaspiro[4.5]decane-2-yl), 3-azaspiro[5.5]undecanyl (e.g. 3-azaspiro[5.5]undecane-3-yl, 3-azaspiro[5.5]undecane-9-yl), 2-azaspiro[5.5]undecanyl, 8-azaspiro[4.5]decanyl, and the like. The 7-12 membered spiro heterobicyclyl group may be optionally substituted with one or more substituents described herein.

In still another embodiment, heterocyclyl refers to a 8-11 membered spiro heterobicyclyl, which refers to a monovalent or multivalent, saturated or partially unsaturated, non-aromatic, spiro heterobicyclyl ring containing 8-11 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. The 8-11 membered spiro heterobicyclyl contains 8-11 membered saturated spiro heterobicyclyl (i.e. 8-11 membered spiro heterobicycloalkyl) and 8-11 membered partially unsaturated spiro heterobicyclyl. Some non-limiting examples of 8-11 membered spiro heterobicyclyl include 2-azaspiro[4.4]nonanyl (e.g. 2-azaspiro[4.4]nonane-4-yl, 2-azaspiro[4.4]nonane-2-yl), 1,6-dioxaspiro[4.4]nonanyl (e.g. 1,6-dioxaspiro[4.4]nonan-9-yl, 1,6-dioxaspiro[4.4]nonane-4-yl), 2-azaspiro[4.5]decanyl (e.g. 2-azaspiro[4.5]decane-8-yl, 2-azaspiro[4.5]decane-2-yl), 7-azaspiro[4.5]decanyl (e.g. 7-azaspiro[4.5]decane-8-yl, 7-azaspiro[4.5]decane-2-yl), 3-azaspiro[5.5]undecanyl (e.g. 3-azaspiro[5.5]undecane-3-yl, 3-azaspiro[5.5]undecane-9-yl), 2-azaspiro[5.5]undecanyl, 8-azaspiro[4.5]decanyl, and the like. The 8-11 membered spiro heterobicyclyl group may be optionally substituted with one or more substituents described herein.

In yet another embodiment, heterocyclyl refers to a 7-12 membered fused heterobicyclyl, which refers to a monovalent or multivalent, saturated or partially unsaturated, non-aromatic fused heterobicyclyl ring containing 7-12 ring atoms, of which at least one ring atom is selected from nitrogen, sulfur and oxygen, and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. The 7-12 membered fused heterobicyclyl contains 7-12 membered saturated fused heterobicyclyl (i.e. 7-12 membered fused heterobicycloalkyl) and 7-12 membered partially unsaturated fused heterobicyclyl. Some non-limiting examples of 7-12 membered fused heterobicyclyl include octahydrocyclopenta[c]pyrrolyl, octahydro-1H-isoindolyl, indolinyl, 1,2,3,4-tetrahydroisoquinolinyl, 1,3-benzodioxolyl, hexahydrofuro[3,2-b]furanyl, hexahydrofuro[2,3-b]furanyl, decahydroisoquinolinyl, and the like. The 7-12 membered fused heterobicyclyl group may be optionally substituted with one or more substituents described herein.

The terms "bridged bicyclic ring", "bridged cyclic", "bridged bicyclyl" and "bridged cyclyl" are used interchangeably refer to a monovalent or multivalent saturated or partially unsaturated, but not aromatic bicyclic ring system, and such that two rings share two atoms and two or more common single bond. Such a system may contain isolated or conjugated unsaturation, but not aromatic or heteroaromatic rings in its core structure (but may have aromatic substitution thereon).

The terms "fused bicyclic ring", "fused cyclic", "fused bicyclyl" and "fused cyclyl" are used interchangeably refer to a monovalent or multivalent saturated or partially unsaturated, but not aromatic bicyclic ring system, and such that two rings share one common bond. Such a system may contain isolated or conjugated unsaturation, but not aromatic or heteroaromatic rings in its core structure (but may have aromatic substitution thereon).

The terms "spirocyclyl", "spirocyclic", "spiro bicyclyl" and "spiro bicyclic" are used interchangeably and refer to a monovalent or multivalent, saturated or partially unsaturated, but not aromatic ring system wherein a ring originating from a particular annular carbon of another ring, and such that two rings only share one atom.

For example, as depicted below in Structure a-1 and Structure a-2, a saturated ring system, ring B and B' is termed as "fused bicyclyl", whereas ring A' and ring B share an atom between the two saturated ring system, which terms as a "spirocyclyl" or "spiro bicyclyl", and ring C and C' is termed as "bridged bicyclyl". Each ring in the fused bicyclyl, the spiro bicyclyl or the bridged bicyclyl can be either a carbocyclyl or a heterocyclyl, and each ring is optionally substituted independently with one or more substituents described herein.

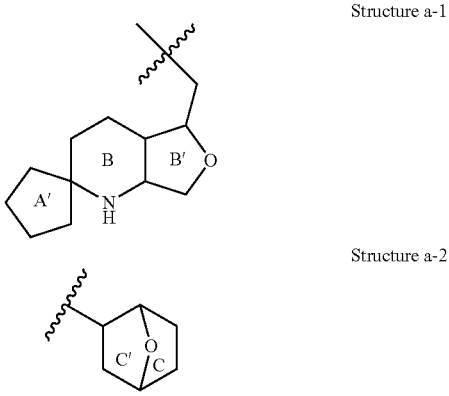

Structure a-1

Structure a-2

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of heterocycloalkyl include azetidinyl, oxetanyl, thietanyl, pyrrolidinyl, pyrazolidinyl, imidazolidinyl, tetrahydrothienyl, tetrahydrofuranyl, piperidinyl, piperazinyl, morpholinyl, dioxanyl, dithianyl, dithiolanyl, isoxazolidinyl, isothiazolidinyl, 1,2-oxazinanyl, 1,2-thiazinanyl, hexahydropyridazinyl, homopiperazinyl, homopiperidinyl, oxepanyl, thiepanyl, oxazepinyl (e.g. 1,4-oxazepinyl, 1,2-oxazepinyl), diazepinyl (e.g. 1,4-diazepinyl, 1,2-diazepinyl), dioxpinyl (e.g. 1,4-dioxpinyl, 1,2-dioxpinyl), thiazepinyl (e.g. 1,4-thiazepinyl, 1,2-thiazepinyl), 2-azaspiro[4.4]nonanyl, 1,6-dioxaspiro[4.4]nonanyl, 2-azaspiro[4.5]decanyl, 8-azaspiro[4.5]decanyl, 7-azaspiro[4.5]decanyl, 3-azaspiro[5.5]undecanyl, 2-azaspiro[5.5]undecanyl, 2-octahydro-1H-isoindolyl, octahydrocyclopenta[c]pyrrolyl, hexahydrofuro[3,2-b]furanyl, decahydroisoquinolinyl, hexahydrofuro[2,3-b]furanyl, and the like. The heterocycloalkyl group may be optionally substituted with one or more substituents described herein.

In one embodiment, heterocycloalkyl refers to a 7-12 membered heterocycloalkyl, which refers to a monovalent or multivalent saturated spiro, fused or bridged heterobicycloalkyl, containing 7-12 ring atoms, of which at least one ring atom is selected from nitrogen, sulfur and oxygen and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. The 7-12 membered heterocycloalkyl group may be optionally substituted with one or more substituents described herein.

In one embodiment, heterocycloalkyl refers to a 4-7 membered heterocycloalkyl, which refers to a monovalent or multivalent saturated heterocyclyl ring containing 4-7 ring atoms, of which at least one ring atom is selected from nitrogen, sulfur and oxygen and which may, unless otherwise specified, be carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 4-7 membered heterocycloalkyl include azetidinyl, oxetanyl, thietanyl, pyrrolidinyl, pyrazolidinyl, imidazolidinyl, piperidinyl, piperazinyl, morpholinyl, dioxanyl, dithianyl, dithiolanyl, isoxazolidinyl, isothiazolidinyl, hexahydropyridazinyl, homopiperazinyl, homopiperidinyl, oxepanyl, thiepanyl, oxazepinyl, diazepinyl, and thiazepinyl. The 4-7 membered heterocycloalkyl group may be optionally substituted with one or more substituents described herein.

In another embodiment, heterocycloalkyl refers to a 7-12 membered spiro heterobicycloalkyl, which refers to a monovalent or multivalent saturated spiro heterobicycloalkyl ring containing 7-12 ring atoms, of which at least one ring atom is selected from nitrogen, sulfur and oxygen. Unless otherwise specified, the 7-12 membered spiro heterobicycloalkyl maybe carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 7-12 membered spiro heterobicycloalkyl include 2-azaspiro[4.4]nonanyl, 1,6-dioxaspiro[4.4]nonanyl, 2-azaspiro[4.5]decanyl, 8-azaspiro[4.5]decanyl, 7-azaspiro[4.5]decanyl, 3-azaspiro[5.5]undecanyl, 2-azaspiro[5.5]undecanyl, and the like. The 7-12 membered spiro heterobicycloalkyl group may be optionally substituted with one or more substituents described herein.

In another embodiment, heterocycloalkyl refers to a 7-12 membered fused heterobicycloalkyl, which refers to a monovalent or multivalent saturated fused heterobicycloalkyl ring containing 7-12 ring atoms, of which at least one ring atom is selected from nitrogen, sulfur and oxygen. Unless otherwise specified, the 7-12 membered fused heterobicycloalkyl maybe carbon or nitrogen linked, and of which a —CH$_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 7-12 membered fused heterobicycloalkyl include octahydro-1H-isoindolyl (e.g. octahydro-1H-isoindole-5-yl, octahydro-1H-isoindole-7-yl), octahydrocyclopenta[c]pyrrolyl (e.g. octahydrocyclopenta[c]pyrrole-5-yl, octahydrocyclopenta[c]pyrrole-2-yl), hexahydrofuro[3,2-b]furanyl (e.g. hexahydrofuro[3,2-b]furan-2-yl, hexahydrofuro[3,2-b]furan-3-yl), decahydroisoquinolinyl, hexahydrofuro[2,3-b]furanyl, and the like. The 7-12 membered fused heterocybicloalkyl group may be optionally substituted with one or more substituents described herein.

In another embodiment, heterocycloalkyl refers to a 8-10 membered fused heterobicycloalkyl, which refers to a monovalent or multivalent saturated fused heterobicycloalkyl ring containing 8-10 ring atoms, of which at least one ring atom is selected from nitrogen, sulfur and oxygen. Unless otherwise specified, the 8-10 membered fused heterobicycloalkyl maybe carbon or nitrogen linked, and of which a —$CH_2$— group can optionally be replaced by a —C(=O)— group. Ring sulfur atoms may be optionally oxidized to form S-oxides. Ring nitrogen atoms maybe optionally oxidized to form N-oxides. Some non-limiting examples of 8-10 membered fused heterobicycloalkyl include octahydro-1H-isoindolyl (e.g. octahydro-1H-isoindole-5-yl, octahydro-1H-isoindole-7-yl), octahydrocyclopenta[c]pyrrolyl (e.g. octahydrocyclopenta[c]pyrrole-5-yl, octahydrocyclopenta[c]pyrrole-2-yl), hexahydrofuro[3,2-b]furanyl (e.g. hexahydrofuro[3,2-b]furan-2-yl, hexahydrofuro[3,2-b]furan-3-yl), decahydroisoquinolinyl, hexahydrofuro[2,3-b]furanyl, and the like. The 8-10 membered fused heterocybicloalkyl group may be optionally substituted with one or more substituents described herein.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydronaphthalenyl is an example of a 10 membered carbocyclyl group.

The term "unsaturated" refers to a moiety having one or more units of unsaturation.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I). The term "azido" or "$N_3$" refers to an azide moiety. This radical may be attached, for example, to a methyl group to form azidomethane (methyl azide, $MeN_3$); or attached to a phenyl group to form phenyl azide ($PhN_3$).

The term "aryl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has one or more points of attachment to the rest of the molecule. The term "aryl" may be used interchangeably with the term "aryl ring" or "aromatic ring". Some non-limiting examples of the aryl group would include phenyl, naphthyl, and anthracenyl. The aryl radical is optionally substituted independently with one or more substituents described herein.

The term "heteroaryl" or "heteroaromatic ring" refers to monocyclic, bicyclic, and tricyclic ring systems having a total of 5 to 12 ring members, preferably, 5 to 10 ring members, and more preferably 5 to 6 ring members, wherein at least one ring in the system is aromatic, at least one aromatic ring in the system contains one or more heteroatoms, wherein each ring in the system contains 5 to 7 ring members and that has one or more points of attachment to the rest of the molecule. The term "heteroaryl" may be used interchangeably with the term "heteroaryl ring" or the term "heteroaromatic ring". In one embodiment, heteroaryl refers to a 5-12 membered heteroaryl comprises 1, 2, 3 or 4 heteroatoms independently selected from O, S and N. In another embodiment, heteroaryl refers to a 5-10 membered heteroaryl comprises 1, 2, 3 or 4 heteroatoms independently selected from O, S and N. In another embodiment, heteroaryl refers to a 5-6 membered heteroaryl comprises 1, 2, 3 or 4 heteroatoms independently selected from O, S and N. The heteroaryl radical is optionally independently substituted with one or more substituents described herein.

Some non-limiting examples of the 5-12 membered heteroaryl group include following bicyclyl heteroaryl: benzimidazolyl, benzofuryl, benzothiophenyl, indolyl (e.g., 2-indolyl, 3-indolyl, 4-indolyl, 5-indolyl, 6-indolyl, 7-indolyl), purinyl, quinolinyl (e.g., 2-quinolinyl, 3-quinolinyl, 4-quinolinyl), isoquinolinyl (e.g., 1-isoquinolinyl, 3-isoquinolinyl, 4-isoquinolinyl), indazolyl (e.g., 3-indazolyl, 4-indazolyl, 5-indazolyl, 6-indazolyl, 7-indazolyl), imidazo[1,2-a]pyridinyl, pyrazolo[1,5-a]pyridinyl, pyrazolo[4,3-c]pyridinyl, pyrazolo[3,4-b]pyridinyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl and [1,2,4]triazolo[1,5-a]pyridinyl, purinyl, and the like. 5-12 membered heteroaryl group also include 5-6 membered heteroaryl group. Some non-limiting examples of the 5-6 membered heteroaryl group include furanyl (e.g., 2-furanyl, 3-furanyl), imidazolyl (e.g., 1-imidazolyl, 2-imidazolyl, 4-imidazolyl, 5-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), pyrrolyl (e.g., 1-pyrrolyl, 2-pyrrolyl, 3-pyrrolyl), pyridyl (e.g., 2-pyridyl, 3-pyridyl, 4-pyridyl), pyridonyl, pyrimidinyl (e.g., 2-pyrimidinyl, 4-pyrimidinyl, 5-pyrimidinyl), pyrimidonyl, pyrimidinedionyl, pyridazinyl (e.g., 3-pyridazinyl, 4-pyridazinyl), pyrazinyl (2-pyrazinyl, 3-pyrazinyl), thiazolyl (e.g., 2-thiazolyl, 4-thiazolyl, 5-thiazolyl), tetrazolyl (e.g., 5-tetrazolyl), triazolyl (e.g., 2-triazolyl and 5-triazolyl), thienyl (e.g., 2-thienyl, 3-thienyl), pyrazolyl (e.g., 1-pyrazolyl, 3-pyrazolyl, 4-pyrazolyl, 5-pyrazolyl), pyrazolonyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the like.

The term "azolyl" refers to a 5-membered or 9-membered heteroaryl ring system containing at least two heteroatoms and wherein at least one heteroatoms is nitrogen atom. Some non-limiting examples of the azolyl include pyrazolyl, imidazolyl, oxazolyl, isoxazolyl, oxadiazolyl, thiazolyl, isothiazolyl, thiadiazolyl, diazolyl, triazolyl, indazolyl, pyrazolo[3,4-b]pyridinyl, pyrazolo[4,3-c]pyridinyl, 1H-imidazo[4,5-b]pyridinyl and 1H-benzo[d]imidazolyl, and the like.

The term "carboxy" or "carboxyl", whether used alone or with other terms, such as "carboxyalkyl", refers to —$CO_2H$. The term "carbonyl", whether used alone or with other terms, such as "aminocarbonyl", denotes —(C=O)—.

The term "alkylamino" embraces "N-alkylamino" and "N,N-dialkylamino" where amino groups are independently substituted with one alkyl radical or with two alkyl radicals, respectively. In one embodiment, alkylamino has one or two alkyl radicals of one to twelve carbon atoms, attached to a nitrogen atom. In another embodiment, alkylamino are "lower alkylamino" radicals having one or two alkyl radicals of one to six carbon atoms, attached to a nitrogen atom. In another embodiment, alkylamino are alkylamino radicals having one or two alkyl radicals of one to four carbon atoms, attached to a nitrogen atom. In still another embodiment, alkylamino are alkylamino radicals having one or two alkyl radicals of one to three carbon atoms, attached to a nitrogen atom. Some non-limiting examples of alkylamino include N-methylamino (—NHCH₃), N-ethylamino, N,N-dimethylamino (—NH(CH₃)₂), N,N-diethylamino, N-ethylpropan-2-amino and the like.

The term "arylamino" refers to amino groups, which have been substituted with one or two aryl radicals, such as N-phenylamino. The arylamino radicals may be further substituted on the aryl ring portion of the radical.

The term "aminoalkyl" refers to linear or branched alkyl radicals having one to about twelve carbon atoms any one of which may be substituted with one or more amino radicals. In one embodiment, the aminoalkyl has 1-12 carbon atoms and one or more amino radicals. In another embodiment, the aminoalkyl radicals are "lower aminoalkyl" radicals having 1-6 carbon atoms and one or more amino radicals. In another embodiment, aminoalkyl has 1-4 carbon atoms and one or more amino radicals. In still another embodiment, aminoalkyl has 1-3 carbon atoms and one or more amino radicals. Examples of such radicals include aminomethyl (—CH₂NH₂), aminoethyl (—CH₂CH₂NH₂, —CH(NH₂)CH₃), aminopropyl, aminobutyl and aminohexyl.

As described herein, a bond drawn from a substituent to the center of one ring within a ring system (as shown below in Structure b) represents substitution of the substituent at any substitutable position on the ring system. For example, as depicted below, Figure b represents possible substitution in any of the positions on the ring D shown in Figure c-Structure e.

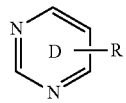

Structure b

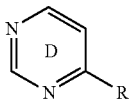

Structure c

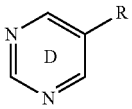

Structure d

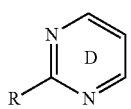

Structure e

As described herein, a connecting bond drawn from the center of one ring within a ring system (as shown in Structure f, wherein each X and X' is independently CH₂, NH or O) represents connection of the connecting bond attached to the rest of the molecule at any substitutable position on the ring system. For example, Structure f represents possible connection attached to the rest of the molecule in any of the position on ring E and ring F (as shown in Structure f-1~Structure f-8).

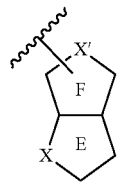

Structure f

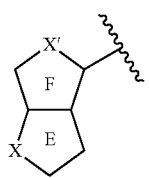

Structure f-1

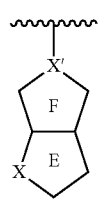

Structure f-2

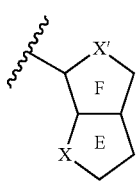

Structure f-3

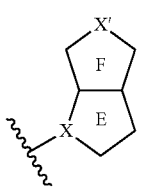

Structure f-4

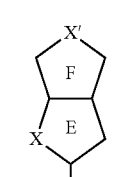

Structure f-5

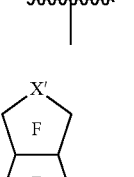

Structure f-6

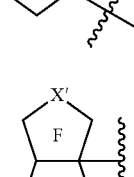

Structure f-7

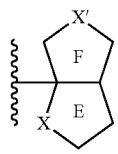

Structure f-8

As described herein, two connecting bonds drawn from the center of one ring within a ring system (as shown in Structure i) represents connection of the connecting bonds attached to the rest of the molecule at any two substitutable positions on the ring system, and the two connecting points (point Q and point Q') can exchange. For example, Structure i represents possible connection attached to the rest of the molecule in any two of the positions on ring G.

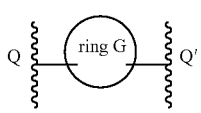

Structure i

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethyl silyl)ethoxy-methyl, 2-(p-toluenesulfonyl)-ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "prodrug" as used herein, represents a compound that is transformed in vivo into a compound of Formula (I) or Formula (II). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., Pro-drugs as Novel Delivery Systems, Vol. 14, A.C.S. Symposium Series; Roche et al., Bioreversible Carriers in Drug Design, American Pharmaceutical Association and Pergamon Press, 1987; Rautio et al., Prodrugs: Design and Clinical Applications, *Nat. Rev. Drug Discovery*, 2008, 7, 255-270, and Hecker et al., Prodrugs of Phosphates and Phosphonates, *J. Med. Chem.*, 2008, 51, 2328-2345, all of which are incorporated herein by reference.

A "metabolite" refers to a product produced through metabolism in the body of a specified compound or salt thereof. The metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in *J. Pharm. Sci.*, 1977, 66, 1-19, which is incorporated herein by reference. Some non-limiting examples of the pharmaceutically acceptable salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid.

Other examples of the pharmaceutically acceptable salt include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable salts derived from appropriate bases include alkali metal, alkaline earth metal, ammonium and $N^+(C_1$-$C_4$ alkyl$)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further examples of the pharmaceutically acceptable salt include, when appropriate, nontoxic ammonium, quaternary ammonium, and amine cations formed using counterions such as halide, hydroxide, carboxylate, sulfate, phosphate, nitrate, $C_1$-$C_8$ sulfonate and aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

"Inflammatory disorder/disease" as used herein can refer to any disease, disorder, or syndrome in which an excessive or unregulated inflammatory response leads to excessive inflammatory symptoms, host tissue damage, or loss of tissue function. "Inflammatory disorder/disease" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (i.e. sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with the compounds disclosed herein encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Description of Compounds of the Invention

In the present invention, novel compounds which are inhibitors of protein kinase activity, in particular JAK kinases, FLT3 kinase and Aurora kinases activity, are disclosed. Compounds which are protein kinase inhibitors may be useful in the treatment of diseases associated with inappropriate protein kinase activity, in particular inappropriate JAK, FLT3 and Aurora kinases activity, for example in the treatment and prevention of diseases mediated by JAK kinases, FLT3 kinase and Aurora kinases involved signalling pathways. Such diseases include proliferative disease, autoimmune disease, allergic disease, inflammatory disease, transplantation rejection, and their co-morbidities. In particular, a compound of the present invention may be useful in the treatment of diseases such as cancer, polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic and cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Crohn's disease, rheumatoid arthritis, juvenile arthritis, psoriatic arthritis, organ transplant rejection, tissue transplant rejection, cell transplant rejection, to name a few.

In one embodiment, the compounds disclosed herein may show potent inhibitory activities against one or more protein kinases.

In one aspect, provided herein is a compound having Formula (I):

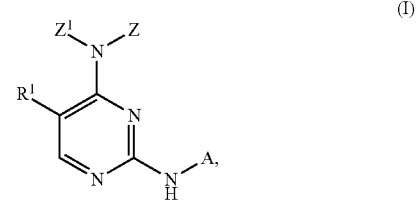

or a stereoisomer, a tautomer, an N-oxide, a solvate, a metabolite, a pharmaceutically acceptable salt or a prodrug thereof, wherein each of Z, $Z^1$, A and $R^1$ is as defined herein.

In one embodiment, Z is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein Z is optionally substituted by 1, 2, 3, 4 or 5 $R^2$ groups;

$Z^1$ is H, $C_1$-$C_{12}$ alkyl, $C_3$-$C_{12}$ cycloalkyl or 3-12 membered heterocyclyl, wherein each of the $C_1$-$C_{12}$ alkyl, $C_3$-$C_{12}$ cycloalkyl and 3-12 membered heterocyclyl is optionally independently substituted by 1, 2, 3, 4 or 5 $R^{2a}$ groups;

A is

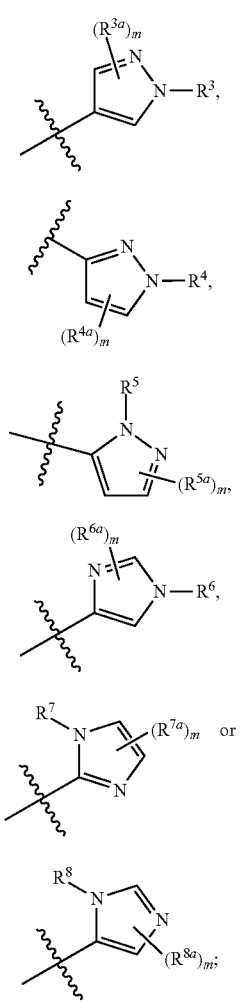

(A1), (A2), (A3), (A4), (A5) or (A6)

$R^1$ is H, F, Cl, Br, I, $N_3$, CN, $—NO_2$, $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, $—NR^{9a}R^{9b}$, $—OR^{9c}$, $—C(=O)R^{9d}$, $—OC(=O)R^{9d}$, $—C(=O)OR^{9c}$, $—N(R^{9e})C(=O)R^{9d}$, $—C(=O)NR^{9a}R^{9b}$, $—N(R^{9e})C(=O)NR^{9a}R^{9b}$, $—S(=O)_2R^{9f}$, $—N(R^{9e})S(=O)_2R^{9f}$ or $—S(=O)_2NR^{9a}R^{9b}$, wherein each of the $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl and 5-12 membered heteroaryl is optionally independently substituted by 1, 2, 3, 4 or 5 $R^{11}$ groups;

each $R^2$ is independently F, Cl, Br, I, $—NO_2$, $N_3$, CN, $—OH$, $—NH_2$, $—C(=O)CH_2CN$, $—NHC(=O)CH_2CN$, $—N(CH_3)C(=O)CH_2CN$, $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, $—NR^{10a}R^{10b}$, $—O—(C_0$-$C_4$ alkylene)-$R^{10c}$, $—O—(C_1$-$C_4$ alkylene)-$OR^{10c}$, $—C(=O)R^{10d}$, $—OC(=O)R^{10d}$, $—N(R^{10e})C(=O)R^{10d}$, $—C(=O)NR^{10a}R^{10b}$, $—N(R^{10e})C(=O)NR^{10a}R^{10b}$, $—C(=O)N(R^{10e})C(=O)R^{10d}$, $—S(=O)_2R^{10f}$, $—N(R^{10e})S(=O)_2R^{10f}$ or $—S(=O)_2NR^{10a}R^{10b}$, or two adjacent $R^2$ taken together with the atoms to which they are attached form a $C_3$-$C_{12}$ cycloalkyl or 3-12 membered heterocycloalkyl group, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, and 3-12 membered heterocycloalkyl group is optionally independently substituted by 1, 2, 3, 4 or 5 $R^{11}$ groups;

each $R^{2a}$ is independently H, F, Cl, Br, I, $—NO_2$, $N_3$, CN, $—OH$, $—NH_2$, $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, $—NR^{10a}R^{10b}$, $—O—(C_0$-$C_4$ alkylene)-$R^{10c}$, $—O—(C_1$-$C_4$ alkylene)-$OR^{10c}$, $—C(=O)R^{10d}$, $—OC(=O)R^{10d}$, $—N(R^{10e})C(=O)R^{10d}$, $—C(=O)NR^{10a}R^{10b}$, $—N(R^{10e})C(=O)NR^{10a}R^{10b}$, $—C(=O)N(R^{10e})C(=O)R^{10d}$, $—S(=O)_2R^{10f}$, $N(R^{10e})S(=O)_2R^{10f}$ or $—S(=O)_2NR^{10a}R^{10b}$, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, and 3-12 membered heterocycloalkyl group is optionally independently substituted by 1, 2, 3, 4 or 5 $R^{11}$ groups;

$R^3$ is H, $C_3$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl or 5-12 membered heteroaryl, wherein each of the $C_3$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl and 5-12 membered heteroaryl is optionally independently substituted by 1, 2, 3, 4 or 5 $R^{11}$ groups;

$R^4$ is $C_1$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl or 5-12 membered heteroaryl, wherein $R^4$ is optionally substituted by 1, 2, 3, 4 or 5 $R^{11}$ groups;

each of $R^5$, $R^6$, $R^7$ and $R^8$ is independently H, $C_1$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl or 5-12 membered heteroaryl, wherein each of the $C_1$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl and 5-12 membered heteroaryl is optionally independently substituted by 1, 2, 3, 4 or 5 $R^{11}$ groups;

each $R^{3a}$, $R^{4a}$, $R^{5a}$, $R^{6a}$, $R^{7a}$ and $R^{8a}$ is independently H, F, Cl, CN, $C_1$-$C_{12}$ alkyl, $C_2$-$C_{12}$ alkenyl, $C_2$-$C_{12}$ alkynyl, $C_1$-$C_{12}$ alkoxyl, $C_1$-$C_{12}$ alkylamino, $—(C_0$-$C_4$ alkylene)-$(C_3$-$C_{12}$ cycloalkyl), $—(C_0$-$C_4$ alkylene)-(3-12 membered heterocyclyl), $C_6$-$C_{12}$ aryl, 5-12 membered heteroaryl, $—NR^{9a}R^{9b}$, $—OR^{9c}$, $—C(=O)R^{9d}$, $—C(=O)OR^{9c}$, $—N(R^{9e})C(=O)R^{9d}$, $—C(=O)NR^{9a}R^{9b}$, $—N(R^{9e})C(=O)NR^{9a}R^{9b}$, $—S(=O)_2R^{9f}$, $—N(R^{9e})S(=O)_2R^{9f}$ or $—S(=O)_2NR^{9a}R^{9b}$, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_1$-$C_{12}$ alkylamino, $—(C_0$-$C_4$ alkylene)-$(C_3$-$C_{12}$ cycloalkyl), $—(C_0$-$C_4$ alkylene)-(3-12 membered heterocyclyl), $C_6$-$C_{12}$ aryl and 5-12 membered heteroaryl is optionally independently substituted by 1, 2, 3, 4 or 5 $R^{11}$ groups;

each $R^{9a}$, $R^{9b}$, $R^{9c}$, $R^{9e}$, $R^{10a}$, $R^{10b}$, $R^{10c}$ and $R^{10e}$ is independently H, $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, $—(C_0$-$C_4$ alkylene)-$(C_3$-$C_{12}$ cycloalkyl), $—(C_0$-$C_4$ alkylene)-(3-12 membered heterocyclyl), $—(C_0$-$C_4$ alkylene)-$(C_6$-$C_{10}$ aryl) or $—(C_0$-$C_4$ alkylene)-(5-12 membered heteroaryl), or $R^{9a}$ and $R^{9b}$, $R^{10a}$ and $R^{10b}$ taken together with the nitrogen atom to which they are attached form a 3-12 membered heterocyclyl group, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, —($C_0$-$C_4$ alkylene)-($C_3$-$C_{12}$ cycloalkyl), —($C_0$-$C_4$ alkylene)-(3-12 membered heterocyclyl), —($C_0$-$C_4$ alkylene)-($C_6$-$C_{10}$ aryl), —($C_0$-$C_4$ alkylene)-(5-12 membered heteroaryl) and 3-12 membered heterocyclyl group is optionally substituted by 1, 2, 3 or 4 substitutents independently selected from F, Cl, Br, CN, $N_3$, —$NO_2$, —OH, —$NH_2$, $C_1$-$C_6$ alkyl, $C_1$-$C_6$ haloalkyl, $C_1$-$C_6$ alkoxy, $C_1$-$C_6$ hydroxyalkyl, $C_1$-$C_6$ aminoalkyl and $C_1$-$C_6$ alkylamino;

each $R^{9d}$, $R^{9f}$, $R^{10d}$ and $R^{10f}$ is independently $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, —($C_1$-$C_4$ alkylene)-($C_3$-$C_{12}$ cycloalkyl), —($C_1$-$C_4$ alkylene)-(3-12 membered heterocyclyl), —($C_1$-$C_4$ alkylene)-($C_6$-$C_{12}$ aryl) or —($C_1$-$C_4$ alkylene)-(5-12 membered heteroaryl), wherein each of the above substituents is optionally substituted by 1, 2, 3 or 4 substitutents independently selected from F, Cl, Br, CN, $N_3$, —OH, —$NH_2$, $C_1$-$C_6$ alkyl, $C_1$-$C_6$ haloalkyl, $C_1$-$C_6$ alkoxy, $C_1$-$C_6$ hydroxyalkyl, $C_1$-$C_6$ aminoalkyl and $C_1$-$C_6$ alkylamino;

each $R^{11}$ is independently F, Cl, Br, I, CN, —$NO_2$, $N_3$, —OH, —$NH_2$, $C_1$-$C_{12}$ alkyl, $C_2$-$C_{12}$ alkenyl, $C_2$-$C_{12}$ alkynyl, $C_1$-$C_{12}$ haloalkyl, $C_3$-$C_{12}$ cycloalkyl, $C_6$-$C_{12}$ aryl, 3-12 membered heterocyclyl, 5-12 membered heteroaryl, $C_1$-$C_{12}$ aminoalkyl, $C_1$-$C_{12}$ alkylamino, $C_1$-$C_{12}$ alkoxyl, $C_1$-$C_{12}$ hydroxyalkyl, —NH($C_0$-$C_4$ alkylene)-($C_3$-$C_{12}$ cycloalkyl), —NH($C_0$-$C_4$ alkylene)-($C_6$-$C_{12}$ aryl), —NH($C_0$-$C_4$ alkylene)-(3-12 membered heterocyclyl), —NH($C_0$-$C_4$ alkylene)-(5-12 membered heteroaryl), —N[($C_0$-$C_4$ alkylene)-($C_3$-$C_{12}$ cycloalkyl)]$_2$, —N[($C_0$-$C_4$ alkylene)-($C_6$-$C_{12}$ aryl)]$_2$, —N[($C_0$-$C_4$ alkylene)-(3-12 membered heterocyclyl)]$_2$, —N[($C_0$-$C_4$ alkylene)-(5-12 membered heteroaryl)]$_2$, —O—($C_0$-$C_4$ alkylene)-($C_3$-$C_{12}$ cycloalkyl), —O—($C_0$-$C_4$ alkylene)-($C_6$-$C_{12}$ aryl), —O—($C_0$-$C_4$ alkylene)-(3-12 membered heterocyclyl) or —O—($C_0$-$C_4$ alkylene)-(5-12 membered heteroaryl); and each m is independently 0, 1 or 2.

In another embodiment, Z is 8-11 membered spiro heterobicyclyl or 8-10 membered fused heterobicycloalkyl, wherein Z is optionally substituted by 1, 2, 3 or 4 $R^2$ groups.

In one embodiment, Z is:

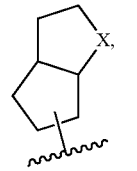

(Z-1)

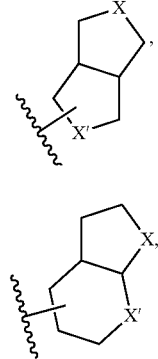

(Z-2)

(Z-3)

(Z-4)

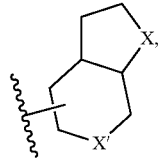

(Z-5)

(Z-6)

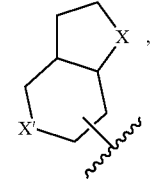

(Z-7)

(Z-8)

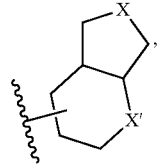

(Z-9)

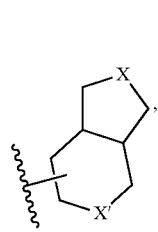

(Z-10)

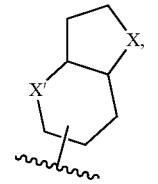

-continued
(Z-11)
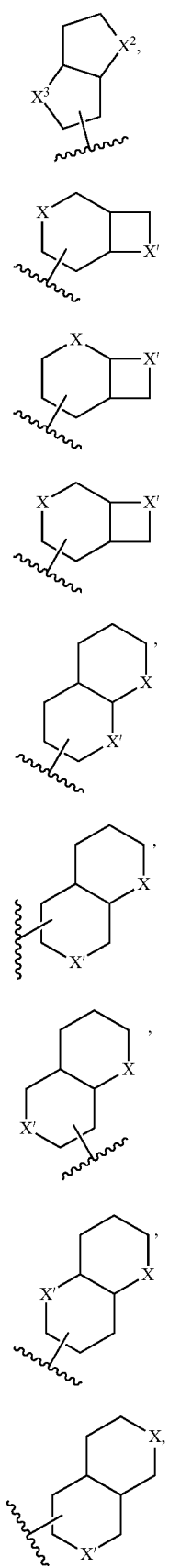
(Z-12)
(Z-13)
(Z-14)
(Z-15)
(Z-16)
(Z-17)
(Z-18)
(Z-19)
-continued
(Z-20)
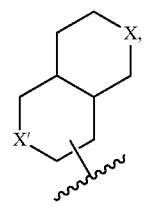
(Z-21)
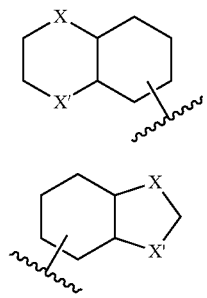
(Z-22)
(Z-23)
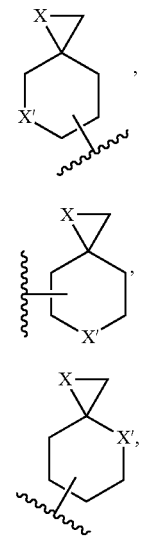
(Z-24)
(Z-25)
(Z-26)
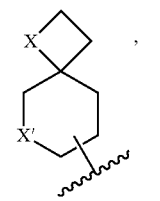
(Z-27)
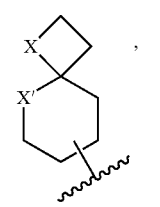
(Z-28)
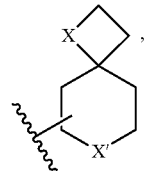

-continued
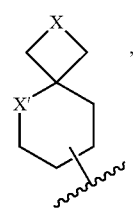
(Z-29)
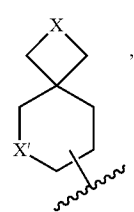
(Z-30)
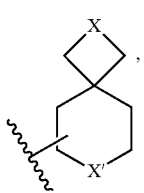
(Z-31)
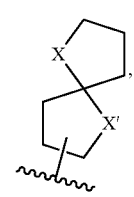
(Z-32)
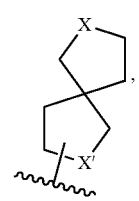
(Z-33)
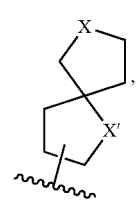
(Z-34)
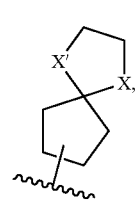
(Z-35)
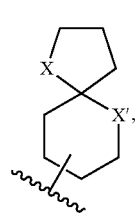
(Z-36)
-continued
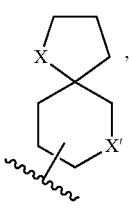
(Z-37)
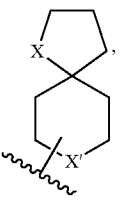
(Z-38)
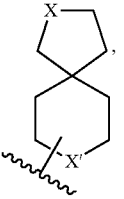
(Z-39)
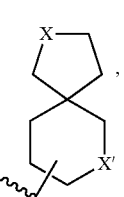
(Z-40)
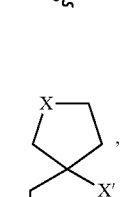
(Z-41)
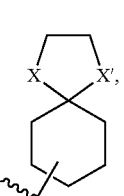
(Z-42)
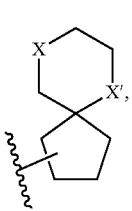
(Z-43)

(Z-44) 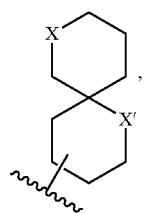
(Z-45) 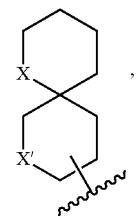
(Z-46) 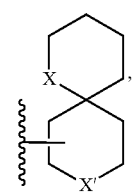
(Z-47) 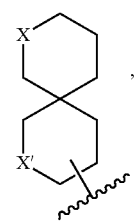
(Z-48) 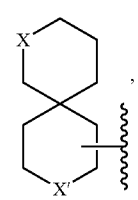
(Z-49) 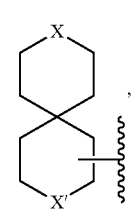
(Z-50) 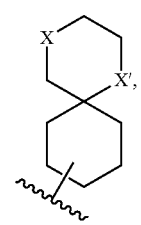
(Z-51) 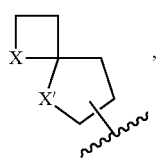
(Z-52) 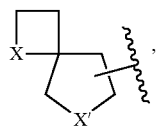
(Z-53) 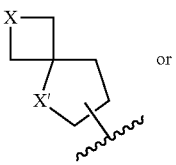
(Z-54) 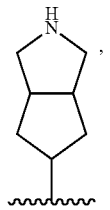
or a stereoisomer thereof, wherein each X, $X^1$, $X^2$, and $X^3$ is independently —$CH_2$—, —NH— or —O—, with the proviso that $X^2$ and $X^3$ are not —O— simultaneously; and wherein Z is optionally substituted by 1, 2 or 3 $R^2$ groups.
In another embodiment, Z is:
(Z-55) 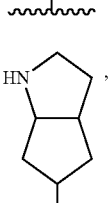
(Z-56) 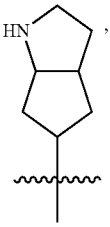
(Z-57) 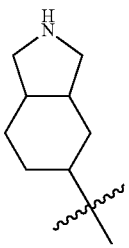

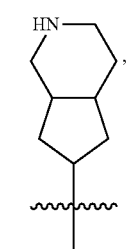 (Z-58)
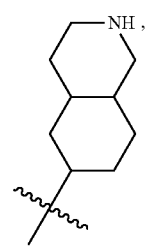 (Z-59)
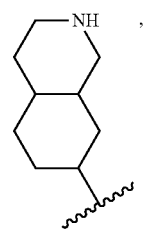 (Z-60)
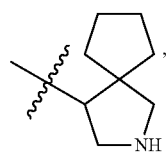 (Z-61)
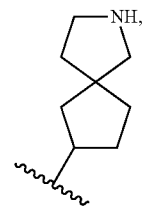 (Z-62)
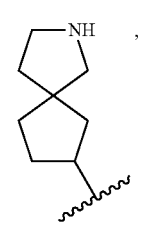 (Z-63)
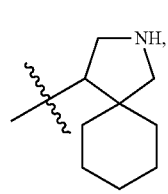 (Z-64)
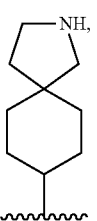 (Z-65)
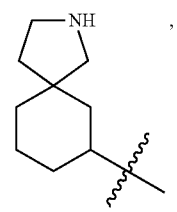 (Z-66)
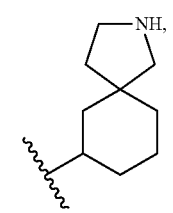 (Z-67)
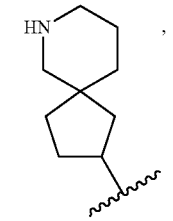 (Z-68)
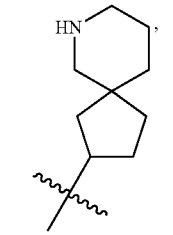 (Z-69)
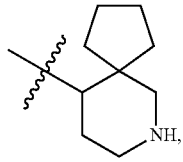 (Z-70)
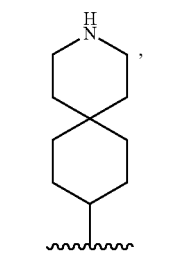 (Z-71)

-continued

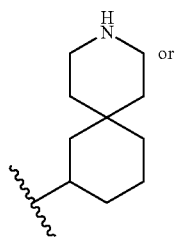
(Z-72)

or

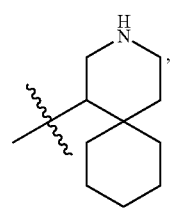
(Z-73)

or a stereoisomer thereof, and wherein Z is optionally substituted by 1, 2 or 3 $R^2$ groups.

In one embodiment, $Z^1$ is H, $C_1$-$C_6$ alkyl, $C_3$-$C_6$ cycloalkyl or 4-7 membered heterocyclyl, wherein each of the $C_1$-$C_6$ alkyl, $C_3$-$C_6$ cycloalkyl and 4-7 membered heterocyclyl is optionally independently substituted by 1, 2 or 3 $R^{2a}$ groups.

In another embodiment, $Z^1$ is H, methyl, ethyl, n-propyl, isopropyl or cyclopropyl.

In one embodiment, $R^1$ is H, F, Cl, Br, I, $N_3$, CN, —$NO_2$, $C_1$-$C_6$ alkyl, $C_1$-$C_6$ alkoxyl, $C_2$-$C_6$ alkenyl, $C_2$-$C_6$ alkynyl, $C_3$-$C_6$ cycloalkyl, 4-7 membered heterocyclyl, —$NR^{9a}R^{9b}$, —$OR^{9c}$, —C(=O)$R^{9d}$, —C(=O)O$R^{9c}$, —C(=O)N$R^{9a}R^{9b}$, —S(=O)$_2R^{9f}$ or —S(=O)$_2$N$R^{9a}R^{9b}$, wherein each of the $C_1$-$C_6$ alkyl, $C_1$-$C_6$ alkoxyl, $C_2$-$C_6$ alkenyl, $C_2$-$C_6$ alkynyl, $C_3$-$C_6$ cycloalkyl and 4-7 membered heterocyclyl is optionally independently substituted by 1, 2 or 3 $R^{11}$ groups.

In another embodiment, each $R^2$ is independently F, Cl, Br, I, —$NO_2$, $N_3$, CN, —OH, —$NH_2$, —C(=O)$CH_2$CN, —NHC(=O)$CH_2$CN, —N($CH_3$)C(=O)$CH_2$CN, $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl, —$NR^{10a}R^{10b}$, —O—($C_0$-$C_3$ alkylene)-$R^{10c}$, —O—($C_1$-$C_3$ alkylene)-O$R^{10c}$, —C(=O)$R^{10d}$, —OC(=O)$R^{10d}$, —N($R^{10e}$)C(=O)$R^{10d}$, —C(=O)N$R^{10a}R^{10b}$, —N($R^{10e}$)C(=O)N$R^{10a}R^{10b}$, —C(=O)N($R^{10e}$)C(=O)$R^{10d}$, —S(=O)$_2R^{10f}$, —N($R^{10e}$)S(=O)$_2R^{10f}$ or —S(=O)$_2$N$R^{10a}R^{10b}$, or two adjacent $R^2$ taken together with the atoms to which they are attached form a $C_3$-$C_6$ cycloalkyl or 4-7 membered heterocycloalkyl group, wherein each of the $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl and 4-7 membered heterocycloalkyl group is optionally independently substituted by 1, 2 or 3 $R^{11}$ groups;

each $R^{2a}$ is independently H, F, Cl, Br, I, —$NO_2$, $N_3$, CN, —OH, —$NH_2$, $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl, —$NR^{10a}R^{10b}$, —O—($C_0$-$C_3$ alkylene)-$R^{1c}$, —O—($C_1$-$C_3$ alkylene)-O$R^{10c}$, —C(=O)$R^{10d}$, —OC(=O)$R^{10d}$, —N($R^{10e}$)C(=O)$R^{10d}$, —C(=O)N$R^{10a}R^{10b}$, —N($R^{10e}$)C(=O)N$R^{10a}R^{10b}$, —C(=O)N($R^{10e}$)C(=O)$R^{10d}$, —S(=O)$_2R^{10f}$, —N($R^{10e}$)S(=O)$_2R^{10f}$ or —S(=O)$_2$N$R^{10a}R^{10b}$.

In one embodiment, $R^3$ is H, $C_3$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_3$-$C_6$ cycloalkyl, phenyl, 4-7 membered heterocyclyl or 5-6 membered heteroaryl, wherein each of the $C_3$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_3$-$C_6$ cycloalkyl, phenyl, 4-7 membered heterocyclyl and 5-6 membered heteroaryl is optionally independently substituted by 1, 2 or 3 $R^{11}$ groups.

In another embodiment, $R^3$ is H, —$CH_2C(CH_3)_2$OH, —$(CH_2)_2CH_2$OOH, —$CH_2CH(OH)CH_3$, piperidinyl, pyrrolidinyl, morpholinyl, piperazinyl, pyridyl, pyrimidinyl, pyridazinyl, pyrazinyl, thiazolyl, pyrrolyl or oxazolyl, wherein each of the piperidinyl, pyrrolidinyl, morpholinyl, piperazinyl, pyridyl, pyrimidinyl, pyridazinyl, thiazolyl, pyrrolyl or oxazolyl is optionally independently substituted by 1, 2 or 3 $R^{11}$ groups.

In one embodiment, $R^4$ is $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, phenyl, 4-7 membered heterocyclyl or 5-6 membered heteroaryl, wherein $R^4$ is optionally substituted by 1, 2, or 3 $R^{11}$ groups.

In another embodiment, each of $R^5$, $R^6$, $R^7$ and $R^8$ is independently H, $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, 4-7 membered heterocyclyl, phenyl or 5-6 membered heteroaryl, wherein each of the $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, 4-7 membered heterocyclyl, phenyl and 5-6 membered heteroaryl is optionally independently substituted by 1, 2 or 3 $R^{11}$ groups.

In one embodiment, each $R^{3a}$, $R^{4a}$, $R^{5a}$, $R^{6a}$, $R^{7a}$ and $R^{8a}$ is independently H, F, Cl, CN, $C_1$-$C_6$ alkyl, $C_2$-$C_6$ alkenyl, $C_1$-$C_6$ alkoxyl, $C_1$-$C_6$ alkylamino, —($C_0$-$C_3$ alkylene)-($C_3$-$C_6$ cycloalkyl), —($C_0$-$C_3$ alkylene)-(4-7 membered heterocyclyl), phenyl, 5-6 membered heteroaryl, —$NR^{9a}R^{9b}$, —$OR^{9c}$, —C(=O)$R^{9d}$, —C(=O)O$R^{9c}$, —C(=O)N$R^{9a}R^{9b}$, —S(=O)$_2R^{9f}$ or —S(=O)$_2$N$R^{9a}R^{9b}$, wherein each of the $C_1$-$C_6$ alkyl, $C_2$-$C_6$ alkenyl, $C_1$-$C_6$ alkoxyl, $C_1$-$C_6$ alkylamino, —($C_0$-$C_3$ alkylene)-($C_3$-$C_6$ cycloalkyl), —($C_0$-$C_3$ alkylene)-(4-7 membered heterocyclyl), phenyl and 5-6 membered heteroaryl is optionally independently substituted by 1, 2 or 3 $R^{11}$ groups.

In another embodiment, each $R^{9a}$, $R^{9b}$, $R^{9c}$, $R^{9e}$, $R^{10a}$, $R^{10b}$, $R^{10c}$ and $R^{10e}$ is independently H, $C_1$-$C_6$ alkyl, $C_2$-$C_6$ alkenyl, $C_2$-$C_6$ alkynyl, $C_1$-$C_6$ alkoxyl, $C_3$-$C_6$ cycloalkyl, —($C_0$-$C_3$ alkylene)-($C_3$-$C_6$ cycloalkyl), —($C_0$-$C_3$ alkylene)-(4-7 membered heterocyclyl), —($C_0$-$C_3$ alkylene)-phenyl, —($C_0$-$C_3$ alkylene)-(5-6 membered heteroaryl), or $R^{9a}$ and $R^{9b}$, $R^{10a}$ and $R^{10b}$ taken together with the nitrogen atom to which they are attached form a 4-7 membered heterocyclyl group, wherein each of the $C_1$-$C_6$ alkyl, $C_2$-$C_6$ alkenyl, $C_2$-$C_6$ alkynyl, $C_1$-$C_6$ alkoxyl, $C_3$-$C_6$ cycloalkyl, —($C_0$-$C_3$ alkylene)-($C_3$-$C_6$ cycloalkyl), —($C_0$-$C_3$ alkylene)-(4-7 membered heterocyclyl), —($C_0$-$C_3$ alkylene)-phenyl, —($C_0$-$C_3$ alkylene)-(5-6 membered heteroaryl), and 4-7 membered heterocyclyl group is optionally substituted by 1, 2 or 3 substitutents independently selected from F, Cl, Br, CN, $N_3$, —$NO_2$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In one embodiment, each $R^{9a}$, $R^{9b}$, $R^{9c}$, $R^{9e}$, $R^{\circ a}$, $R^{10b}$, $R^{10c}$ and $R^{10e}$ is independently H, methyl, ethyl, n-propyl, isopropyl, n-butyl, isobutyl, sec-butyl, tert-butyl, allyl, vinyl, propenyl, $C_1$-$C_4$ alkoxyl, cyclopropyl, cyclobutyl, cyclopentyl, cyclohexyl, piperidinyl, pyrrolidinyl, morpholinyl, piperazinyl, -methylene-cyclopropy, -ethylidene-cyclopropyl, -methylene-cyclobutyl, -ethylidene-cyclobutyl, -methylene-cyclopentyl, -ethylidene-cyclopentyl, -methylene-cyclohexyl, -ethylidene-cyclohexyl, —($C_1$-$C_3$ alkylene)-(4-7 membered heterocyclyl), phenyl, pyridyl, pyridazinyl, pyrimidinyl, —($C_1$-$C_3$ alkylene)-phenyl or —($C_1$-$C_3$ alkylene)-(5-6 membered heteroaryl), wherein each of the methyl, ethyl, n-propyl, isopropyl, n-butyl, isobutyl, sec-butyl, tert-butyl, allyl, vinyl, propenyl, $C_1$-$C_4$ alkoxyl, cyclopropyl, cyclobutyl, cyclopentyl, cyclohexyl, piperidinyl, pyrrolidinyl, morpholinyl, piperazinyl, -methylene-cyclopropyl, -ethylidene-cyclopropyl, -methylene-cyclobutyl, -ethylidene-cyclobutyl, -methylene-cyclopentyl, -ethylidene-cyclopentyl, -methylene-cyclohexyl, -ethylidene-cyclohexyl, —($C_1$-$C_3$ alkylene)-(4-7 membered heterocyclyl), phenyl, pyridyl, pyridazinyl, pyrimidinyl, —($C_1$-$C_3$ alkylene)-phenyl and —($C_1$-$C_3$ alkylene)-(5-6 membered heteroaryl) is optionally substituted by 1, 2 or 3 substitutents independently selected from F, Cl, Br, CN, $N_3$, —$NO_2$, —OH, —$NH_2$, —$CF_3$, —$OCH_3$, —$CH_2OH$, —$CH_2CH_2OH$, —$NHCH_3$, —$N(CH_3)_2$ and —$CH_2NH_2$.

In another embodiment, each $R^{9d}$, $R^{9f}$, $R^{10d}$ and $R^{10f}$ is independently $C_1$-$C_4$ alkyl, $C_2$-$C_4$ alkenyl, $C_2$-$C_4$ alkynyl, $C_1$-$C_4$ alkoxyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl or —($C_1$-$C_3$ alkylene)-(5-6 membered heteroaryl), wherein each of the above substituents is optionally substituted by 1, 2 or 3 substitutents independently selected from F, Cl, Br, CN, $N_3$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In one embodiment, each $R^{9d}$, $R^{9f}$, $R^{10d}$ and $R^{10f}$ is independently methyl, ethyl, n-propyl, isopropyl, n-butyl, isobutyl, sec-butyl, tert-butyl, cyclopropyl, cyclobutyl, cyclopentyl, cyclohexyl, allyl, vinyl, propenyl, phenyl, piperidinyl, pyrrolidinyl, morpholinyl, piperazinyl, $C_1$-$C_4$ alkoxyl, -methylene-cyclopropy, -ethylidene-cyclopropyl, -methylene-cyclobutyl, -ethylidene-cyclobutyl, -methylene-cyclopentyl, -ethylidene-cyclopentyl, -methylene-cyclohexyl or -ethylidene-cyclohexyl, wherein each of the above substituents is optionally substituted by 1, 2 or 3 substitutents independently selected from F, Cl, Br, CN, $N_3$, —OH, —$NH_2$, —$CF_3$, —$OCH_3$, —$CH_2OH$, —$CH_2CH_2OH$, —$NHCH_3$, —$N(CH_3)_2$ and —$CH_2NH_2$.

In another embodiment, each $R^{11}$ is independently F, Cl, Br, I, CN, —$NO_2$, $N_3$, —OH, —$NH_2$, $C_1$-$C_4$ alkyl, $C_2$-$C_4$ alkenyl, $C_2$-$C_4$ alkynyl, $C_1$-$C_4$ haloalkyl, $C_3$-$C_6$ cycloalkyl, phenyl, 4-7 membered heterocyclyl, 5-6 membered heteroaryl, $C_1$-$C_4$ aminoalkyl, $C_1$-$C_4$ alkylamino, $C_1$-$C_4$ alkoxyl, $C_1$-$C_4$ hydroxyalkyl, —NH($C_0$-$C_3$ alkylene)-($C_3$-$C_6$ cycloalkyl), —NH($C_0$-$C_3$ alkylene)-(4-7 membered heterocyclyl), —N[($C_0$-$C_3$ alkylene)-($C_3$-$C_6$ cycloalkyl)]$_2$, —N[($C_0$-$C_3$ alkylene)-(4-7 membered heterocyclyl)]$_2$, —O($C_0$-$C_3$ alkylene)-($C_3$-$C_6$ cycloalkyl) or —O($C_0$-$C_3$ alkylene)-(4-7 membered heterocyclyl).

In one embodiment, each $R^{11}$ is independently F, Cl, Br, I, CN, —$NO_2$, $N_3$, —OH, —$NH_2$, methyl, ethyl, n-propyl, isopropyl, cyclopropyl, methoxy, ethyoxyl, n-propoxy, isopropoxy, hydroxymethyl, hydroxyethyl, methylamino, dimethylamino or aminomethyl.

In yet another embodiment, some non-limiting examples of the compound disclosed herein, and their stereoisomer, tautomer, N-oxide, solvate, pharmaceutically acceptable salts and solvates thereof, are shown in the following:

TABLE 1

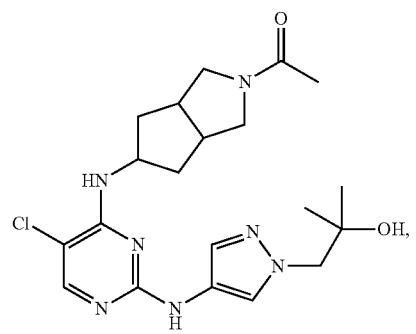 [SMILES: CC(=O)N1CC2CC(Nc3nc(Nc4cnn(CC(C)(C)O)c4)ncc3Cl)CC2C1]

(1)

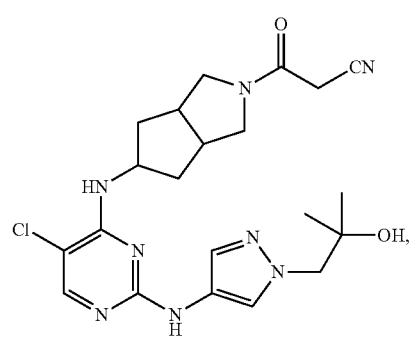 [SMILES: CC(C)(O)Cn1cc(Nc2ncc(Cl)c(NC3CC4CN(C(=O)CC#N)CC4C3)n2)cn1]

(2)

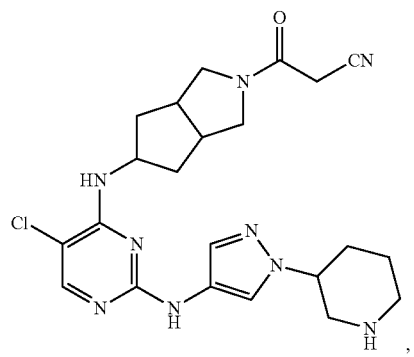 [SMILES: N#CCC(=O)N1CC2CC(Nc3nc(Nc4cnn(C5CCCNC5)c4)ncc3Cl)CC2C1]

(3)

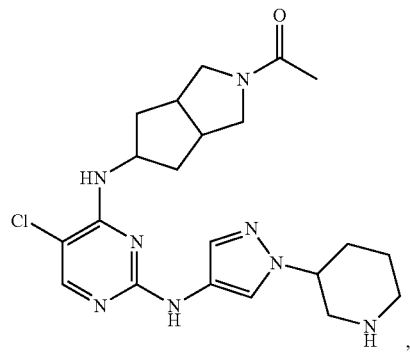 [SMILES: CC(=O)N1CC2CC(Nc3nc(Nc4cnn(C5CCCNC5)c4)ncc3Cl)CC2C1]

(4)

TABLE 1-continued
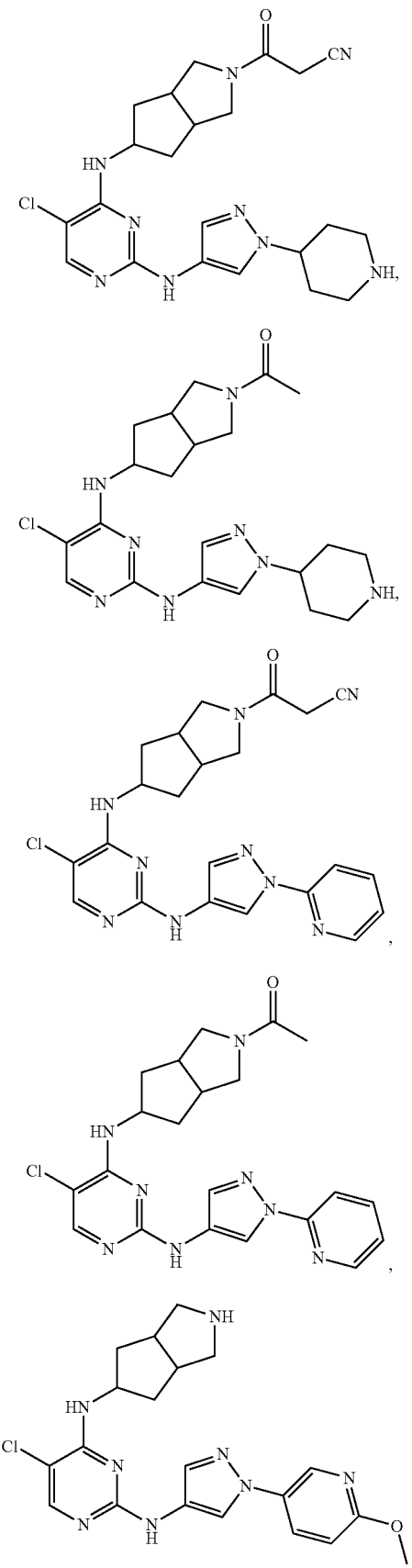
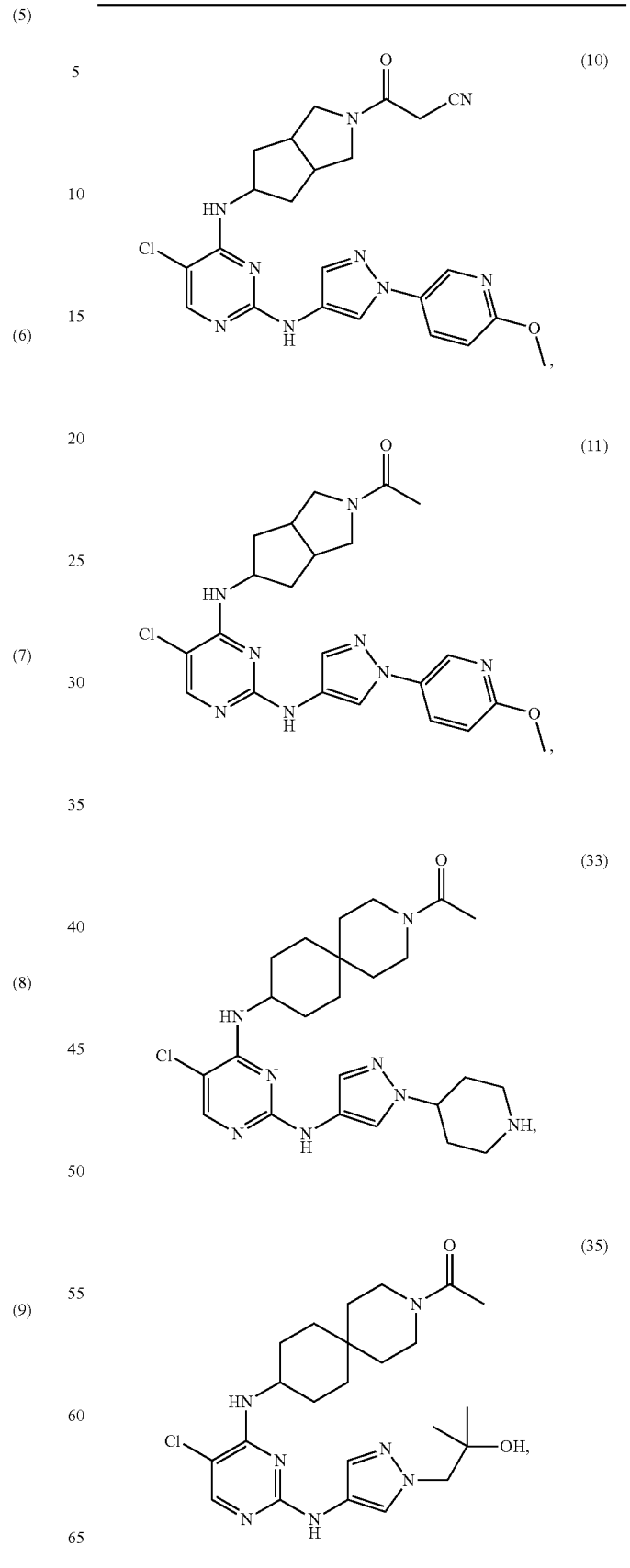

TABLE 1-continued
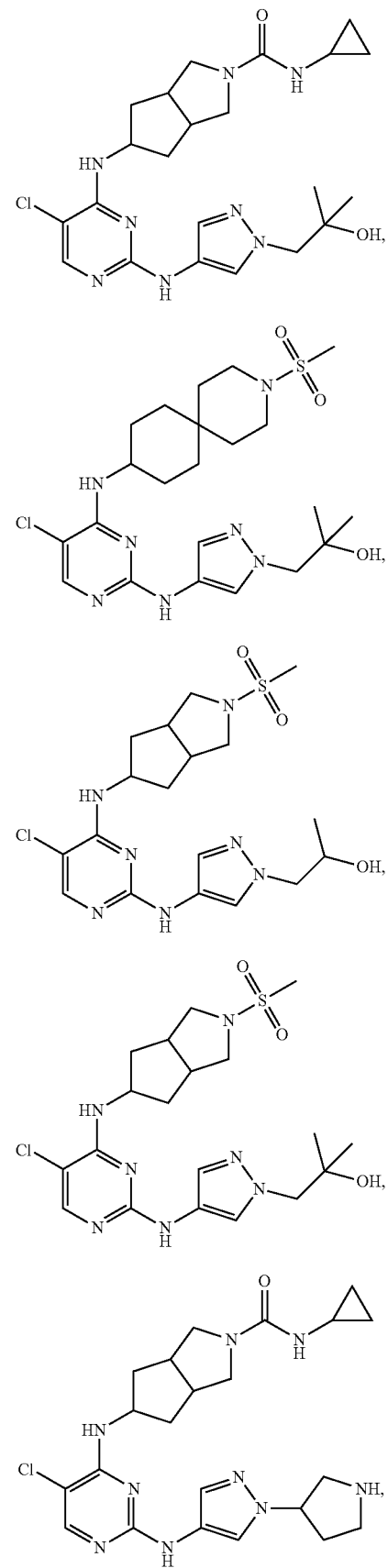
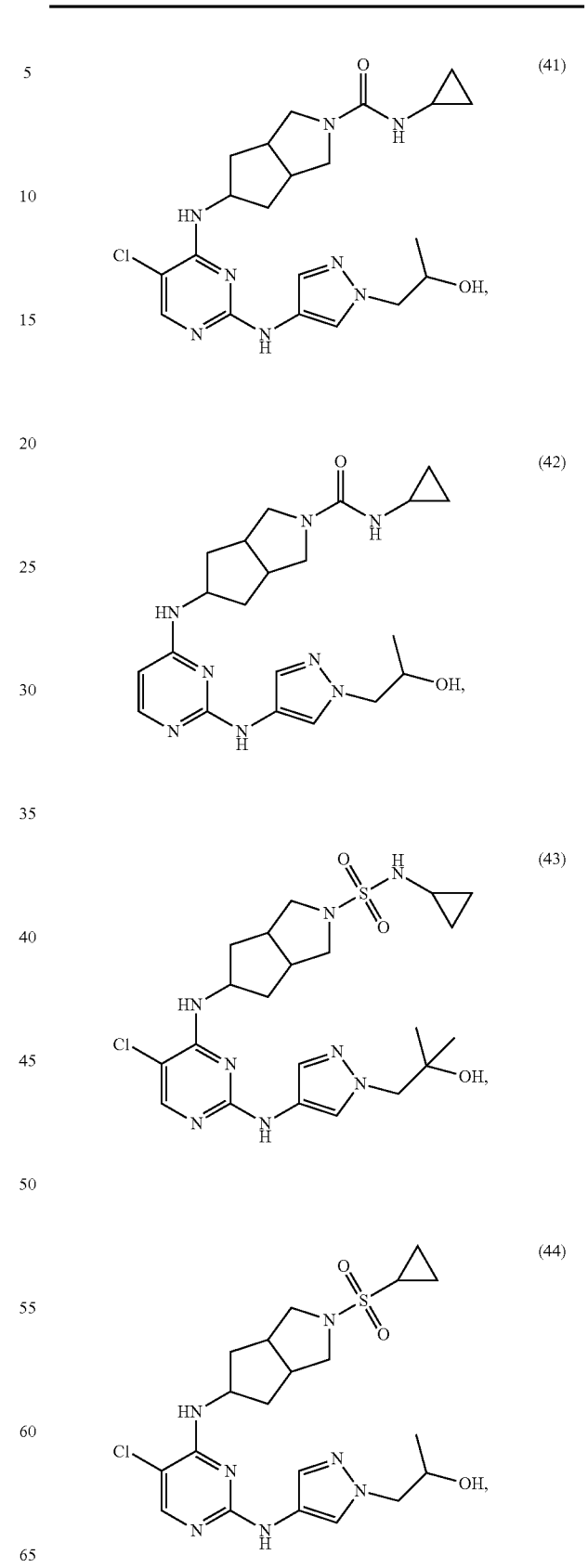

TABLE 1-continued

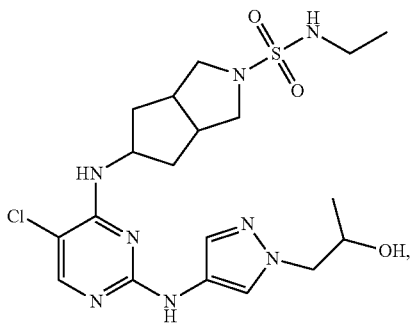 [SMILES: CCNS(=O)(=O)N1CC2CC(Nc3nc(Nc4cnn(CC(C)O)c4)ncc3Cl)CC2C1]
(45)

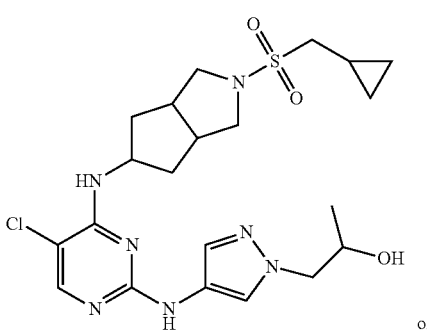
(46)

or

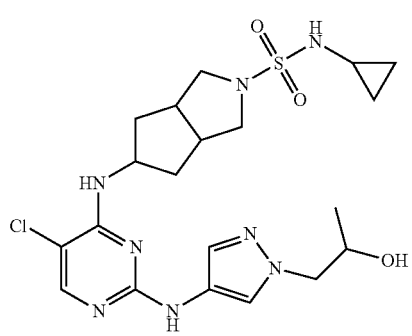 [SMILES: CC(O)Cn1cc(Nc2ncc(Cl)c(NC3CC4CN(S(=O)(=O)NC5CC5)CC4C3)n2)cn1]
(47)

In another aspect, provided herein is a compound having Formula (II):

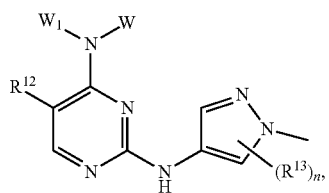
(II)

or a stereoisomer, a tautomer, an N-oxide, a solvate, a metabolite, a pharmaceutically acceptable salt or a prodrug thereof, wherein each of W, $W_1$, $R^{12}$, $R^{13}$ and n is as defined herein.

In one embodiment, W is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein W is substituted by 1, 2, 3, 4 or 5 $R^{14}$ groups;

$W_1$ is H, $C_1$-$C_6$ alkyl, $C_1$-$C_6$ haloalkyl, $C_1$-$C_6$ alkoxyl, $C_1$-$C_6$ aminoalkyl, $C_1$-$C_6$ hydroxyalkyl, $C_3$-$C_6$ cycloalkyl or 4-7 membered heterocyclyl;

$R^{12}$ is H, F, Cl, Br, I, $N_3$, CN, —$NO_2$, $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, —$NR^{15a}R^{15b}$, —$OR^{15c}$, —C(=O)$R^{15d}$, —OC(=O)$R^{15d}$, —C(=O)O$R^{15c}$, —N($R^{15e}$)C(=O)$R^{15d}$, —C(=O)N$R^{15a}R^{15b}$, —N($R^{15e}$)C(=O)N$R^{15a}R^{15b}$, —S(=O)$_2R^{15f}$, —N($R^{15e}$)S(=O)$_2R^{15f}$ or —S(=O)$_2$N$R^{15a}R^{15b}$, wherein each of the $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl and 5-12 membered heteroaryl is optionally independently substituted by 1, 2, 3, 4 or 5 $R^{17}$ groups;

each $R^{13}$ is independently H, F, Cl, CN, $C_1$-$C_{12}$ alkyl, $C_2$-$C_{12}$ alkenyl, $C_1$-$C_{12}$ alkoxyl, —($C_0$-$C_4$ alkylene)-($C_3$-$C_{12}$ cycloalkyl), —($C_0$-$C_4$ alkylene)-(3-12 membered heterocyclyl), $C_6$-$C_{12}$ aryl, 5-12 membered heteroaryl, —$NR^{15a}R^{15b}$, —$OR^{15c}$, —C(=O)$R^{15d}$, —C(=O)O$R^{15c}$, —C(=O)N$R^{15a}R^{15b}$, —S(=O)$_2R^{15f}$, —N($R^1$Se)S(=O)$_2R^{15f}$ or —S(=O)$_2$N$R^{15a}R^{15b}$, wherein each of the $C_1$-$C_{12}$ alkyl, $C_2$-$C_{12}$ alkenyl, $C_1$-$C_{12}$ alkoxyl, —($C_0$-$C_4$ alkylene)-($C_3$-$C_{12}$ cycloalkyl), —($C_0$-$C_4$ alkylene)-(3-12 membered heterocyclyl), $C_6$-$C_{12}$ aryl and 5-12 membered heteroaryl is optionally independently substituted by 1, 2, 3, 4 or 5 $R^{17}$ groups;

each $R^{14}$ is independently F, Cl, Br, I, $NO_2$, $N_3$, CN, $C_3$-$C_{12}$ alkyl, $C_2$-$C_{12}$ alkenyl, $C_2$-$C_{12}$ alkynyl, $C_1$-$C_{12}$ hydroxyalkyl, $C_3$-$C_{12}$ alkoxyl, $C_1$-$C_{12}$ alkylamino, $C_1$-$C_{12}$ aminoalkyl, $C_3$-$C_{12}$ cycloalkyl, 4-7 membered heterocyclyl, $C_6$-$C_{12}$ aryl, 6-cyanopyridazine-3-yl, —$CH_2CN$, —$CH_2CH_2CN$, —C(=O)$R^{16d}$, —S(=O)$_2R^{16e}$, —C(=O)N$R^{16a}R^{16b}$, —S(=O)$_2$N$R^{16a}R^{16b}$, —C(=O)O—$R^{16c}$, —N($R^{16a}$)C(=O)$R^{16f}$, —N($R^{16a}$)S(=O)$_2R^{16g}$ or —OC(=O)$R^{16f}$, wherein each of the —$CH_2CN$, —$CH_2CH_2CN$, $C_3$-$C_{12}$ alkyl, $C_2$-$C_{12}$ alkenyl, $C_2$-$C_{12}$ alkynyl, $C_1$-$C_{12}$ hydroxyalkyl, $C_3$-$C_{12}$ alkoxyl, $C_1$-$C_{12}$ alkylamino, $C_1$-$C_{12}$ aminoalkyl, $C_3$-$C_{12}$ cycloalkyl, 4-7 membered heterocyclyl, $C_6$-$C_{12}$ aryl and 6-cyanopyridazine-3-yl is optionally independently substituted by 1, 2, 3, 4 or 5 $R^{17}$ groups;

each $R^{15a}$, $R^{15b}$, $R^{15c}$, $R^{15e}$, $R^{16a}$ and $R^{16b}$ is independently H, $C_1$-$C_{12}$ alkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, —($C_1$-$C_4$ alkylene)-($C_3$-$C_{12}$ cycloalkyl), —($C_1$-$C_4$ alkylene)-(3-12 membered heterocyclyl), —($C_1$-$C_4$ alkylene)-($C_6$-$C_{12}$ aryl), or —($C_1$-$C_4$ alkylene)-(5-12 membered heteroaryl), or $R^{15a}$ and $R^{15b}$, taken together with the nitrogen atom to which they are attached form a 3-12 membered heterocyclyl group, wherein each of the $C_1$-$C_{12}$ alkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, —($C_1$-$C_4$ alkylene)-($C_3$-$C_{12}$ cycloalkyl), —($C_1$-$C_4$ alkylene)-(3-12 membered heterocyclyl), —($C_1$-$C_4$ alkylene)-($C_6$-$C_{12}$ aryl), and —($C_1$-$C_4$ alkylene)-(5-12 membered heteroaryl) is optionally substituted by 1, 2 or 3 substitutents independently selected from F, Cl, Br, CN, $N_3$, —$NO_2$, —OH, —$NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino;

each $R^{15d}$ and $R^{15f}$ is independently $C_1$-$C_{12}$ alkyl, $C_2$-$C_{12}$ alkenyl, $C_2$-$C_{12}$ alkynyl, $C_1$-$C_{12}$ alkoxyl, —($C_0$-$C_4$ alkylene)-($C_3$-$C_{12}$ cycloalkyl), —($C_0$-$C_4$ alkylene)-(3-12 membered heterocyclyl), —($C_0$-$C_4$ alkylene)-($C_6$-$C_{12}$ aryl) or —($C_0$-$C_4$ alkylene)-(5-12 membered heteroaryl), wherein each of the above substituents is optionally substituted by 1, 2, 3 or 4 substitutents independently selected from F, Cl, Br, CN, $N_3$, —OH, —$NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino;

each $R^{16d}$, $R^{16e}$ and $R^{16g}$ is independently $C_2$-$C_{12}$ alkyl, $C_3$-$C_{12}$ cycloalkyl, 3-12 membered heterocyclyl, $C_6$-$C_{12}$ aryl, 5-12 membered heteroaryl, —($C_1$-$C_4$ alkylene)-($C_3$-

$C_{12}$ cycloalkyl), —($C_1$-$C_4$ alkylene)-(3-12 membered heterocyclyl), —($C_1$-$C_4$ alkylene)-($C_6$-$C_{12}$ aryl) or —($C_1$-$C_4$ alkylene)-(5-12 membered heteroaryl), wherein each of the above substituents is optionally substituted by 1, 2, 3 or 4 substitutents independently selected from F, Cl, Br, CN, $N_3$, —OH, —$NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino;

each $R^{16e}$ and $R^{16f}$ is independently $C_1$-$C_3$ alkyl, $C_3$-$C_{12}$ cycloalkyl, 3-12 membered heterocyclyl, $C_6$-$C_{12}$ aryl, 5-12 membered heteroaryl, —($C_1$-$C_4$ alkylene)-($C_3$-$C_{12}$ cycloalkyl), —($C_1$-$C_4$ alkylene)-(3-12 membered heterocyclyl), —($C_1$-$C_4$ alkylene)-($C_6$-$C_{12}$ aryl), or —($C_1$-$C_4$ alkylene)-(5-12 membered heteroaryl), wherein each of the above substituents is optionally substituted by 1, 2, 3 or 4 substitutents independently selected from F, Cl, Br, CN, $N_3$, —OH, —$NH_2$, $C_1$-$C_4$ alkyl, $C_1$-$C_4$ haloalkyl, $C_1$-$C_4$ alkoxy, $C_1$-$C_4$ hydroxyalkyl, $C_1$-$C_4$ aminoalkyl and $C_1$-$C_4$ alkylamino;

each $R^{17}$ is independently F, Cl, Br, I, CN, $NO_2$, $N_3$, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, $C_6$-$C_{12}$ aryl, 4-7 membered heterocyclyl, 5-12 membered heteroaryl, $C_1$-$C_6$ aminoalkyl, $C_1$-$C_6$ alkylamino, $C_1$-$C_6$ alkoxyl, $C_1$-$C_6$ hydroxyalkyl, —NH($C_0$-$C_4$ alkylene)-($C_3$-$C_6$ cycloalkyl), —NH($C_0$-$C_4$ alkylene)-(4-7 membered heterocyclyl), —N[($C_0$-$C_4$ alkylene)-($C_3$-$C_6$ cycloalkyl)]$_2$, —N[($C_0$-$C_4$ alkylene)-(4-7 membered heterocyclyl)]$_2$, —O($C_0$-$C_4$ alkylene)-($C_3$-$C_6$ cycloalkyl) or —O($C_0$-$C_4$ alkylene)-(4-7 membered heterocyclyl); and n is 0, 1 or 2.

In another embodiment, W is 8-11 membered spiro heterobicyclyl or 8-10 membered fused heterobicycloalkyl, wherein W is substituted by 1, 2, 3 or 4 $R^{14}$ groups.

In one embodiment, W is:

(W-1)

(W-2)

(W-3)

(W-4)

-continued

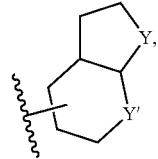
(Z-5)

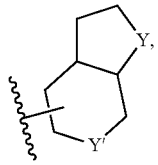
(W-6)

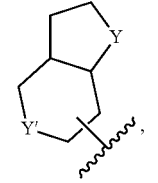
(W-7)

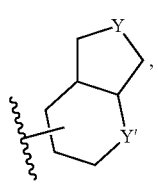
(W-8)

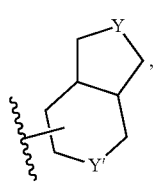
(W-9)

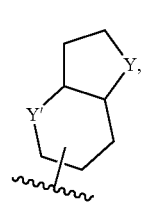
(W-10)

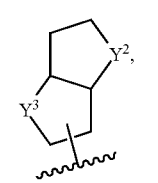
(W-11)

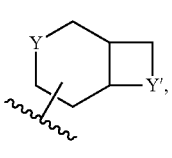
(W-12)

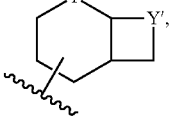
(W-13)

(W-14) 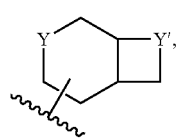
(W-15) 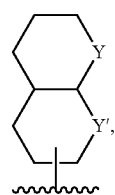
(W-16) 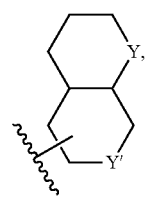
(W-17) 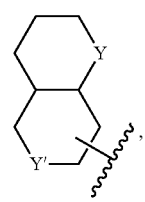
(W-18) 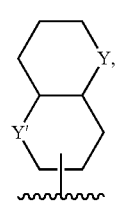
(W-19) 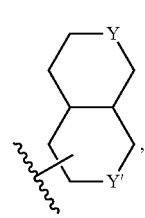
(W-20) 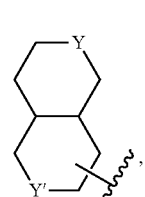
(W-21) 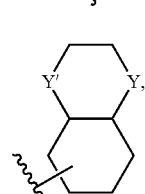
(W-22) 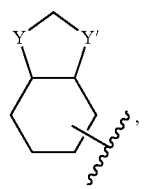
(W-23) 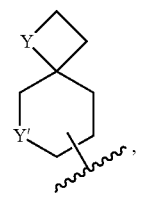
(W-24) 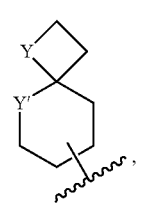
(W-25) 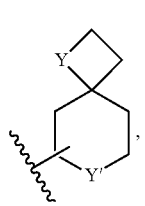
(W-26) 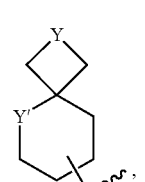
(W-27) 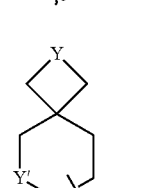
(W-28) 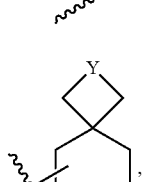
(W-29) 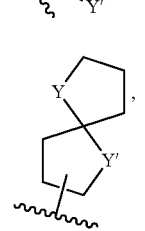

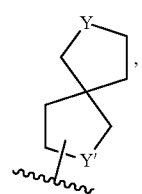 (W-30)
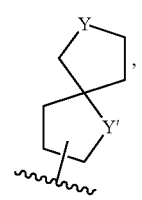 (W-31)
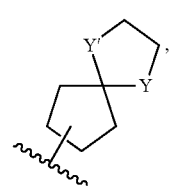 (W-32)
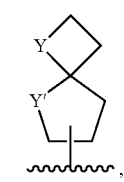 (W-33)
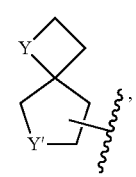 (W-34)
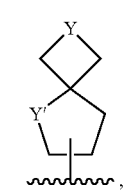 (W-35)
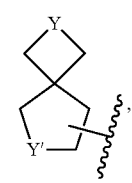 (W-36)
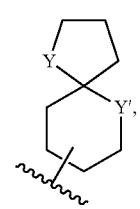 (W-37)
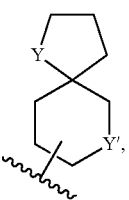 (W-38)
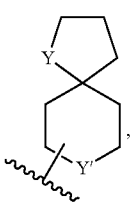 (W-39)
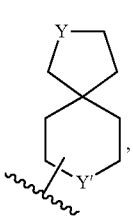 (W-40)
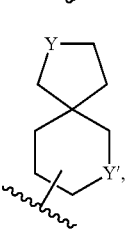 (W-41)
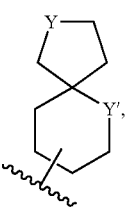 (W-42)
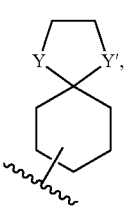 (W-43)
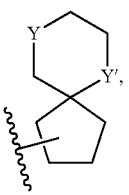 (W-44)

-continued
(W-45) 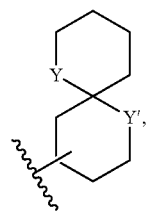
(W-46) 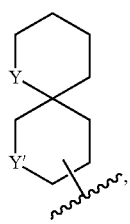
(W-47) 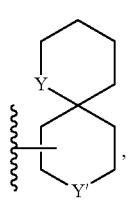
(W-48) 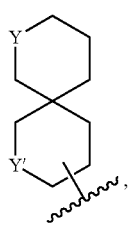
(W-49) 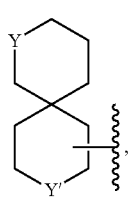
(W-50) 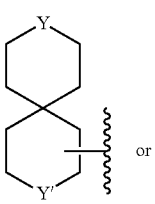 or
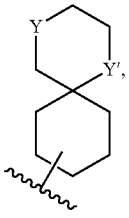
or a stereoisomer thereof, wherein each Y, $Y^1$, $Y^2$ and $Y^3$ is independently —$CH_2$—, —NH— or —O—, with the proviso that $Y^2$ and $Y^3$ are not —O— simultaneously; and wherein W is substituted by 1, 2 or 3 $R^{14}$ groups.
In another embodiment, W is:
(W-52) 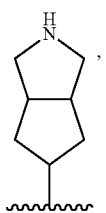
(W-53) 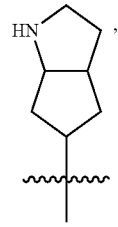
(W-54) 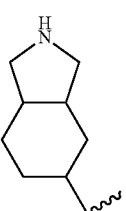
(W-55) 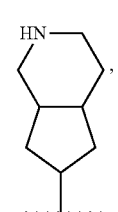
(W-56) 
(W-57) 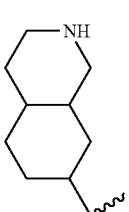
(W-58) 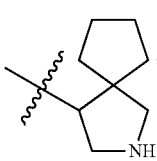

(W-59) 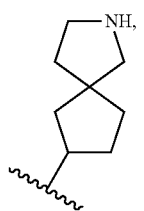

(W-60) 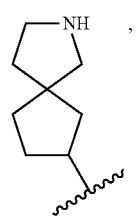

(W-61) 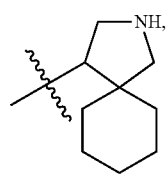

(W-62) 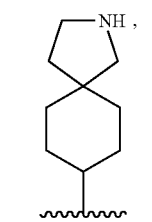

(W-63) 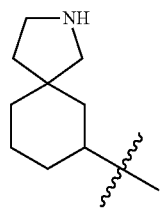

(W-64) 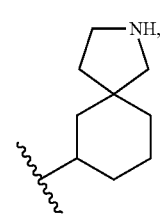

(W-65) 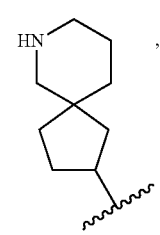

(W-66) 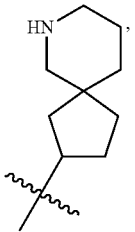

(W-67) 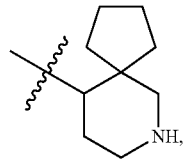

(W-68) 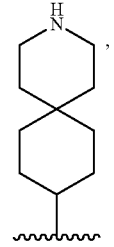

(W-69) or 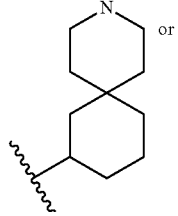

(W-70) 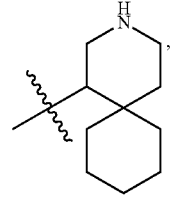

or a stereoisomer thereof, and wherein W is substituted by 1, 2 or 3 $R^{14}$ groups.

In one embodiment, $W_1$ is H, methyl, ethyl, n-propyl, isopropyl or cyclopropyl.

In another embodiment, $R^{12}$ is H, F, Cl, Br, I, $N_3$, CN, —$NO_2$, $C_1$-$C_4$ alkyl, $C_1$-$C_4$ alkoxyl, $C_2$-$C_4$ alkenyl, $C_2$-$C_4$ alkynyl, $C_3$-$C_6$ cycloalkyl, 4-7 membered heterocyclyl, —$NR^{15a}R^{15b}$, —$OR^{5c}$, —C(=O)$R^{15d}$, —C(=O)$OR^{15c}$, —C(=O)$NR^{15a}R^{15b}$, —S(=O)$_2R^{15f}$, or —S(=O)$_2NR^{15a}R^{15b}$, wherein each of the $C_1$-$C_4$ alkyl, $C_1$-$C_4$ alkoxyl, $C_2$-$C_4$ alkenyl, $C_2$-$C_4$ alkynyl, $C_3$-$C_6$ cycloalkyl and 4-7 membered heterocyclyl is optionally independently substituted by 1, 2 or 3 $R^{17}$ groups.

In one embodiment, each $R^{13}$ is independently H, F, Cl, CN, $C_1$-$C_4$ alkyl, $C_2$-$C_4$ alkenyl, $C_1$-$C_4$ alkoxyl, —($C_0$-$C_3$ alkylene)-($C_3$-$C_6$ cycloalkyl), —($C_0$-$C_3$ alkylene)-(4-7 membered heterocyclyl), —$NR^{15a}R^{15b}$, —$OR^{15}$, —C(=O)$R^{15d}$, —C(=O)$OR^{15c}$, —C(=O)$NR^{15a}R^{15b}$, —S(=O)$_2R^{15f}$ or —S(=O)$_2NR^{15a}R^{15b}$, wherein each of the $C_1$-$C_4$ alkyl, $C_2$-$C_4$ alkenyl, $C_1$-$C_4$ alkoxyl, —($C_0$-$C_3$ alkylene)-(C$_3$-C$_6$ cycloalkyl) and —(C$_0$-C$_3$ alkylene)-(4-7 membered heterocyclyl) is optionally independently substituted by 1, 2 or 3 R$^{17}$ groups.

In another embodiment, each R$^{14}$ is independently F, Cl, Br, I, —NO$_2$, N$_3$, CN, C$_3$-C$_6$ alkyl, C$_2$-C$_6$ alkenyl, C$_2$-C$_6$ alkynyl, C$_1$-C$_6$ hydroxyalkyl, C$_3$-C$_6$ alkoxyl, C$_1$-C$_6$ alkylamino, C$_1$-C$_6$ aminoalkyl, C$_3$-C$_6$ cycloalkyl, 4-7 membered heterocyclyl, phenyl, 6-cyanopyridazine-3-yl, —CH$_2$CN, —CH$_2$CH$_2$CN, —C(=O)R$^{16d}$, —S(=O)$_2$R$^{16e}$, —C(=O)NR$^{16a}$R$^{6b}$, —S(=O)$_2$NR$^{16a}$R$^{16b}$, —C(=O)O—R$^{16c}$, —N(R$^{16a}$)C(=O)R$^{16f}$, —N(R$^{16a}$)S(=O)$_2$R$^{16g}$ or —OC(=O)R$^{16f}$, wherein each of the —CH$_2$CN, —CH$_2$CH$_2$CN, C$_3$-C$_6$ alkyl, C$_2$-C$_6$ alkenyl, C$_2$-C$_6$ alkynyl, C$_1$-C$_6$ hydroxyalkyl, C$_3$-C$_6$ alkoxyl, C$_1$-C$_6$ alkylamino, C$_1$-C$_6$ aminoalkyl, C$_3$-C$_6$ cycloalkyl, 4-7 membered heterocyclyl, phenyl and 6-cyanopyridazine-3-yl is optionally independently substituted by 1, 2 or 3 R$^{17}$ groups.

In one embodiment, each R$^{14}$ is independently F, Cl, Br, —NO$_2$, CN,

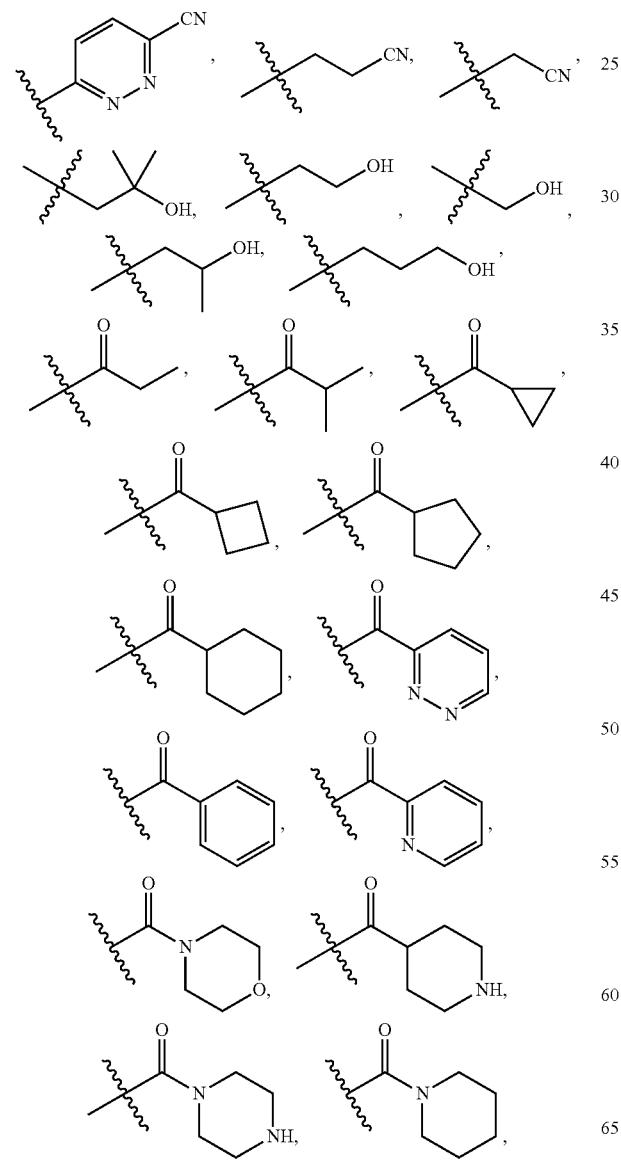

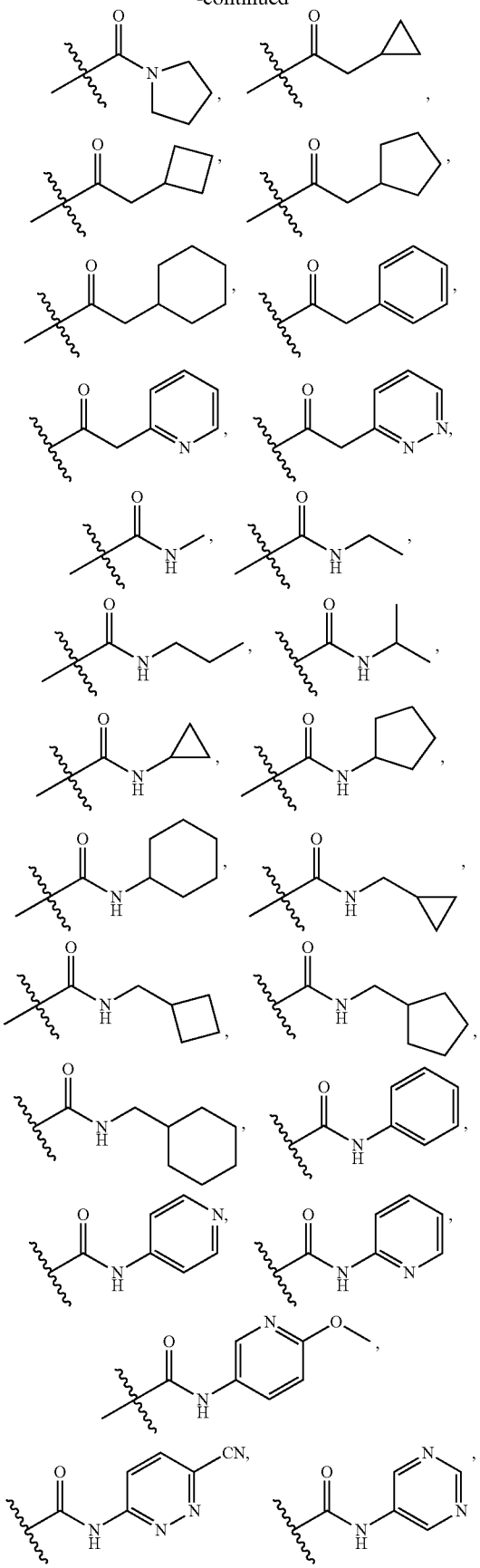

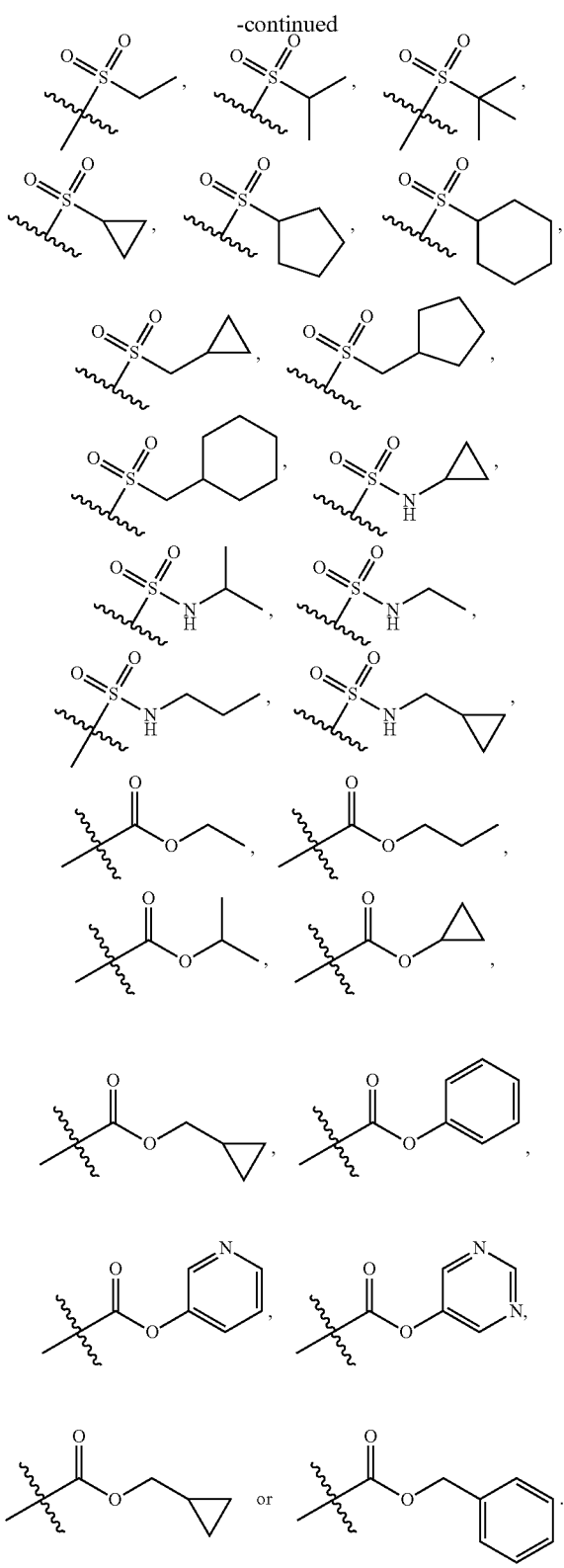

In another embodiment, each $R^{15a}$, $R^{15b}$, $R^{15c}$, $R^{15e}$, $R^{16a}$ and $R^{16b}$ is independently H, $C_1$-$C_4$ alkyl, $C_2$-$C_4$ alkenyl, $C_2$-$C_4$ alkynyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl or —($C_1$-$C_3$ alkylene)-(5-6 membered heteroaryl), or $R^{15a}$ and $R^{15b}$, taken together with the nitrogen atom to which they are attached form a 4-7 membered heterocyclyl group, wherein each of the $C_1$-$C_4$ alkyl, $C_2$-$C_4$ alkenyl, $C_2$-$C_4$ alkynyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl and —($C_1$-$C_3$ alkylene)-(5-6 membered heteroaryl) is optionally substituted by 1, 2 or 3 substitutents independently selected from F, Cl, Br, CN, $N_3$, —$NO_2$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In one embodiment, each $R^{15d}$ and $R^{15f}$ is independently $C_1$-$C_4$ alkyl, $C_2$-$C_4$ alkenyl, $C_2$-$C_4$ alkynyl, $C_1$-$C_4$ alkoxyl, —($C_0$-$C_3$ alkylene)-($C_3$-$C_6$ cycloalkyl), —($C_0$-$C_3$ alkylene)-(4-7 membered heterocyclyl), —($C_0$-$C_3$ alkylene)-phenyl, or —($C_0$-$C_3$ alkylene)-(5-6 membered heteroaryl), wherein each of the above substituents is optionally substituted by 1, 2 or 3 substitutents independently selected from F, Cl, Br, CN, $N_3$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In another embodiment, each $R^{16d}$, $R^{16e}$ and $R^{16g}$ is independently $C_2$-$C_6$ alkyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl, or —($C_1$-$C_3$ alkylene)-(5-6 membered heteroaryl), wherein each of the above substituents is optionally substituted by 1, 2, 3 or 4 substitutents independently selected from F, Cl, Br, CN, $N_3$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In one embodiment, each $R^{16c}$ and $R^{16f}$ is independently $C_1$-$C_3$ alkyl, $C_3$-$C_6$ cycloalkyl, 4-7 membered heterocyclyl, phenyl, 5-6 membered heteroaryl, —($C_1$-$C_3$ alkylene)-($C_3$-$C_6$ cycloalkyl), —($C_1$-$C_3$ alkylene)-(4-7 membered heterocyclyl), —($C_1$-$C_3$ alkylene)-phenyl, or —($C_1$-$C_3$ alkylene)-(5-6 membered heteroaryl), wherein each of the above substituents is optionally substituted by 1, 2, 3 or 4 substitutents independently selected from F, Cl, Br, CN, $N_3$, —OH, —$NH_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

In another embodiment, each $R^{17}$ is independently F, Cl, Br, I, CN, $NO_2$, $N_3$, —OH, —$NH_2$, $C_1$-$C_4$ alkyl, $C_2$-$C_4$ alkenyl, $C_2$-$C_4$ alkynyl, $C_1$-$C_4$ haloalkyl, $C_3$-$C_6$ cycloalkyl, phenyl, 4-7 membered heterocyclyl, 5-6 membered heteroaryl, $C_1$-$C_4$ aminoalkyl, $C_1$-$C_4$ alkylamino, $C_1$-$C_4$ alkoxyl, $C_1$-$C_4$ hydroxyalkyl, —NH($C_0$-$C_3$ alkylene)-($C_3$-$C_6$ cycloalkyl), —NH($C_0$-$C_3$ alkylene)-(4-7 membered heterocyclyl), —N[($C_0$-$C_3$ alkylene)-($C_3$-$C_6$ cycloalkyl)]$_2$, —N[($C_0$-$C_3$ alkylene)-(4-7 membered heterocyclyl)]$_2$, —O($C_0$-$C_3$ alkylene)-($C_3$-$C_6$ cycloalkyl) or —O($C_0$-$C_3$ alkylene)-(4-7 membered heterocyclyl).

In yet another embodiment, some non-limiting examples of the compound disclosed herein, and their stereoisomer, tautomer, N-oxide, solvate, pharmaceutically acceptable salts and solvates thereof, are shown in the following:

TABLE 2
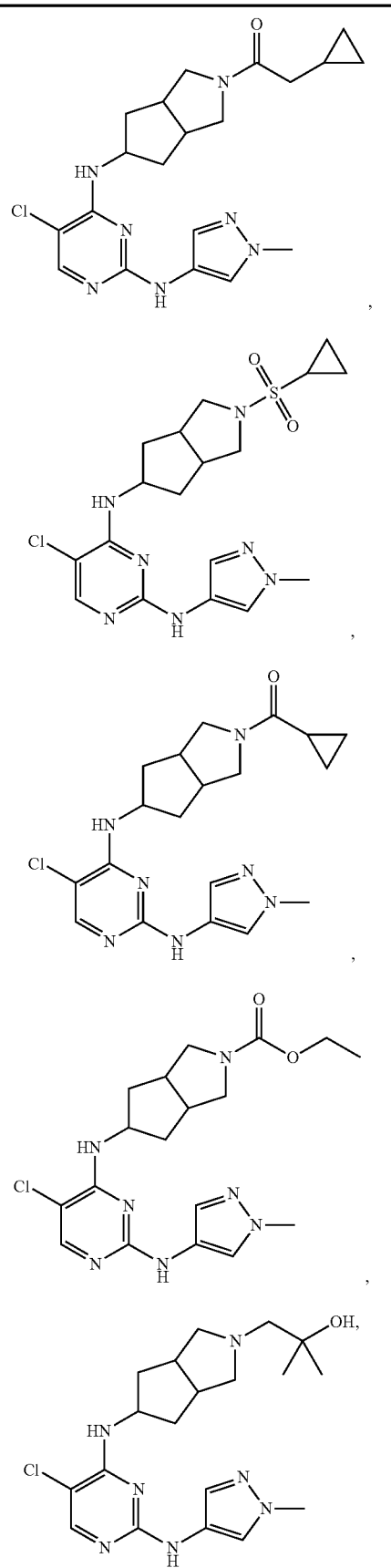
TABLE 2-continued
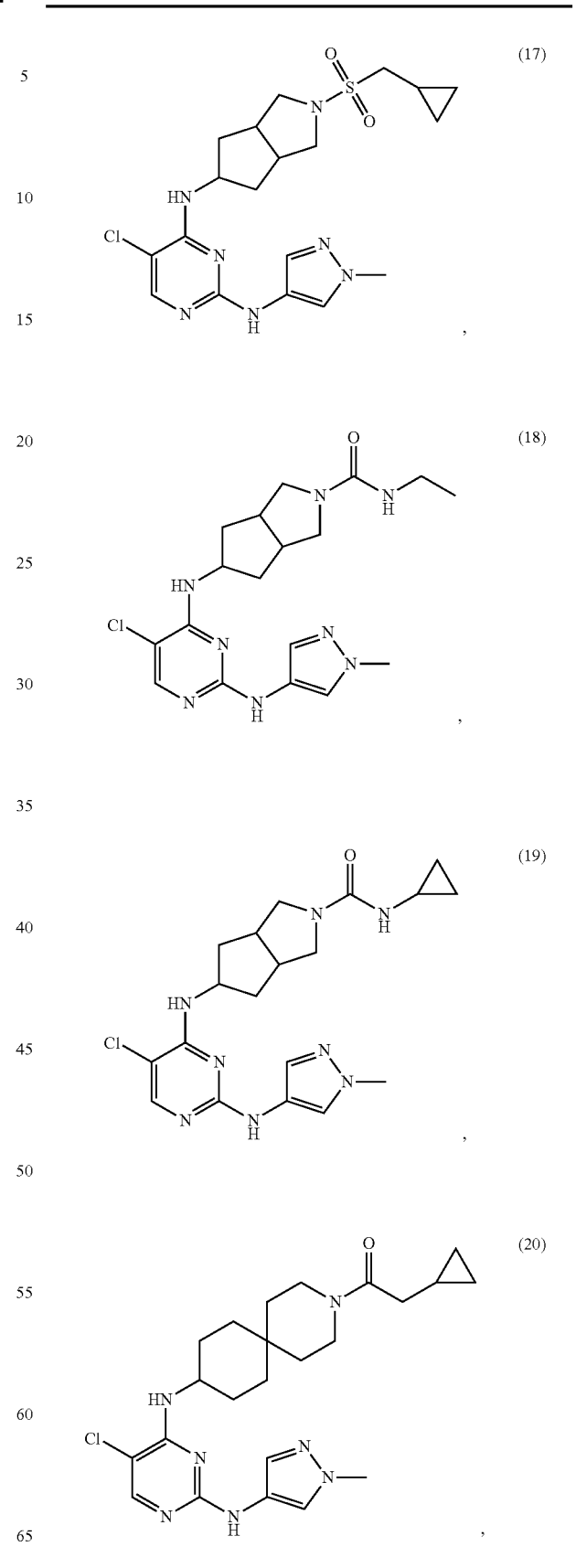

TABLE 2-continued
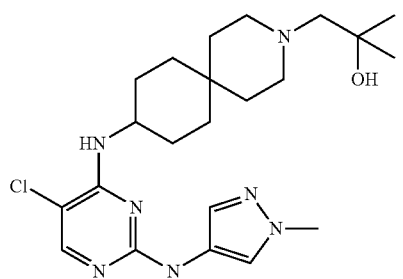
(21)
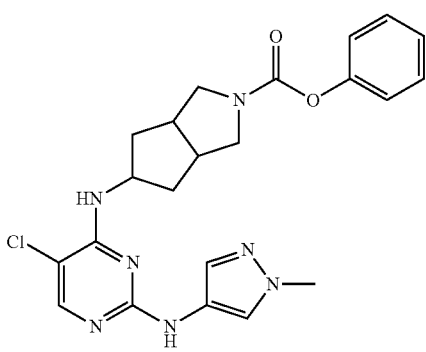
(25)
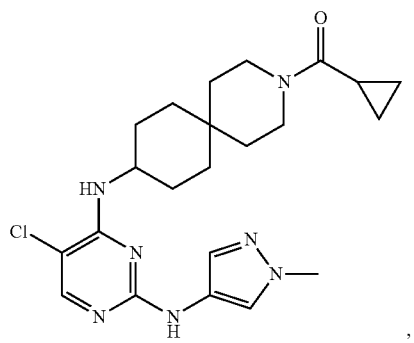 [SMILES: Cn1cc(Nc2ncc(Cl)c(NC3CCC4(CC3)CCN(C(=O)C3CC3)CC4)n2)cn1]
(22)
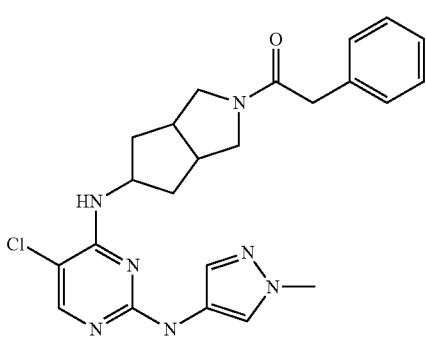
(26)
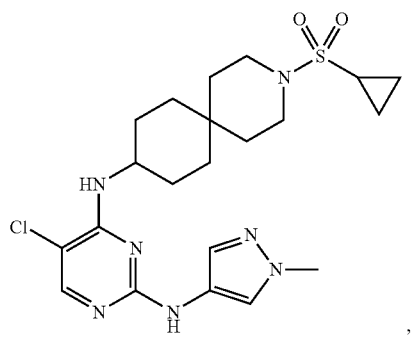 [SMILES: Cn1cc(Nc2ncc(Cl)c(NC3CCC4(CC3)CCN(S(=O)(=O)C3CC3)CC4)n2)cn1]
(23)
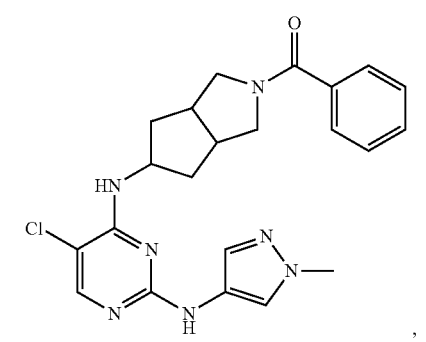
(27)
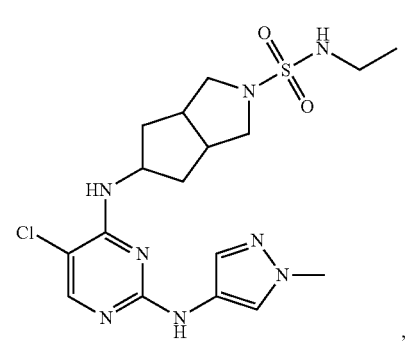 [SMILES: CCNS(=O)(=O)N1CC2CC(Nc3nc(Nc4cnn(C)c4)ncc3Cl)CC2C1]
(24)
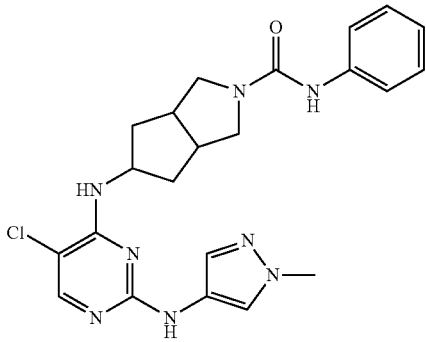
(28)

TABLE 2-continued

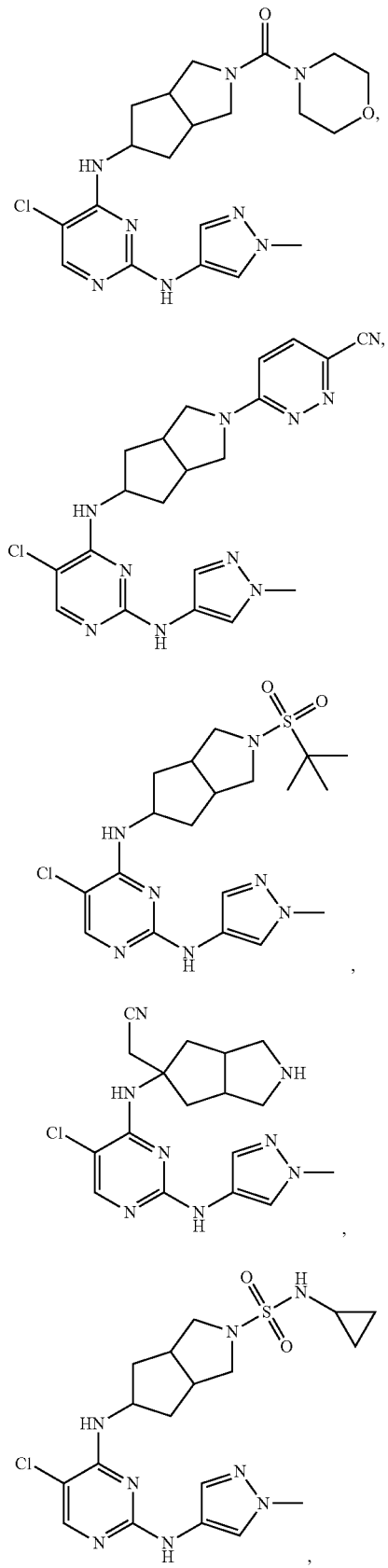

TABLE 2-continued

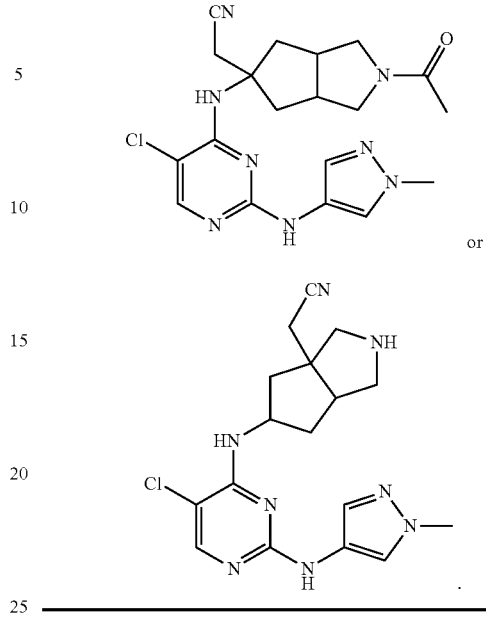

Unless otherwise stated, all stereoisomers, tautomers, solvates, metabolites, salts, and pharmaceutically acceptable prodrugs of the compounds of Formula (I) and Formula (II) are within the scope of the invention.

The compounds disclosed herein may contain asymmetric or chiral centers, and therefore exist in different stereoisomeric forms. It is intended that all stereoisomeric forms of compounds of Formula (I) and Formula (II), including but not limited to, diastereomers, enantiomers, atropisomers, conformers (rotamers) and geometric (cis/trans) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula (I) and Formula (II) may exist in different tautomeric forms, and all such forms are embraced within the scope of the invention, as defined by the claims.

The compounds of Formula (I) and Formula (II) can be in the form of salts. In one embodiment, the salts are pharmaceutically acceptable salts. The phrase "pharmaceutically acceptable" indicates that the substance or composition must be compatible chemically and/or toxicologically, with the other ingredients comprising a formulation, and/or the mammal being treated therewith. In another embodiment, the salts are not necessarily pharmaceutically acceptable salts, and which may be useful as intermediates for preparing and/or purifying compounds of Formula (I) and Formula (II) and/or for separating enantiomers of compounds of Formula (I) and Formula (II).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) and Formula (II) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I) and Formula (II). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. D$_2$O, acetone-d$_6$, DMSO-d$_6$.

In another aspect, provided herein are intermediates for preparing the compounds disclosed herein.

In another aspect, provided herein are methods of preparing, methods of separating, and methods of purifying the compounds disclosed herein.

In another aspect, provided herein is a pharmaceutical composition comprising a therapeutically effective amount of the compound disclosed herein, and a pharmaceutically acceptable excipient, carrier, adjuvant, vehicle or a combination thereof. In some embodiments, the composition is a liquid, solid, semi-solid, gel, or an aerosol form.

In another aspect, provided herein is a method of treating a disease or disorder modulated by one or more protein kinases such as JAK kinases, FLT3 kinase and Aurora kinases, comprising administering to a mammal in need of such treatment an effective amount of a compound or a pharmaceutical composition disclosed herein. In one embodiment, the disease or disorder is selected from proliferative disease, autoimmune disease, allergic disease, inflammatory disease or transplantation rejection.

In another aspect, provided herein is the compound or the pharmaceutical composition disclosed herein for use in the treatment of disease or disorder selected from proliferative disease, autoimmune disease, allergic disease, inflammatory disease or transplantation rejection.

In another aspect, provided herein is the use of the compound or the pharmaceutical composition disclosed herein in the manufacture of a medicament for the treatment of disease or disorder selected from proliferative disease, autoimmune disease, allergic disease, inflammatory disease or transplantation rejection.

In still another aspect, provided herein is use of the compound or the pharmaceutical composition disclosed herein in the manufacture of a medicament for modulating the activity of protein kinase.

Pharmaceutical Composition, Formulations and Administration of the Compounds of the Invention The present invention provides a pharmaceutical composition that include a compound disclosed herein, or a compound listed in Table 1 and Table 2; and a pharmaceutically acceptable excipient, carrier, adjuvant, vehicle or a combination thereof. The amount of compound in the pharmaceutical composition disclosed herein is such that is effective to detectably inhibit a protein kinase in a biological sample or in a patient.

It will also be appreciated that certain compounds disclosed herein can exist in free form for treatment, or where appropriate, as a pharmaceutically acceptable derivative thereof. Some non-limiting examples of pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

The pharmaceutical compositions disclosed herein may be prepared and packaged in bulk form wherein a safe and effective amount of the compound disclosed herein can be extracted and then given to the patient such as with powders or syrups. Alternatively, the pharmaceutical compositions disclosed herein may be prepared and packaged in unit dosage form wherein each physically discrete unit contains the compound disclosed herein. When prepared in unit dosage form, the pharmaceutical compositions of the invention typically may contain, for example, from 0.5 mg to 1 g, or from 1 mg to 700 mg, or from 5 mg to 100 mg of the compound disclosed herein.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound disclosed herein when administered to a patient and interactions which would result in pharmaceutical compositions that are not pharmaceutically acceptable are avoided. In addition, each excipient must be pharmaceutically-acceptable, e.g., of sufficiently high purity.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds disclosed herein once administered to the patient from one organ, or portion of the body, to another organ, or portion of the body. Certain pharmaceutically acceptable excipients may be chosen for their ability to enhance patient compliance.

Suitable pharmaceutically acceptable excipients comprise the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

The pharmaceutical compositions disclosed herein are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising the compound disclosed herein and a pharmaceutically acceptable excipient, carrier, adjuvant, vehicle or a combination thereof, which comprises mixing the ingredients. A pharmaceutical composition comprising the compound disclosed herein may be prepared by, for example, admixture at ambient temperature and atmospheric pressure.

The compounds disclosed herein will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, granula, and cachets;

(2) parenteral administration such as sterile solutions, suspensions, and freeze drying powder; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein will be formulated for oral administration. In another embodiment, the compounds disclosed herein will be formulated for inhaled administration. In a further embodiment, the compounds disclosed herein will be formulated for intranasal administration. In another embodiment, the compounds disclosed herein will be formulated for transdermal administration. In a further embodiment, the compounds disclosed herein will be formulated for topical administration.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable nonaqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The composition can also be prepared to prolong or sustain the release as for example by coating or embedding particulate material in polymers, wax or the like.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms. The compounds disclosed herein may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds disclosed herein may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The pharmaceutical compositions provided herein can be formulated as immediate or modified release dosage forms, including delayed-, sustained-, pulsed-, controlled-, targeted-, and programmed-release forms.

The pharmaceutical compositions provided herein can be co-formulated with other active ingredients which do not impair the desired therapeutic action, or with substances that supplement the desired action.

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, 3-cyclodextrin, hydroxypropyl-P-cyclodextrin, sulfobutylether-β-cyclodextrin, and sulfobutylether 7-P-cyclodextrin (CAPTISOL®, CyDex, Lenexa, Kans.).

The pharmaceutical compositions provided herein can be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate. Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In another aspect, the pharmaceutical compositions disclosed herein can be formulated in any dosage forms that are adapted for administration to a patient by inhalation, for example as a dry powder, an aerosol, a suspension, or a solution composition. In one embodiment, the pharmaceutical compositions disclosed herein can be formulated in a dosage form adapted for administration to a patient by inhalation as a dry powder. In a further embodiment, the pharmaceutical compositions disclosed herein can be formulated in a dosage form adapted for administration to a patient by inhalation via a nebulizer. Dry powder compositions for delivery to the lung by inhalation typically comprise the compounds disclosed herein as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

Aerosols may be formed by suspending or dissolving the compound disclosed herein in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising the compound disclosed herein will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 1986, 3(6), 318.

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound disclosed herein may be employed with either a paraffinic or a water-miscible ointment base. Alternatively, the compound disclosed herein may be formulated in a cream with an oil-in-water cream base or a water-in-oil base.

Use of the Compounds and Compositions of the Invention

The present invention provides a method of using a compound disclosed herein, or a pharmaceutical composition comprising the compound disclosed herein for the treatment, prevention, or amelioration of a disease or disorder that is mediated or otherwise affected via one or more protein kinases activity, such as JAK kinases (including JAK1, JAK2, JAK3 or TYK2 kinase), FLT3 kinase, and Aurora kinases (including Aurora-A, Aurora-B and Aurora-C) activity or one or more symptoms of diseases or disorders that are mediated or otherwise affected via one or more protein kinases activity, such as JAK kinases (including JAK1, JAK2, JAK3 or TYK2 kinase), FLT3 kinase and Aurora kinases (including Aurora-A, Aurora-B and Aurora-C kinase) activity.

FLT3 kinase can be wild type and/or mutant form of FLT3 kinase.

JAK kinases can be wild type and/or mutant form of JAK1, JAK2, JAK3 or TYK2 kinase.

In one embodiment, provided herein is a method of using a compound disclosed herein or a pharmaceutical composition comprising a compound disclosed herein for the treatment, prevention, or amelioration of a disease or disorder that is mediated or otherwise affected via inappropriate JAK1 kinase activity or one or more symptoms of diseases or disorders that are mediated or otherwise affected via inappropriate JAK1 kinase activity. In another embodiment, a disease, a disorder or one or more symptoms of diseases or disorders is related to the inappropriate activity of JAK2 kinase. In yet another embodiment, a disease, a disorder or one or more symptoms of diseases or disorders is related to the inappropriate activity of JAK3 kinase.

In one embodiment, provided herein is a method of using a compound disclosed herein or a pharmaceutical composition comprising a compound disclosed herein for the treatment, prevention, or amelioration of a disease or disorder that is mediated or otherwise affected via inappropriate FLT3 kinase activity or one or more symptoms of diseases or disorders that are mediated or otherwise affected via inappropriate FLT3 kinase activity.

In one embodiment, provided herein is a method of using a compound disclosed herein or a pharmaceutical composition comprising a compound disclosed herein for the treatment, prevention, or amelioration of a disease or disorder that is mediated or otherwise affected via inappropriate Aurora-A kinase activity or one or more symptoms of diseases or disorders that are mediated or otherwise affected via inappropriate Aurora-A kinase activity. In another embodiment, a disease, a disorder or one or more symptoms of diseases or disorders is related to the inappropriate activity of Aurora-B kinase. In yet another embodiment, a disease, a disorder or one or more symptoms of diseases or disorders is related to the inappropriate activity of Aurora-C kinase.

"Inappropriate JAK kinase activity" refers to any JAK kinase activity that deviates from the normal JAK kinase activity expected in a particular patient. Inappropriate JAK kinase may take the form of, for instance, an abnormal increase in activity, or an aberration in the timing and or control of JAK kinase activity. Such inappropriate activity may result then, for example, from overexpression or mutation of the protein kinase leading to inappropriate or uncontrolled activation. Accordingly, in another aspect the invention is directed to methods of treating such diseases and disorders.

Consistent with the description above, such diseases or disorders include without limitation: myeloproliferative disorders such as polycythemia vera (PCV), essential thrombocythemia and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as acute lymphocytic leukemia (ALL) and myeloma; cancer including head and neck cancer, prostate cancer, breast cancer, ovarian cancer, melanoma, lung cancer, brain tumor, pancreatic cancer and renal carcinoma; and allergic or inflammatory diseases or disorders related to immune dysfunction, immunodeficiency, immunomodulation, autoimmune diseases, transplantation rejection, graft-versus-host disease, wound healing, kidney disease, multiple sclerosis, thyroiditis, type 1 diabetes, sarcoidosis, psoriasis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD) and dry eye syndrome (or keratoconjunctivitis sicca (KCS)).

In one aspect, provided herein is the compound or the pharmaceutical composition disclosed herein for preventing and/or treating proliferative disease, autoimmune disease, allergic disease, inflammatory disease or transplantation rejection in mammals including humans.

In yet another aspect, provided herein is a method of treating a mammal having, or at risk of having a disease or disorder disclosed herein, said method comprising administering an effective condition-treating or condition-preventing amount of one or more of the pharmaceutical compositions or the compounds disclosed herein. In a particular aspect, provided here is a method of treating a mammal having, or at risk of having proliferative disease, autoimmune disease, allergic disease, inflammatory disease or transplantation rejection.

In additional method of treatment aspects, provided herein is a method of treatment and/or prophylaxis of a mammal susceptible to or afflicted with a proliferative disease, said methods comprising administering an effective condition-treating or condition-preventing amount of one or more of the pharmaceutical compositions or compounds disclosed herein. In a specific embodiment, the proliferative disease is selected from cancer (e.g. solid tumors such as uterine leiomyosarcoma or prostate cancer), polycythemia vera, essential thrombocytosis, myelofibrosis, leukemia (e.g. AML, CML, ALL or CLL), and multiple myeloma.

In another aspect, provided herein is the compound or the pharmaceutical composition disclosed herein for use in the treatment, and/or prophylaxis of a proliferative disease. In a specific embodiment, the proliferative disease is selected from cancer (e.g. solid tumors such as uterine leiomyosarcoma or prostate cancer), polycythemia vera, essential thrombocytosis, myelofibrosis, leukemia (e.g. AML, CML, ALL or CLL), and multiple myeloma.

In yet another aspect, provided herein is the use of the compound or the pharmaceutical composition disclosed herein for use in the manufacture of a medicament for the treatment, and/or prophylaxis of a proliferative disease. In a specific embodiment, the proliferative disease is selected from cancer (e.g. solid tumors such as uterine leiomyosarcoma or prostate cancer), polycythemia vera, essential thrombocytosis, myelofibrosis, leukemia (e.g. AML, CML, ALL or CLL), and multiple myeloma.

In another aspect, provided herein is a method of treatment and/or prophylaxis of a mammal susceptible to or afflicted with an autoimmune disease. The methods comprise administering an effective condition-treating or condition-preventing amount of one or more of the pharmaceutical compositions or compounds disclosed herein. In a specific embodiment, the autoimmune disease is selected from COPD, asthma, systemic and cutaneous lupus erythematosis, lupus nephritis, dermatomyositis, Sjogren's syndrome, psoriasis and type I diabetes mellitus.

In another aspect, provided herein is the compound or the pharmaceutical composition disclosed herein for use in the treatment, and/or prophylaxis of an autoimmune disease. In a specific embodiment, the autoimmune disease is selected from COPD, asthma, systemic and cutaneous lupus erythematosis, lupus nephritis, dermatomyositis, Sjogren's syndrome, psoriasis and type I diabetes mellitus.

In yet another aspect, provided here is the use of the compound or the pharmaceutical composition disclosed herein in the manufacture of a medicament for the treatment, and/or prophylaxis of an autoimmune disease. In a specific embodiment, the autoimmune disease is selected from COPD, asthma, systemic and cutaneous lupus erythematosis, lupus nephritis, dermatomyositis, Sjogren's syndrome, psoriasis and type I diabetes mellitus.

In a method of treatment aspects, provided herein are methods of treatment and/or prophylaxis of a mammal susceptible to or afflicted with an allergic disease. The methods comprising administering an effective condition-treating or condition-preventing amount of one or more of the pharmaceutical compositions or the compounds disclosed herein. In a specific embodiment, the allergic disease is selected from allergic airway disease, sinusitis, eczema and hives, food allergies and allergies to insect venom.

In another aspect, provided herein is the compound or the pharmaceutical composition disclosed herein for use in the treatment, and/or prophylaxis of an allergic disease. In a specific embodiment, the allergic disease is selected from allergic airway disease, sinusitis, eczema and hives, food allergies and allergies to insect venom.

In yet another aspect, provided herein is the use of the compound or the pharmaceutical composition disclosed herein in the manufacture of a medicament for the treatment, or prophylaxis of an allergic disease. In a specific embodiment, the allergic disease is selected from allergic airway disease, sinusitis, eczema and hives, food allergies and allergies to insect venom.

In another aspect, provided herein are methods of treatment and/or prophylaxis of a mammal susceptible to or afflicted with an inflammatory disease. The methods comprise administering an effective condition-treating or condition-preventing amount of one or more of the pharmaceutical compositions or the compounds disclosed herein. In a specific embodiment, the inflammatory disease is selected from inflammatory bowel syndrome, Crohn's disease, rheumatoid arthritis, juvenile arthritis and psoriatic arthritis.

In another aspect, provided herein is the compound or the pharmaceutical composition disclosed herein for use in the treatment, and/or prophylaxis of an inflammatory disease. In a specific embodiment, the inflammatory disease is selected from inflammatory bowel syndrome, Crohn's disease, rheumatoid arthritis, juvenile arthritis and psoriatic arthritis.

In yet another aspect, provided herein is the use of the compound or the pharmaceutical composition disclosed herein in the manufacture of a medicament for the treatment, and/or prophylaxis of an inflammatory disease. In a specific embodiment, the inflammatory disease is selected from inflammatory bowel syndrome, Crohn's disease, rheumatoid arthritis, juvenile arthritis and psoriatic arthritis.

In another aspect, provided herein are methods of treatment and/or prophylaxis of a mammal susceptible to or afflicted with transplantation rejection. The methods comprising administering an effective condition-treating or condition-preventing amount of one or more of the pharmaceutical compositions or the compound of the invention herein described. In a specific embodiment, the transplantation rejection is organ transplant rejection, tissue transplant rejection and cell transplant rejection.

In another aspect, provided herein is the compound or the pharmaceutical composition disclosed herein for use in the treatment, and/or prophylaxis of transplantation rejection. In a specific embodiment, the transplantation rejection is organ transplant rejection, tissue transplant rejection and cell transplant rejection.

In yet another aspect, provided herein is the use of the compound or the pharmaceutical composition disclosed herein for use in the manufacture of a medicament for the treatment and/or prophylaxis of transplantation rejection. In a specific embodiment, the transplantation rejection is organ transplant rejection, tissue transplant rejection and cell transplant rejection.

The present invention provides the compound or the pharmaceutical composition disclosed herein for use as a pharmaceutical especially in the treatment and/or prophylaxis of the aforementioned diseases or disorders. Also provided herein is the use of the compound or the pharmaceutical composition disclosed herein in the manufacture of a medicament for the treatment and/or prophylaxis of one of the aforementioned diseases or disorders.

A particular regimen of the present method comprises the administration to a subject suffering from a disease involving inflammation, of an effective amount of a compound disclosed herein for a period of time sufficient to reduce the level of inflammation in the subject, and preferably terminate the processes responsible for said inflammation. A special embodiment of the method comprises administering of an effective amount of a compound disclosed herein to a subject patient suffering from or susceptible to the development of rheumatoid arthritis, for a period of time sufficient to reduce or prevent, respectively, inflammation in the joints of said patient, and preferably terminate, the processes responsible for said inflammation.

A further particular regimen of the present method comprises the administration to a subject suffering from a disease involving proliferative disease, of an effective amount of a compound disclosed herein for a period of time sufficient to reduce the level of proliferative disease in the subject, and preferably terminate the processes responsible for said proliferative disease. A particular embodiment of the method comprises administering of an effective amount of a compound disclosed herein to a subject patient suffering from or susceptible to the development of cancer, for a period of time sufficient to reduce or prevent, respectively, solid tumor of said patient, and preferably terminate, the processes responsible for said solid.

Combination Therapy

A compound disclosed herein can be administered as the sole active agent or it can be administered in combination with other therapeutic agents, including other compounds that demonstrate the same or a similar therapeutic activity and that are determined to be safe and efficacious for such combined administration.

In one aspect, provided herein is a method of treating, preventing, managing, or ameliorating a disease or disorder comprising administering a safe and effective amount of a combination comprising the compound disclosed herein together with one or more therapeutically active agents. In one embodiment, the combinations comprising one or two other therapeutic agents.

Example of other therapeutic agents may include without limitation anti-cancer agents, including chemotherapeutic agents and antiproliferative agents; anti-inflammatory agents and immunomodulatory agents or immunosuppressive agents.

In another aspect, provided herein is a product comprising a compound disclosed herein and at least one other therapeutic agent as a combined preparation for simultaneous, separate or sequential use in therapy. In one embodiment, the therapy is the treatment of a disease or disorder mediated by the activity of one or more protein kinases activity, such as JAK kinases, FLT3 kinase and Aurora kinases. Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In another aspect, provided herein is a pharmaceutical composition comprising a compound disclosed herein and another therapeutic agent(s). In one embodiment, the pharmaceutical composition may comprise a pharmaceutically acceptable excipient, carrier, adjuvant or vehicle as described above.

In another aspect, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The invention also provides the use of a compound disclosed herein for treating a disease or condition mediated by the activity of one or more protein kinases, such as JAK kinases, FLT3 kinase and Aurora kinases, wherein the patient has previously (e.g. within 24 hours) been treated with another therapeutic agent. The invention also provides the use of another therapeutic agent for treating a disease or condition mediated by the activity of one or more protein kinases, such as JAK kinases, FLT3 kinase and Aurora kinases, wherein the patient has previously (e.g. within 24 hours) been treated with a compound disclosed herein.

The compounds disclosed herein may be administered as the sole active ingredient or in conjunction with, e.g. as an adjuvant to, other therapeutic agent.

In one embodiment, other therapeutic agent refers to chemotherapeutic agents or antiproliferative agents. Some non-limiting examples of known chemotherapeutic agents include other therapies or anticancer agents that may be used in combination with the inventive anticancer agents of the present invention and include surgery, radiotherapy (in but a few examples, gamma radiation, neutron beam radiotherapy, electron beam radiotherapy, proton therapy, brachytherapy, and systemic radioactive isotopes, to name a few), endocrine therapy, taxanes (taxol, taxotere etc), platinum derivatives (cisplatin, carboplatin), biologic response modifiers (interferons, interleukins), tumor necrosis factor (TNF, TRAIL receptor targeting agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, ifosfamide), antimetabolites (methotrexate, pemetrexed etc), purine antagonists and pyrimidine antagonists (6-mercaptopurine, 5-fluorouracil, cytarabile, gemcitabine), spindle poisons (vinblastine, vincristine, vinorelbine), podophyllotoxins (etoposide, irinotecan, topotecan), antibiotics (doxorubicin, bleomycin, mitomycin), nitrosoureas (carmustine, lomustine), cell cycle inhibitors (KSP mitotic kinesin inhibitors, CENP-E and CDK inhibitors), enzymes (asparaginase), hormones (tamoxifen, leuprolide, flutamide, megestrol, dexamethasone), antiangiogenic agents (avastin and others), monoclonal antibodies (BENLYSTA®), brentuximab (ADCETRIS®), cetuximab (ERBITUX®), gemtuzumab (MYLOTARG®), ipilimumab (YERVOY®), ofatumumab (ARZERRA®), panitumumab (VECTIBIX®), ranibizumab (LUCERTIS®), rituximab (RITUXAN®), tositumomab (BEXXAR®), trastuzumab (HERCEPTIN®)), kinase inhibitors (imatinib (GLEEVEC®), sunitinib (SUTENT®), sorafenib (NEXAVAR®), erlotinib, (TARCEVA®), gefitinib (IRESSA®), dasatinib (SPRYCEL®), nilotinib (TASIGNA®), lapatinib (TYKERB®), crizotinib (XALKORI®), ruxolitinib (JAKAFI®), vemurafenib (ZELBORAF®), vandetanib (CAPRELSA®), pazopanib (VOTRIENT®), and others), and agents inhibiting or activating cancer pathways such as the mTOR, HIF (hypoxia induced factor) pathways (such as everolimus and temsirolimus) and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, all of which are herein incorporated by reference in their entireties. In another embodiment, the compounds of the present invention can be combined, with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine and vindesine. Other cytotoxic drugs suitable for use with the compounds of the invention include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2,2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds of the invention also include newly discovered cytotoxic principles such as oxaliplatin, vemurafenib, capecitabine, epothilone and its natural or synthetic derivatives, temozolomide (Quinn et al., *J. Clin. Oncol.*, 2003, 21(4), 646-651), tositumomab (BEXXAR®), trabedectin (Vidal et al., Proceedings of the American Society for Clinical Oncology, 2004, 23, abstract 3181), and the inhibitors of the kinesin spindle protein Eg5 (Wood et al., *Curr. Opin. Pharmacol.*, 2001, 1, 370-377).

In another embodiment, the compounds of the present invention can be combined with other signal transduction inhibitors. EGFR family as one of the target signal transduction inhibitors, such as EGFR, HER-2 and HER-4 (Raymond et al., *Drugs*, 2000, 60 (Suppl.1), 15-23; Harari et al., *Oncogene*, 2000, 19 (53), 6102-6114) and ligands thereof. Examples of such therapies also include, by no way of limitation, small-molecule kinase inhibitors such as imatinib (GLEEVEC®), sunitinib (SUTENT®), sorafenib (NEXAVAR®), erlotinib (TARCEVA®), gefitinib (IRESSA®), dasatinib (SPRYCEL®), nilotinib (TASIGNA®), lapatinib (TYKERB®), crizotinib (XALKORI®), ruxolitinib (JAKAFI®), vemurafenib (ZELBORAF®), vandetanib (CAPRELSA®), pazopanib (VOTRIENT®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TKI258, GDC-0941 (Folkes et al. *J. Med. Chem.* 2008, 51: 5522), BZE235, and others.

In one embodiment, the compounds disclosed herein may be administered in conjunction with, e.g. as an adjuvant to, other drugs e.g. immunosuppressive or immunomodulating agents or other anti-inflammatory agents, e.g. for the treatment or prevention of alio- or xenograft acute or chronic rejection or inflammatory or autoimmune disorders, or a chemotherapeutic agent, e.g a malignant cell anti-proliferative agent. For example, the compounds disclosed herein may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, TAFA-93, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4lg (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

Where the compounds disclosed herein are administered in conjunction with other immunosuppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth.

In one aspect, provided herein is a combination comprising a compound disclosed herein together with a $\beta_2$-adrenoreceptor agonist. Examples of $\beta_2$-adrenoreceptor agonists include salmeterol, salbutamol, formoterol, salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 h or longer, are preferred.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

In another aspect, provided herein is a combination comprising a compound disclosed herein together with corticosteroids. Suitable corticosteroids refer to those oral and inhaled corticosteroids and their pro-drugs which have anti-inflammatory activity. Examples include methyl prednisolone, prednisolone, dexamethasone, fluticasone propionate, 6α, 9α-difluoro-11p3-hydroxy-16α-methyl-17α-[(4-methyl-1,3-thiazole-5-carbonyl)oxy]-3-oxo-androsta-1,4-diene-17β-carbothioic acid S-fluoromethyl ester, 6α, 9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-ethycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(cis)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methyl cyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanyl carbonyl)oxy]-11β-hydroxy-16α-methyl-3-oxo-androsta-1,4-diene-17β-carbothioic acid S-fluoromethyl ester.

In another aspect, provided herein is a combination comprising a compound disclosed herein together with non-steroidal GR agonist. Non-steroidal compounds having glucocorticoid agonism that may possess selectivity for transrepression over transactivation and that may be useful in combination therapy include those covered in the following patents: WO 03/082827, WO 98/54159, WO 04/005229, WO 04/009017, WO 04/018429, WO 03/104195, WO 03/082787, WO 03/082280, WO 03/059899, WO 03/101932, WO 02/02565, WO 01/16128, WO 00/66590, WO 03/086294, WO 04/026248, WO 03/061651 and WO 03/08277. Further non-steroidal compounds are covered in: WO 2006/000401, WO 2006/000398 and WO 2006/015870.

In another aspect, provided herein is a combination comprising a compound disclosed herein together with non-steroidal anti-inflammatory drugs (NSAID's). Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO 93/13055, WO 98/30537, WO 02/50021, WO 95/34534 and WO 99/62875. Examples of CCR3 inhibitors include those disclosed in WO 02/26722.

In one embodiment, the invention provides the use of the compounds disclosed herein in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4. Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

In another aspect, provided herein is a combination comprising a compound disclosed herein together with an anticholinergic agent. Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name ATROVENT®), oxitropium (for example, as the bromide, CAS 30286-75-0) and tiotropium (for example, as the bromide, CAS 136310-93-5, sold under the name SPIRIVA®). Also of interest are revatropate (for example, as the hydrobromide, CAS 262586-79-8) and LAS-34273 which is disclosed in WO 01/04118. Exemplary compounds for oral administration include pirenzepine (CAS 28797-61-7), darifenacin (CAS 133099-04-4, or CAS 133099-07-7 for the hydrobromide sold under the name ENABLEX®), oxybutynin (CAS 5633-20-5, sold under the name DITROPAN®), terodiline (CAS 15793-40-5), tolterodine (CAS 124937-51-5, or CAS 124937-52-6 for the tartrate, sold under the name DETROL®), otilonium (for example, as the bromide, CAS 26095-59-0, sold under the name SPASMOMEN®), trospium chloride (CAS 10405-02-4) and solifenacin (CAS 242478-37-1, or CAS 242478-38-2 for the succinate also known as YM-905 and sold under the name VESICARE®).

In another aspect, provided herein is a combination comprising a compound disclosed herein together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound disclosed herein together with an H3 antagonist (and/or inverse agonist). Examples of H3 antagonists include, for example, those compounds disclosed in WO 2004/035556 and in WO 2006/045416. Other histamine receptor antagonists which may be used in combination with the compounds disclosed herein include antagonists (and/or inverse agonists) of the H4 receptor, for example, the compounds disclosed in Jablonowski et al., *J. Med. Chem.*, 2003, 46:3957-3960.

In still another aspect, provided herein is a combination comprising a compound disclosed herein together with a PDE4 inhibitor and a $\beta_2$-adrenoreceptor agonist.

In yet another aspect, provided herein is a combination comprising a compound disclosed herein together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable excipient or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound disclosed herein together with another therapeutically active agent.

In one embodiment, the pharmaceutical composition comprises a combination of a compound disclosed herein together with a chemotherapeutic agents.

In one embodiment, the pharmaceutical composition comprises a combination of a compound disclosed herein together with an anti-proliferative agents.

In one embodiment, the pharmaceutical composition comprises a combination of a compound disclosed herein together with a PDE4 inhibitor.

In another embodiment, the pharmaceutical composition comprises a combination of a compound disclosed herein together with a $\beta_2$-adrenoreceptor agonist.

In another embodiment, the pharmaceutical composition comprises a combination of a compound disclosed herein together with a corticosteroid.

In another embodiment, the pharmaceutical composition comprises a combination of a compound disclosed herein together with a non-steroidal GR agonist.

In another embodiment, the pharmaceutical composition comprises a combination of a compound disclosed herein together with an anticholinergic agent.

In still another embodiment, the pharmaceutical composition comprises a combination of a compound disclosed herein together with an antihistamine.

In another embodiment, the pharmaceutical composition comprises a combination of a compound disclosed herein together with an anti-inflammatory agents.

In another embodiment, the pharmaceutical composition comprises a combination of a compound disclosed herein together with an immunomodulators.

In another embodiment, the pharmaceutical composition comprises a combination of a compound disclosed herein together with an agents for treating atherosclerosis In another embodiment, the pharmaceutical composition comprises a combination of a compound disclosed herein together with an agents for treating pulmonary fibrosis.

In the field of medical oncology it is normal practice to use a combination of different forms of treatment to treat each patient with cancer. In medical oncology the other component(s) of such conjoint treatment in addition to compositions disclosed herein may be, for example, surgery, radiotherapy, chemotherapy, signal transduction inhibitors or modulators (e.g. kinase inhibitors or modulators) and/or monoclonal antibodies.

A compound disclosed herein may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds that induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; antiandrogens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, nonsteroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN®. Formestane can be administered, e.g., in the form as it is marketed, e.g., under the trademark LENTARON®. Fadrozole can be administered, e.g., in the form as it is marketed, e.g., under the trademark AFEMA®. Anastrozole can be administered, e.g., in the form as it is marketed, e.g., under the trademark ARIMIDEX®. Letrozole can be administered, e.g., in the form as it is marketed, e.g., under the trademark FEMARA® or FEMAR®. Aminoglutethimide can be administered, e.g., in the form as it is marketed, e.g., under the trademark ORIMETEN®. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX®. Raloxifene hydrochloride can be administered, e.g., in the form as it is marketed, e.g., under the trademark EVISTA®. Fulvestrant can be formulated as disclosed in U.S. Pat. No. 4,659,516 or it can be administered, e.g., in the form as it is marketed, e.g., under the trademark FASLODEX®. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX®), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR®. Topotecan can be administered, e.g., in the form as it is marketed, e.g., under the trademark HYCAMTIN®.

The term "topoisomerase II inhibitor", as used herein, includes, but is not limited to, the anthracyclines, such as doxorubicin, including liposomal formulation, e.g., CAELYX; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS®. Teniposide can be administered, e.g., in the form as it is marketed, e.g., under the trademark VM 26-BRISTOL®. Doxorubicin can be administered, e.g., in the form as it is marketed, e.g., under the trademark ADRIBLASTIN® or ADRIAMYCIN®.

Epirubicin can be administered, e.g., in the form as it is marketed, e.g., under the trademark FARMORUBICIN®. Idarubicin can be administered, e.g., in the form as it is marketed, e.g., under the trademark ZAVEDOS®. Mitoxantrone can be administered, e.g., in the form as it is marketed, e.g., under the trademark NOVANTRON®.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL. Docetaxel can be administered, e.g., in the form as it is marketed, e.g., under the trademark TAXOTERE®. Vinblastine sulfate can be administered, e.g., in the form as it is marketed, e.g., under the trademark VINBLASTIN R.P®. Vincristine sulfate can be administered, e.g., in the form as it is marketed, e.g., under the trademark FARMISTIN®. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN®. Ifosfamide can be administered, e.g., in the form as it is marketed, e.g., under the trademark HOLOXAN®.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA®. Gemcitabine can be administered, e.g., in the form as it is marketed, e.g., under the trademark GEMZAR®. Also included is the monoclonal antibody trastuzumab which can be administered, e.g., in the form as it is marketed, e.g., under the trademark HERCEPTIN®.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT®. Oxaliplatin can be administered, e.g., in the form as it is marketed, e.g., under the trademark ELOXATIN®.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;
b) compounds targeting, decreasing or inhibiting the activity of the fibroblast growth factor-receptors (FGFR);
c) compounds targeting, decreasing or inhibiting the activity of the insulin-like growth factor receptor I (IGF-IR), such as compounds which target, decrease or inhibit the activity of IGF-IR, especially compounds which inhibit the IGF-IR receptor, such as those compounds disclosed in WO 02/092599;
d) compounds targeting, decreasing or inhibiting the activity of the Trk receptor tyrosine kinase family;
e) compounds targeting, decreasing or inhibiting the activity of the Axl receptor tyrosine kinase family;
f) compounds targeting, decreasing or inhibiting the activity of the c-Met receptor;
g) compounds targeting, decreasing or inhibiting the activity of the Kit/SCFR receptor tyrosine kinase;
h) compounds targeting, decreasing or inhibiting the activity of the c-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;
i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;
j) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; llmofosine; RO 318220 and RO 320432; GO 6976; Isis 3521; LY333531/LY379196; isochinoline compounds, such as those disclosed in WO 00/09495; FTIs; PD184352; or QAN697 (a PI3K inhibitor);
k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC®) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG957 and adaphostin (4-{[(2,5-dihydroxyphenyl)methyl]amino}-benzoic acid adamantyl ester, NSC 680410, adaphostin; and 1) compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0564409; WO 99/03854; EP 0520722; EP 0566226; EP 0787722; EP 0837063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d]pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID®) and TNP-470.

Compounds which target, decrease or inhibit the activity of a protein or lipid phosphatase are, e.g., inhibitors of phosphatase 1, phosphatase 2A, PTEN or $CDC_{25}$, e.g., okadaic acid or a derivative thereof.

Compounds that induce cell differentiation processes are e.g. retinoic acid, α-, γ- or δ-tocopherol or α-, γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX®), rofecoxib (VIOXX®), etoricoxib, valdecoxib or a 5-alkyl-2-arylaminophenylacetic acid, e.g., 5-methyl-2-(2'-chloro-6'-fluoroanilino)phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL®. "Clodronic acid" can be administered, e.g., in the form as it is marketed, e.g., under the trademark BONEFOS®. "Tiludronic acid" can be administered, e.g., in the form as it is marketed, e.g., under the trademark SKELID®. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX®. "Ibandronic acid" can be administered, e.g., in the form as it is marketed, e.g., under the trademark BONDRANAT®. "Risedronic acid" can be administered, e.g., in the form as it is marketed, e.g., under the trademark ACTONEL. "Zoledronic acid" can be administered, e.g., in the form as it is marketed, e.g., under the trademark ZOMETA®.

The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88. The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R1 15777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI1270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU1 1248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (HERCEPTIN™), Trastuzumab-$DM_1$, erlotinib (TARCEVA™), bevacizumab (AVASTIN™), rituximab (RITUXAN®), PR064553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity. For the treatment of acute myeloid leukemia (AML), compounds disclosed herein can be used in combination with standard leukemia therapies, especially in combination with therapies used for the treatment of AML. In particular, compounds disclosed herein can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

A compound disclosed herein may also be used to advantage in combination with each other or in combination with other therapeutic agents, especially other anti-malarial agents. Such anti-malarial agents include, but are not limited to proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, inhaled NO, L-arginine, Dipropylenetri-amine NONOate (NO donor), Rosiglitzone (PPAR-γ agonist), activated charcoal, Erythropoietin, Levamisole, and pyronaridine.

A compound disclosed herein may also be used to advantage in combination with each other or in combination with other therapeutic agents, such as used for the treatment of Leishmaniosis, Trypanosomiasis, Toxoplasmosis and Neurocysticercosis. Such agents include, but are not limited to chloroquine sulfate, atovaquone-proguanil, artemether-lumefantrine, quinine-sulfate, artesunate, quinine, doxycycline, clindamycin, meglumine antimoniate, sodium stibogluconate, miltefosine, ketoconazole, pentamidine, amphotericin B (AmB), liposomal-AmB, paromomycine, eflornithine, nifurtimox, suramin, melarsoprol, prednisolone, benznidazole, sulfadiazine, pyrimethamine, clindamycin, trimetropim, sulfamethoxazole, azitromycin, atovaquone, dexamethasone, praziquantel, albendazole, beta-lactams, fluoroquinolones, macrolides, aminoglycosides, sulfadiazine and pyrimethamine.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound disclosed herein, can be prepared and administered as described in the art, such as in the documents cited above.

A compound disclosed herein may also be used to advantage in combination with known therapeutic processes, e.g., the administration of hormones or especially radiation. A compound disclosed herein may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound disclosed herein and a combination partner may be administered independently at the same time or separately within time intervals that especially allow that the combination partners show a cooperative, e.g., synergistic, effect or any combination thereof. The terms "coadministration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound disclosed herein and a combination partner, are both administered to a patient simultaneously in the form of a single entity or dosage. The term "non-fixed combination" means that the active ingredients, e.g. a compound disclosed herein and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Methods of Treatment

In one embodiment, the methods of treatment disclosed herein comprise administering a safe and effective amount of a compound or a pharmaceutically composition disclosed herein to a patient in need thereof. Individual embodiments disclosed herein include methods of treating any one of the above-mentioned disorders by administering a safe and effective amount of a compound disclosed herein or a pharmaceutical composition containing a compound disclosed herein to a patient in need thereof.

In one embodiment, the compounds disclosed herein or pharmaceutically compositions containing the compounds disclosed herein may be administered by any suitable route of administration, including both systemic administration and topical administration. Systemic administration includes oral administration, parenteral administration, transdermal administration and rectal administration. Parenteral administration is typically by injection or infusion, including intravenous, intramuscular, and subcutaneous injection or infusion. Topical administration includes application to the skin as well as intraocular, otic, intravaginal, inhaled and intranasal administration. In one embodiment, the compounds disclosed herein or pharmaceutical compositions containing the compounds disclosed herein may be administered orally. In another embodiment, the compounds disclosed herein or pharmaceutically compositions containing the compounds disclosed herein may be administered by inhalation. In a further embodiment, the compounds disclosed herein or pharmaceutical compositions containing the compounds disclosed herein may be administered intranasally.

In another embodiment, the compounds disclosed herein or pharmaceutically compositions containing the compounds disclosed herein may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound disclosed herein or a pharmaceutical composition containing a compound disclosed herein depend on the pharmacokinetic properties of that compound, such as absorption, distribution, and half-life, which can be determined by the skilled artisan. In addition, suitable dosing regimens, including the duration such regimens are administered, for a compound disclosed herein or a pharmaceutical composition containing a compound disclosed herein depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compound of the present invention may be administered either simultaneously with, or before or after, one or more other therapeutic agent. The compound of the present invention may be administered separately, by the same or different route of administration, or together in the same pharmaceutical composition as the other agents.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Additionally, the compounds disclosed herein may be administered as prodrugs. As used herein, a "prodrug" of a compound disclosed herein is a functional derivative of the compound which, upon administration to a patient, eventually liberates the compound disclosed herein in vivo. Administration of a compound disclosed herein as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for Formula (I) and Formula (II), above, except where further noted. The following non-limiting schemes and examples are presented to further exemplify the invention. Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded with a Bruker 400 MHz or 600 MHz spectrometer at ambient temperature. $^1$H NMR spectra were obtained as $CDCl_3$, DMSO-$d_6$, $CD_3OD$ or acetone-$d_6$ solutions (reported in ppm), using TMS (0 ppm) or chloroform (7.26 ppm) as the reference standard. When peak multiplicities are reported, the following abbreviations are used: s (singlet), d (doublet), t (triplet), m (multiplet), br (broadened), dd (doublet of doublets), dt (doublet of triplets), td (triplet of doublets). Coupling constants J, when given, are reported in Hertz (Hz).

Low-resolution mass spectral (MS) data were generally determined on an Agilent 6120 quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210/254 nm and electrospray ionization (ESI).

Purities of compounds were assessed by Agilent 1260 pre-HPLC or Calesep pump 250 pre-HPLC (column: NOVASEP 50/80 mm DAC) with UV detection at 210 nm and 254 nm.

The following abbreviations are used throughout the specification:
AcOH, HAc, $CH_3COOH$ acetic acid
$Ac_2O$ acetic anhydride
BnBr benzyl bromide
BOC, Boc butyloxycarbony
$(Boc)_2O$ di-tert-butyl dicarbonate
$BH_3$-DMS borane-methyl sulfide complex
BINAP 2,2'-bis(diphenylphosphino)-1,1'-binaphthyl
n-BuOH n-butyl alcohol
$Cs_2CO_3$ cesium carbonate
$CH_2Cl_2$, DCM methylene chloride
$CDCl_3$ chloroform deuterated
$CH_3I$ iodomethane
DIEA, DIPEA, i-$Pr_2NEt$ N,N-diisopropylethylamine
DMF dimethylformamide
DMP dimethyl phthalate
DMAP 4-dimethylaminopyridine, N,N-dimethylpyridin-4-amine
DMSO dimethylsulfoxide
DHP dihydropyran
DIAD diisopropyl azodicarboxylate
PPTs pyridinium toluene-4-sulphonate
$Et_3N$, TEA triethylamine
EtOAc, EA ethyl acetate
EtOH ethanol
$Et_2O$ diethyl ether
EDCI N-(3-dimethylaminopropyl)-N'-ethylcarbodiimide hydrochloride
g gram
h hour
HATU 2-(7-aza-1H-benzotriazole-1-yl)-1,1,3,3-tetramethyluronium hexafluorophosphate
HCl hydrochloric acid
HOAT 1-hydroxy-7-azabenzotriazole
KOH potassium hydroxide
$KMnO_4$ potassium permanganate
$K_2CO_3$ potassium carbonate
LiCl lithium chloride
LiHMDS, LHMDS lithium bis(trimethylsilyl)amide
LAH lithium aluminium hydride
MeCN, $CH_3CN$ acetonitrile
MsCl methanesulfonyl chloride
$(NH_4)_2SO_4$ ammonium sulfate
$NH_4Cl$ ammonium chloride
NaH sodium hydride
$NaBH_3CN$ sodium cyanoborohydride
$Na_2CO_3$ sodium carbonate
$NaHCO_3$ sodium bicarbonate
NaOH sodium hydroxide
$Na_2SO_4$ sodium sulfate
$Na_2S_2O_3$ sodium thiosulfate
NaOAc ammonium acetate
NBS bromosuccinimide MeOH methanol
mCPBA 3-chlorobenzenecarboperoxoic acid
mL, ml milliliter
Pd/C palladium on carbon
PTSA p-toluenesulfonic acid
PE petroleum ether (60-90° C.)
PDC pyridinium dichromate
RT, rt, r.t. room temperature
PTSA p-toluenesulfonamide
Pd(OAc)$_2$ palladium diacetate
Pd/C palladium on activated carbon
PCl$_5$ phosphorus pentachloride
PDC pyridinium dichromate
Rt retention time
THF tetrahydrofuran
TBAF tetrabutylammonium fluoride
TFAA trifluoroacetic anhydride
TFA, CF$_3$COOH trifluoroacetic acid
Ti(Oi-Pr)$_4$ titanium tetraisopropanolate
TsCl tosyl chloride Representative synthetic procedures for the preparation of the compounds disclosed herein is outlined below in following Scheme 1 to Scheme 5. Unless otherwise indicated, each of Z, Z$^1$, W, W$_1$, A, R$^1$, R$^2$, R$^3$, R$^{3a}$, R$^4$, R$^{4a}$, R$^5$, R$^{5a}$, R$^6$, R$^{6a}$, R$^7$, R$^{7a}$, R$^8$, R$^{8a}$, R$^{12}$, R$^{13}$, R$^{14}$, n and m carry the definitions set forth above in connection with Formula (I) and Formula (II); p is 0, 1, 2, 3, or 4; q is 0, 1, 2 or 3; PG is a protecting group; each R$^{ss}$ is independently R$^3$, R$^{3a}$, R$^4$, R$^{4a}$, R$^5$, R$^{5a}$, R$^6$, R$^{6a}$, R$^7$, R$^{7a}$, R$^8$ or R$^{8a}$.

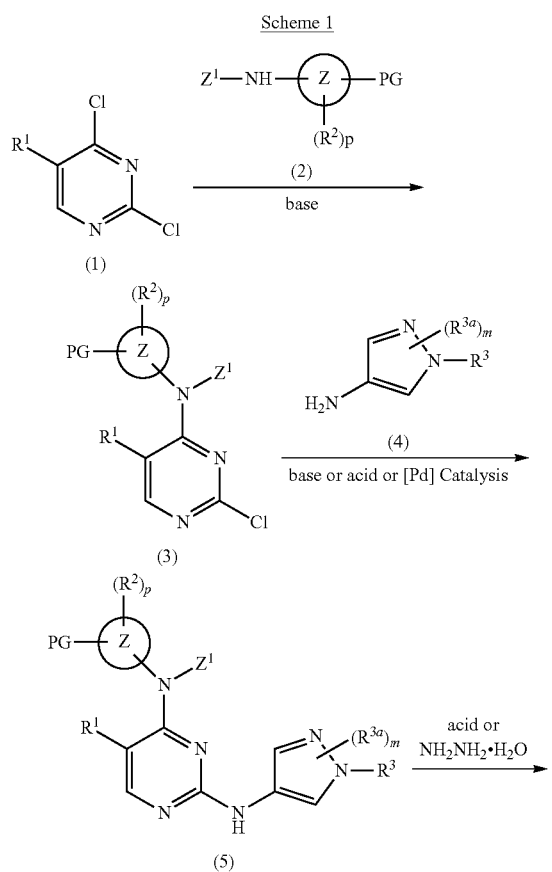

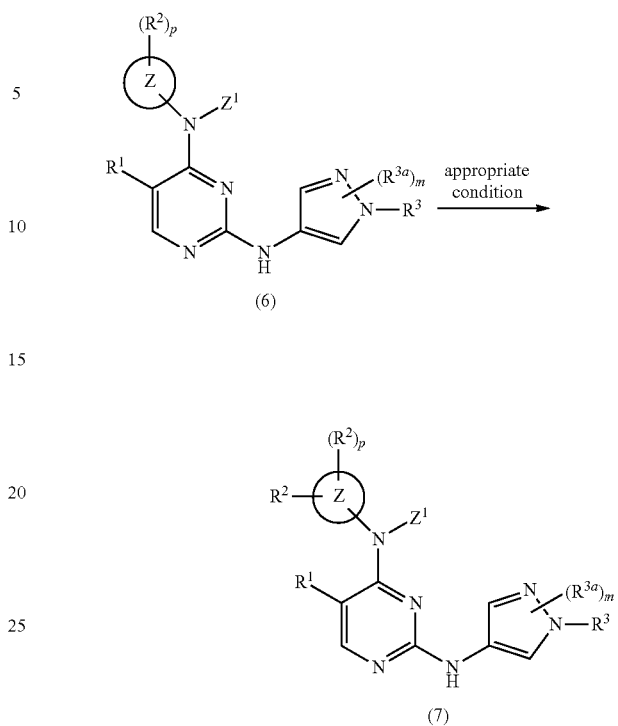

Some compounds having Formula (6) or Formula (2) can be prepared by a general method illustrated in Scheme 1 and described in details in the Examples. As showing in Scheme 1, substituted dichloropyrimidine compound (1) is reacted with optionally substituted heterocyclic compound (2) with an aid of a base, such as Et$_3$N, DIPEA or Cs$_2$CO$_3$ to give optionally substituted heteroaryl compound (3). Compound (3) is then coupled with optionally substituted aminopyrazole (4) or a hydrochloride thereof in the presence of a base, such as DIPEA, Et$_3$N, or in the presence of an acid, such as trifluoroacetic acid, a solution of HCl in EtOAc, or in the presence of a suitable Pd catalyst, such as Pd(OAc)$_2$, to afford the compound (5). The protecting group of compound (5) is removed under acidic conditions, such as trifluoroacetic acid, a solution of HCl in EtOAc, or with an aid of hydrazine hydrate, or any other appropriate condition, such as with the aid of TBAF to give the desired protein kinase inhibitor (6). Other protein kinase inhibitor having Formula (2) is obtained by introducing various substituents to the compound (6) under appropriate conditions.

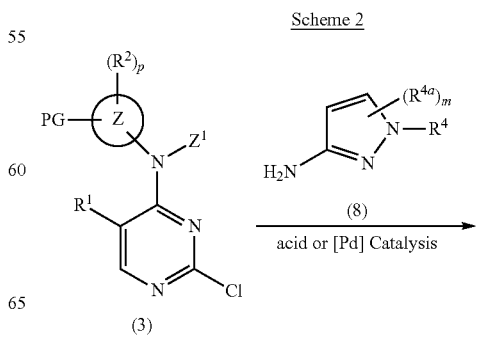

-continued

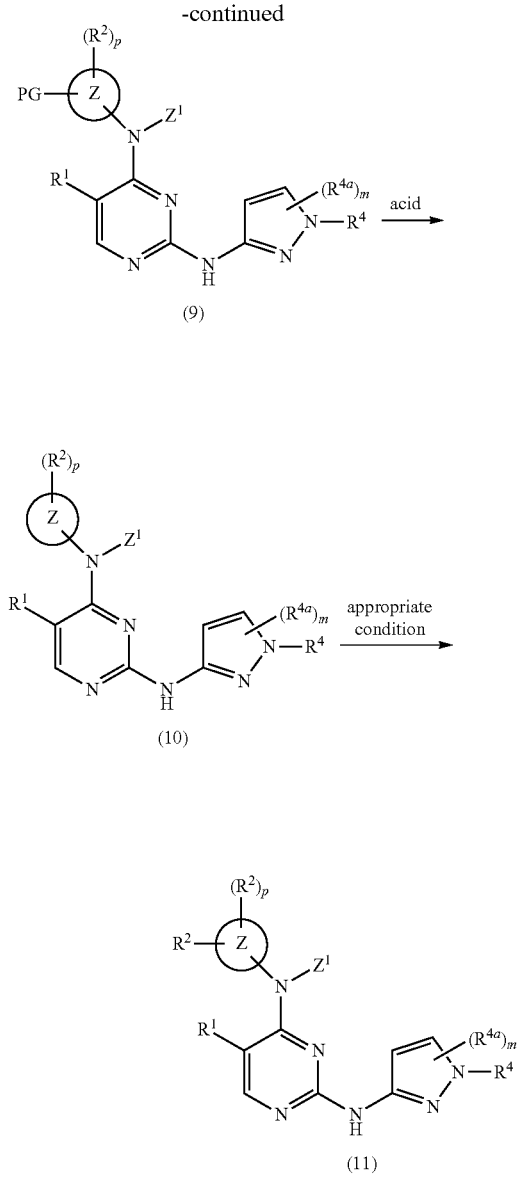

Scheme 3

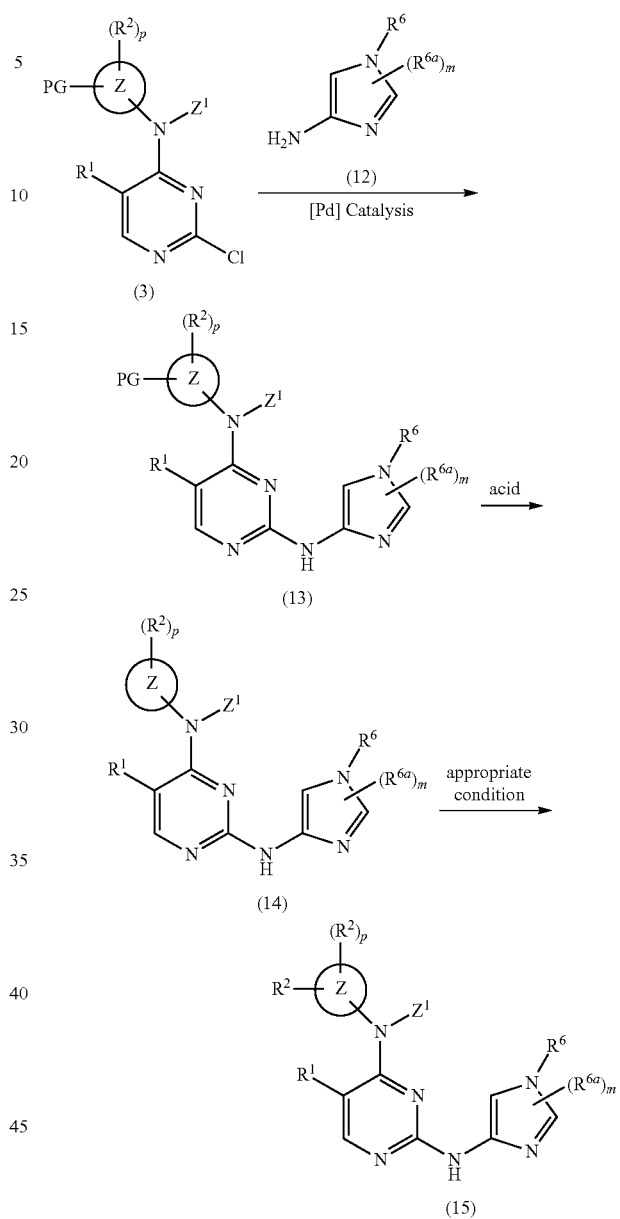

Some compounds having Formula (10) or Formula (11) can be prepared by a general method illustrated in Scheme 2 and described in details in the Examples. As showing in Scheme 2, Compound (3) is coupled with optionally substituted aminopyrazole (8) or a hydrochloride thereof in the presence of a base, such as DIPEA, Et$_3$N, Cs$_2$CO$_3$ or in the presence of an acid, such as trifluoroacetic acid, a solution of HCl in EtOAc, or in the presence of a suitable Pd catalyst, such as Pd(OAc)$_2$, to afford the compound (9). The protecting group of compound (9) is removed under acidic conditions, such as trifluoroacetic acid, a solution of HCl in EtOAc, or with an aid of hydrazine hydrate, or any other appropriate condition, such as with the aid of TBAF to give the desired protein kinase inhibitor (10). Other desired protein kinase inhibitor having Formula (11) is obtained by introducing various substituents to the compound 10) under appropriate conditions.

Some compounds having Formula (14) or Formula (15) can be prepared by a general method illustrated in Scheme 3 and described in details in the Examples. As showing in Scheme 3, Compound (3) is coupled with optionally substituted aminoimidazole (2) or a hydrochloride thereof in the presence of a suitable Pd catalyst, such as Pd(OAc)$_2$, affords the compound (13). The protecting group of compound 13) is removed under acidic conditions, such as trifluoroacetic acid, a solution of HCl in EtOAc, or with an aid of hydrazine hydrate, or any other appropriate condition, such as with the aid of TBAF to give the desired protein kinase inhibitor (14). Other desired protein kinase inhibitor having Formula (15) is obtained by introducing various substituents to the compound (4) under appropriate conditions.

Scheme 4

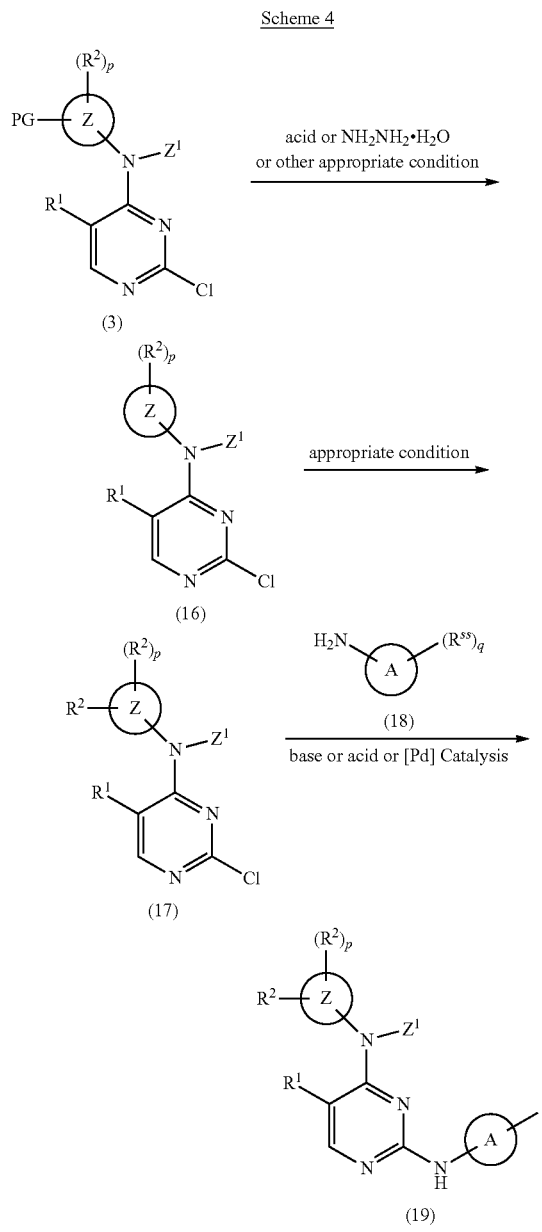

Scheme 5

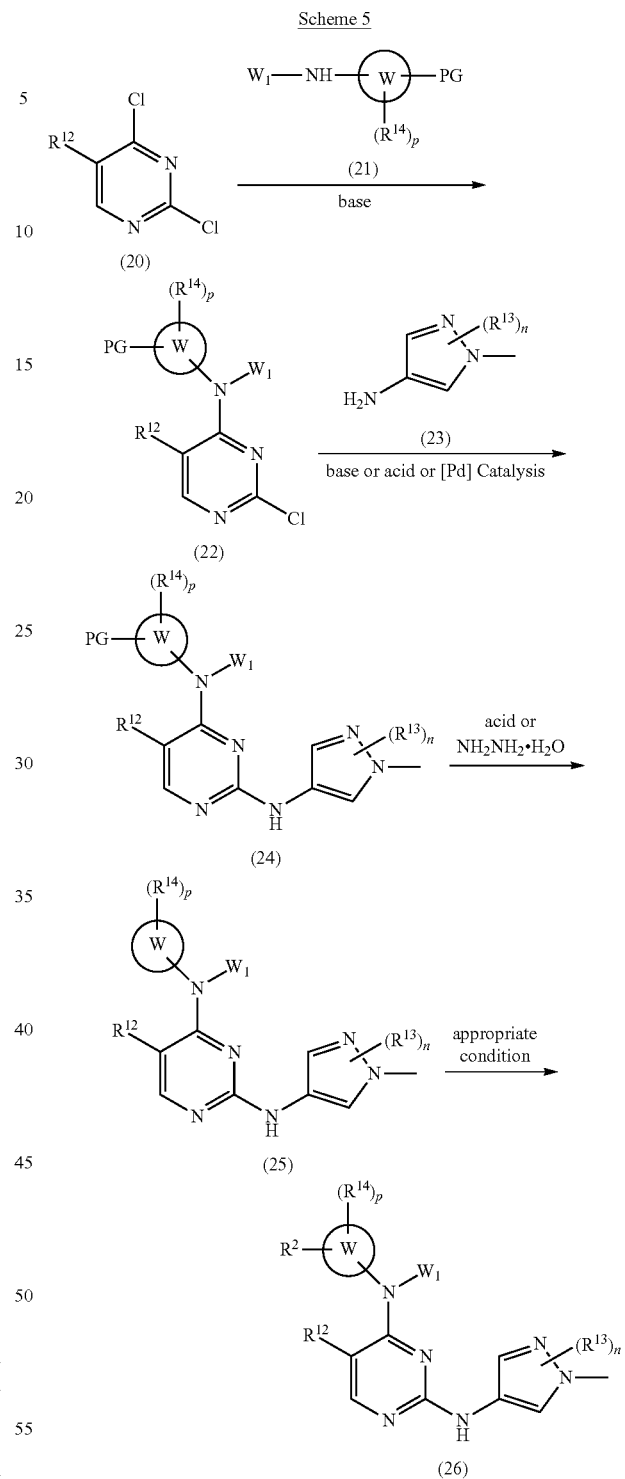

Some compounds having Formula (19) can be prepared by a general method illustrated in Scheme 4 and described in details in the Examples. As showing in Scheme 4, the protecting group of compound (3) is removed under acidic conditions, such as trifluoroacetic acid, a solution of HCl in EtOAc, or with an aid of hydrazine hydrate, or any other appropriate condition, such as with the aid of TBAF to give the compound (16). Then, various substituents are introduced to the compound (16) under appropriate conditions to give the compound (17). Compound (17) is coupled with optionally substituted aminoazole compound (18) or a hydrochloride thereof in the presence of a base, such as DIPEA, Et$_3$N, Cs$_2$CO$_3$ or in the presence of a suitable Pd catalyst, such as Pd(OAc)$_2$, to afford the desired protein kinase inhibitor (19).

Some compounds having Formula (25) or Formula (26) can be prepared by a general method illustrated in Scheme 5 and described in details in the Examples. As showing in Scheme 5, optionally substituted dichloropyrimidine compound (20) is reacted with optionally substituted heterocyclic compound (21 with an aid of a base, such as Et$_3$N, DIPEA to give optionally substituted heteroaryl compound (22). Compound (22) is then coupled with optionally substituted 1-methyl-H-pyrazole-4-amine (2 or a hydrochloride thereof in the presence of a base, such as DIPEA, Et₃N, Cs₂CO₃ or in the presence of an acid, such as trifluoroacetic acid, a solution of HCl in EtOAc, or in the presence of a suitable Pd catalyst, such as Pd(OAc)₂, to afford the compound (2). The protecting group of compound (24) is removed under acidic conditions, such as trifluoroacetic acid, a solution of HCl in EtOAc, or with an aid of hydrazine hydrate, or any other appropriate condition, such as with the aid of TBAF to give the other protein kinase inhibitor having Formula (26) is obtained by introducing various substituents to the compound (25) under appropriate conditions.

EXAMPLES

Example 1 1-(5-((5-chloro-2-((1-(2-hydroxy-2-methylpropyl)-1H-pyrazol-4-yl)amino)pyrimidin-4-yl)amino)hexahydrocyclopenta[c]pyrrol-2(1H)-yl)ethanone

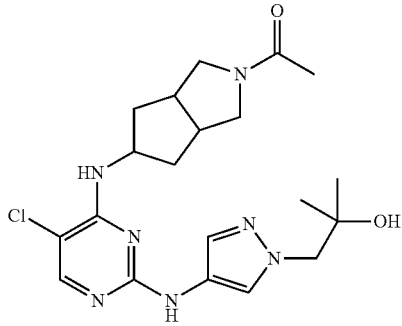 [SMILES: CC(=O)N1CC2CC(Nc3nc(Nc4cnn(CC(C)(C)O)c4)ncc3Cl)CC2C1]

Step 1) tert-butyl 3α,4,7,7a-tetrahydro-1H-isoindole-2(3H)-carboxylate

To a suspension of LAH (22.80 g, 600 mmol) in THF (600 mL) at 0° C. was added tetrahydrophthalimide (39.45 g, 260.9 mmol) portion-wise. After addition, the reaction mixture was stirred at 60° C. for 18 h, then cooled down to 0° C. and quenched carefully with water (25 mL), followed by 15% KOH aqueous solution (25 mL) and another 75 mL of water. The resulting mixture was stirred at rt for 1 h and filtered through a pad of Celite. Then the filtrate was washed with DCM (500 mL) and concentrated in vacuo to give isoindole as yellow oil, which was used in the next step without purification.

Accordingly, the isoindole in DCM (300 mL) was treated with Et₃N (39.61 g, 391.4 mmol) and (Boc)₂O (68.32 g, 313.1 mmol) at 0° C. for 0.5 h, and then warmed to rt and stirred for another 21 h. The mixture was concentrated in vacuo and the residue was dissolved in EtOAc (600 mL), then the resulting solution was washed with citric acid aqueous solution (1 M, 130 mL×2), followed by saturated NaHCO₃ (2×130 mL) and brine (250 mL). The separated organic layer was dried over anhydrous Na₂SO₄, then filtered and concentrated in vacuo. The residue was purified by silica gel column chromatography (EtOAc/PE (v/v)=1/5) to give the title compound as orange red oil (45.00 g, yield 77.3%).

LC-MS (ESI, pos. ion) m/z: 168.2 [(M-C₄H₈)+H]⁺;
¹H NMR (400 MHz, CDCl₃) δ (ppm): 5.64 (s, 2H), 3.40 (m, 2H), 3.16 (m, 1H), 3.07 (m, 1H), 2.25 (m, 4H), 1.90 (m, 2H), 1.46 (s, 9H).

Step 2) 2,2'-(1-(tert-butoxycarbonyl)pyrrolidine-3,4-diyl)diacetic acid

To a solution of tert-butyl 3α,4,7,7a-tetrahydro-1H-isoindole-2(3H)-carboxylate (4.91 g, 22 mmol) and (NH₄)₂SO₄ (1.55 g, 12 mmol) in H₂O (40 mL) was added KMnO₄ (8.20 g, 52 mmol) portionwise at 5° C. in 0.5 h. The reaction mixture was stirred at 5° C. for 6 h, then filtered and the filter cake was washed with H₂O (40 mL×3). The filtrate was extracted with CH₂Cl₂ (40 mL×3) and the aqueous layer was adjusted to pH=2-3 with 3 M HCl aqueous solution, then extracted with EtOAc (50 mL×3). The combined organic phases were washed with brine (50 mL×3), dried over anhydrous Na₂SO₄, filtered and concentrated in vacuo to give the title compound as a pale yellow solid (4.52 g, yield 71.5%).

LC-MS (ESI, pos. ion) m/z: 232.2 [(M-C₄H₈)+H]⁺;
¹H NMR (400 MHz, CDCl₃) δ (ppm): 3.53 (m, 2H), 3.04 (m, 2H), 2.80 (m, 2H), 2.44 (m, 4H), 1.43 (s, 9H).

Step 3) tert-butyl 5-oxohexahydrocyclopenta[c]pyrrole-2(1H)-carboxylate

To a suspension of 2,2'-(1-(tert-butoxycarbonyl)pyrrolidine-3,4-diyl)diacetic acid (3.40 g, 11.8 mmol) in Ac₂O (21 mL) was added NaOAc (0.78 g, 9.5 mmol) and the reaction mixture was stirred at 120° C. for 3 h. After that, the resulting mixture was cooled down to rt, then filtered and the filter cake was washed with EtOAc (20 mL×2). The filtrate was concentrated in vacuo and the residue was purified by silica gel column chromatography (EtOAc/PE (v/v)=1/4) to give the title compound as orange yellow oil (1.38 g, yield 55.0%).

LC-MS (ESI, pos. ion) m/z: 170.2 [(M-C₄H₈)+H]⁺;
¹H NMR (400 MHz, CDCl₃) δ (ppm): 3.69 (m, 2H), 3.00 (m, 4H), 2.61 (dd, J=8.2, 18.4 Hz, 2H), 2.29 (dd, J=5.8, 18.4 Hz, 2H), 1.43 (s, 9H).

Step 4) tert-butyl 5-(benzylamino)hexahydrocyclopenta[c]pyrrole-2(1H)-carboxylate To a solution of tert-butyl 5-oxohexahydrocyclopenta[c]pyrrole-2(1H)-carboxylate (9.57 g, 42.5 mmol) in DCM (170 mL) were added BnNH₂ (4.56 g, 42.5 mmol) and AcOH (2.55 g, 42.5 mmol) at 0° C. and the reaction mixture was stirred at 0° C. for 0.5 h. Then NaBH(OAc)₃ (18.00 g, 85.0 mmol) was added to the above mixture. The resulting mixture was stirred at rt for another 20 h, then quenched with saturated NaHCO₃ aqueous solution (142 mL), and extracted with DCM (250 mL×3). The combined organic phases were washed with brine (250 mL×3), dried over anhydrous Na₂SO₄, filtered and concentrated in vacuo. The residue was purified by silica gel column chromatography (EtOAc, 100%) to give the title compound as a yellow solid (7.44 g, yield 55.3%).

LC-MS (ESI, pos. ion) m/z: 317.3 [M+H]⁺;
¹H NMR (400 MHz, CDCl₃) δ (ppm): 7.31 (m, 4H), 7.26 (m, 1H), 3.79 (s, 2H), 3.46 (m, 2H), 3.28 (d, J=8.8 Hz, 1H), 3.16 (tt, J=9.6, 6.9 Hz, 1H), 2.55 (m, 2H), 2.28 (s, 2H), 2.22 (m, 2H), 1.45 (s, 9H), 1.31 (m, 2H).

Step 5) tert-butyl 5-aminohexahydrocyclopenta[c]pyrrole-2(1H)-carboxylate

To a solution of tert-butyl 5-(benzylamino)hexahydrocyclopenta[c]pyrrole-2(1H)-carboxylate (6.50 g, 20.5 mmol) and AcOH (1.23 g, 20.5 mmol) in MeOH (150 mL) was added Pd(OH)$_2$/C (mass %=10%, 1.00 g), and the suspension was stirred at 40° C. under H$_2$ atmosphere overnight. The mixture was filtered through a pad of Celite and the filtrate was concentrated in vacuo. The residue was dissolved in saturated NaHCO$_3$ aqueous solution (70 mL) and the mixture was extracted with DCM (100 mL×3). The combined organic phases were washed with brine (100 mL×3), dried over anhydrous Na$_2$SO$_4$, then filtered and concentrated in vacuo to give the title compound as a yellow solid (4.00 g, yield 86.2%).

LC-MS (ESI, pos. ion) m/z: 227.2 [M+H]$^+$;

$^1$H NMR (400 MHz, CDCl$_3$) δ (ppm): 3.44 (m, 2H), 3.31 (m, 3H), 2.98 (br. s, 2H), 2.57 (m, 2H), 2.22 (dt, J=14.0, 7.2 Hz, 2H), 1.44 (s, 9H).

Step 6) tert-butyl 5-((2,5-dichloropyrimidin-4-yl)amino)hexahydrocyclopenta[c]pyrrole-2(1H)-carboxylate To a solution of 2,4,5-trichloropyrimidine (1.46 g, 7.96 mmol) and tert-butyl 5-aminohexahydrocyclopenta[c]pyrrole-2(1H)-carboxylate (3.11 g, 13.74 mmol) in EtOH (60 mL) was added Et$_3$N (2.21 g, 21.84 mmol), and the reaction mixture was stirred at rt overnight and then concentrated in vacuo. The residue was dissolved in a mixture of EtOAc (50 mL) and water (50 mL), and the solution was extracted with EtOAc (150 mL×3). The combined organic phases were washed with brine (150 mL), dried over anhydrous Na$_2$SO$_4$, and then concentrated in vacuo. The residue was purified by silica gel column chromatography (EtOAc/PE (v/v)=1/5) to give the title compound as a pale yellow solid (2.97 g, yield 100%).

LC-MS (ESI, pos. ion) m/z: 373.0 [M+H]$^+$.

Step 7) N-(2,5-dichloropyrimidin-4-yl)octahydrocyclopenta[c]pyrrol-5-amine

To a solution of tert-butyl 5-((2,5-dichloropyrimidin-4-yl)amino)-hexahydrocyclopenta[c]pyrrole-2(1H)-carboxylate (3.36 g, 9.00 mmol) in dichloromethane (40 mL) was added a solution of HCl in EtOAc (20 mL, 80 mmol, 4M). The reaction mixture was stirred at rt for 2 h and concentrated in vacuo. The residue was dissolved in water (20 mL) and the resulting mixture was adjusted to pH=8-9 with a saturated NaHCO$_3$ aqueous solution, then extracted with DCM/MeOH (v/v=10/1, 50 mL×6). The combined organic phases were washed with brine (100 mL), dried over anhydrous Na$_2$SO$_4$, then filtered and concentrated in vacuo. The residue was purified by silica gel column chromatography (MeOH/DCM (v/v)=1/10 to 1/5) to give the title compound as a light yellow solid (2.45 g, yield 99.6%).

LC-MS (ESI, pos. ion) m/z: 273.2 [M+H].

Step 8) 1-(5-((2, 5-dichloropyrimidin-4-yl)amino) hexahydrocyclopenta[c]pyrrol-2(1H)-yl)ethanone To a solution of N-(2,5-dichloropyrimidin-4-yl)octahydrocyclopenta[c]pyrrol-5-amine (1.3 g, 4.8 mmol) and acetyl acetate (0.58 g, 5.7 mmol) in dichloromethane (30 mL) was added N,N-diethylethanamine (0.96 g, 9.5 mmol). The mixture was stirred at room temperature for 10 min. Then the mixture was concentrated in vacuo. The residue was purified by silica gel column chromatography (DCM/MeOH (v/v)=100/1) to give the title product as a white solid (1.14 g, yield 76%).

LC-MS (ESI, pos. ion) m/z: 315.2 [M+H]$^+$;

$^1$H NMR (400 MHz, CDCl$_3$) δ (ppm): 8.01 (s, 1H), 5.57 (d, J=6.9 Hz, 1H), 4.56-4.40 (m, 1H), 3.65-3.55 (m, 3H), 3.39 (dd, J=10.9, 3.4 Hz, 1H), 2.84-2.65 (m, 2H), 2.52 (dq, J=15.5, 7.6 Hz, 2H), 2.06 (s, 3H), 1.44-1.31 (m, 2H).

Step 9) 2-methyl-1-(4-nitro-1H-pyrazol-1-yl)propan-2-ol

To a solution of 4-nitro-1H-pyrazole (1.01 g, 8.93 mmol) and 2, 2-dimethyloxirane (1.94 g, 26.9 mmol) in DMF (20 mL) was added cesium carbonate (5.76 g, 17.7 mmol) and the reaction mixture was stirred at 100° C. for 3.5 h. The reaction was quenched with water (100 mL) and extracted with EtOAc (250 mL×3). The combined organic phases were washed with brine (100 mL), dried over anhydrous Na$_2$SO$_4$, filtered and concentrated in vacuo. The residue was purified by silica gel column chromatography (EtOAc/PE (v/v)=1/4) to give the title compound as yellow oil (1.52 g, yield 91.9%).

LC-MS (ESI, pos. ion) m/z: 186.3 [M+H]$^+$;

$^1$H NMR (400 MHz, CDCl$_3$) δ (ppm): 8.26 (s, 1H), 8.07 (s, 1H), 4.11 (s, 2H), 1.22 (s, 6H).

Step 10) 1-(4-amino-1H-pyrazol-1-yl)-2-methylpropan-2-ol

To a solution of 2-methyl-1-(4-nitro-1H-pyrazol-1-yl)propan-2-ol (1.52 g, 8.21 mmol) in methanol (50 mL) was added Pd/C (150 mg, mass %=10%). The reaction mixture was stirred at rt in a high pressure autoclave under 2 MPa H$_2$ atmosphere overnight and then filtered. The filtrate was concentrated in vacuo to give the title compound as purple oil (1.2 g, yield 94%).

LC-MS (ESI, pos. ion) m/z: 156.3 [M+H]$^+$;

$^1$H NMR (400 MHz, CDCl$_3$) δ (ppm): 7.19 (s, 1H), 7.03 (s, 1H), 3.91 (s, 2H), 1.82 (s, 2H), 1.13 (s, 6H).

Step 11) 1-(5-((5-chloro-2-((1-(2-hydroxy-2-methylpropyl)-1H-pyrazol-4-yl)amino)pyrimidin-4-yl)amino)hexahydrocyclopenta[c]pyrrol-2(1H)-yl)ethanone To a solution of 1-(4-amino-1H-pyrazol-1-yl)-2-methylpropan-2-ol (63 mg, 0.405 mmol) and 1-(5-((2,5-dichloropyrimidin-4-yl)amino)hexahydrocyclopenta[c]pyrrol-2 (1H)-yl)ethanone (100 mg, 0.317 mmol) in 1,4-dioxane (6 mL) were added cesium carbonate (207 mg, 0.635 mmol), Pd(OAc)$_2$ (14 mg, 0.063 mmol) and BINAP (39 mg, 0.063 mmol). The reaction mixture was stirred at 100° C. overnight and concentrated in vacuo. The residue was purified by silica gel column chromatography (MeOH/DCM (v/v)=1/25) to give the title compound as a yellow solid (82 mg, yield 59.6%).

LC-MS (ESI, pos. ion) m/z: 434.2 [M+H]$^+$;

$^1$H NMR (400 MHz, CDCl$_3$) δ (ppm): 7.86 (s, 1H), 7.74 (s, 1H), 7.60 (s, 1H), 6.77 (s, 1H), 5.24 (d, J=7.2 Hz, 1H), 4.40 (m, 1H), 4.01 (s, 2H), 3.63 (m, 3H), 3.39 (dd, J=10.8, 3.4 Hz, 2H), 2.81-2.69 (m, 2H), 2.52-2.45 (m, 2H), 2.07 (s, 3H), 1.49-1.41 (m, 2H), 1.18 (s, 6H).

139

Example 2 3-(5-((5-chloro-2-((1-(2-hydroxy-2-methylpropyl)-1H-pyrazol-4-yl)amino)pyrimidin-4-yl)amino)hexahydrocyclopenta[c]pyrrol-2(1H)-yl)-3-oxopropanenitrile

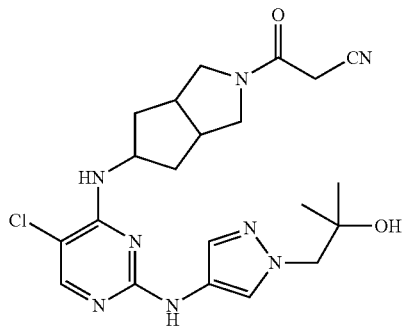 [SMILES: CC(C)(O)Cn1cc(Nc2ncc(Cl)c(NC3CC4CN(C(=O)CC#N)CC4C3)n2)cn1]

Step 1) 3-(5-((2,5-dichloropyrimidin-4-yl)amino)hexahydrocyclopenta[c]pyrrol-2(1H)-yl)-3-oxopropanenitrile To a solution of N-(2,5-dichloropyrimidin-4-yl)-octahydrocyclopenta[c]pyrrol-5-amine (1.3 g, 4.8 mmol), 2-cyanoacetic acid (0.81 g, 9.5 mmol), EDCI (1.8 g, 9.4 mmol) and HOAT (1.3 g, 9.6 mmol) in dichloromethane (30 mL) was added TEA (1.4 g, 14 mmol). The mixture was stirred at room temperature for 3.5 h. Then, the mixture was concentrated in vacuo. The residue was purified by silica gel column chromatography (DCM/MeOH (v/v)=100/1) to give the title product as a white solid (1.16 g, yield 72%).

LC-MS (ESI, pos. ion) m/z: 340.2 [M+H]$^+$;

$^1$H NMR (400 MHz, CDCl$_3$) δ (ppm): 8.00 (s, 1H), 5.75 (d, J=7.4 Hz, 1H), 4.51 (ddd, J=17.4, 7.5, 2.6 Hz, 1H), 3.71-3.58 (m, 3H), 3.50-3.42 (m, 3H), 2.90-2.67 (m, 2H), 2.51 (dq, J=14.4, 7.2 Hz, 2H), 1.50-1.37 (m, 2H).

Step 2) 3-(5-((5-chloro-2-((1-(2-hydroxy-2-methylpropyl)-1H-pyrazol-4-yl)amino)pyrimidin-4-yl)amino)hexahydrocyclopenta[c]pyrrol-2(1H)-yl)-3-oxopropanenitrile To a solution of 1-(4-amino-1H-pyrazol-1-yl)-2-methylpropan-2-ol (63 mg, 0.405 mmol) and 3-(5-((2,5-dichloropyrimidin-4-yl)amino)hexahydrocyclopenta[c]pyrrol-2(1H)-yl)-3-oxopropanenitrile (100 mg, 0.293 mmol) in 1,4-dioxane (6 mL) were added cesium carbonate (192 mg, 0.589 mmol), Pd(OAc)$_2$ (13 mg, 0.057 mmol) and BINAP (39 mg, 0.057 mmol). The reaction mixture was stirred at 100° C. overnight and concentrated in vacuo. The residue was purified by silica gel column chromatography (MeOH/DCM (v/v)=1/30) to give the title compound as a yellow solid (64 mg, yield 47.5%).

LC-MS (ESI, pos. ion) m/z: 459.4 [M+H]$^+$;

$^1$H NMR (400 MHz, CDCl$_3$) δ (ppm): 7.87 (s, 1H), 7.73 (s, 1H), 7.61 (s, 1H), 6.78 (s, 1H), 5.25 (d, J=6.0 Hz, 1H), 4.41 (d, J=7.4 Hz, 1H), 4.02 (s, 2H), 3.66 (d, J=24.5 Hz, 4H), 3.43 (s, 2H), 2.89-2.73 (m, 2H), 2.56-2.47 (m, 2H), 1.47-1.42 (m, 2H), 1.19 (s, 6H).

140

Example 3 3-(5-((5-chloro-2-((1-(piperidin-3-yl)-1H-pyrazol-4-yl)amino)pyrimidin-4-yl)amino) hexahydrocyclopenta[c]pyrrol-2(1H)-yl)-3-oxopropanenitrile

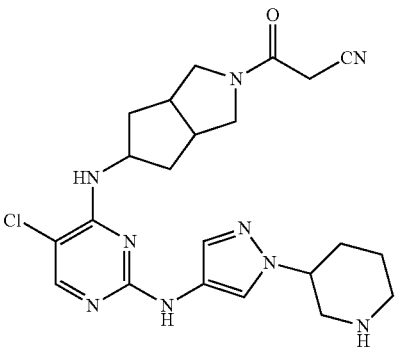 [SMILES: N#CCC(=O)N1CC2CC(Nc3nc(Nc4cnn(C5CCCNC5)c4)ncc3Cl)CC2C1]

Step 1) tert-butyl 3-hydroxypiperidine-1-carboxylate

To a solution of piperidin-3-ol (1.13 g, 11.2 mmol) and triethylamine (3.05 g, 30.2 mmol) in DCM (20 mL) was added (Boc)$_2$O (2.60 g, 11.9 mmol). The reaction mixture was stirred at rt for 1 h and concentrated in vacuo. The residue was purified by silica gel column chromatography (DCM/MeOH (v/v)=50/1) to give the title compound as light yellow liquid (1.88 g, yield 83.6%).

LC-MS (ESI, pos. ion) m/z: 146.3 [(M+H)-56]$^+$.

Step 2) tert-butyl 3-(4-nitro-1H-pyrazol-1-yl)piperidine-1-carboxylate

Under an inert atmosphere, to a solution of 4-nitro-1H-pyrazole (801.2 mg, 7.085 mmol), triphenylphosphane (2.79 g, 10.6 mmol) and tert-butyl 3-hydroxypiperidine-1-carboxylate (1.64 g, 8.15 mmol) in THF (30 mL) at 0° C. was dropwise added a solution of DIAD (2.17 g, 10.7 mmol) in THF (20 mL) in 30 min. The reaction mixture was stirred at 0° C. for 1 h then stirred at rt for another 18 h and concentrated in vacuo. The residue was purified by silica gel column chromatography (PE/EtOAc (v/v)=10/1) to give the title compound as a white solid (1.92 g, yield 91%).

LC-MS (ESI, pos. ion) m/z: 241.3 [M+H-56]$^+$;

$^1$H NMR (400 MHz, CDCl$_3$) δ (ppm): 8.26 (s, 1H), 8.09 (s, 1H), 4.28-4.20 (m, 1H), 4.13 (d, J=10.9 Hz, 1H), 3.79 (dt, J=13.2, 4.3 Hz, 1H), 3.51-3.41 (m, 1H), 3.13 (ddd, J=13.3, 9.7, 3.4 Hz, 1H), 2.21-2.13 (m, 2H), 1.80-1.70 (m, 1H), 1.65-1.62 (m, 1H), 1.47 (s, 9H).

Step 3) tert-butyl 3-(4-amino-1H-pyrazol-1-yl)piperidine-1-carboxylate

To a solution of tert-butyl 3-(4-nitropyrazol-1-yl)piperidine-1-carboxylate (1.08 g, 3.64 mmol) in EtOH (30 mL) was added Pd/C (300 mg, mass %=10%). The reaction mixture was stirred at rt under H$_2$ atmosphere for 2.5 h. Filtered, the filter cake was washed with MeOH (150 mL), and the filtrate was concentrated in vacuo to give the title compound as yellow oil (860 mg, yield 88%).

LC-MS (ESI, pos. ion) m/z: 267.4 [M+H]+.

Step 4) tert-butyl 3-(4-((5-chloro-4-((2-(2-cyano-acetyl)octahydrocyclopenta[c]pyrrol-5-yl)amino)pyrimidin-2-yl)amino)-1H-pyrazol-1-yl)piperidine-1-carboxylate A mixture of tert-butyl 3-(4-amino-1H-pyrazol-1-yl)piperidine-1-carboxylate (253.6 mg, 0.9523 mmol), 3-(5-((2,5-dichloropyrimidin-4-yl)amino)hexahydrocyclopenta[c]pyrrol-2(1H)-yl)-3-oxopropanenitrile (208.7 mg, 0.6135 mmol), Pd(OAc)$_2$ (14.7 mg, 0.0655 mmol), BINAP (35.4 mg, 0.0568 mmol) and cesium carbonate (578.3 mg, 1.775 mmol) were dissolved in 1,4-dioxane (10 mL). The reaction mixture was heated to reflux and stirred for 3 h under an inert atmosphere and then concentrated in vacuo. The residue was purified by silica gel column chromatography (DCM/MeOH (v/v)=45/1) to give the title compound as an off-white solid (86 mg, yield 24.6%).

LC-MS (ESI, pos. ion) m/z: 570.3 [M+H]+;
$^1$H NMR (400 MHz, CDCl$_3$) δ (ppm): 7.87 (s, 1H), 7.73 (s, 1H), 7.57 (s, 1H), 6.75 (s, 1H), 5.24 (d, J=7.1 Hz, 1H), 4.49-4.36 (m, 1H), 4.33-4.25 (m, 1H), 4.15-4.06 (m, 1H), 4.05-3.94 (m, 1H), 3.74-3.58 (m, 3H), 3.47-3.41 (m, 3H), 3.20-3.06 (m, 1H), 2.90-2.74 (m, 3H), 2.57-2.47 (m, 2H), 2.26-2.17 (m, 1H), 2.10-1.95 (m, 1H), 1.86-1.75 (m, 2H), 1.47-1.42 (m, 11H).

Step 5) 3-(5-((5-chloro-2-((1-(piperidin-3-yl)-1H-pyrazol-4-yl)amino)pyrimidin-4-yl)amino) hexahydrocyclopenta[c]pyrrol-2(1H)-yl)-3-oxopropanenitrile tert-butyl 3-(4-((5-chloro-4-((2-(2-cyanoacetyl)octahydrocyclopenta[c]pyrrol-5-yl)amino)pyrimidin-2-yl)amino)-1H-pyrazol-1-yl)piperidine-1-carboxylate (86 mg, 0.1509 mmol) was dissolved in a solution of HCl in EtOAc (5 mL, 3 mmol, 0.5 M) and the reaction mixture was stirred at rt for 30 min. The reaction was quenched with saturated Na$_2$CO$_3$ aqueous solution (20 mL), extracted with DCM/MeOH (v/v=10/1, 40 mL×6), the combined organic layers were dried over anhydrous Na$_2$SO$_4$, filtered and concentrated in vacuo. The residue was purified by preparative TLC (DCM/(a solution of NH$_3$ in MeOH (7M) (v/v)=10/1) to give the title compound as a light yellow solid (20.3 mg, yield 28.6%).

LC-MS (ESI, pos. ion) m/z: 470.4 [M+H]+;
$^1$H NMR (400 MHz, CDCl$_3$+CD$_3$OD) δ (ppm): 7.74 (d, J=5.6 Hz, 2H), 7.55 (d, J=3.9 Hz, 1H), 4.65-4.57 (m, 1H), 4.42-4.32 (m, 1H), 3.70-3.56 (m, 3H), 3.34-3.23 (m, 6H), 3.02-2.93 (m, 1H), 2.89-2.82 (m, 1H), 2.78-2.70 (m, 1H), 2.48-2.39 (m, 2H), 2.16-2.09 (m, 1H), 2.06-2.00 (m, 1H), 1.98-1.90 (m, 2H), 1.44-1.34 (m, 2H).

Example 4 1-(5-((5-chloro-2-((1-(piperidin-3-yl)-1H-pyrazol-4-yl)amino)pyrimidin-4-yl)amino)hexahydrocyclopenta[c]pyrrol-2(1H)-yl)ethanone

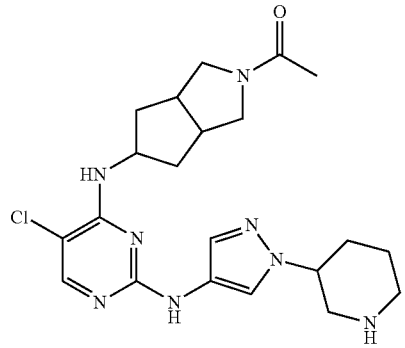 [SMILES: CC(=O)N1CC2CC(Nc3nc(Nc4cnn(C5CCCNC5)c4)ncc3Cl)CC2C1]

Step 1) tert-butyl 3-(4-((4-((2-acetyloctahydrocyclopenta[c]pyrrol-5-yl)amino)-5-chloropyrimidin-2-yl)amino)-1H-pyrazol-1-yl)piperidine-1-carboxylate A mixture of tert-butyl 3-(4-amino-1H-pyrazol-1-yl)piperidine-1-carboxylate (251.8 mg, 0.9456 mmol), 1-(5-((2,5-dichloropyrimidin-4-yl)amino)hexahydrocyclopenta[c]pyrrol-2(1H)-yl)ethanone (204.3 mg, 0.6482 mmol), Pd(OAc)$_2$ (14.9 mg, 0.0664 mmol), BINAP (37.6 mg, 0.0604 mmol) and cesium carbonate (618.6 mg, 1.899 mmol) was dissolved in 1,4-dioxane (10 mL). The reaction was heated to reflux and stirred for 3 h under an inert atmosphere and the reaction was concentrated in vacuo. The residue was purified by silica gel column chromatography (DCM/MeOH (v/v)=40/1) to give the title compound as a light yellow solid (185 mg, yield 52.4%).

LC-MS (ESI, pos. ion) m/z: 545.3 [M+H]+;
$^1$H NMR (400 MHz, CDCl$_3$) δ (ppm): 7.85 (s, 1H), 7.74 (s, 1H), 7.57 (s, 1H), 6.78 (s, 1H), 5.39 (d, J=7.0 Hz, 1H), 5.11-5.04 (m, 1H), 5.00-4.94 (m, 1H), 4.47-4.36 (m, 1H), 4.35-4.24 (m, 1H), 4.14-4.05 (m, 1H), 4.05-3.94 (m, 1H), 3.65-3.49 (m, 3H), 3.37 (ddd, J=11.0, 7.6, 3.5 Hz, 1H), 3.18-3.07 (m, 1H), 2.86-2.63 (m, 3H), 2.56-2.43 (m, 2H), 2.25-2.17 (m, 1H), 2.05 (d, J=3.2 Hz, 3H), 2.03-1.95 (m, 1H), 1.45 (s, 9H), 1.38-1.34 (m, 2H).

Step 2) 1-(5-((5-chloro-2-((1-(piperidin-3-yl)-1H-pyrazol-4-yl)amino)pyrimidin-4-yl)amino)hexahydrocyclopenta[c]pyrrol-2(1H)-yl)ethanone tert-butyl 3-(4-((4-((2-acetyloctahydrocyclopenta[c]pyrrol-5-yl)amino)-5-chloropyrimidin-2-yl)amino)-1H-pyrazol-1-yl)piperidine-1-carboxylate (185 mg, 0.3394 mmol) was dissolved in a solution of HCl in EtOAc (6 mL, 3 mmol, 0.5 M) and the reaction mixture was stirred at rt for 30 min. The reaction mixture was washed with water (20 mL×2), and the combined aqueous phases were adjusted to pH=10 with Na$_2$CO$_3$ power and then extracted with DCM/MeOH (v/v=10/1, 50 mL×6). The combined organic layers were dried over anhydrous Na$_2$SO$_4$, filtered and concentrated in vacuo. The residue was purified by a preparative TLC (DCM/(a solution of NH$_3$ in MeOH (7M)) (v/v)=10/1) to give the title compound as a light yellow solid (68.3 mg, yield 45.2%).

LC-MS (ESI, pos. ion) m/z: 445.4 [M+H]+;

1H NMR (400 MHz, CDCl3) δ (ppm): 7.86 (s, 1H), 7.79 (s, 1H), 7.57 (s, 1H), 6.81 (s, 1H), 5.25 (d, J=7.1 Hz, 1H), 4.52-4.35 (m, 2H), 3.68-3.58 (m, 3H), 3.55 (dd, J=12.5, 3.2 Hz, 1H), 3.39 (dd, J=10.9, 3.3 Hz, 1H), 3.32-3.22 (m, 2H), 2.98-2.90 (m, 1H), 2.83-2.70 (m, 2H), 2.54-2.43 (m, 2H), 2.26-2.18 (m, 1H), 2.11-2.03 (m, 4H), 1.96-1.82 (m, 2H), 1.49-1.38 (m, 2H).

Example 5 3-(5-((5-chloro-2-((1-(piperidin-4-yl)-1H-pyrazol-4-yl)amino)pyrimidin-4-yl)amino) hexahydrocyclopenta[c]pyrrol-2(1H)-yl)-3-oxopropanenitrile

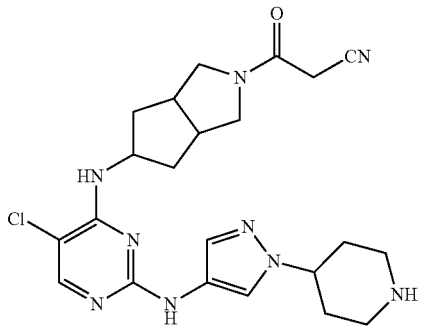 [SMILES: N#CCC(=O)N1CC2CC(Nc3nc(Nc4cnn(C5CCNCC5)c4)ncc3Cl)CC2C1]

Step 1) tert-butyl 4-hydroxypiperidine-1-carboxylate

To a solution of piperidin-4-ol (2 g, 19.773 mmol) and TEA (4 g, 39.530 mmol) in tetrahydrofuran (20 mL) were dropwise added (Boc)2O (5.2 g, 24 mmol). The mixture was stirred at rt overnight and concentrated in vacuo. The residue was purified by silica gel column chromatography (PE/EA (v/v)=10/1 to 5/1) to give the title product as a white solid (3.91 g, yield 98.3%).

LC-MS (ESI, pos. ion) m/z: 146.1 [M-55]+;

1H NMR (400 MHz, CDCl3) δ (ppm): 3.82 (d, J=8.4 Hz, 3H), 3.01 (ddd, J=13.3, 9.8, 3.2 Hz, 2H), 1.92 (s, 1H), 1.83 (dd, J=11.0, 5.5 Hz, 3H), 1.44 (s, 9H).

Step 2) tert-butyl 4-(4-nitro-1H-pyrazol-1-yl)piperidine-1-carboxylate

To a solution of tert-butyl 4-hydroxypiperidine-1-carboxylate (1 g, 4.9687 mmol), 4-nitro-1H-pyrazole (675 mg, 5.9692 mmol) and triphenylphosphane (1.96 g, 7.47 mmol) in anhydrous THF (50 mL) was dropwise added DIAD (1.5 mL, 7.6 mmol) at 0° C. for 30 min. The reaction mixture was stirred at rt for 1 h, and then moved to rt overnight. The resulting mixture was concentrated in vacuo, and the residue was purified by silica gel column chromatography (PE/EtOAc (v/v)=20/1 to 4/1) to give the title product as a white solid (1.35 g, yield 91.7%).

LC-MS (ESI, pos. ion) m/z: 241.2 [M-55].

Step 3) tert-butyl 4-(4-amino-1H-pyrazol-1-yl)piperidine-1-carboxylate

To a solution of tert-butyl 4-(4-nitro-1H-pyrazol-1-yl) piperidine-1-carboxylate (1.35 g, 4.56 mmol) in ethanol (30 mL) was added Pd/C (135 mg, 1.269 mmol, mass %=10%). The mixture was stirred under a H2 atmosphere at rt for 2 h. The resulting mixture was filtered and the filtrate was concentrated in vacuo. The residue was purified by silica gel column chromatography (DCM/MeOH (v/v)=50/1 to 25/1) to give the title product as brown oil (955 mg, yield 78.7%).

LC-MS (ESI, pos. ion) m/z: 211.1 [M-55]+

Step 4) tert-butyl 4-(4-((5-chloro-4-((2-(2-cyanoacetyl)octahydrocyclopenta[c]pyrrol-5-yl)amino) pyrimidin-2-yl)amino)-1H-pyrazol-1-yl)piperidine-1-carboxylate To a solution of 3-(5-((2,5-dichloropyrimidin-4-yl)amino) hexahydrocyclopenta[c]pyrrol-2(1H)-yl)-3-oxopropanenitrile (350 mg, 1.029 mmol), tert-butyl 4-(4-amino-1H-pyrazol-1-yl)piperidine-1-carboxylate (411 mg, 1.543 mmol) and cesium carbonate (1.1 g, 3.4 mmol) in 1,4-dioxane (25 mL) were added Pd(OAc)2 (23.1 mg, 0.103 mmol) and BINAP (64.1 mg, 0.103 mmol). The reaction mixture was degassed for 2 min and refilled with N2 and then stirred at 105° C. for 2 h. The mixture was concentrated in vacuo and the residue was purified by silica gel column chromatography (DCM/MeOH (v/v)=50/1 to 25/1) to give the title compound as a light yellow solid (254 mg, yield 43.31%).

LC-MS (ESI, pos. ion) m/z: 570.3 [M+H]+.

Step 5) 3-(5-((5-chloro-2-((1-(piperidin-4-yl)-1H-pyrazol-4-yl)amino)pyrimidin-4-yl)amino)hexahydrocyclopenta[c]pyrrol-2(1H)-yl)-3-oxopropanenitrile To a solution of tert-butyl 4-(4-((5-chloro-4-((2-(2-cyanoacetyl)octahydrocyclopenta[c]pyrrol-5-yl)amino)pyrimidin-2-yl)amino)-1H-pyrazol-1-yl)piperidine-1-carboxylate (254 mg, 0.4455 mmol) in dichloromethane (12 mL) was added a solution of HCl in EtOAc (6 mL, 24 mmol, 4M). The reaction mixture was stirred at rt for 30 min and concentrated in vacuo. The residue was dissolved in water (20 mL) and the resulting solution was adjusted to pH=8-9 with saturated NaHCO3 aqueous solution, then extracted with DCM/MeOH (v/v=10/1, 50 mL×6). The combined organic phases were washed with brine (100 mL), dried over anhydrous Na2SO4, then filtered and concentrated in vacuo. The residue was purified by silica gel column chromatography (MeOH/DCM (v/v)=1/10) to give the title compound as a light yellow solid (77 mg, yield 36.77%).

LC-MS (ESI, pos. ion) m/z: 470.5 [M+H]+;

1H NMR (400 MHz, DMSO-d6) δ (ppm): 9.04 (s, 1H), 7.86 (s, 1H), 7.83 (s, 1H), 7.45 (s, 1H), 6.91 (d, J=7.6 Hz, 1H), 4.49 (dd, J=15.6, 7.8 Hz, 1H), 4.21 (t, J=11.3 Hz, 1H), 3.93 (s, 2H), 3.39 (d, J=6.2 Hz, 2H), 3.14 (d, J=17.7 Hz, 4H), 2.71 (dd, J=34.0, 23.2 Hz, 4H), 2.24 (dd, J=12.0, 6.3 Hz, 2H), 2.01 (d, J=11.4 Hz, 2H), 1.84 (dd, J=20.6, 11.5 Hz, 2H), 1.53 (dd, J=13.9, 7.9 Hz, 2H).

Example 6 1-(5-((5-chloro-2-((1-(piperidin-4-yl)-1H-pyrazol-4-yl)amino)pyrimidin-4-yl)amino) hexahydrocyclopenta[c]pyrrol-2(1H)-yl)ethanone

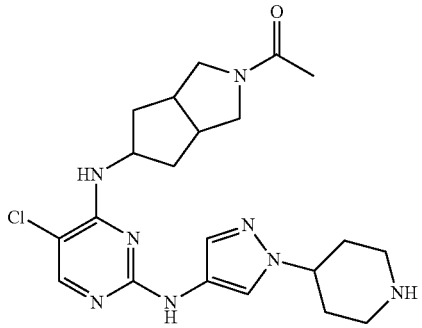 [SMILES: CC(=O)N1CC2CC(Nc3nc(Nc4cnn(C5CCNCC5)c4)ncc3Cl)CC2C1]

Step 1) tert-butyl 4-(4-((4-((2-acetyloctahydrocyclopenta[c]pyrrol-5-yl)amino)-5-chloropyrimidin-2-yl)amino)-1H-pyrazol-1-yl)piperidine-1-carboxylate To a solution of 1-(5-((2,5-dichloropyrimidin-4-yl)amino)hexahydrocyclopenta[c]pyrrol-2(1H)-yl)ethanone (350 mg, 1.110 mmol), tert-butyl 4-(4-amino-1H-pyrazol-1-yl)piperidine-1-carboxylate (443.6 mg, 1.666 mmol) and cesium carbonate (1.1 g, 3.4 mmol) in 1,4-dioxane (25 mL) were added Pd(OAc)$_2$ (25 mg, 0.1114 mmol) and BINAP (69.2 mg, 0.111 mmol). The mixture was degassed for 2 min and refilled with N$_2$. The reaction mixture was stirred at 105° C. for 2 h and concentrated in vacuo. The residue was purified by silica gel column chromatography (DCM/MeOH (v/v)=50/1 to 25/1) to give the title compound as a light yellow solid (585 mg, yield 96.65%).

LC-MS (ESI, pos. ion) m/z: 545.5 [M+H]$^+$.

Step 2) 1-(5-((5-chloro-2-((1-(piperidin-4-yl)-1H-pyrazol-4-yl)amino)pyrimidin-4-yl)amino) hexahydrocyclopenta[c]pyrrol-2(1H)-yl)ethanone To a solution of tert-butyl 4-(4-((4-((2-acetyloctahydrocyclopenta[c]pyrrol-5-yl)amino)-5-chloropyrimidin-2-yl)amino)-1H-pyrazol-1-yl)piperidine-1-carboxylate (585 mg, 1.073 mmol) in dichloromethane (12 mL) was added a solution of HCl in EtOAc (6 mL, 24 mmol, 4M). The reaction mixture was stirred at rt for 30 min and concentrated in vacuo. The residue was dissolved in water (20 mL), and the resulting solution was adjusted to pH=8-9 with a saturated NaHCO$_3$ aqueous solution, then extracted with DCM/MeOH (v/v=10/1, 50 mL×6). The combined organic phases were washed with brine (100 mL), dried over anhydrous Na$_2$SO$_4$, then filtered and concentrated in vacuo. The residue was purified by silica gel column chromatography (MeOH/DCM (v/v)=1/10) to give the title compound as an off white solid (375 mg, yield 78.52%).

LC-MS (ESI, pos. ion) m/z: 445.4 [M+H]$^+$;
$^1$H NMR (400 MHz, DMSO-d$_6$) δ (ppm): 9.04 (s, 1H), 7.86 (s, 1H), 7.84 (s, 1H), 7.45 (s, 1H), 6.94 (d, J=7.7 Hz, 1H), 4.49 (td, J=9.8, 2.1 Hz, 1H), 4.18 (td, J=11.3, 5.7 Hz, 1H), 3.41 (dd, J=8.8, 5.2 Hz, 4H), 3.12 (d, J=12.6 Hz, 2H), 2.71 (t, J=11.3 Hz, 3H), 2.64-2.53 (m, 1H), 2.24 (dd, J=12.0, 5.8 Hz, 2H), 2.00 (d, J=10.8 Hz, 2H), 1.95 (s, 3H), 1.82 (tt, J=11.8, 6.1 Hz, 2H), 1.59-1.45 (m, 2H).

Example 7 3-(5-((5-chloro-2-((1-(pyridin-2-yl)-1H-pyrazol-4-yl)amino)pyrimidin-4-yl)amino)hexahydrocyclopenta[c]pyrrol-2(1H)-yl)-3-oxopropanenitrile

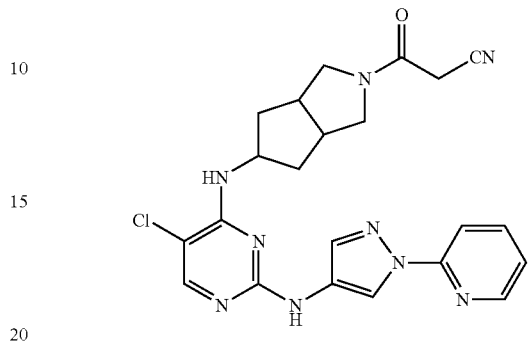

Step 1) 2-(4-nitro-1H-pyrazol-1-yl)pyridine

To a solution of 4-nitro-1H-pyrazole (2.01 g, 17.7 mmol) and 2-iodopyridine (4.37 g, 21.3 mmol) in DMF (20 mL) were added iodocopper (674 mg, 3.54 mmol), cesium carbonate (11.6 g, 35.5 mmol) and cyclohexane-1,2-diamine (407 mg, 3.56 mmol) and then the reaction mixture was stirred at 100° C. for 4 h. The reaction was quenched with water (100 mL) and extracted with EtOAc (250 mL×3). The combined organic phases were washed with brine (100 mL), dried over anhydrous Na$_2$SO$_4$, filtered and concentrated in vacuo. The residue was purified by silica gel column chromatography (EtOAc/PE (v/v)=1/15) to give the title compound as a white solid (1.8 g, 53.6%).

LC-MS (ESI, pos. ion) m/z: 191.3 [M+H]$^+$;
$^1$H NMR (400 MHz, CDCl$_3$) δ (ppm): 9.28 (s, 1H), 8.51-8.47 (m, 1H), 8.26 (s, 1H), 8.06-8.02 (m, 1H), 7.94-7.88 (m, 1H), 7.37-7.33 (m, 1H).

Step 2) 1-(pyridin-2-yl)-1H-pyrazol-4-amine

To a solution of 2-(4-nitro-1H-pyrazol-1-yl)pyridine (1.52 g, 8.21 mmol) in MeOH (80 mL) was added Pd/C (210 mg, mass %=10%). The reaction mixture was stirred at rt in a high pressure autoclave under 2 MPa H$_2$ atmosphere overnight and filtered. The filtrate was concentrated in vacuo to give the title compound as purple oil (1.62 g, yield 98.6%).

LC-MS (ESI, pos. ion) m/z: 161.3 [M+H]$^+$;
$^1$H NMR (400 MHz, CDCl$_3$) δ (ppm): 8.35 (d, J=3.9 Hz, 1H), 8.09 (d, J=0.4 Hz, 1H), 7.89 (d, J=8.3 Hz, 1H), 7.78-7.72 (m, 1H), 7.41 (s, 1H), 7.13-7.08 (m, 1H), 3.10 (s, 2H).

Step 3) tert-butyl 5-((5-chloro-2-((1-(pyridin-2-yl)-1H-pyrazol-4-yl)amino)pyrimidin-4-yl)amino)hexahydrocyclopenta[c]pyrrole-2(1H)-carboxylate To a solution of tert-butyl 5-((2,5-dichloropyrimidin-4-yl)amino)hexahydrocyclopenta[c]pyrrole-2(1H)-carboxylate (501 mg, 1.34 mmol) and 1-(pyridin-2-yl)-1H-pyrazol-4-amine (259 mg, 1.62 mmol) in 1,4-dioxane (20 mL) were added Pd(OAc)$_2$ (60 mg, 0.267 mmol), BINAP (167 mg, 0.268 mmol) and caesium carbonate (872 mg, 2.67 mmol). The reaction mixture was stirred at 108° C. overnight and concentrated in vacuo. The residue was purified by silica gel column chromatography (EtOAc/PE (v/v)=1/3) to give the title compound as a yellow solid (589 mg, yield 88.3%).

LC-MS (ESI, pos. ion) m/z: 497.4 [M+H]$^+$;

$^1$H NMR (400 MHz, CDCl$_3$) δ (ppm): 8.91 (s, 1H), 8.35 (d, J=4.5 Hz, 1H), 7.95 (d, J=8.3 Hz, 1H), 7.90 (s, 1H), 7.81-7.75 (m, 2H), 7.17-7.12 (m, 1H), 6.85 (s, 1H), 5.35-5.31 (m, 1H), 4.54-4.50 (m, 1H), 3.51-3.38 (m, 4H), 2.80-2.78 (m, 2H), 2.60-2.51 (m, 2H), 1.47 (s, 9H), 1.44-1.39 (m, 2H).

Step 4) 5-chloro-N$^4$-(octahydrocyclopenta[c]pyrrol-5-yl)-N$^2$-(1-(pyridin-2-yl)-1H-pyrazol-4-yl)pyrimidine-2,4-diamine To a solution of 5-((5-chloro-2-((1-(pyridin-2-yl)-1H-pyrazol-4-yl)amino)pyrimidin-4-yl)amino)hexahydrocyclopenta[c]pyrrole-2(1H)-carboxylate (589 mg, 1.19 mmol) in dichloromethane (20 mL) was added a solution of HCl in EtOAc (10 mL, 30 mmol, 3 M). The reaction mixture was stirred at rt overnight and concentrated in vacuo. The residue was dissolved in EtOAc (20 mL), and the resulting solution was adjusted to pH=10 with a saturated NaHCO$_3$ aqueous solution, then extracted with EtOAc (50 mL×3). The combined organic phases were washed with brine (50 mL×3), dried over anhydrous Na$_2$SO$_4$, filtered and concentrated in vacuo to give the title compound as a yellow solid (400 mg, yield 85.1%).

LC-MS (ESI, pos. ion) m/z: 397.2 [M+H]$^+$;

$^1$H NMR (400 MHz, CDCl$_3$) δ (ppm): 8.85 (s, 1H), 8.37 (d, J=3.8 Hz, 1H), 7.94 (d, J=8.3 Hz, 1H), 7.84 (d, J=9.0 Hz, 2H), 7.80-7.75 (m, 1H), 7.59 (d, J=9.0 Hz, 1H), 7.16-7.12 (m, 1H), 6.68 (s, 1H), 4.61-4.56 (m, 1H), 2.89-2.87 (m, 4H), 2.74-2.72 (m, 2H), 2.38-2.32 (m, 2H), 1.49-1.44 (m, 2H).

Step 5) 3-(5-((5-chloro-2-((1-(pyridin-2-yl)-1H-pyrazol-4-yl)amino)pyrimidin-4-yl)amino) hexahydrocyclopenta[c]pyrrol-2(1H)-yl)-3-oxopropanenitrile To a solution of 5-chloro-N$^4$-(octahydrocyclopenta[c]pyrrol-5-yl)-N$^2$-(1-(pyridin-2-yl)-1H-pyrazol-4-yl)pyrimidine-2,4-diamine (100 mg, 0.252 mmol) and 2-cyanoacetic acid (25 mg, 0.294 mmol) in dichloromethane (5 mL) were added EDCI (97 mg, 0.506 mmol), HOAT (68 mg, 0.501 mmol) and Et$_3$N (54 mg, 0.533 mmol). The reaction mixture was stirred at rt for 6 h and concentrated in vacuo. The residue was purified by silica gel column chromatography (MeOH/DCM (v/v)=1/10) to give the title compound as a white solid (50.1 mg, yield 72.8%).

LC-MS (ESI, pos. ion) m/z: 464.2 [M+H]$^+$;

$^1$H NMR (400 MHz, DMSO-d$_6$) δ (ppm): 9.41 (s, 1H), 8.91 (s, 1H), 8.42 (d, J=4.1 Hz, 1H), 7.96 (d, J=6.4 Hz, 1H), 7.88 (d, J=8.2 Hz, 1H), 7.78 (s, 1H), 7.31-7.26 (m, 1H), 7.09 (s, 1H), 4.60-4.57 (m, 1H), 3.94 (s, 2H), 3.65-3.48 (m, 3H), 3.46-3.41 (m, 2H), 2.76-2.72 (m, 2H), 2.35-2.31 (m, 2H), 1.58-1.51 (m, 2H).

Example 8 1-(5-((5-chloro-2-((1-(pyridin-2-yl)-1H-pyrazol-4-yl)amino)pyrimidin-4-yl)amino) hexahydrocyclopenta[c]pyrrol-2(1H)-yl)ethanone

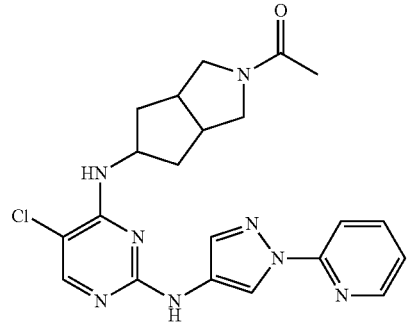 [SMILES: CC(=O)N1CC2CC(Nc3nc(Nc4cnn(-c5ccccn5)c4)ncc3Cl)CC2C1]

To a solution of 5-chloro-N$^4$-(octahydrocyclopenta[c]pyrrol-5-yl)-N$^2$-(1-(pyridin-2-yl)-1H-pyrazol-4-yl)pyrimidine-2,4-diamine (100 mg, 0.252 mmol) and acetic anhydride (31 mg, 0.304 mmol) in dichloromethane (5 mL) was added triethylamine (57 mg, 0.563 mmol). The reaction mixture was stirred at rt overnight and concentrated in vacuo. The residue was purified by preparative TLC (MeOH/DCM (v/v)=1/20) to afford the title compound as a yellow solid (80 mg, yield 72.3%).

LC-MS (ESI, pos. ion) m/z: 439.2 [M+H]$^+$;

$^1$H NMR (400 MHz, CDCl$_3$) δ (ppm): 8.91 (s, 1H), 8.34 (d, J=4.0 Hz, 1H), 7.96 (d, J=8.3 Hz, 1H), 7.90 (s, 1H), 7.82-7.76 (m, 2H), 7.17-7.13 (m, 1H), 6.96 (s, 1H), 5.32-5.28 (m, 1H), 4.57-4.53 (m, 1H), 3.69-3.61 (m, 3H), 3.44-3.39 (m, 1H), 2.94-2.80 (m, 2H), 2.65-2.59 (m, 2H), 2.08 (s, 3H), 1.48-1.41 (m, 2H).

Example 9 5-chloro-N$^2$-(1-(6-methoxypyridin-3-yl)-1H-pyrazol-4-yl)-N$^4$-(octahydrocyclopenta[c]pyrrol-5-yl)pyrimidine-2,4-diamine

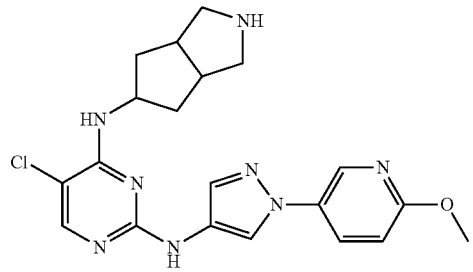 [SMILES: COc1ccc(-n2cc(Nc3ncc(Cl)c(NC4CC5CNCC5C4)n3)cn2)cn1]

Step 1) 2-chloro-5-(4-nitro-1H-pyrazol-1-yl)pyridine

To s suspension of 3-nitro-1H-pyrazole (2.50 g, 22.11 mmol) in anhydrous DMF (80.0 mL) were added 2-chloro-5-iodopyridine (6.36 g, 26.55 mmol), iodocopper (0.85 g, 4.47 mmol, cyclohexane-1,2-diamine (0.52 g, 4.54 mmol) and cesium carbonate (14.54 g, 44.62 mmol). The reaction mixture was degassed for 2 min and refilled with N$_2$ and stirred at 100° C. overnight. Then the mixture was diluted with EtOAc (100 mL), filtered and washed with MeOH (550 mL). The filtrate was concentrated in vacuo. The residue was purified by silica gel column chromatography (EA/PE (v/v)=1/4 to 1/2) to afford the title compound as a light yellow solid (0.36 g, yield 7%).

LC-MS (ESI, pos. ion) m/z: 225.1 [M+H]⁺;

¹H NMR (400 MHz, CDCl₃) δ (ppm): 8.80 (d, J=2.8 Hz, 1H), 8.66 (s, 1H), 8.32 (s, 1H), 8.07 (dd, J=8.6, 2.9 Hz, 1H), 7.53 (d, J=8.6 Hz, 1H).

Step 2) 2-methoxy-5-(4-nitro-1H-pyrazol-1-yl)pyridine

To a suspension of 2-chloro-5-(4-nitro-1H-pyrazol-1-yl)pyridine (0.36 g, 1.60 mmol) in MeOH (15.0 mL) was added a solution of sodium methanolate in MeOH (5.0 mL, 25.0 mmol, 5 M). The reaction mixture was heated to 50° C. and stirred for 12 h and concentrated in vacuo. The residue was diluted with water (15.0 mL), and then filtered. The filter cake was washed with water (5.0 mL) and the filtrate was extracted with DCM (20 mL×3). The combined organic layers were dried over anhydrous Na₂SO₄, filtered and concentrated in vacuo. The residue and the filter cake was combined and dried in vacuo to afford the title compound as a yellow solid (0.32 g, yield 91%).

LC-MS (ESI, pos. ion) m/z: 221.2 [M+H]⁺;

¹H NMR (400 MHz, CDCl₃) δ (ppm): 8.53 (s, 1H), 8.49 (d, J=2.7 Hz, 1H), 8.27 (s, 1H), 7.92 (dd, J=8.9, 2.8 Hz, 1H), 6.90 (d, J=8.9 Hz, 1H), 4.00 (s, 3H).

Step 3) 1-(6-methoxypyridin-3-yl)-1H-pyrazol-4-amine

To a suspension of 2-methoxy-5-(4-nitro-1H-pyrazol-1-yl)pyridine (0.32 g, 1.50 mmol) in MeOH (10.0 mL) was added Pd/C (0.067 g, mass %=10%). The reaction mixture was stirred at room temperature for 1 h under H₂ atmosphere and then filtered. The filter cake was washed with MeOH (10.0 mL) and the filtrate was concentrated in vacuo. The residue was purified by silica gel column chromatography (EtOAc/PE (v/v)=1/1 to DCM/(a solution of NH₃ in MeOH (3M) (v/v)=20/1) to afford the title compound as a black solid (0.15 g, yield 54%).

LC-MS (ESI, pos. ion) m/z: 191.3 [M+H]⁺;

¹H NMR (400 MHz, DMSO-d₆) δ (ppm): 8.48 (d, J=2.7 Hz, 1H), 8.02 (dd, J=8.9, 2.8 Hz, 1H), 7.66 (s, 1H), 7.26 (s, 1H), 6.90 (d, J=8.9 Hz, 1H), 4.17 (s, 2H), 3.87 (s, 3H).

Step 4) tert-butyl 5-((5-chloro-2-((1-(6-methoxypyridin-3-yl)-1H-pyrazol-4-yl)amino)pyrimidin-4-yl)amino)hexahydrocyclopenta[c]pyrrole-2(1H)-carboxylate To a suspension of tert-butyl 5-((2,5-dichloropyrimidin-4-yl)amino) hexahydrocyclopenta[c]pyrrole-2(1H)-carboxylate (0.30 g, 0.81 mmol) in anhydrous 1,4-dioxane (10.0 mL) were added 1-(6-methoxypyridin-3-yl)-1H-pyrazol-4-amine (0.15 g, 0.79 mmol), Pd(OAc)₂ (0.037 g, 0.17 mmol), BINAP (0.10 g, 0.16 mmol) and cesium carbonate (0.53 g, 1.64 mmol). The mixture was degassed for 2 min and refilled with N₂, then and heated to 100° C. and stirred overnight. The mixture was concentrated in vacuo and the residue was purified by silica chromatography (EtOAc/PE (v/v)=1/2 to 2/1) to afford the title compound as a yellow solid (0.24 g, yield 57%).

LC-MS (ESI, pos. ion) m/z: 527.3 [M+H]⁺;

¹H NMR (400 MHz, CDCl₃) δ (ppm): 8.43 (d, J=2.6 Hz, 1H), 8.23 (s, 1H), 7.93 (dd, J=8.9, 2.8 Hz, 1H), 7.90 (s, 1H), 7.75 (s, 1H), 6.83 (d, J=8.9 Hz, 1H), 6.80 (s, 1H), 5.34 (d, J=7.1 Hz, 1H), 4.48-4.35 (m, 1H), 3.97 (s, 3H), 3.53-3.45 (m, 2H), 3.43-3.33 (m, 2H), 2.74-2.65 (m, 2H), 2.52-2.41 (m, 2H), 1.48-1.45 (m, 11H).

Step 5) 5-chloro-N²-(1-(6-methoxypyridin-3-yl)-1H-pyrazol-4-yl)-N⁴-(octahydrocyclopenta[c]pyrrol-5-yl)pyrimidine-2,4-diamine To a suspension of tert-butyl 5-((5-chloro-2-((1-(6-methoxypyridin-3-yl)-1H-pyrazol-4-yl)amino)pyrimidin-4-yl)amino)hexahydrocyclopenta[c]pyrrole-2(1H)-carboxylate (0.24 g, 0.46 mmol) in DCM (10.0 mL) was added a solution of HCl in EtOAc (10.0 mL, 3 M). The reaction mixture was stirred at room temperature for 30 min and then concentrated in vacuo. The residue was diluted with DCM (10 mL) and saturated Na₂CO₃ aqueous solution (10 mL) and the resulting mixture was stirred for another 15 min. The resulting mixture was extracted with DCM (20 mL×3) and DCM/MeOH (v/v)=10/1, 20 mL×3). The combined organic layers were dried over anhydrous Na₂SO₄, filtered and concentrated in vacuo. The residue was purified by silica gel column chromatography (DCM/(a solution of NH₃ in MeOH (3M)) (v/v)=50/1 to 25/1) to afford the title compound as a yellow solid (0.17 g, yield 87%).

LC-MS (ESI, pos. ion) m/z: 427.4 [M+H]⁺;

¹H NMR (400 MHz, DMSO-d₆) δ (ppm): 9.25 (s, 1H), 8.53 (d, J=2.6 Hz, 1H), 8.38 (s, 1H), 8.06 (dd, J=8.9, 2.8 Hz, 1H), 7.90 (s, 1H), 7.78 (s, 2H), 6.95 (d, J=8.9 Hz, 1H), 4.53-4.41 (m, 1H), 3.89 (s, 3H), 2.89-2.82 (m, 2H), 2.82-2.74 (m, 2H), 2.64-2.55 (m, 2H), 2.27-2.15 (m, 2H), 1.53-1.40 (m, 2H).

Example 10 3-(5-((5-chloro-2-((1-(6-methoxypyridin-3-yl)-1H-pyrazol-4-yl)amino)pyrimidin-4-yl)amino)hexahydrocyclopenta[c]pyrrol-2(1H)-yl)-3-oxopropanenitrile

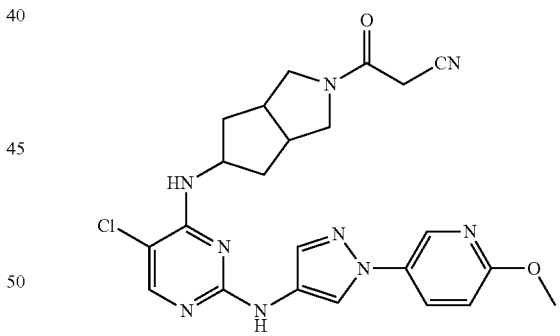

To a suspension of 5-chloro-N²-(1-(6-methoxypyridin-3-yl)-1H-pyrazol-4-yl)-N⁴-(octahydrocyclopenta[c]pyrrol-5-yl)pyrimidine-2,4-diamine (75 mg, 0.18 mmol) in anhydrous DCM (2.0 mL) were added 2-cyanoacetic acid (0.004 g, 0.045 mmol), EDCI (0.007 g, 0.037 mmol), HOAT (0.006 g, 0.043 mmol) and Et₃N (0.005 g, 0.051 mmol). The reaction mixture was stirred at room temperature for 30 min. The mixture was diluted with DCM (30 mL), washed with water (10 mL×2), dried over anhydrous Na₂SO₄, filtered and concentrated in vacuo. The residue was purified by silica gel column chromatography (DCM/(a solution of NH₃ in MeOH (3M)) (v/v)=100/1 to 50/1) to afford the title compound as a light yellow solid (75 mg, yield 86%).

LC-MS (ESI, pos. ion) m/z: 494.0 [M+H]⁺;

$^1$H NMR (400 MHz, CDCl$_3$) δ (ppm): 8.42 (d, J=2.7 Hz, 1H), 8.20 (s, 1H), 7.96-7.90 (m, 2H), 7.77 (s, 1H), 6.86-6.81 (m, 2H), 5.29 (d, J=7.1 Hz, 1H), 4.51-4.38 (m, 1H), 3.97 (s, 3H), 3.75-3.64 (m, 3H), 3.49-3.43 (m, 3H), 2.92-2.71 (m, 2H), 2.61-2.48 (m, 2H), 1.55-1.41 (m, 2H).

Example 11 1-(5-((5-chloro-2-((1-(6-methoxypyridin-3-yl)-1H-pyrazol-4-yl)amino)pyrimidin-4-yl)amino)hexahydrocyclopenta[c]pyrrol-2(1H)-yl)ethanone

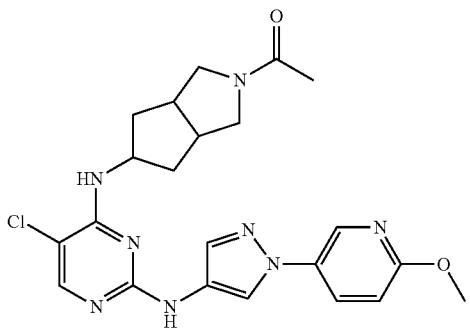 [SMILES: COc1ccc(-n2cc(Nc3ncc(Cl)c(NC4CC5CN(C(C)=O)CC5C4)n3)cn2)cn1]

To a suspension of 5-chloro-N$^2$-(1-(6-methoxypyridin-3-yl)-1H-pyrazol-4-yl)-N$^4$-(octahydrocyclopenta[c]pyrrol-5-yl)pyrimidine-2,4-diamine (0.050 g, 0.12 mmol) in DCM (3.0 mL) were added Et$_3$N (0.020 g, 0.19 mmol) and acetyl acetate (0.015 g, 0.15 mmol). The reaction mixture was stirred at room temperature for 30 min and then concentrated in vacuo. The residue was purified by silica gel column chromatography (DCM/(a solution of NH$_3$ in MeOH (3M)) (v/v)=100/1 to 50/1) to afford the title compound as a white solid (37 mg, yield 67%).

LC-MS (ESI, pos. ion) m/z: 469.1 [M+H]$^+$;

$^1$H NMR (400 MHz, CDCl$_3$) δ (ppm): 8.42 (d, J=2.6 Hz, 1H), 8.21 (s, 1H), 7.93 (dd, J=9.0, 2.8 Hz, 1H), 7.91 (s, 1H), 7.76 (s, 1H), 6.86-6.81 (m, 2H), 5.28 (d, J=7.1 Hz, 1H), 4.50-4.37 (m, 1H), 3.97 (s, 3H), 3.67-3.59 (m, 3H), 3.44-3.37 (m, 1H), 2.83-2.69 (m, 2H), 2.57-2.46 (m, 2H), 2.07 (s, 3H), 1.50-1.43 (m, 2H).

Example 12 1-(5-((5-chloro-2-((1-methyl-1H-pyrazol-4-yl)amino)pyrimidin-4-yl)amino) hexahydrocyclopenta[c]pyrrol-2(1H)-yl)-2-cyclopropylethanone

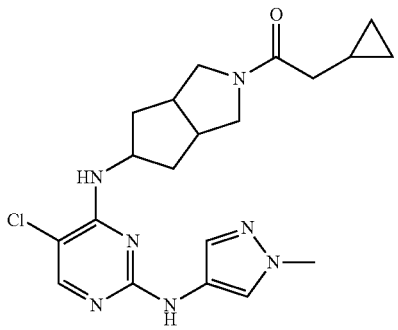 [SMILES: Cn1cc(Nc2ncc(Cl)c(NC3CC4CN(C(=O)CC5CC5)CC4C3)n2)cn1]

Step 1) tert-butyl 5-((5-chloro-2-((1-methyl-1H-pyrazol-4-yl)amino)pyrimidin-4-yl)amino) hexahydrocyclopenta[c]pyrrole-2(1H)-carboxylate To a suspension of tert-butyl 5-((2,5-dichloropyrimidin-4-yl)amino)hexahydrocyclopenta[c]pyrrole-2(1H)-carboxylate (579.6 mg, 1.55 mmol) and 1-methyl-1H-pyrazol-4-amine hydrochloride (213.0 mg, 1.34 mmol) in n-BuOH (5 mL) was added N-ethyldiisopropylamine (668.2 mg, 5.17 mmol). The reaction mixture was stirred at 150° C. in a sealed tube overnight and concentrated in vacuo. The residue was purified by silica gel column chromatography (MeOH/DCM (v/v)=1/80) to give the title compound as a beige solid (672.6 mg, yield 100%).

LC-MS (ESI, pos. ion) m/z: 434.3 [M+H]$^+$.

Step 2) 5-chloro-N$^2$-(1-methyl-1H-pyrazol-4-yl)-N$^4$-(octahydrocyclopenta[c]pyrrol-5-yl)pyrimidine-2,4-diamine To a solution of tert-butyl 5-((5-chloro-2-((1-methyl-1H-pyrazol-4-yl)amino)pyrimidin-4-yl)amino)hexahydrocyclopenta[c]pyrrole-2(1H)-carboxylate (672.6 mg, 1.55 mmol) in DCM (10 mL) was added a solution of HCl in EtOAc (10 mL, 40 mmol). The reaction mixture was stirred at rt overnight and concentrated in vacuo. The residue was dissolved in water (30 mL), and the resulting solution was adjusted to pH=10 with saturated Na$_2$CO$_3$ aqueous solution, then extracted with DCM (250 mL×3). The combined organic phases were washed with brine (250 mL), dried over anhydrous Na$_2$SO$_4$, then filtered and concentrated in vacuo. The residue was purified by silica gel column chromatography (MeOH/DCM (v/v)=1/5) to give the title compound as a beige solid (410 mg, yield 79.2%).

LC-MS (ESI, pos. ion) m/z: 334.2 [M+H]$^+$;

$^1$H NMR (400 MHz, DMSO-d$_6$) δ (ppm): 10.01 (s, 1H), 7.88 (s, 1H), 7.66 (s, 1H), 7.55 (s, 1H), 6.70 (s, 1H), 5.54 (s, 1H), 4.40 (m, 1H), 3.89 (s, 3H), 3.39 (d, J=11.6 Hz, 2H), 3.29 (m, 2H), 2.94 (m, 2H), 2.51 (m, 2H), 1.83 (m, 2H).

Step 3) 1-(5-((5-chloro-2-((1-methyl-1H-pyrazol-4-yl)amino)pyrimidin-4-yl)amino) hexahydrocyclopenta[c]pyrrol-2(1H)-yl)-2-cyclopropylethanone To a solution of 5-chloro-N$^2$-(1-methyl-1H-pyrazol-4-yl)-N$^4$-(octahydrocyclopenta[c]pyrrol-5-yl)pyrimidine-2,4-diamine (101.0 mg, 0.30 mmol) and 2-cyclopropylacetic acid (64.6 mg, 0.64 mmol) in DCM (15 mL) were added HOAT (89.2 mg, 0.66 mmol), EDCI (122.4 mg, 0.63 mmol) and Et$_3$N (104.0 mg, 1.03 mmol). The reaction mixture was stirred at rt for 0.5 h, then quenched with H$_2$O (30 mL) and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/30) to give the title compound as a beige solid (83.2 mg, yield 66.1%).

LC-MS (ESI, pos. ion) m/z: 416.3 [M+H]$^+$;

$^1$H NMR (400 MHz, CDCl$_3$) δ (ppm): 7.89 (s, 1H), 7.68 (s, 1H), 7.56 (s, 1H), 6.71 (s, 1H), 5.25 (d, J=7.2 Hz, 1H), 4.42 (m, 1H), 3.90 (s, 3H), 3.65 (d, J=6.2 Hz, 2H), 3.61 (m, 1H), 3.41 (dd, J=10.8, 3.2 Hz, 1H), 2.78 (m, 2H), 2.50 (td, J=15.8, 7.9 Hz, 2H), 2.25 (m, 2H), 1.45 (m, 2H), 1.11 (m, 1H), 0.59 (q, J=5.4 Hz, 2H), 0.19 (q, J=5.0 Hz, 2H).

Example 13 5-chloro-N⁴-(2-(cyclopropylsulfonyl)octahydrocyclopenta[c]pyrrol-5-yl)-N²-(1-methyl-1H-pyrazol-4-yl)pyrimidine-2,4-diamine

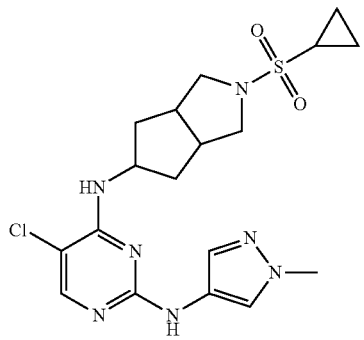 [SMILES: Cn1cc(Nc2ncc(Cl)c(NC3CC4CN(S(=O)(=O)C5CC5)CC4C3)n2)cn1]

Under the protection of nitrogen, to a suspension of 5-chloro-N²-(1-methyl-1H-pyrazol-4-yl)-N⁴-(octahydrocyclopenta[c]pyrrol-5-yl)pyrimidine-2,4-diamine (60 mg, 0.18 mmol) and triethylamine (28 mg, 0.28 mmol) in a mixture of anhydrous DCM (10.0 mL) and DMF (0.50 mL) was added cyclopropanesulfonyl chloride (31 mg, 0.22 mmol). The reaction mixture was stirred at room temperature overnight and then concentrated in vacuo. The residue was purified by silica gel column chromatography (DCM/MeOH (v/v)=50/1 to 30/1 to 20/1) to afford the title compound as a white solid (31 mg, yield 39%).

LC-MS (ESI, pos, ion) m/z: 438.2 [M+H]⁺;

¹H NMR (400 MHz, CDCl₃) δ (ppm): 7.89 (s, 1H), 7.67 (s, 1H), 7.54 (s, 1H), 6.58 (s, 1H), 5.38 (d, J=7.5 Hz, 1H), 4.42-4.29 (m, 1H), 3.90 (s, 3H), 3.42-3.29 (m, 4H), 2.83-2.74 (m, 2H), 2.54-2.45 (m, 2H), 2.42-2.33 (m, 1H), 1.55-1.45 (m, 2H), 1.26-1.20 (m, 2H), 1.07-0.99 (m, 2H).

Example 14 (5-((5-chloro-2-((1-methyl-1H-pyrazol-4-yl)amino)pyrimidin-4-yl)amino) hexahydrocyclopenta[c]pyrrol-2(1H)-yl)(cyclopropyl)methanone

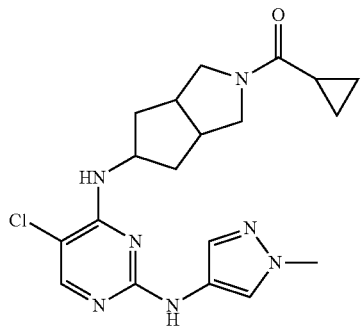 [SMILES: Cn1cc(Nc2ncc(Cl)c(NC3CC4CN(C(=O)C5CC5)CC4C3)n2)cn1]

To a solution of 5-chloro-N²-(1-methyl-1H-pyrazol-4-yl)-N⁴-(octahydrocyclopenta[c]pyrrol-5-yl)pyrimidine-2,4-diamine (70 mg, 0.210 mmol) and triethylamine (35 mg, 0.346 mmol) in dichloromethane (5 mL) was added cyclopropanecarbonyl chloride (27 mg, 0.258 mmol). The reaction mixture was stirred at rt for 20 min and concentrated in vacuo. The residue was purified by preparative TLC (MeOH/DCM (v/v)=1/20) to afford the title compound as a yellow solid (26 mg, yield 30.9%).

LC-MS (ESI, pos. ion) m/z: 402.1 [M+H]⁺;

1H NMR (400 MHz, CDCl₃) δ (ppm): 7.87 (s, 1H), 7.66 (s, 1H), 7.53 (s, 1H), 6.69 (s, 1H), 5.25 (d, J=7.1 Hz, 1H), 4.46-4.38 (m, 1H), 3.88 (s, 3H), 3.84-3.77 (m, 1H), 3.63 (d, J=6.6 Hz, 2H), 2.83-2.69 (m, 2H), 2.53-2.44 (m, 2H), 1.69-1.58 (m, 4H), 1.01 (t, J=3.6 Hz, 2H), 0.79-0.74 (m, 2H).

Example 15 ethyl 5-((5-chloro-2-((1-methyl-1H-pyrazol-4-yl)amino)pyrimidin-4-yl)amino)hexahydrocyclopenta[c]pyrrole-2(1H)-carboxylate

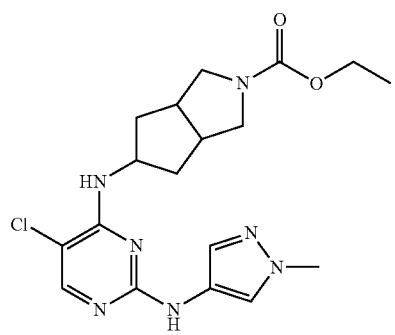 [SMILES: CCOC(=O)N1CC2CC(Nc3nc(Nc4cnn(C)c4)ncc3Cl)CC2C1]

To a solution of 5-chloro-N²-(1-methyl-1H-pyrazol-4-yl)-N⁴-(octahydrocyclopenta[c]pyrrol-5-yl)pyrimidine-2,4-diamine (71 mg, 0.213 mmol) and triethylamine (35 mg, 0.346 mmol) in DCM (5 mL) was added ethyl carbonochloridate (27 mg, 0.249 mmol). The reaction mixture was stirred at rt for 20 min and concentrated in vacuo. The residue was purified by preparative TLC (MeOH/DCM (v/v)=1/20) to afford the title compound as a yellow solid (22 mg, yield 25.5%).

LC-MS (ESI, pos. ion) m/z: 406.2 [M+H]⁺;

¹H NMR (400 MHz, CDCl₃) δ (ppm): 7.86 (s, 1H), 7.66 (s, 1H), 7.51 (s, 1H), 6.60 (s, 1H), 5.26 (d, 1H), 4.39 (m, 9.2 Hz, 1H), 4.14 (q, 2H), 3.87 (s, 3H), 3.47 (d, 4H), 2.74-2.67 (m, 2H), 2.50-2.41 (m, 2H), 1.46-1.40 (m, 2H), 1.26 (s, 3H).

Example 16 1-(5-((5-chloro-2-((1-methyl-1H-pyrazol-4-yl)amino)pyrimidin-4-yl)amino)hexahydrocyclopenta[c]pyrrol-2(1H)-yl)-2-methylpropan-2-ol

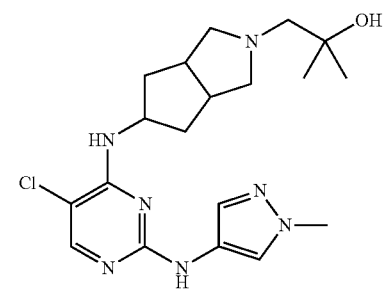 [SMILES: Cn1cc(Nc2ncc(Cl)c(NC3CC4CN(CC(C)(C)O)CC4C3)n2)cn1]

To a solution of 5-chloro-N²-(1-methyl-1H-pyrazol-4-yl)-N⁴-(octahydrocyclopenta[c]pyrrol-5-yl)pyrimidine-2,4-diamine (118.9 mg, 0.36 mmol) in MeOH (10 mL) was added 2,2-dimethyloxirane (44.1 mg, 0.61 mmol). The reaction mixture was stirred at 80° C. in a sealed tube overnight, then cooled down to rt and concentrated in vacuo. The residue was purified by silica gel column chromatography (MeOH/DCM (v/v)=1/10) to give the title compound as a beige solid (107.9 mg, yield 74.6%).

LC-MS (ESI, pos. ion) m/z: 406.3 [M+H]$^+$;

$^1$H NMR (400 MHz, CDCl$_3$ and MeOH-d$_4$) δ (ppm): 7.75 (s, 1H), 7.64 (s, 1H), 7.53 (s, 1H), 4.33 (m, 1H), 3.83 (s, 3H), 3.33 (m, 2H), 2.94 (d, J=9.3 Hz, 2H), 2.74 (m, 1H), 2.67 (m, 1H), 2.63 (s, 2H), 2.38 (dt, J=12.9, 6.6 Hz, 2H), 1.49 (m, 2H), 1.24 (s, 6H).

Example 17 5-chloro-N$^4$-(2-((cyclopropylmethyl)sulfonyl)octahydrocyclopenta[c]pyrrol-5-yl)-N$^2$-(1-methyl-1H-pyrazol-4-yl)pyrimidine-2,4-diamine

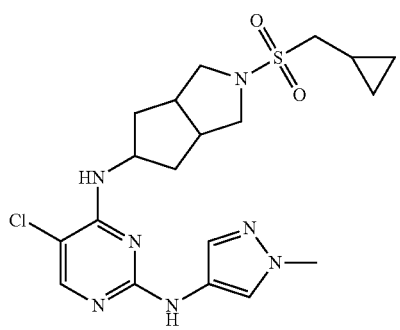 [SMILES: Cn1cc(Nc2ncc(Cl)c(NC3CC4CN(S(=O)(=O)CC5CC5)CC4C3)n2)cn1]

Step 1) sodium cyclopropyl methanesulfonate

To the solid of (bromomethyl)cyclopropane (2.0 g, 14.83 mmol) was added saturated Na$_2$SO$_3$ aqueous solution (20.0 mL). The reaction mixture was heated to reflux and stirred for 24 h and concentrated in vacuo. To the residue was added EtOH (30 mL), and the mixture was stirred at 50° C. for 30 min, then filtered immediately. The filtrate was concentrated in vacuo and the residue was diluted with toluene (20 mL), and then concentrated in vacuo again. The residue was dried in vacuo to afford the title compound as a white solid (1.25 g, yield 53%).

LC-MS (ESI, neg. ion) m/z: 135.1 [M-Na]$^-$;

$^1$H NMR (600 MHz, DMSO-d$_6$) δ (ppm): 2.34 (d, J=6.5 Hz, 2H), 0.99-0.89 (m, 1H), 0.45-0.33 (m, 2H), 0.19-0.09 (m, 2H).

Step 2) cyclopropylmethanesulfonyl chloride

To a suspension of sodium cyclopropylmethanesulfonate (0.48 g, 3.04 mmol) in anhydrous THF (10.0 mL) were added DMF (0.26 mL, 3.40 mmol) and thionyl chloride (0.73 g, 6.15 mmol). The reaction mixture was heated to reflux and stirred for 3 h, then cooled down to room temperature and filtered. The filtrate was concentrated in vacuo to afford the title compound as brown liquid (0.47 g, 100%). The crude product was used for next reaction without further purification.

Step 3) 5-chloro-N$^4$-(2-((cyclopropylmethyl)sulfonyl)octahydrocyclopenta[c]pyrrol-5-yl)-N$^2$-(1-methyl-1H-pyrazol-4-yl)pyrimidine-2,4-diamine Under the protection of nitrogen, to a suspension of 5-chloro-N$^2$-(1-methyl-1H-pyrazol-4-yl)-N$^4$-(octahydrocyclopenta[c]pyrrol-5-yl)pyrimidine-2,4-diamine (0.20 g, 0.60 mmol) and triethylamine (0.20 mL, 1.40 mmol) in anhydrous DCM (20.0 mL) was added cyclopropylmethanesulfonyl chloride (0.14 g, 0.91 mmol) slowly. The reaction mixture was stirred at room temperature for 2 h and concentrated in vacuo. The residue was purified by silica gel column chromatography (DCM/(a solution of NH$_3$ in MeOH) (3M) (v/v)=50/1 to 30/1) to afford the title compound as a light yellow solid (50 mg, yield 18%).

LC-MS (ESI, pos. ion) m/z: 452.2 [M+H]$^+$;

$^1$H NMR (600 MHz, CDCl$_3$) δ (ppm): 7.87 (s, 1H), 7.65 (s, 1H), 7.52 (s, 1H), 6.58 (s, 1H), 5.29 (d, J=5.8 Hz, 1H), 4.35-4.27 (m, 1H), 3.88 (s, 3H), 3.44-3.37 (m, 2H), 3.36-3.30 (m, 2H), 2.94 (d, J=7.1 Hz, 2H), 2.77-2.70 (m, 2H), 2.51-2.44 (m, 2H), 1.50-1.44 (m, 2H), 1.19-1.13 (m, 1H), 0.76-0.70 (m, 2H), 0.41-0.35 (m, 2H).

Example 18 5-((5-chloro-2-((1-methyl-1H-pyrazol-4-yl)amino)pyrimidin-4-yl)amino)-N-ethylhexahydrocyclopenta[c]pyrrole-2(1H)-carboxamide

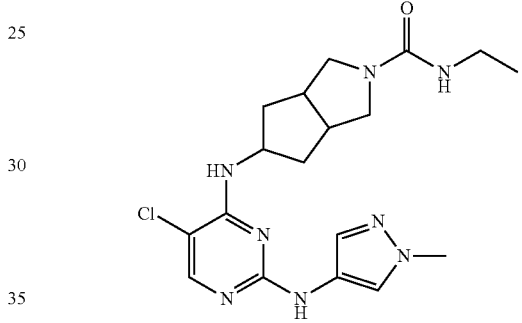

To a solution of phenyl carbonochloridate (506.5 mg, 3.235 mmol) at 0° C. was dropwise added a solution of ethanamine in THF (6 mL, 12 mmol, 2 M). The reaction mixture was stirred at rt for 10 min. The reaction was quenched with H$_2$O (20 mL), extracted with EtOAc (30 mL×3). The combined organic phases were dried over anhydrous Na$_2$SO$_4$, filtered and concentrated in vacuo to give phenyl ethylcarbamate as a colorless liquid. To the solution of phenyl ethylcarbamate in DCM (20 mL) were added N,N-diethylethanamine (162.8 mg, 1.609 mmol) and 5-chloro-N$^2$-(1-methyl-1H-pyrazol-4-yl)-N$^4$-(octahydrocyclopenta[c]pyrrol-5-yl)pyrimidine-2,4-diamine (107.6 mg, 0.3223 mmol). The reaction mixture was stirred at rt overnight and then concentrated in vacuo. The residue was purified by silica gel column chromatography (DCM/MeOH (v/v)=15/1) to give the title compound as a white solid (95 mg, yield 59%).

LC-MS (ESI, pos. ion) m/z: 405.3 [M+H]$^+$;

$^1$H NMR (400 MHz, CDCl$_3$) δ (ppm): 7.85 (s, 1H), 7.66 (s, 1H), 7.52 (s, 1H), 6.72 (s, 1H), 5.36 (d, J=7.2 Hz, 1H), 4.42 (dd, J=15.3, 7.7 Hz, 1H), 4.18-4.26 (m, 1H), 3.87 (s, 3H), 3.48 (dd, J=10.1, 7.5 Hz, 2H), 3.37-3.23 (m, 4H), 2.79-2.69 (m, 2H), 2.49-2.38 (m, 2H), 1.53-1.41 (m, 2H), 1.15 (t, J=7.2 Hz, 3H).

157

Example 19 5-((5-chloro-2-((1-methyl-1H-pyrazol-4-yl)amino)pyrimidin-4-yl)amino)-N-cyclopropyl-hexahydrocyclopenta[c]pyrrole-2(1H)-carboxamide

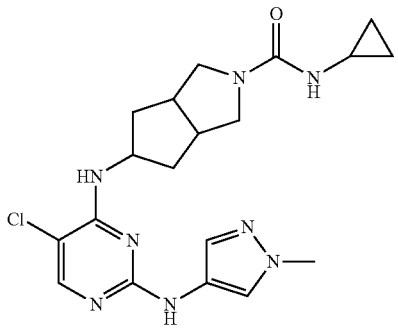 [SMILES: Cn1cc(Nc2ncc(Cl)c(NC3CC4CN(C(=O)NC5CC5)CC4C3)n2)cn1]

Step 1) Phenyl Cyclopropylcarbamate

To a suspension of phenyl carbonochloridate (2.00 g, 12.78 mmol) and triethylamine (3.60 mL, 25.08 mmol) in anhydrous DCM (20.0 mL) was added cyclopropanamine (1.10 g, 19.24 mmol) slowly at 0° C. The reaction mixture was stirred at room temperature overnight. The mixture was diluted with DCM (50 mL), washed with water (40 mL×2) and brine (40 mL). The separated organic layer was dried over anhydrous $Na_2SO_4$, filtered and concentrated in vacuo. The residue was purified by silica gel column chromatography (EtOAc/PE (v/v)=1/20 to 1/10) to afford the title compound as a white solid (0.85 g, yield 38%).

LC-MS (ESI, pos. ion) m/z: 178.3 [M+H]$^+$;

$^1$H NMR (400 MHz, CDCl$_3$) δ (ppm): 7.40-7.31 (m, 2H), 7.23-7.16 (m, 1H), 7.16-7.08 (m, 2H), 5.22 (s, 1H), 2.81-2.63 (m, 1H), 0.83-0.75 (m, 2H), 0.67-0.59 (m, 2H).

Step 2) 5-((5-chloro-2-((1-methyl-1H-pyrazol-4-yl)amino)pyrimidin-4-yl)amino)-N-cyclopropyl hexahydrocyclopenta[c]pyrrole-2(1H)-carboxamide To a suspension of 5-chloro-N$^2$-(1-methyl-1H-pyrazol-4-yl)-N$^4$-(octahydrocyclopenta[c]pyrrol-5-yl)pyrimidine-2,4-diamine (0.10 g, 0.30 mmol) in THF (5.0 mL) were added phenyl cyclopropylcarbamate (0.12 g, 0.68 mmol) and triethylamine (0.15 mL, 1.10 mmol). The mixture was heated to reflux and stirred for 24 h, and then concentrated in vacuo. The residue was purified by silica gel column chromatography (DCM/(a solution of NH$_3$ in MeOH) (3M) (v/v)=100/1 to 50/1 to 30/1) to afford the title compound as a light yellow solid (50 mg, yield 40%).

LC-MS (ESI, pos. ion) m/z: 417.0 [M+H]$^+$;

$^1$H NMR (400 MHz, CDCl$_3$) δ (ppm): 7.86 (s, 1H), 7.65 (s, 1H), 7.52 (s, 1H), 6.64 (s, 1H), 5.33 (d, J=7.2 Hz, 1H), 4.49 (s, 1H), 4.47-4.35 (m, 1H), 3.87 (s, 3H), 3.50-3.43 (m, 2H), 3.35-3.29 (m, 2H), 2.78-2.70 (m, 2H), 2.68-2.62 (m, 1H), 2.48-2.39 (m, 2H), 1.52-1.43 (m, 2H), 0.75-0.70 (m, 2H), 0.50-0.45 (m, 2H).

158

Example 20 1-(9-((5-chloro-2-((1-methyl-1H-pyrazol-4-yl)amino)pyrimidin-4-yl)amino)-3-azaspiro[5.5]undecan-3-yl)-2-cyclopropyl ethanone

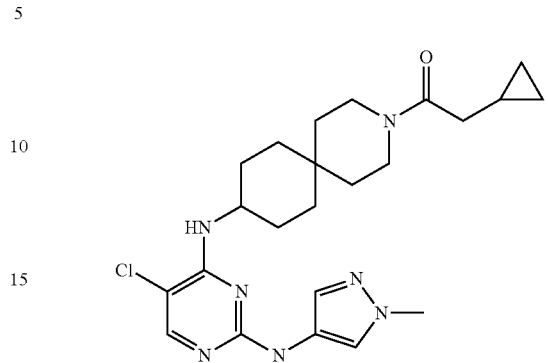

Step 1) tert-butyl 9-oxo-3-azaspiro[5.5]undec-7-ene-3-carboxylate

To a solution of tert-butyl 4-formylpiperidine-1-carboxylate (10.0 g, 46.9 mmol) and KOH (1.3 g, 23.5 mmol) in EtOH (200 mL) was added but-3-en-2-one (3.9 g, 56.3 mmol), the mixture was stirred at 70° C. for 16 h and concentrated in vacuo. The residue was purified by silica gel column chromatography (EtOAc/PE (v/v)=1/4) to give the product as brown oil (5.2 g, yield 41.8%).

LC-MS (ESI, pos. ion) m/z: 210.2 [M-55]$^+$.

Step 2) tert-butyl 9-oxo-3-azaspiro[5.5]undecane-3-carboxylate

To a solution of tert-butyl 9-oxo-3-azaspiro[5.5]undec-7-ene-3-carboxylate (5.2 g, 19.6 mmol) in DCM (80 mL) was added Pd/C (0.5 g, mass %=10%) and the suspension was stirred at room temperature under a H$_2$ atmosphere overnight. The reaction mixture was filtered and concentrated in vacuo, then the residue was purified by silica gel column chromatography (EtOAc/PE (v/v)=1/4) to give the product as brown oil (3.1 g, yield 59.0%).

LC-MS (ESI, pos. ion) m/z: 212.1 [M-55]$^+$.

Step 3) tert-butyl 9-amino-3-azaspiro[5.5]undecane-3-carboxylate

To a solution of tert-butyl 9-oxo-3-azaspiro[5.5]undecane-3-carboxylate (5.35 g, 20.0 mmol) in EtOH (40 mL) were added a solution of NH$_3$ in MeOH (7M, 40 mL, 280.0 mmol) and Ti(Oi-Pr)$_4$ (11.30 g, 40.0 mmol), the mixture was stirred at room temperature overnight. And then NaBH$_4$ (1.51 g, 40.0 mmol) was added portion-wise. After addition, the resulting mixture was stirred at room temperature for another 5 h, then quenched with water (40 mL), stirred for 1 h and filtered. The filtrate was concentrated in vacuo, and the residue was purified by silica gel column chromatography (MeOH/DCM (v/v)=1/25) to give the product as a light yellow solid (1.20 g, yield 22.4%).

LC-MS (ESI, pos. ion) m/z: 269.3 [M+H]$^+$.

Step 4) tert-butyl 9-((2,5-dichloropyrimidin-4-yl)amino)-3-azaspiro[5.5]undecane-3-carboxylate To a solution of 2,4,5-trichloropyrimidine (495.9 mg, 2.7 mmol) in ethanol (20 mL) were added tert-butyl 9-amino- 3-azaspiro[5.5]undecane-3-carboxylate (1.08 g, 4.0 mmol) and Et$_3$N (413.6 mg, 4.1 mmol). The mixture was stirred at room temperature for 12 h and then concentrated in vacuo. The residue was purified by silica gel column chromatography (EtOAc/PE (v/v)=1/10 to 1/7) to give the product as a light yellow solid (387.1 mg, yield 34.5%).

LC-MS (ESI, pos. ion) m/z: 415.0 [M+H]$^+$.

Step 5) tert-butyl 9-((5-chloro-2-((1-methyl-1H-pyrazol-4-yl)amino)pyrimidin-4-yl)amino)-3-azaspiro[5.5]undecane-3-carboxylate To a solution of tert-butyl 9-((2,5-dichloropyrimidin-4-yl)amino)-3-azaspiro[5.5]undecane-3-carboxylate (230.0 mg, 0.55 mmol) and 1-methyl-1H-pyrazol-4-amine hydrochloride (185.4 mg, 1.39 mmol) in n-BuOH (3 mL) was added DIPEA (215.7 mg, 1.67 mmol). The mixture was stirred at 150° C. overnight and then concentrated in vacuo. The residue was purified by silica gel column chromatography (MeOH/DCM (v/v)=1/100 to 1/70) to give the title product as a light yellow solid (87.0 mg, yield 33.0%).

LC-MS (ESI, pos. ion) m/z: 476.1 [M+H]$^+$.

Step 6) 5-chloro-N$^2$-(1-methyl-1H-pyrazol-4-yl)-N$^4$-(3-azaspiro[5.5]undecan-9-yl)pyrimidine-2,4-diamine To a solution of tert-butyl 9-((5-chloro-2-((1-methyl-1H-pyrazol-4-yl)amino)pyrimidin-4-yl)amino)-3-azaspiro[5.5]undecane-3-carboxylate (87.0 mg, 0.18 mmol) in dichloromethane (5 mL) was added a solution of HCl in EtOAc (2 mL, 8 mmol). The mixture was stirred at room temperature for 5 h and then concentrated in vacuo. The residue was dissolved in MeOH (2 mL) and adjusted to pH=10 with a saturated Na$_2$CO$_3$ aqueous solution, then extracted with DCM (20 mL×3). The combined organic phases were washed with brine (20 mL), dried over anhydrous Na$_2$SO$_4$, then filtered and concentrated in vacuo. The residue was purified by preparative TLC (MeOH/DCM (v/v)=1/5) to give the title product as a light yellow solid (54.0 mg, yield 78.6%).

LC-MS (ESI, pos. ion) m/z: 376.1 [M+H]$^+$;
$^1$H NMR (400 MHz, DMSO-d$_6$) δ (ppm): 8.73 (s, 1H), 7.85 (s, 1H), 7.72 (s, 1H), 7.44 (s, 1H), 6.62 (s, 1H), 3.77 (s, 3H), 3.03 (m, 5H), 1.84-1.23 (m, 12H).

Step 7) 1-(9-((5-chloro-2-((1-methyl-1H-pyrazol-4-yl)amino)pyrimidin-4-yl)amino)-3-azaspiro[5.5]undecan-3-yl)-2-cyclopropyl ethanone To a solution of 5-chloro-N$^2$-(1-methyl-1H-pyrazol-4-yl)-N$^4$-(3-azaspiro[5.5]undecan-9-yl)pyrimidine-2,4-diamine (60.2 mg, 0.16 mmol), 2-cyclopropylacetic acid (24.7 mg, 0.25 mmol) and triethylamine (34.5 mg, 0.34 mmol) in dichloromethane (5 mL) were added EDCI (61.4 mg, 0.32 mmol) and HOAT (44.2 mg, 0.33 mmol), the reaction mixture was stirred at room temperature for 3 h. The reaction was quenched with H$_2$O (15 mL) and extracted with DCM (3×10 mL). The combined organic layers were dried over anhydrous Na$_2$SO$_4$, filtered and concentrated in vacuo. The residue was purified by silica gel column chromatography (MeOH/DCM (v/v)=1/30) to afford the target product as a white solid (47.5 mg, yield 64.8%).

LC-MS (ESI, pos. ion) m/z: 458.2 [M+H]$^+$;
$^1$H NMR (400 MHz, CDCl$_3$) δ (ppm): 7.86 (s, 1H), 7.69-7.62 (m, 1H), 7.54-7.47 (m, 1H), 6.63 (s, 1H), 5.12 (s, 1H), 4.00-3.91 (m, 1H), 3.87 (s, 3H), 3.64-3.54 (m, 2H), 3.46-3.33 (m, 2H), 2.28 (d, J=6.6 Hz, 2H), 2.02-1.94 (m, 2H), 1.82-1.70 (m, 2H), 1.60-1.55 (m, 2H), 1.43-1.27 (m, 6H), 1.09-1.01 (m, 1H), 0.61-0.52 (m, 2H), 0.21-0.12 (m, 2H).

Example 21 1-(9-((5-chloro-2-((1-methyl-1H-pyrazol-4-yl)amino)pyrimidin-4-yl)amino)-3-azaspiro[5.5]undecan-3-yl)-2-methylpropan-2-ol

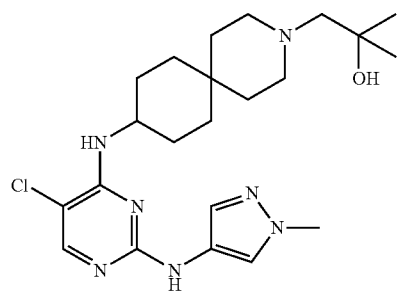 [SMILES: Cn1cc(Nc2ncc(Cl)c(NC3CCC4(CC3)CCN(CC(C)(C)O)CC4)n2)cn1]

To a solution of 5-chloro-N$^2$-(1-methyl-1H-pyrazol-4-yl)-N$^4$-(3-azaspiro[5.5]undecan-9-yl)pyrimidine-2,4-diamine (100.3 mg, 0.27 mmol) in N,N-dimethylformamide (2 mL) was added 2,2-dimethyloxirane (58.5 mg, 0.81 mmol), the reaction mixture was stirred in a sealed tube at 80° C. overnight. The reaction was quenched with H$_2$O (20 mL) and extracted with DCM (3×10 mL). The combined organic layers were dried over anhydrous Na$_2$SO$_4$, filtered and concentrated in vacuo. The residue was purified by silica gel column chromatography (MeOH/DCM (v/v)=1/80 to 1/50) to afford the target product as a light yellow solid (69.4 mg, yield 58.1%).

LC-MS (ESI, pos. ion) m/z: 448.5 [M+H]$^+$;
$^1$H NMR (400 MHz, CDCl$_3$) δ (ppm): 7.85 (s, 1H), 7.68 (s, 1H), 7.48 (s, 1H), 6.60 (s, 1H), 5.11 (d, J=7.1 Hz, 1H), 3.95-3.90 (m, 1H), 3.87 (s, 3H), 3.57-3.46 (m, 1H), 3.37-3.29 (m, 1H), 2.67-2.52 (m, 2H), 2.31 (s, 2H), 1.99-1.90 (m, 2H), 1.78-1.71 (m, 2H), 1.50-1.35 (m, 6H), 1.29-1.26 (m, 2H), 1.15 (s, 6H).

Example 22 (9-((5-chloro-2-((1-methyl-1H-pyrazol-4-yl)amino)pyrimidin-4-yl)amino)-3-azaspiro[5.5]undecan-3-yl)(cyclopropyl)methanone

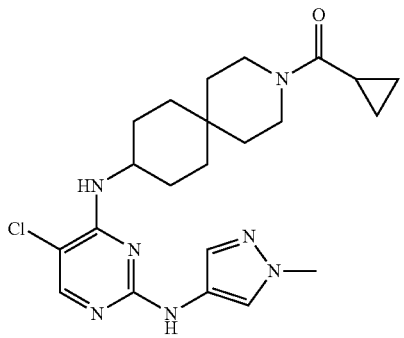 [SMILES: Cn1cc(Nc2ncc(Cl)c(NC3CCC4(CC3)CCN(C(=O)C3CC3)CC4)n2)cn1]

To a solution of 5-chloro-N$^2$-(1-methyl-1H-pyrazol-4-yl)-N$^4$-(3-azaspiro[5.5]undecan-9-yl)pyrimidine-2,4-diamine (150 mg, 0.3990 mmol) and cyclopropanecarbonyl chloride (51 mg, 0.48785 mmol) in dichloromethane (10 mL) was added N,N-diethylethanamine (61 mg, 0.60283 mmol). The reaction mixture was stirred at rt overnight and concentrated in vacuo. The residue was purified by silica gel column chromatography (DCM/MeOH (v/v)=50/1 to 25/1) to give the title product as a white solid (105 mg, yield 59.26%).

LC-MS (ESI, pos. ion) m/z: 444.3 [M+H]+;

$^1$H NMR (400 MHz, DMSO-$d_6$) δ (ppm): 9.01 (s, 1H), 7.85 (s, 1H), 7.73 (s, 1H), 7.44 (s, 1H), 6.66 (d, J=7.8 Hz, 1H), 3.94 (s, 1H), 3.77 (s, 3H), 3.63 (s, 2H), 3.45 (s, 2H), 1.97 (s, 2H), 1.78 (d, J=13.2 Hz, 2H), 1.68 (d, J=15.1 Hz, 2H), 1.61 (d, J=13.4 Hz, 3H), 1.47 (s, 1H), 1.36 (s, 1H), 1.22-1.13 (m, 2H), 0.69 (dd, J=9.8, 5.8 Hz, 4H).

Example 23 5-chloro-N-(3-(cyclopropylsulfonyl)-3-azaspiro[5.5]undecan-9-yl)-N$^2$-(1-methyl-1H-pyrazol-4-yl)pyrimidine-2,4-diamine

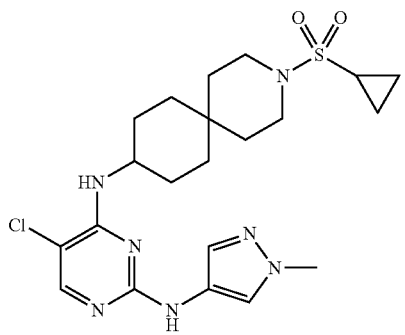 [SMILES: Cn1cc(Nc2ncc(Cl)c(NC3CCC4(CC3)CCN(S(=O)(=O)C3CC3)CC4)n2)cn1]

To a solution of 5-chloro-N$^2$-(1-methyl-1H-pyrazol-4-yl)-N$^4$-(3-azaspiro[5.5]undecan-9-yl)pyrimidine-2,4-diamine (150 mg, 0.3990 mmol) and cyclopropanesulfonyl chloride (67.5 mg, 0.480 mmol) in dichloromethane (10 mL) was added TEA (61 mg, 0.60283 mmol). The mixture was stirred at rt overnight and concentrated in vacuo. The residue was purified by silica gel column chromatography (DCM/MeOH (v/v)=50/1 to 25/1) to give the title product as a white solid (150 mg, yield 78.31%).

LC-MS (ESI, pos. ion) m/z: 480.3 [M+H]+;

$^1$H NMR (400 MHz, CDCl3) δ (ppm): 7.86 (s, 1H), 7.65 (s, 1H), 7.51 (s, 1H), 6.68 (s, 1H), 5.11 (d, J=7.4 Hz, 1H), 3.94 (dd, J=7.3, 3.6 Hz, 1H), 3.87 (s, 3H), 3.29 (dd, J=11.0, 5.2 Hz, 4H), 2.27 (ddd, J=12.9, 8.1, 4.9 Hz, 1H), 2.02-1.93 (m, 2H), 1.77 (d, J=13.2 Hz, 2H), 1.72-1.67 (m, 2H), 1.56-1.50 (m, 2H), 1.43 (t, J=12.1 Hz, 2H), 1.37-1.32 (m, 2H), 1.18 (dd, J=4.8, 2.0 Hz, 2H), 0.98 (dd, J=7.7, 2.1 Hz, 2H).

Example 24 5-((5-chloro-2-((1-methyl-1H-pyrazol-4-yl)amino)pyrimidin-4-yl)amino)-N-ethylhexahydrocyclopenta[c]pyrrole-2(1H)-sulfonamide

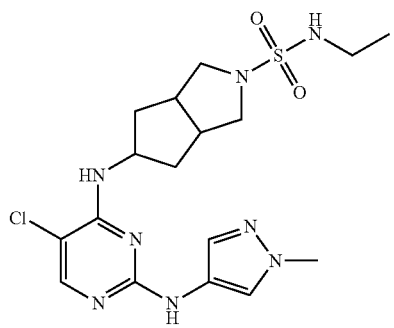 [SMILES: CCNS(=O)(=O)N1CC2CC(Nc3nc(Nc4cnn(C)c4)ncc3Cl)CC2C1]

To a suspension of 5-chloro-N$^2$-(1-methyl-1H-pyrazol-4-yl)-N$^4$-(octahydrocyclopenta[c]pyrrol-5-yl)pyrimidine-2,4-diamine (0.20 g, 0.60 mmol) in anhydrous DCM (5.0 mL) were added Et$_3$N (0.25 mL, 1.80 mmol) and N-ethylsulfamoyl chloride (0.18 g, 1.24 mmol) and the reaction mixture was stirred at room temperature overnight. The reaction was quenched by addition of water (10 mL), extracted with DCM (50 mL×3). The combined organic layers were dried over anhydrous Na$_2$SO$_4$, filtered and concentrated in vacuo. The residue was purified by silica gel column chromatography (DCM/(a solution of NH$_3$ in MeOH) (3M) (v/v)=100/1 to 50/1) to afford the title compound as a white solid (0.12 g, yield 45%).

LC-MS (ESI, pos. ion) m/z: 441.2 [M+H]+;

$^1$H NMR (400 MHz, CDCl$_3$) δ (ppm): 7.86 (s, 1H), 7.64 (s, 1H), 7.51 (s, 1H), 6.62 (s, 1H), 5.38 (d, J=7.5 Hz, 1H), 4.39-4.26 (m, 1H), 4.16 (t, J=5.9 Hz, 1H), 3.87 (s, 3H), 3.25-3.17 (m, 6H), 2.81-2.69 (m, 2H), 2.52-2.41 (m, 2H), 1.49-1.38 (m, 2H), 1.22 (t, J=7.2 Hz, 3H).

Example 25 phenyl 5-((5-chloro-2-((1-methyl-1H-pyrazol-4-yl)amino)pyrimidin-4-yl)amino) hexahydrocyclopenta[c]pyrrole-2(1H)-carboxylate

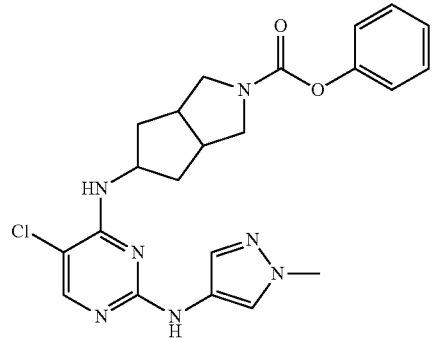 [SMILES: Cn1cc(Nc2ncc(Cl)c(NC3CC4CN(C(=O)Oc5ccccc5)CC4C3)n2)cn1]

To a suspension of 5-chloro-N$^2$-(1-methyl-1H-pyrazol-4-yl)-N$^4$-(octahydrocyclopenta[c]pyrrol-5-yl)pyrimidine-2,4-diamine (0.10 g, 0.30 mmol) in DCM (8 mL) were added triethylamine (0.047 g, 0.47 mmol) and phenyl carbonochloridate (0.059 g, 0.38 mmol). The reaction mixture was stirred at room temperature for 2 h, then quenched by the addition of water (20 mL), extracted with DCM (50 mL×3). The combined organic layers were dried over anhydrous Na$_2$SO$_4$, filtered and concentrated in vacuo. The residue was purified by silica gel column chromatography (DCM/(a solution of NH$_3$ in MeOH) (3M) (v/v)=100/1 to 50/1 to 30/1) to afford the title compound as a yellow solid (85 mg, yield 62%).

LC-MS (ESI, pos. ion) m/z: 454.3 [M+H]+;

$^1$H NMR (400 MHz, CDCl$_3$) δ (ppm): 7.87 (s, 1H), 7.64 (s, 1H), 7.52 (s, 1H), 7.35 (t, J=7.9 Hz, 2H), 7.19 (t, J=7.4 Hz, 1H), 7.13 (d, J=7.6 Hz, 2H), 6.69 (s, 1H), 5.31 (d, J=7.3 Hz, 1H), 4.50-4.36 (m, 1H), 3.87 (s, 3H), 3.78-3.64 (m, 2H), 3.64-3.49 (m, 2H), 2.86-2.73 (m, 2H), 2.59-2.46 (m, 2H), 1.54-1.45 (m, 2H).

Example 26 1-(5-((5-chloro-2-((1-methyl-1H-pyrazol-4-yl)amino)pyrimidin-4-yl)amino)hexahydrocyclopenta[c]pyrrol-2(1H)-yl)-2-phenylethanone

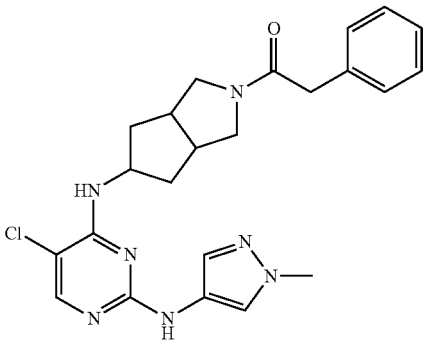 [SMILES: Cn1cc(Nc2ncc(Cl)c(NC3CC4CN(C(=O)Cc5ccccc5)CC4C3)n2)cn1]

To a suspension of 5-chloro-$N^2$-(1-methyl-1H-pyrazol-4-yl)-$N^4$-(octahydrocyclopenta[c]pyrrol-5-yl)pyrimidine-2,4-diamine (51 mg, 0.15 mmol) in DCM (5 mL) were added triethylamine (0.026 g, 0.26 mmol) and 2-phenylacetyl chloride (0.033 g, 0.21 mmol). The reaction mixture was stirred at room temperature overnight, then quenched by addition of water (10 mL), extracted with DCM (30 mL×3). The combined organic layers were dried over anhydrous $Na_2SO_4$, filtered and concentrated in vacuo. The residue was purified by silica chromatography (DCM/3M $NH_3$ in MeOH (v/v)=100/1 to 50/1 to 30/1) to afford the crude product as a yellow solid. The solid was purified further by preparative TLC (DCM/(a solution of $NH_3$ in MeOH (3M)) (v/v)=40/1) to afford the title compound as a yellow solid (28 mg, yield 41%).

LC-MS (ESI, pos. ion) m/z: 452.5 $[M+H]^+$;

$^1$H NMR (400 MHz, $CDCl_3$) δ (ppm): 7.86 (s, 1H), 7.63 (s, 1H), 7.51 (s, 1H), 7.37-7.27 (m, 4H), 6.62 (s, 1H), 5.12 (d, J=6.7 Hz, 1H), 4.39-4.27 (m, 1H), 3.86 (s, 3H), 3.73-3.64 (m, 3H), 3.61-3.50 (m, 2H), 3.46-3.38 (m, 1H), 2.75-2.61 (m, 2H), 2.53-2.31 (m, 2H), 1.36-1.29 (m, 2H).

Example 27 (5-((5-chloro-2-((1-methyl-1H-pyrazol-4-yl)amino)pyrimidin-4-yl)amino) hexahydrocyclopenta[c]pyrrol-2(1H)-yl)(phenyl)methanone

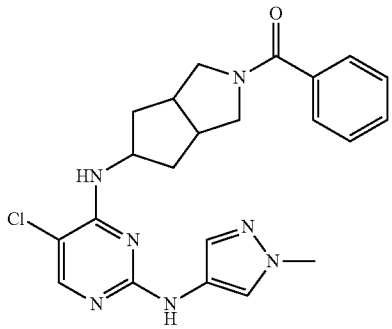 [SMILES: Cn1cc(Nc2ncc(Cl)c(NC3CC4CN(C(=O)c5ccccc5)CC4C3)n2)cn1]

To a suspension of 5-chloro-$N^2$-(1-methyl-1H-pyrazol-4-yl)-$N^4$-(octahydrocyclopenta [c]pyrrol-5-yl)pyrimidine-2,4-diamine (0.058 g, 0.17 mmol) in DCM (3 mL) was added triethylamine (0.023 g, 0.23 mmol). The reaction mixture was cooled down to 0° C., then added benzoyl chloride (0.027 g, 0.19 mmol). The mixture was stirred at 0° C. for 30 min and then quenched by addition of water (20 mL), extracted with DCM (30 mL×3). The combined organic layers were dried over anhydrous $Na_2SO_4$, filtered and concentrated in vacuo. The residue was purified by silica gel column chromatography (DCM/(a solution of $NH_3$ in MeOH) (3M) (v/v)=100/1 to 50/1 to 30/1) to afford the crude product as a yellow solid. The solid was purified further by preparative TLC (DCM/3M $NH_3$ in MeOH (v/v)=40/1) to afford the title compound as a yellow solid (32 mg, yield 42%).

LC-MS (ESI, pos. ion) m/z: 438.4 $[M+H]^+$;

$^1$H NMR (400 MHz, $CDCl_3$) δ (ppm): 7.87 (s, 1H), 7.66 (s, 1H), 7.54 (s, 1H), 7.52-7.48 (m, 2H), 7.43-7.38 (m, 3H), 6.80 (s, 1H), 5.26 (d, J=6.8 Hz, 1H), 4.39-4.27 (m, 1H), 3.99-3.89 (m, 1H), 3.86 (s, 3H), 3.78-3.69 (m, 1H), 3.67-3.58 (m, 1H), 3.46-3.35 (m, 1H), 2.80-2.65 (m, 2H), 2.58-2.47 (m, 1H), 2.41-2.29 (m, 1H), 1.58-1.47 (m, 2H).

Example 28 5-((5-chloro-2-((1-methyl-1H-pyrazol-4-yl)amino)pyrimidin-4-yl)amino)-N-phenylhexahydrocyclopenta[c]pyrrole-2(1H)-carboxamide

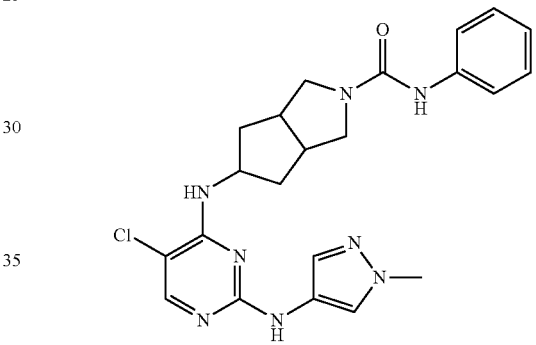

Step 1) phenyl phenylcarbamate

To a solution of aniline (941.3 mg, 10.11 mmol) and $Et_3N$ (2.07 g, 20.46 mmol) in DCM (20 mL) was added phenyl carbonochloridate (3.80 g, 24.27 mmol) at 0° C. After addition, the reaction mixture was stirred at 0° C. for 0.5 h and then moved to rt for another 2 h. The reaction was quenched with water (30 mL), and extracted with DCM (100 mL×3). The combined organic phases were washed with brine (100 mL), dried over anhydrous $Na_2SO_4$, filtered and concentrated in vacuo. The residue was purified by silica gel column chromatography (EtOAc/PE (v/v)=1/20) to give the title compound as a white solid (2.16 g, 100%).

LC-MS (ESI, pos. ion) m/z: 214.2 $[M+H]^+$.

Step 2) 5-((5-chloro-2-((1-methyl-1H-pyrazol-4-yl)amino)pyrimidin-4-yl)amino)-N-phenylhexahydrocyclopenta[c]pyrrole-2(1H)-carboxamide To a solution of 5-chloro-$N^2$-(1-methyl-1H-pyrazol-4-yl)-$N^4$-(octahydrocyclopenta[c]pyrrol-5-yl)pyrimidine-2,4-diamine (164.9 mg, 0.49 mmol) and $Et_3N$ (224.6 mg, 2.22 mmol) in EtOH (20 mL) was added phenyl phenylcarbamate (202.1 mg, 0.95 mmol). The reaction mixture was stirred at rt overnight, then quenched with water (30 mL), and extracted with DCM (100 mL×3). The combined organic phases were washed with brine (100 mL), dried over anhydrous Na$_2$SO$_4$, filtered and concentrated in vacuo. The residue was purified by silica gel column chromatography (DCM/MeOH (v/v)=20/1) to give the title compound as a beige solid (165.2 mg, yield 73.8%).

LC-MS (ESI, pos. ion) m/z: 453.3 [M+H]$^+$;
$^1$H NMR (400 MHz, CDCl$_3$) δ (ppm): 7.88 (s, 1H), 7.67 (s, 1H), 7.56 (s, 1H), 7.42 (d, J=7.7 Hz, 2H), 7.32 (d, J=7.5 Hz, 2H), 7.06 (t, J=7.4 Hz, 1H), 6.74 (s, 1H), 6.22 (s, 1H), 5.38 (d, J=7.3 Hz, 1H), 448 (m, 1H), 3.90 (s, 3H), 3.80 (m, 2H), 3.52 (dd, J=10.6, 2.2 Hz, 2H), 2.85 (m, 2H), 2.52 (dt, J=14.6, 7.5 Hz, 2H), 1.56 (m, 2H).

Example 29 (5-((5-chloro-2-((1-methyl-1H-pyrazol-4-yl)amino)pyrimidin-4-yl)amino) hexahydrocyclopenta[c]pyrrol-2(1H)-yl)(morpholino)methanone

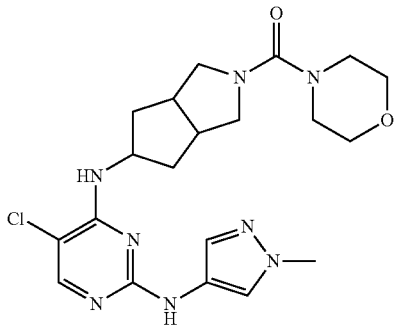 [SMILES: Cn1cc(Nc2ncc(Cl)c(NC3CC4CN(C(=O)N5CCOCC5)CC4C3)n2)cn1]

Step 1) 4-nitrophenyl morpholine-4-carboxylate

To a solution of 4-nitrophenyl carbonochloridate (389.3 mg, 1.93 mmol) and Et$_3$N (304.3 mg, 3.01 mmol) in DCM (10 mL) was added morpholine (185.0 mg, 2.12 mmol). The reaction mixture was stirred at rt for 3.5 h, then quenched with water (30 mL), and extracted with DCM (100 mL×3). The combined organic phases were washed with brine (100 mL), dried over anhydrous Na$_2$SO$_4$, filtered and concentrated in vacuo. The residue was purified by silica gel column chromatography (EtOAc/PE (v/v)=1/2) to give the title compound as a yellow green solid (487.2 mg, yield 100%).

LC-MS (ESI, pos. ion) m/z: 253.2 [M+H]$^+$;
$^1$H NMR (400 MHz, CDCl$_3$) δ (ppm): 8.28 (d, J=9.1 Hz, 2H), 7.33 (d, J=9.1 Hz, 2H), 3.79 (m, 4H), 3.71 (s, 2H), 3.61 (s, 2H).

Step 2) (5-((5-chloro-2-((1-methyl-1H-pyrazol-4-yl)amino)pyrimidin-4-yl)amino)hexahydrocyclopenta[c]pyrrol-2(1H)-yl)(morpholino)methanone To a solution of 5-chloro-N$^2$-(1-methyl-1H-pyrazol-4-yl)-N$^4$-(octahydrocyclopenta[c]pyrrol-5-yl)pyrimidine-2,4-diamine (85.7 mg, 0.26 mmol) and Et$_3$N (276.2 mg, 2.73 mmol) in EtOH (10 mL) was added 4-nitrophenyl morpholine-4-carboxylate (82.4 mg, 0.33 mmol). The reaction mixture was stirred at 100° C. in a sealed tube overnight, then cooled down to rt, and quenched with water (30 mL), then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/40) to give the title compound as a beige solid (72.7 mg, yield 63.4%).

LC-MS (ESI, pos. ion) m/z: 447.4 [M+H]$^+$;
$^1$H NMR (600 MHz, CDCl$_3$) δ (ppm): 7.86 (s, 1H), 7.68 (s, 1H), 7.56 (s, 1H), 7.29 (s, 1H), 5.38 (d, J=4.6 Hz, 1H), 4.30 (s, 1H), 3.88 (s, 3H), 3.71 (m, 6H), 3.47 (m, 4H), 2.66 (s, 2H), 2.41 (s, 2H), 2.32 (s, 2H), 1.51 (s, 2H); $^{13}$C NMR (150 MHz, CDCl$_3$) δ (ppm): 163.0, 157.9, 157.6, 152.8, 131.0, 123.4, 120.9, 104.1, 72.4, 66.7, 61.7, 54.0, 53.5, 46.9, 40.8, 39.4, 38.7.

Example 30 6-(5-((5-chloro-2-((1-methyl-1H-pyrazol-4-yl)amino)pyrimidin-4-yl)amino) hexahydrocyclopenta[c]pyrrol-2(1H)-yl)pyridazine-3-carbonitrile

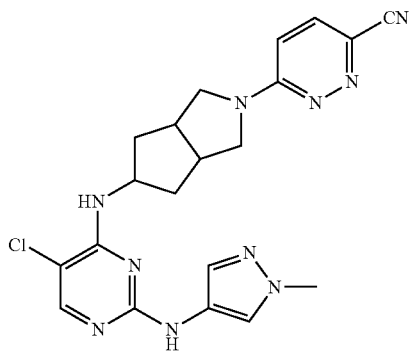 [SMILES: Cn1cc(Nc2ncc(Cl)c(NC3CC4CN(c5ccc(C#N)nn5)CC4C3)n2)cn1]

To a solution of 5-chloro-N$^2$-(1-methyl-1H-pyrazol-4-yl)-N$^4$-(octahydrocyclopenta[c]pyrrol-5-yl)pyrimidine-2,4-diamine (85.8 mg, 0.26 mmol) and Et$_3$N (80.4 mg, 0.80 mmol) in EtOH (10 mL) was added 6-chloropyridazine-3-carbonitrile (72.8 mg, 0.52 mmol). The reaction mixture was stirred at rt overnight, quenched with water (30 mL), and extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/50) to give the title compound as a beige solid (109.6 mg, yield 97.6%).

LC-MS (ESI, pos. ion) m/z: 437.4 [M+H]$^+$;
$^1$H NMR (600 MHz, DMSO-d$_6$) δ (ppm): 9.03 (s, 1H), 7.85 (m, 2H), 7.75 (s, 1H), 7.45 (s, 1H), 7.02 (d, J=9.6 Hz, 1H), 6.93 (d, J=7.8 Hz, 1H), 4.59 (m, 1H), 3.79 (s, 3H), 3.72 (m, 4H), 2.84 (s, 2H), 2.33 (m, 2H), 1.62 (m, 2H); $^{13}$C NMR (150 MHz, CDCl$_3$) δ (ppm): 158.2, 157.5, 131.1, 130.1, 128.2, 124.2, 118.2, 111.8, 72.7, 60.7, 52.9, 40.8, 39.1, 37.6.

Example 31 N$^4$-(2-(tert-butylsulfonyl)octahydrocyclopenta[c]pyrrol-5-yl)-5-chloro-N$^2$-(1-methyl-1H-pyrazol-4-yl)pyrimidine-2,4-diamine

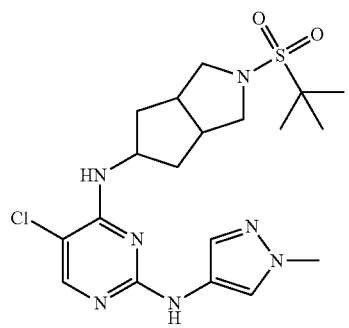 [SMILES: Cn1cc(Nc2ncc(Cl)c(NC3CC4CN(S(=O)(=O)C(C)(C)C)CC4C3)n2)cn1]

Step 1) N⁴-(2-(tert-butylsulfinyl)octahydrocyclopenta[c]pyrrol-5-yl)-5-chloro-N²-(1-methyl-1H-pyrazol-4-yl)pyrimidine-2,4-diamine To a solution of 5-chloro-N²-(1-methyl-1H-pyrazol-4-yl)-N⁴-(octahydrocyclopenta[c]pyrrol-5-yl)pyrimidine-2,4-diamine (98.5 mg, 0.30 mmol) and Et₃N (132.8 mg, 1.31 mmol) in DCM (8 mL) was added a solution of 2-methylpropane-2-sulfinic chloride (92.8 mg, 0.66 mmol) in DCM (2 mL) at 0° C. The reaction mixture was stirred at 0° C. for 1 h, then quenched with water (50 mL), and the resulting mixture was extracted with DCM (100 mL×3). The combined organic phases were washed with brine (100 mL), dried over anhydrous Na₂SO₄, filtered and concentrated in vacuo. The residue was purified by silica gel column chromatography (MeOH/DCM (v/v)=1/50) to give the title compound as a pale yellow solid (129.5 mg, yield 100%).

LC-MS (ESI, pos. ion) m/z: 438.2 [M+H]⁺;

¹H NMR (600 MHz, CDCl₃) δ (ppm): 7.86 (s, 1H), 7.69 (s, 1H), 7.52 (s, 1H), 6.98 (s, 1H), 5.50 (d, J=5.0 Hz, 1H), 4.29 (m, 1H), 3.89 (s, 3H), 3.49 (dd, J=11.5, 6.9 Hz, 1H), 3.41 (dd, J=11.0, 2.9 Hz, 1H), 3.17 (m, 2H), 2.66 (m, 2H), 2.38 (m, 2H), 1.59 (m, 2H), 1.22 (s, 9H).

Step 2) N⁴-(2-(tert-butylsulfonyl)octahydrocyclopenta[c]pyrrol-5-yl)-5-chloro-N²-(1-methyl-1H-pyrazol-4-yl)pyrimidine-2,4-diamine To a solution of N⁴-(2-(tert-butylsulfinyl)octahydrocyclopenta[c]pyrrol-5-yl)-5-chloro-N²-(1-methyl-1H-pyrazol-4-yl)pyrimidine-2,4-diamine (133.6 mg, 0.30 mmol) in DCM (10 mL) was added mCPBA (138.6 mg, 0.68 mmol) portionwise. The reaction mixture was stirred at reflux overnight and mCPBA (131.5 mg, 0.65 mmol) was added portionwise again. The reaction mixture was continued to stir at reflux overnight. The mixture was cooled down to rt, and adjusted to pH=10 with a saturated Na₂CO₃ aqueous solution, then extracted with DCM (100 mL×3). The combined organic phases were washed with brine (100 mL), dried over anhydrous Na₂SO₄, filtered and concentrated in vacuo. The residue was purified by silica gel column chromatography (MeOH/DCM (v/v)=1/80) to give the title compound as a beige solid (42.7 mg, yield 30.8%).

LC-MS (ESI, pos. ion) m/z: 454.1 [M+H]⁺;

HRMS (ESI, pos. ion) m/z: 454.1795 [M+H]⁺, calculated value for C₁₉H₂₉ClN₇O₂S [M+H]⁺ is 454.1792;

¹H NMR (400 MHz, CDCl₃) δ (ppm): 7.87 (s, 1H), 7.66 (s, 1H), 7.53 (s, 1H), 7.02 (s, 1H), 5.29 (d, J=7.0 Hz, 1H), 4.26 (m, 1H), 3.88 (s, 3H), 3.55 (d, J=10.8 Hz, 2H), 3.39 (dd, J=10.5, 6.0 Hz, 2H), 2.69 (d, J=4.5 Hz, 2H), 2.44 (m, 2H), 1.50 (m, 2H), 1.41 (s, 9H);

¹³C NMR (150 MHz, CDCl₃) δ (ppm): 169.0, 158.0, 157.7, 152.9, 131.0, 123.3, 120.9, 64.8, 60.8, 55.2, 52.9, 41.3, 39.2, 38.1, 30.6, 24.5, 19.1.

Example 32 2-(5-((5-chloro-2-((1-methyl-1H-pyrazol-4-yl)amino)pyrimidin-4-yl)amino) octahydrocyclopenta[c]pyrrol-5-yl)acetonitrile

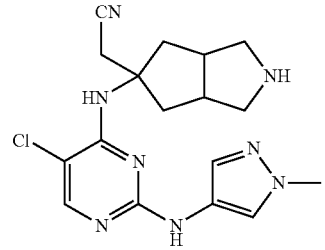 [SMILES: Cn1cc(Nc2ncc(Cl)c(NC3(CC#N)CC4CNCC4C3)n2)cn1]

Step 1) tert-butyl 5-(cyanomethylene)hexahydrocyclopenta[c]pyrrole-2(1H)-carboxylate To a suspension of NaH (60% [w/w] mineral oil suspension, 5.65 g, 141.25 mmol) in THF (200 mL) at 0° C. was dropwise added diethyl(cyanomethyl)phosphonate (25.98 g, 146.66 mmol). After addition, the reaction mixture was stirred at 0° C. for 1 h and then moved to rt for another 2 h. A solution of tert-butyl 5-oxohexahydrocyclopenta[c]pyrrole-2(1H)-carboxylate (15.34 g, 68.09 mmol) in THF (100 mL) was dropwise added to the above mixture. The reaction mixture was stirred at rt overnight, then quenched with water (150 mL), and extracted with EtOAc (250 mL×3). The combined organic phases were washed with brine (250 mL), dried over anhydrous Na₂SO₄, filtered and concentrated in vacuo. The residue was purified by silica gel column chromatography (EtOAc/PE (v/v)=1/10) to give the title compound as orange oil (12.94 g, yield 76.5%).

LC-MS (ESI, pos. ion) m/z: 193.2 [M-C₄H₈+H]⁺;

¹H NMR (400 MHz, CDCl₃) δ (ppm): 5.29 (s, 1H), 3.58 (s, 2H), 3.39 (s, 1H), 3.13 (m, 3H), 2.82 (m, 2H), 2.59 (d, J=18.3 Hz, 1H), 2.44 (d, J=14.3 Hz, 1H), 1.48 (s, 9H).

Step 2) tert-butyl 5-amino-5-(cyanomethyl)hexahydrocyclopenta[c]pyrrole-2(1H)-carboxylate To a solution of tert-butyl 5-(cyanomethylene)hexahydrocyclopenta[c]pyrrole-2(1H)-carboxylate (14.69 g, 59.16 mmol) in MeOH (30 mL) was added concentrated ammonia (28% [w/w] in water, 163.03 g, 1.30 mol). The reaction was stirred in a autoclave at 110° C. for 64 h, then cooled down to rt and concentrated in vacuo. The residue was purified by silica gel column chromatography (MeOH/DCM (v/v)=1/60) to give the title compound as yellow oil (6.28 g, yield 40%).

LC-MS (ESI, pos. ion) m/z: 266.3 [M+H]⁺;

¹H NMR (400 MHz, CDCl₃) δ (ppm): 3.50 (s, 2H), 3.46 (m, 2H), 3.28 (d, J=8.7 Hz, 2H), 2.96 (m, 2H), 2.58 (s, 2H), 1.97 (dd, J=13.2, 8.0 Hz, 2H), 1.55 (m, 2H), 1.47 (s, 9H).

Step 3) tert-butyl 5-(cyanomethyl)-5-((2, 5-dichloropyrimidin-4-yl)amino)hexahydro cyclopenta[c]pyrrole-2(1H)-carboxylate To a solution of 2,4,5-trichloropyrimidine (3.65 g, 19.90 mmol) and tert-butyl 5-amino-5-(cyanomethyl)hexahydrocyclopenta[c]pyrrole-2(1H)-carboxylate (5.23 g, 19.71 mmol) in n-BuOH (80 mL) was added Et₃N (4.13 g, 40.81 mmol). After addition, the reaction mixture was stirred in a sealed tube at 150° C. overnight, then cooled down to rt and concentrated in vacuo. The residue was purified by silica gel column chromatography (EtOAc/PE (v/v)=1/4) to give the title compound as yellow oil (1.11 g, yield 13.5%).

LC-MS (ESI, pos. ion) m/z: 412.2 [M+H]$^+$;

$^1$H NMR (400 MHz, CDCl$_3$) δ (ppm): 8.13 and 8.12 (s, 1H), 5.82 and 5.40 (s, 1H), 3.50 (m, 2H), 3.38 (s, 2H), 3.30 and 3.19 (s, 2H), 2.85 (m, 2H), 2.72 (m, 2H), 1.92 and 1.73 (dd, J=13.6, 6.1 Hz, 2H), 1.49 and 1.47 (s, 9H).

Step 4) tert-butyl 5-((5-chloro-2-((1-methyl-1H-pyrazol-4-yl)amino)pyrimidin-4-yl)amino)-5-(cyanomethyl)hexahydrocyclopenta[c]pyrrole-2(1H)-carboxylate To a suspension of tert-butyl 5-(cyanomethyl)-5-((2,5-dichloropyrimidin-4-yl)amino) hexahydrocyclopenta[c]pyrrole-2(1H)-carboxylate (631.5 mg, 1.53 mmol) and 1-methyl-1H-pyrazol-4-amine hydrochloride (213.2 mg, 1.60 mmol) in n-BuOH (10 mL) was added Et$_3$N (322.1 mg, 3.18 mmol). The reaction mixture was stirred at 150° C. in a sealed tube overnight and concentrated in vacuo. The residue was purified by silica gel column chromatography (MeOH/DCM (v/v)=1/50) to give the title compound as a yellow solid (283.0 mg, yield 39.1%).

LC-MS (ESI, pos. ion) m/z: 473.3 [M+H]$^+$.

Step 5) 2-(5-((5-chloro-2-((1-methyl-1H-pyrazol-4-yl)amino)pyrimidin-4-yl)amino) octahydrocyclopenta[c]pyrrol-5-yl)acetonitrile To a solution of tert-butyl 5-((5-chloro-2-((1-methyl-1H-pyrazol-4-yl)amino)pyrimidin-4-yl)amino)-5-(cyanomethyl)hexahydrocyclopenta[c]pyrrole-2(1H)-carboxylate (272.0 mg, 0.58 mmol) in DCM (10 mL) was added a solution of HCl in EtOAc (10 mL, 40 mmol). The reaction mixture was stirred at rt for 0.5 h and concentrated in vacuo. The residue was dissolved in water (10 mL) and the resulting mixture was adjusted to pH=10 with a saturated Na$_2$CO$_3$ aqueous solution, then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/10) to give the title compound as a beige solid (109.9 mg, yield 51.2%).

LC-MS (ESI, pos. ion) m/z: 373.2 [M+H]$^+$;

HRMS (ESI, pos. ion) m/z: 373.1658 [M+H]$^+$, calculated value for C$_{17}$H$_{22}$ClN$_8$ [M+H]$^+$ is 373.1656;

$^1$H NMR (400 MHz, CDCl$_3$) δ (ppm): 7.91 (s, 1H), 7.64 (s, 1H), 7.44 (s, 1H), 6.57 (s, 1H), 6.43 (s, 1H), 3.90 (s, 3H), 3.24 (s, 2H), 2.86 (m, 2H), 2.78 (d, J=10.2 Hz, 2H), 2.69 (d, J=2.6 Hz, 2H), 2.49 (dd, J=13.3, 7.7 Hz, 2H), 1.79 (dd, J=13.4, 5.2 Hz, 2H);

$^{13}$C NMR (150 MHz, CDCl$_3$) δ (ppm): 158.0, 157.6, 153.6, 122.7, 122.4, 118.1, 105.4, 63.1, 53.5, 44.4, 41.6, 39.3, 29.7, 25.0.

Example 33 1-(9-((5-chloro-2-((1-(piperidin-4-yl)-1H-pyrazol-4-yl)amino)pyrimidin-4-yl)amino)-3-azaspiro[5.5]undecan-3-yl)ethanone

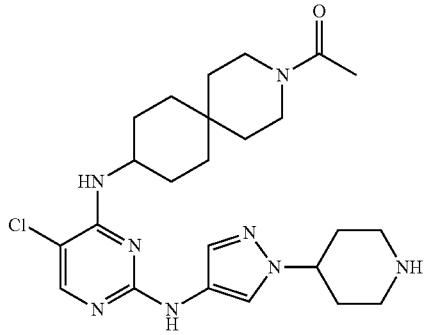 [SMILES: CC(=O)N1CCC2(CCC(Nc3nc(Nc4cnn(C5CCNCC5)c4)ncc3Cl)CC2)CC1]

Step 1) tert-butyl 9-oxo-3-azaspiro[5.5]undec-7-ene-3-carboxylate

To a solution of tert-butyl 4-formylpiperidine-1-carboxylate (10.0 g, 46.9 mmol) and KOH (1.3 g, 23.5 mmol) in EtOH (200 mL) was added but-3-en-2-one (3.9 g, 56.3 mmol), the mixture was stirred at 70° C. for 16 h and concentrated in vacuo. The residue was purified by silica gel column chromatography (EtOAc/PE (v/v)=1/4) to give the product as brown oil (5.2 g, yield 41.8%).

MS (ESI, pos. ion) m/z: 210.2 [M-55]$^+$.

Step 2) tert-butyl 9-oxo-3-azaspiro[5.5]undecane-3-carboxylate

To a solution of tert-butyl 9-oxo-3-azaspiro[5.5]undec-7-ene-3-carboxylate (5.2 g, 19.6 mmol) in DCM (80 mL) was added Pd/C (0.5 g, mass %=10%) and the suspension was stirred under a H$_2$ atmosphere at room temperature overnight. The reaction mixture was filtered and concentrated in vacuo, then the residue was purified by silica gel column chromatography (EtOAc/PE (v/v)=1/4) to give the title compound as brown oil (3.1 g, yield 59.0%).

MS (ESI, pos. ion) m/z: 212.1 [M-55]$^+$.

Step 3) tert-butyl 9-amino-3-azaspiro[5.5]undecane-3-carboxylate

To a solution of tert-butyl 9-oxo-3-azaspiro[5.5]undecane-3-carboxylate (5.35 g, 20.0 mmol) in EtOH (40 mL) were added a solution of NH$_3$ in MeOH (7M, 40 mL, 280.0 mmol) and Ti(Oi-Pr)$_4$ (11.30 g, 40.0 mmol), the mixture was stirred at room temperature overnight. And then NaBH$_4$ (1.51 g, 40.0 mmol) was added portionwise. After addition, the resulting mixture was stirred at room temperature for another 5 h, then quenched with water (40 mL), stirred for 1 h and filtered. The filtrate was concentrated in vacuo, and the residue was purified by silica gel column chromatography (MeOH/DCM (v/v)=1/25) to give the product as a light yellow solid (1.20 g, yield 22.4%).

MS (ESI, pos. ion) m/z: 269.3 [M+H]$^+$.

Step 4) tert-butyl 9-((2,5-dichloropyrimidin-4-yl)amino)-3-azaspiro[5.51] undecane-3-carboxylate To a solution of 2,4,5-trichloropyrimidine (495.9 mg, 2.7 mmol) in ethanol (20 mL) were added tert-butyl 9-amino- 3-azaspiro[5.5]undecane-3-carboxylate (1.08 g, 4.0 mmol) and Et$_3$N (413.6 mg, 4.1 mmol). The mixture was stirred at room temperature for 12 h and then concentrated in vacuo. The residue was purified by silica gel column chromatography (EtOAc/PE (v/v)=1/10 to 1/7) to give the product as a light yellow solid (387.1 mg, yield 34.5%).

MS (ESI, pos. ion) m/z: 415.0 [M+H]$^+$.

Step 5) N-(2,5-dichloropyrimidin-4-yl)-3-azaspiro[5.5]undecan-9-amine

To a solution of tert-butyl 3-[(2,5-dichloropyrimidin-4-yl)amino]-9-azaspiro[5.5]undecane-9-carboxylate (1.05 g, 2.53 mmol) in DCM (10 mL) was added a solution of HCl in EtOAc (25 mL, 3 mmol, 2 M). The reaction mixture was stirred at rt for 1 h. The reaction solution was directly washed with water (50 mL×2). The combined aqueous phases were adjusted to pH=12 with NaOH aqueous solution (4 M) and then extracted with the mixture solvent of DCM and MeOH (10/1 (v/v), 100 mL×5). The combined organic layers were dried with Na$_2$SO$_4$, filtered and concentrated in vacuo to give the title compound as a white solid (708 mg, yield 89%).

MS (ESI, pos. ion) m/z: 315.2 [M+H]$^+$.

Step 6) 1-(9-((2,5-dichloropyrimidin-4-yl)amino)-3-azaspiro[5.5]undecan-3-yl)ethanone To a solution of N-(2,5-dichloropyrimidin-4-yl)-3-azaspiro[5.5]undecan-9-amine (301.8 mg, 0.9575 mmol) and TEA (202.6 mg, 2.002 mmol) in DCM (20 mL) was added acetyl acetate (120.4 mg, 1.179 mmol). The reaction mixture was stirred at rt for 30 min and concentrate in vacuo. The residue was purified by silica gel column chromatography (DCM/MeOH (v/v)=70/1) to give the title compound as a white solid (190 mg, yield 55.54%).

MS (ESI, pos. ion) m/z: 357.3 [M+H]$^+$.

Step 7) tert-butyl 4-(4-((4-((3-acetyl-3-azaspiro[5.5]undecan-9-yl)amino)-5-chloropyrimidin-2-yl)amino)-1H-pyrazol-1-yl)piperidine-1-carboxylate To a solution of 1-(9-((2,5-dichloropyrimidin-4-yl)amino)-3-azaspiro[5.5]undecan-3-yl)ethanone (312.4 mg, 0.8743 mmol), tert-butyl 4-(4-amino-1H-pyrazol-1-yl)piperidine-1-carboxylate (337.8 mg, 1.268 mmol) and cesium carbonate (817.4 mg, 2.509 mmol) in 1,4-dioxane (14 mL) were added BINAP (54.1 mg, 0.0869 mmol) and Pd(OAc)$_2$ (20.3 mg, 0.0904 mmol). The reaction mixture was heated to 100° C. and stirred for 6 h and then concentrated in vacuo. The residue was purified by silica gel column chromatography (DCM/MeOH (v/v)=40/1) to give the title compound as a yellow solid (280 mg, yield 54.5%).

MS (ESI, pos. ion) m/z: 587.6 [M+H]$^+$;
$^1$H NMR (400 MHz, CDCl$_3$) δ (ppm): 7.85 (s, 1H), 7.70 (s, 1H), 7.53 (s, 1H), 6.92 (s, 1H), 5.13 (d, J=7.1 Hz, 1H), 4.31-4.13 (m, 3H), 3.99-3.88 (m, 1H), 3.72-3.66 (m, 2H), 3.56 (dd, J=11.4, 6.1 Hz, 2H), 3.40 (dd, J=11.4, 6.3 Hz, 2H), 2.87 (t, J=11.6 Hz, 2H), 2.15-2.09 (m, 2H), 2.08 (s, 3H), 2.01-1.91 (m, 4H), 1.89-1.86 (m, 2H), 1.80-1.70 (m, 3H), 1.62-1.53 (m, 3H), 1.46 (s, 9H).

Step 8) 1-(9-((5-chloro-2-((1-(piperidin-4-yl)-1H-pyrazol-4-yl)amino)pyrimidin-4-yl)amino)-3-azaspiro[5.5]undecan-3-yl)ethanone tert-butyl 4-(4-((4-((3-acetyl-3-azaspiro[5.5]undecan-9-yl)amino)-5-chloropyrimidin-2-yl)amino)-1H-pyrazol-1-yl)piperidine-1-carboxylate (280 mg, 0.4768 mmol) was added to a solution of HCl in EtOAc (8 mL, 16 mmol, 2 M). The reaction mixture was stirred for 2 h at rt, then concentrated directly in vacuo. The residue was purified by silica gel column chromatography (DCM/(a solution of NH$_3$ in MeOH (7 M) (v/v)=20/1) to give the title compound as a yellow solid (57.2 mg, yield 24.6%).

MS (ESI, pos. ion) m/z: 487.4 [M+H]$^+$;
HRMS (ESI, pos. ion) m/z: 487.2672 [M+H]$^+$, calculated value for C$_{24}$H$_{36}$ClN$_8$O [M+H]$^+$ is 487.2701;
$^1$H NMR (400 MHz, CDCl$_3$) δ (ppm): 7.84 (s, 1H), 7.74 (s, 1H), 7.57 (d, J=6.6 Hz, 1H), 7.18-6.96 (m, 1H), 5.13 (d, J=4.9 Hz, 1H), 4.31-4.21 (m, 1H), 3.98-3.87 (m, 1H), 3.58-3.51 (m, 2H), 3.45-3.36 (m, 4H), 2.96 (t, J=11.8 Hz, 2H), 2.28-2.21 (m, 2H), 2.19-2.11 (m, 2H), 2.07 (d, J=1.4 Hz, 3H), 2.00-1.89 (m, 2H), 1.77-1.67 (m, 2H), 1.58-1.50 (m, 2H), 1.47-1.29 (m, 6H);
$^{13}$C NMR (100 MHz, CDCl$_3$) δ (ppm): 169.0, 158.0, 157.4, 153.0, 130.7, 123.4, 117.6, 104.2, 57.6, 50.7, 49.9, 44.1, 42.5, 39.4, 37.4, 34.2, 31.3, 30.9, 29.7, 27.5, 21.4.

Example 34 5-((5-chloro-2-((1-methyl-1H-pyrazol-4-yl)amino)pyrimidin-4-yl)amino)-N-cyclopropyl-hexahydrocyclopenta[c]pyrrole-2(1H)-sulfonamide

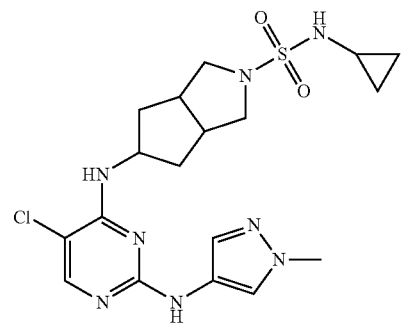 [SMILES: Cn1cc(Nc2ncc(Cl)c(NC3CC4CN(S(=O)(=O)NC5CC5)CC4C3)n2)cn1]

Step 1) cyclopropanaminium cyclopropylsulfamate

To a solution of cyclopropanamine (2.94 g, 51.5 mmol) in anhydrous DCM (50.0 mL) was slowly added a solution of sulfurochloridic acid (2.00 g, 17.18 mmol) in anhydrous DCM (9.0 mL) over 30 min at 0° C. The reaction mixture was stirred at 0° C. for another 30 min, then move to room temperature and stirred for another 1 h, then filtered. The filtrate cake was washed with anhydrous DCM (10.0 mL) and dried in vacuo to give the title compound as a white solid (3.33 g, yield 100%).

MS (ESI, pos. ion) m/z: 58.2 [M$_1$]$^+$;
MS (ESI, neg. ion) m/z: 136.0 [M$_2$]$^-$.

Step 2) cyclopropylsulfamoyl chloride

To a suspension of cyclopropanaminium cyclopropylsulfamate (3.33 g, 17.1 mmol) in anhydrous toluene (50.0 mL) was added phosphorus pentachloride (3.57 g, 17.1 mmol). The mixture was heated to 75° C. and stirred for 2 h and then cooled down to room temperature and filtered. The filtrate cake was washed with anhydrous toluene (10.0 mL). The filtrate was concentrated in vacuo to afford the title compound as brown liquid (0.65 g, yield 24%).

Step 3) 5-((5-chloro-2-((1-methyl-1H-pyrazol-4-yl)amino)pyrimidin-4-yl)amino)-N-cyclopropylhexahydrocyclopenta[c]pyrrole-2(1H)-sulfonamide To a suspension of 5-chloro-$N^2$-(1-methyl-1H-pyrazol-4-yl)-$N^4$-(octahydrocyclopenta[c]pyrrol-5-yl)pyrimidine-2,4-diamine (0.10 g, 0.30 mmol) and TEA (0.21 mL, 1.50 mmol) in anhydrous DCM (10.0 mL) was added cyclopropylsulfamoyl chloride (0.10 g, 0.63 mmol) at 0° C. The mixture was stirred at 0° C. for 15 min and then move to room temperature and stirred overnight. The resulting mixture was concentrated in vacuo. The residue was purified by silica gel column chromatography (DCM/(a solution of $NH_3$ in MeOH (3 M) (v/v)=100/1 to 50/1) to get the title compound as a white solid (30 mg, yield 22%).

MS (ESI, pos. ion) m/z: 453.2 $[M+H]^+$;
HRMS (ESI, pos. ion) m/z: 453.1585 $[M+H]^+$, calculated value for $C18H_{26}ClN_8O_2S$ $[M+H]^+$ is 453.1582;
$^1$H NMR (600 MHz, $CDCl_3$) δ (ppm): 7.86 (s, 1H), 7.64 (s, 1H), 7.49 (s, 1H), 6.62 (s, 1H), 5.33 (d, J=7.3 Hz, 1H), 4.72 (d, J=4.5 Hz, 1H), 4.38-4.27 (m, 1H), 3.88 (s, 3H), 3.32-3.25 (m, 4H), 2.78-2.72 (m, 2H), 2.62-2.57 (m, 1H), 2.51-2.45 (m, 2H), 1.48-1.41 (m, 2H), 0.73-0.65 (m, 4H);
$^{13}$C NMR (150 MHz, $CDCl_3$) δ (ppm): 158.03, 157.65, 153.02, 131.05, 123.19, 121.01, 104.35, 54.24, 52.70, 40.51, 39.27, 24.82, 18.45, 6.90.

Example 35 1-(9-((5-chloro-2-((1-(2-hydroxy-2-methylpropyl)-1H-pyrazol-4-yl)amino)pyrimidin-4-yl)amino)-3-azaspiro[5.5]undecan-3-yl)ethanone

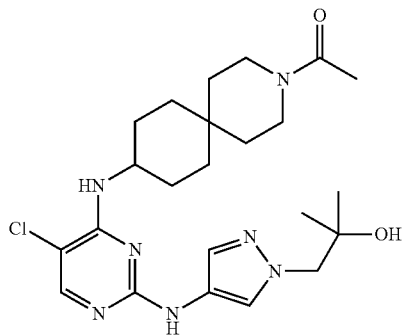 [SMILES: CC(=O)N1CCC2(CCC(Nc3nc(Nc4cnn(CC(C)(C)O)c4)ncc3Cl)CC2)CC1]

To a solution of 1-(9-((2,5-dichloropyrimidin-4-yl)amino)-3-azaspiro[5.5]undecan-3-yl)ethanone (83 mg, 0.534 mmol) and 1-(4-amino-1H-pyrazol-1-yl)-2-methylpropan-2-ol (129 mg, 0.361 mmol) in 1,4-dioxane (20 mL) were added cesium carbonate (225 mg, 0.690 mmol), Pd(OAc)$_2$ (15 mg, 0.067 mmol) and BINAP (45 mg, 0.072 mmol). The reaction mixture was stirred at 100° C. overnight and concentrated in vacuo. The residue was purified by silica gel column chromatography (MeOH/DCM=1/30) to give the title compound as a yellow solid (30 mg, yield 17.5%).

MS (ESI, pos. ion) m/z: 476.2 $[M+H]^+$;
HRMS (ESI, pos. ion) m/z: 476.2540 $[M+H]^+$, calculated value for $C_{23}H_{35}ClN_7O_2[M+H]^+$ is 476.2463;
$^1$H NMR (400 MHz, $CDCl_3$) δ (ppm): 7.85 (s, 1H), 7.75 (d, J=11.3 Hz, 1H), 7.57 (d, J=12.3 Hz, 1H), 7.00 (s, 1H), 5.16 (s, 1H), 4.02-3.90 (m, 2H), 3.93 (d, J=16.2 Hz, 1H), 3.60-3.52 (m, 2H), 3.42-3.99 (m, 2H), 2.09 (s, 3H), 1.99-1.94 (m, 2H), 1.76-1.72 (s, 2H), 1.59-1.53 (m 2H), 1.48-1.33 (m, 6H), 1.18 (s, 6H);

$^{13}$C NMR (100 MHz, $CDCl_3$) δ (ppm): 169.11, 157.86, 157.50, 152.72, 131.52, 130.04, 123.10, 121.78, 70.92, 62.25, 42.59, 37.48, 34.38, 30.97, 29.82, 27.67, 27.03, 26.92, 21.62.

Example 36 5-((5-chloro-2-((1-(2-hydroxy-2-methylpropyl)-1H-pyrazol-4-yl)amino)pyrimidin-4-yl)amino)-N-cyclopropylhexahydrocyclopenta[c]pyrrole-2(1H)-carboxamide

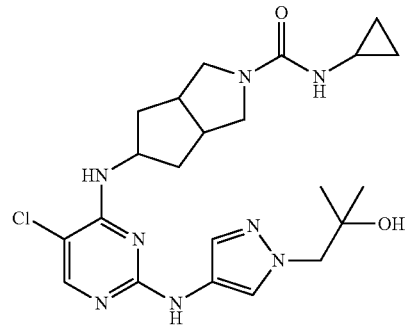 [SMILES: CC(C)(O)Cn1cc(Nc2ncc(Cl)c(NC3CC4CN(C(=O)NC5CC5)CC4C3)n2)cn1]

Step 1) tert-butyl 5-((5-chloro-2-((1-(2-hydroxy-2-methylpropyl)-1H-pyrazol-4-yl)amino)pyrimidin-4-yl)amino)hexahydrocyclopenta[c]pyrrole-2(1H)-carboxylate To a suspension of tert-butyl 5-((2,5-dichloropyrimidin-4-yl)amino)hexahydro cyclopenta[c]pyrrole-2(1H)-carboxylate (143.5 mg, 0.38 mmol) and 1-(4-amino-1H-pyrazol-1-yl)-2-methylpropan-2-ol (68.8 mg, 0.44 mmol) in 1,4-dioxane (20 mL) were added Pd(OAc)$_2$ (19.3 mg, 0.09 mmol), BINAP (98%, 54.4 mg, 0.08 mmol) and cesium carbonate (98%, 272.3 mg, 0.82 mmol). The reaction mixture was stirred at 100° C. overnight and concentrated in vacuo. The residue was purified by silica gel column chromatography (EtOAc/PE (v/v)=2/1) to give the title compound as a yellow solid (56.2 mg, yield 29.7%).

MS (ESI, pos. ion) m/z: 492.4 $[M+H]^+$;
$^1$H NMR (400 MHz, $CDCl_3$) δ (ppm): 7.85 (s, 1H), 7.75 (s, 1H), 7.64 (s, 1H), 5.36 (d, J=5.8 Hz, 1H), 4.41 (m, 1H), 4.03 (s, 2H), 3.50 (m, 2H), 3.38 (d, J=9.5 Hz, 2H), 2.71 (m, 2H), 2.46 (m, 2H), 1.46 (m, 11H), 1.20 (s, 6H).

Step 2) 1-(4-((5-chloro-4-((octahydrocyclopenta[c]pyrrol-5-yl)amino)pyrimidin-2-yl)amino)-1H-pyrazol-1-yl)-2-methylpropan-2-ol To a solution of tert-butyl 5-((5-chloro-2-((1-(2-hydroxy-2-methylpropyl)-1H-pyrazol-4-yl)amino)pyrimidin-4-yl)amino)hexahydrocyclopenta[c]pyrrole-2(1H)-carboxylate (176.4 mg, 0.45 mmol) in DCM (10 mL) was added a solution of HCl in EtOAc (10 mL, 40 mmol, 4M). The reaction mixture was stirred at rt for 0.5 h and then concentrated in vacuo. The residue was dissolved in water (10 mL) and adjusted to pH=10 with a saturated $Na_2CO_3$ aqueous solution, then extracted with DCM (100 mL×3). The combined organic phases were washed with brine (100 mL), dried over anhydrous $Na_2SO_4$, then concentrated in vacuo.

The residue was purified by silica gel column chromatography (MeOH/DCM (v/v)=1/8) to give the title compound as a pale yellow solid (64.5 mg, yield 45.9%).

MS (ESI, pos. ion) m/z: 392.0 [M+H]$^+$;

$^1$H NMR (600 MHz, CDCl$_3$) δ (ppm): 7.82 (s, 2H), 7.79 (s, 1H), 7.58 (s, 1H), 6.64 (s, 1H), 4.52 (m, 1H), 4.03 (s, 2H), 3.51 (s, 1H), 2.90 (m, 4H), 2.71 (s, 2H), 2.26 (m, 2H), 1.51 (d, J=13.4 Hz, 2H), 1.20 (s, 6H).

Step 3) 5-((5-chloro-2-((1-(2-hydroxy-2-methylpropyl)-1H-pyrazol-4-yl)amino)pyrimidin-4-yl)amino)-N-cyclopropylhexahydrocyclopenta[c]pyrrole-2 (1H)-carboxamide To a solution of 1-(4-((5-chloro-4-((octahydrocyclopenta[c]pyrrol-5-yl)amino)pyrimidin-2-yl)amino)-1H-pyrazol-1-yl)-2-methylpropan-2-ol (55.9 mg, 0.14 mmol) and Et$_3$N (110.1 mg, 1.09 mmol) in EtOH (10 mL) was added phenyl cyclopropylcarbamate (45.2 mg, 0.26 mmol). The reaction mixture was stirred at 50° C. overnight, cooled down to rt, and quenched with water (30 mL), then extracted with DCM (100 mL×3). The combined organic phases were washed with brine (100 mL), dried over anhydrous Na$_2$SO$_4$, filtered and concentrated in vacuo. The residue was purified by silica gel column chromatography (MeOH/DCM (v/v)=1/20) to give the title compound as a beige solid (52.6 mg, yield 77.6%).

MS (ESI, pos. ion) m/z: 475.2[M+H]$^+$;

HRMS (ESI, pos. ion) m/z: 475.2339 [M+H]$^+$, calculated value for C$_{22}$H$_{32}$ClN$_8$O$_2$[M+H]$^+$ is 475.2337;

$^1$H NMR (600 MHz, CDCl$_3$) δ (ppm): 7.86 (s, 1H), 7.76 (s, 1H), 7.62 (s, 1H), 7.20 (s, 1H), 5.42 (s, 1H), 4.56 (s, 1H), 4.42 (s, 1H), 4.03 (s, 2H), 3.47 (2, 2H), 3.34 (s, 2H), 2.75 (s, 2H), 2.66 (s, 1H), 2.43 (s, 2H), 1.49 (s, 2H), 1.20 (s, 6H), 0.73 (s, 2H), 0.49 (s, 2H);

$^{13}$C NMR (150 MHz, CDCl$_3$) δ (ppm): 158.2, 157.8, 157.6, 152.6, 131.6, 122.9, 121.9, 70.8, 62.1, 53.2, 52.2, 41.1, 39.1, 29.7, 26.9, 23.3, 6.9.

Example 37 1-(4-((5-chloro-4-((3-(methylsulfonyl)-3-azaspiro[5.5]undecan-9-yl)amino)pyrimidin-2-yl)amino)-1H-pyrazol-1-yl)-2-methylpropan-2-ol

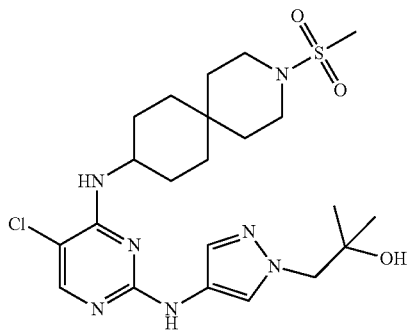 [SMILES: CC(C)(O)Cn1cc(Nc2ncc(Cl)c(NC3CCC4(CC3)CCN(S(C)(=O)=O)CC4)n2)cn1]

Step 1) N-(2, 5-dichloropyrimidin-4-yl)-3-(methyl sulfonyl)-3-azaspiro[5.5]undecan-9-amine To a solution of N-(2,5-dichloropyrimidin-4-yl)-3-azaspiro[5.5]undecan-9-amine (220 mg, 0.698 mmol) in DCM (10 mL) were added TEA (109 mg, 1.07 mmol) and DMAP (19.1 mg, 0.223 mmol). The reaction mixture was cooled to 0° C. and methanesulfonyl chloride (102 mg, 0.890 mmol) was added. The resulting mixture was stirred at 0° C. overnight and then concentrated in vacuo. The residue was purified by silica gel column chromatography (MeOH/DCM (v/v)=1/80) to give the title compound as a yellow solid (176 mg, yield 64.1%).

MS (ESI, pos. ion) m/z: 393.0 [M+H]$^+$.

Step 2) 1-(4-((5-chloro-4-((3-(methylsulfonyl)-3-azaspiro[5.5]undecan-9-yl)amino)pyrimidin-2-yl)amino)-1H-pyrazol-1-yl)-2-methylpropan-2-ol To a solution of N-(2,5-dichloropyrimidin-4-yl)-3-(methylsulfonyl)-3-azaspiro[5.5]undecan-9-amine (142 mg, 0.361 mmol) and 1-(4-amino-1H-pyrazol-1-yl)-2-methylpropan-2-ol (70 mg, 0.451 mmol) in 1,4-dioxane (20 mL) were added cesium carbonate (234 mg, 0.718 mmol), Pd(OAc)$_2$ (16 mg, 0.071 mmol) and BINAP (45 mg, 0.072 mmol). The mixture was stirred at 105° C. overnight and concentrated in vacuo. The residue was purified by silica gel column chromatography (DCM/MeOH=40/1) to give the title compound as a yellow solid (80 mg, yield 43.3%).

MS (ESI, pos. ion) m/z: 512.0 [M+H]$^+$;

HRMS (ESI, pos. ion) m/z: 512.2209 [M+H]$^+$, calculated value for C$_{22}$H$_{35}$N$_7$O$_3$S [M+H]$^+$ is 512.2131;

$^1$H NMR (600 MHz, DMSO-d$_6$) δ (ppm): 9.96 (s, 2H), 8.02 (s, 1H), 7.86 (s, 1H), 7.73 (s, 1H), 7.50 (s, 1H), 3.96 (s, 2H), 3.12-3.10 (m, 4H), 2.86 (s, 3H), 2.00-1.98 (m, 1H), 1.77-1.64 (m, 10H), 1.44-1.42 (m, 2H), 1.06 (s, 6H).

Example 38 1-(4-((5-chloro-4-((2-(methyl sulfonyl) octahydrocyclopenta[c]pyrrol-5-yl)amino)pyrimidin-2-yl)amino)-1H-pyrazol-1-yl)propan-2-ol

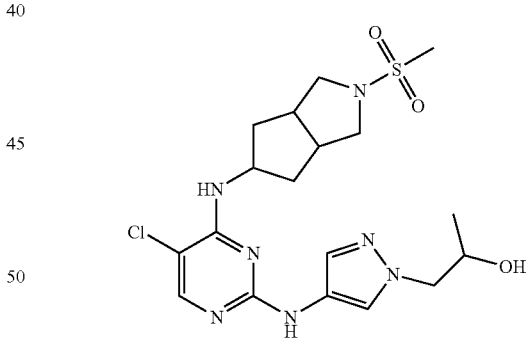

Step 1)-(4-nitro-1H-pyrazol-1-yl)propan-2-ol

To a solution of 4-nitro-1H-pyrazole (1.02 g, 9.02 mmol) and 1-bromopropan-2-ol (3.65 g, 26.3 mmol) in DMF (10 mL) was added cesium carbonate (8.65 g, 26.5 mmol). The mixture was stirred at 100° C. for 3.5 h. The reaction was quenched with water (50 mL) and extracted with EtOAc (100 mL×3). The combined organic phases were dried over anhydrous Na$_2$SO$_4$, filtered and concentrated in vacuo to give the title compound as yellow oil (1.51 g, yield 97.8%).

MS (ESI, pos. ion) m/z: 172.2 [M+H]$^+$.

Step 2) 1-(4-amino-1H-pyrazol-1-yl)propan-2-ol

To a solution of 1-(4-nitro-1H-pyrazol-1-yl)propan-2-ol (1.51 g, 8.82 mmol) in EtOH (20 mL) was added Pd/C (300 mg, mass %=10%). The mixture was stirred at rt in a high pressure autoclave under 2 MPa H$_2$ atmosphere overnight and filtered. The filtrate was concentrated in vacuo and the residue was purified by silica gel column chromatography (DCM/MeOH (v/v)=1/30) to give the title compound as a brown solid (1.0 g, yield 80.3%).

MS (ESI, pos. ion) m/z: 142.2 [M+H]$^+$;

$^1$H NMR (400 MHz, CDCl$_3$) δ (ppm): 7.17 (s, 1H), 7.03 (s, 1H), 4.16-4.10 (m, 1H), 4.02 (dd, J=13.8, 2.7 Hz, 1H), 3.85 (dd, J=13.8, 7.9 Hz, 1H), 2.95 (s, 2H), 1.19 (d, J=6.3 Hz, 3H).

Step 3) N-(2,5-dichloropyrimidin-4-yl)-2-(methylsulfonyl)octahydrocyclopenta[c]pyrrol-5-amine To a solution of N-(2,5-dichloropyrimidin-4-yl)octahydrocyclopenta[c]pyrrol-5-amine (500 mg, 1.83 mmol) in DCM (10 mL) were added triethylamine (340 mg, 3.36 mmol) and DMAP (45 mg, 0.368 mmol). The mixture was cooled to 0° C. and methanesulfonyl chloride (310 mg, 2.71 mmol) was added. The mixture was stirred at 0° C. overnight and concentrated in vacuo. The residue was purified by silica gel column chromatography (MeOH/DCM (v/v)=1/100) to give the title compound as a yellow solid (300 mg, yield 46.7%).

MS (ESI, pos. ion) m/z: 351.2 [M+H]$^+$.

Step 4) 1-(4-((5-chloro-4-((2-(methylsulfonyl)octahydrocyclopenta[c]pyrrol-5-yl)amino)pyrimidin-2-yl)amino)-1H-pyrazol-1-yl)propan-2-ol To a solution of N-(2,5-dichloropyrimidin-4-yl)-2-(methylsulfonyl)octahydro-cyclopenta[c]pyrrol-5-amine (132 mg, 0.375 mmol) and 1-(4-amino-1H-pyrazol-1-yl)propan-2-ol (82 mg, 0.580 mmol) in 1,4-dioxane (20 mL) were added cesium carbonate (241 mg, 0.739 mmol), Pd(OAc)$_2$ (16 mg, 0.071 mmol) and BINAP (46 mg, 0.073 mmol). The reaction mixture was stirred at 105° C. overnight and concentrated in vacuo. The residue was purified by silica gel column chromatography (MeOH/DCM (v/v)=1/30) to give the title compound as a yellow solid (100 mg, yield 58.4%).

MS (ESI, pos. ion) m/z: 456.4 [M+H]$^+$;

HRMS (ESI, pos. ion) m/z: 456.1580 [M+H]$^+$, calculated value for C18H$_{27}$ClN$_7$O$_3$S [M+H]$^+$ is 456.1506;

$^1$H NMR (600 MHz, DMSO-d$_6$) δ (ppm): 9.04 (s, 1H), 7.85 (d, J=8.1 Hz, 1H), 7.82 (s, 1H), 7.42 (s, 1H), 6.97 (d, J=7.4 Hz, 1H), 4.91 (s, 1H), 4.43-4.37 (m, 1H), 3.96-3.89 (m, 3H), 3.23 (dd, J=9.3, 7.1 Hz, 2H), 3.13-3.10 (m, 2H), 2.91 (s, 3H), 2.69 (s, 2H), 2.25 (s, 2H), 1.52 (dd, J=18.4, 10.1 Hz, 2H), 1.01 (d, J=5.8 Hz, 3H);

$^{13}$C NMR (150 MHz, DMSO-d$_6$) δ (ppm): 157.65, 157.37, 153.29, 129.43, 123.35, 119.87, 65.70, 58.91, 53.59, 40.06, 39.99, 37.56, 32.85, 20.90.

Example 39 1-(4-((5-chloro-4-((2-(methyl sulfonyl)octahydrocyclopenta[c]pyrrol-5-yl)amino)pyrimidin-2-yl)amino)-1H-pyrazol-1-yl)-2-methylpropan-2-ol

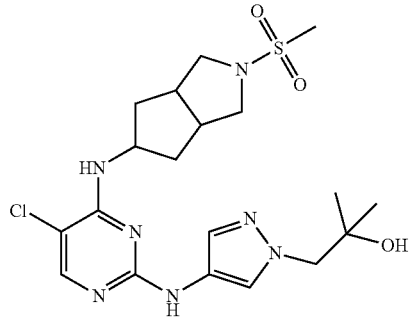 [SMILES: CC(C)(O)Cn1cc(Nc2ncc(Cl)c(NC3CC4CN(S(C)(=O)=O)CC4C3)n2)cn1]

To a solution of N-(2,5-dichloropyrimidin-4-yl)-2-(methylsulfonyl)octahydro-cyclopenta[c]pyrrol-5-amine (160 mg, 0.455 mmol) and 1-(4-amino-1H-pyrazol-1-yl)-2-methylpropan-2-ol (110 mg, 0.708 mmol) in 1,4-dioxane (20 mL) were added cesium carbonate (310 mg, 0.951 mmol), Pd(OAc)$_2$ (21 mg, 0.093 mmol) and BINAP (57 mg, 0.091 mmol). The reaction mixture was stirred at 105° C. overnight and concentrated in vacuo. The residue was purified by silica gel column chromatography (MeOH/DCM (v/v)=1/30) to give the title compound as a yellow solid (100 mg, yield 46.7%).

MS (ESI, pos. ion) m/z: 470.1 [M+H]$^+$;

HRMS (ESI, pos. ion) m/z: 470.1773 [M+H]$^+$, calculated value for C$_{19}$H29ClN$_7$O$_3$S [M+H]$^+$ is 470.1663;

$^1$H NMR (600 MHz, DMSO-d$_6$) δ (ppm): 9.04 (s, 1H), 7.85 (d, J=5.8 Hz, 2H), 7.42 (s, 1H), 6.96 (d, J=7.7 Hz, 1H), 4.44-4.37 (m, 1H), 3.93 (s, 2H), 3.23 (dd, J=9.3, 7.0 Hz, 2H), 3.17 (d, J=5.2 Hz, 1H), 3.13-3.10 (m, 2H), 2.91 (s, 3H), 2.69 (s, 2H), 2.25 (s, 2H), 1.51 (dd, J=18.9, 11.7 Hz, 2H), 1.04 (s, 6H);

$^{13}$C NMR (150 MHz, DMSO-d$_6$) δ (ppm): 157.69, 157.39, 153.34, 129.25, 123.35, 120.32, 69.42, 62.42, 53.62, 48.63, 40.02, 37.61, 32.86, 27.22.

Example 40 5-((5-chloro-2-((1-(pyrrolidin-3-yl)-1H-pyrazol-4-yl)amino)pyrimidin-4-yl)amino)-N-cyclopropylhexahydrocyclopenta[c]pyrrole-2(1H)-carboxamide

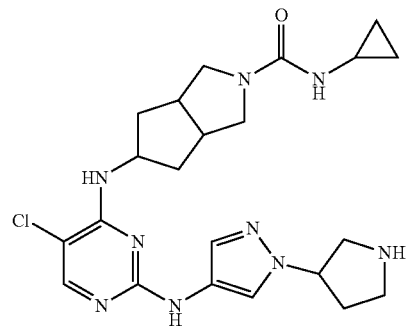 [SMILES: O=C(NC1CC1)N1CC2CC(Nc3nc(Nc4cnn(C5CCNC5)c4)ncc3Cl)CC2C1]

Step 1) tert-butyl 3-hydroxypyrrolidine-1-carboxylate

To a suspension of pyrrolidin-3-ol hydrochloride (2.00 g, 16.2 mmol) and triethylamine (6.80 mL, 48.8 mmol) in anhydrous DCM (40.0 mL) was added (Boc)$_2$O (4.24 g, 19.4 mmol). The mixture was stirred at room temperature for 3 h, then concentrated in vacuo. The residue was purified by silica gel column chromatography (EtOAc/PE (v/v)=1/4 to 1/2 to 1/1) to afford the title compound as colorless sticky liquid (2.20 g, 76%).

MS (ESI, pos. ion) m/z: 132.2 [(M-56)+H]$^+$;

$^1$H NMR (400 MHz, CDCl$_3$) δ (ppm): 4.48-4.33 (m, 1H), 3.51-3.24 (m, 4H), 1.97-1.82 (m, 2H), 1.44 (s, 9H).

Step 2) tert-butyl 3-(4-nitro-1H-pyrazol-1-yl)pyrrolidine-1-carboxylate

To a suspension of 4-nitro-1H-pyrazole (0.50 g, 4.43 mmol) in THF (35.0 mL) were added tert-butyl 3-hydroxypyrrolidine-1-carboxylate (1.00 g, 5.33 mmol) and triphenylphosphane (1.75 g, 6.68 mmol), and the mixture was cooled down to 0° C. To the above mixture was added a solution of DIAD (1.36 g, 6.73 mmol) in anhydrous THF (15.0 mL) over 20 min. After addition, the resulting mixture was stirred at 0° C. for 30 min, and then move to room temperature and stirred overnight. The mixture was concentrated in vacuo and the residue was purified by silica gel column chromatography (EtOAc/PE (v/v)=10/1 to 5/1) to afford the crude title compound as brown sticky liquid (2.10 g, containing impurity, the target product was just for 1.25 g, yield 100%).

MS (ESI, pos. ion) m/z: 227.0 [(M-56)+H]$^+$.

Step 3) tert-butyl 3-(4-amino-1H-pyrazol-1-yl)pyrrolidine-1-carboxylate

To a suspension of tert-butyl 3-(4-nitro-1H-pyrazol-1-yl)pyrrolidine-1-carboxylate (1.25 g, 4.43 mmol) in EtOH (30.0 mL) was added Pd/C (mass %=10%, 0.30 g). The mixture was stirred at room temperature overnight under hydrogen atmosphere. Then the mixture was filtered and the filter cake was washed with MeOH (10.0 mL). The filtrate was concentrated in vacuo, and the residue was purified by silica chromatography (DCM 100% to DCM/(a solution of NH$_3$ in MeOH (3M)) (v/v)=100/1 to 50/1) to afford the title compound as brown sticky liquid (0.65 g, yield 58%).

MS (ESI, pos. ion) m/z: 253.2 [M+H]$^+$;

$^1$H NMR (400 MHz, CDCl$_3$) δ (ppm): 7.16 (s, 1H), 7.01 (s, 1H), 4.79-4.67 (m, 1H), 3.82-3.73 (m, 1H), 3.70-3.44 (m, 3H), 2.90 (s, 2H), 2.36-2.24 (m, 2H), 1.45 (s, 9H).

Step 4) N-cyclopropyl-5-((2,5-dichloropyrimidin-4-yl)amino)hexahydrocyclopenta[c]pyrrole-2(1H)-carboxamide To a solution of N-(2,5-dichloropyrimidin-4-yl)octahydrocyclopenta[c]pyrrol-5-amine (110.5 mg, 0.41 mmol) in ethanol (2 mL) was added phenyl N-cyclopropylcarbamate (144.2 mg, 0.81 mmol). The reaction mixture was stirred at 50° C. for 10 h and then concentrated in vacuo. The residue was purified by silica gel column chromatography (DCM/MeOH (v/v)=30/1) to afford the title compound as brown oil (138.2 mg, yield 96%).

MS (ESI, pos. ion) m/z: 356.0 [M+H]$^+$.

Step 5) tert-butyl 3-(4-((5-chloro-4-((2-(cyclopropylcarbamoyl)octahydrocyclopenta[c]pyrrol-5-yl)amino)pyrimidin-2-yl)amino)-1H-pyrazol-1-yl)pyrrolidine-1-carboxylate To a solution of N-cyclopropyl-5-((2,5-dichloropyrimidin-4-yl)amino)hexahydrocyclopenta[c]pyrrole-2(1H)-carboxamide (152.2 mg, 0.43 mmol) and tert-butyl 3-(4-aminopyrazol-1-yl)pyrrolidine-1-carboxylate (130.4 mg, 0.52 mmol) in 1,4-dioxane (4 mL) were added Pd(OAc)$_2$ (10.2 mg, 0.05 mmol), BINAP (27.3 mg, 0.04 mmol) and cesium carbonate (275.6 mg, 0.85 mmol). The reaction mixture was stirred at 100° C. for 6 h under N$_2$ atmosphere and then concentrated in vacuo. The residue was purified by silica gel column chromatography (DCM/MeOH (v/v)=60/1 to 30/1) to afford the title compound as a brown solid (124.3 mg, yield 51%).

MS (ESI, pos. ion) m/z: 572.3 [M+H]$^+$.

Step 6) 5-((5-chloro-2-((1-(pyrrolidin-3-yl)-1H-pyrazol-4-yl)amino)pyrimidin-4-yl)amino)-N-cyclopropylhexahydrocyclopenta[c]pyrrole-2(1H)-carboxamide A solution of HCl in EtOAc (8 mL, 24 mmol, 3M) was added to a solution of tert-butyl 3-(4-((5-chloro-4-((2-(cyclopropylcarbamoyl)octahydrocyclopenta[c]pyrrol-5-yl)amino)pyrimidin-2-yl)amino)-1H-pyrazol-1-yl)pyrrolidine-1-carboxylate (124.2 mg, 0.22 mmol) in DCM (2 mL). The resulting mixture was stirred at room temperature for 1 h and then concentrated in vacuo. The residue was diluted with water (4 mL), and the resulting mixture was adjusted to pH=9 with 1M NaOH aqueous solution and concentrated in vacuo. The residue was purified by silica gel column chromatography (DCM/MeOH (v/v)=20/1 to DCM/(a solution of NH$_3$ in MeOH (7M)) (v/v)=10/1) to afford the target compound as a red solid (45.4 mg, yield 44%).

MS (ESI, pos. ion) m/z: 236.6 [(M+2H)/2]$^+$;

HRMS (ESI, pos. ion) m/z: 472.2303 [M+H]$^+$, calculated value for C$_{22}$H$_{31}$ClN$_9$O [M+H]$^+$ is 472.2335;

$^1$H NMR (600 MHz, CDCl$_3$) δ (ppm): 7.86 (s, 1H), 7.78 (s, 1H), 7.54 (s, 1H), 6.78 (s, 1H), 5.35 (d, J=7.5 Hz, 1H), 4.79 (ddd, J=10.9, 7.2, 3.5 Hz, 1H), 4.52 (s, 1H), 4.41 (dd, J=15.3, 7.7 Hz, 1H), 3.47 (dd, J=10.1, 7.6 Hz, 2H), 3.35-3.31 (m, 3H), 3.27 (dd, J=12.1, 6.4 Hz, 1H), 3.12-3.06 (m, 1H), 2.73 (t, J=10.7 Hz, 2H), 2.65 (dd, J=5.3, 3.4 Hz, 1H), 2.47-2.40 (m, 2H), 2.38-2.31 (m, 1H), 2.28-2.18 (m, 3H), 1.53-1.45 (m, 2H), 0.76-0.68 (m, 2H), 0.50-0.44 (m, 2H);

$^{13}$C NMR (150 MHz, CDCl$_3$) δ (ppm): 158.2, 157.9, 157.5, 153.0, 131.1, 129.9, 123.3, 119.0, 61.9, 53.6, 53.2, 52.2, 46.3, 41.2, 39.1, 33.0, 23.4, 6.9.

Example 41 5-((5-chloro-2-((1-(2-hydroxypropyl)-1H-pyrazol-4-yl)amino)pyrimidin-4-yl)amino)-N-cyclopropylhexahydrocyclopenta[c]pyrrole-2(1H)-carboxamide and

Example 42 N-cyclopropyl-5-((2-((1-(2-hydroxypropyl)-1H-pyrazol-4-yl)amino)pyrimidin-4-yl)amino)hexahydrocyclopenta[c]pyrrole-2(1H)-carboxamide

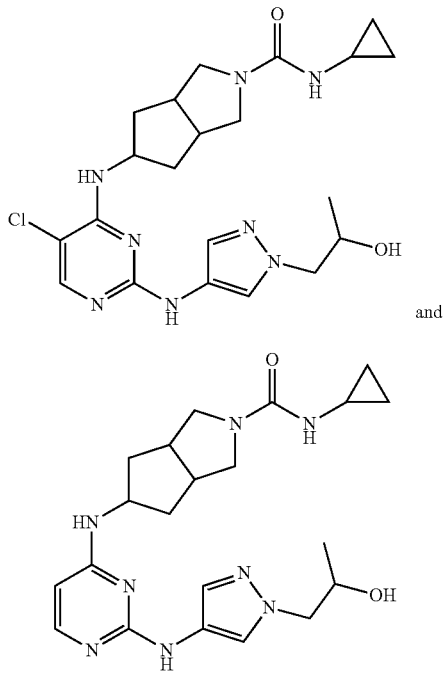

To a suspension of N-cyclopropyl-5-((2,5-dichloropyrimidin-4-yl)amino) hexahydrocyclopenta[c]pyrrole-2(1H)-carboxamide (535.5 mg, 1.50 mmol) and 1-(4-amino-1H-pyrazol-1-yl)propan-2-ol (271.2 mg, 1.92 mmol) in 1,4-dioxane (30 mL) were added Pd(OAc)$_2$ (73.0 mg, 0.32 mmol), BINAP (98%, 194.8 mg, 0.31 mmol) and cesium carbonate (98%, 1.04 g, 3.13 mmol). The reaction mixture was stirred at 100° C. overnight and concentrated in vacuo. The residue was purified by silica gel column chromatography (DCM/MeOH (v/v)=20/1) to give 5-((5-chloro-2-((1-(2-hydroxypropyl)-1H-pyrazol-4-yl)amino)pyrimidin-4-yl)amino)-N-cyclopropylhexahydrocyclopenta[c]pyrrole-2(1H)-carboxamide as a light pink solid (279.8 mg, yield 40.4%) and used another elution system (DCM/MeOH (v/v)=10/1) to give N-cyclopropyl-5-((2-((1-(2-hydroxypropyl)-1H-pyrazol-4-yl)amino)pyrimidin-4-yl)amino) hexahydrocyclopenta[c]pyrrole-2(1H)-carboxamide as a light pink solid (134.2 mg, yield 20.9%). Characterization Data of Example 41 5-((5-chloro-2-((1-(2-hydroxypropyl)-1H-pyrazol-4-yl)amino)pyrimidin-4-yl)amino)-N-cyclopropylhexahydrocyclopenta[c]pyrrole-2(1H)-carboxamide MS (ESI, pos. ion) m/z: 461.1 [M+H]$^+$;
HRMS (ESI, pos. ion) m/z: 461.2150 [M+H]$^+$, calculated value for $C_{21}H_{30}ClN_8O_2$ [M+H]$^+$ is 461.2180;

$^1$H NMR (600 MHz, CDCl$_3$) δ (ppm): 7.86 (s, 1H), 7.76 (s, 1H), 7.59 (s, 1H), 6.82 (s, 1H), 5.37 (d, J=7.4 Hz, 1H), 4.54 (s, 1H), 4.42 (m, 1H), 4.22 (m, 1H), 4.13 (dd, J=13.8, 2.7 Hz, 1H), 3.96 (dd, J=13.8, 8.0 Hz, 1H), 3.57 (s, 1H), 3.48 (dd, J=9.9, 7.3 Hz, 2H), 3.34 (d, J=10.0 Hz, 2H), 2.76 (m, 2H), 2.67 (m, 1H), 2.45 (m, 2H), 1.51 (m, 2H), 1.25 (d, J=6.3 Hz, 3H), 0.74 (m, 2H), 0.50 (m, 2H);

$^{13}$C NMR (150 MHz, CDCl$_3$) δ (ppm): 158.2, 158.0, 157.5, 153.0, 131.6, 123.0, 121.4, 67.2, 58.9, 53.2, 52.2, 41.1, 39.1, 23.3, 20.1, 6.9.

Characterization Data of Example 42

N-cyclopropyl-5-((2-((1-(2-hydroxypropyl)-1H-pyrazol-4-yl)amino)pyrimidin-4-yl)amino)hexahydrocyclopenta[c]pyrrole-2(1H)-carboxamide MS (ESI, pos. ion) m/z: 427.2 [M+H]$^+$;
HRMS (ESI, pos. ion) m/z: 427.2542 [M+H]$^+$, calculated value for $C_{21}H_{31}N_8O_2$ [M+H]$^+$ is 427.2570;

$^1$H NMR (600 MHz, CDCl$_3$) δ (ppm): 7.90 (d, J=4.7 Hz, 1H), 7.83 (s, 1H), 7.53 (s, 1H), 6.70 (s, 1H), 5.78 (d, J=5.8 Hz, 1H), 4.97 (s, 1H), 4.52 (s, 1H), 4.22 (m, 2H), 4.14 (dd, J=13.8, 2.4 Hz, 1H), 3.96 (dd, J=13.8, 8.1 Hz, 1H), 3.77 (s, 1H), 3.48 (dd, J=10.1, 7.6 Hz, 2H), 3.31 (d, J=10.4 Hz, 2H), 2.75 (m, 2H), 2.65 (m, 1H), 2.42 (m, 2H), 1.44 (m, 2H), 1.25 (d, J=6.3 Hz, 3H), 0.74 (m, 2H), 0.49 (m, 2H);

$^{13}$C NMR (150 MHz, CDCl$_3$) δ (ppm): 162.6, 159.8, 158.1, 132.0, 124.8, 122.8, 122.1, 67.2, 59.0, 52.0, 50.8, 41.2, 39.2, 23.3, 20.1, 6.9.

Example 43 5-((5-chloro-2-((1-(2-hydroxy-2-methylpropyl)-1H-pyrazol-4-yl)amino)pyrimidin-4-yl)amino)-N-cyclopropylhexahydrocyclopenta[c]pyrrole-2(1H)-sulfonamide

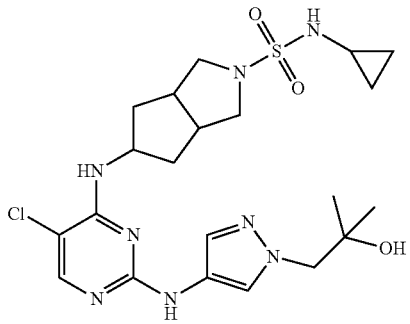 [SMILES: CC(C)(O)Cn1cc(Nc2ncc(Cl)c(NC3CC4CN(S(=O)(=O)NC5CC5)CC4C3)n2)cn1]

Step 1) N-cyclopropyl-5-((2,5-dichloropyrimidin-4-yl)amino)hexahydrocyclopenta[c]pyrrole-2(1H)-sulfonamide To a suspension of N-(2,5-dichloropyrimidin-4-yl)octahydrocyclopenta[c]pyrrol-5-amine (0.27 g, 0.987 mmol7) and TEA (0.70 mL, 5.00 mmol) in anhydrous DCM (10.0 mL) was slowly added a solution of cyclopropylsulfamoyl chloride (0.31 g, 1.98 mmol) in anhydrous DCM (5.0 mL) at 0° C. After addition, the mixture was move to room temperature and stirred for another 30 min. The reaction was quenched by addition of water (20 mL) and allowed to stratification. The organic layer was separated and the aqueous layer was extracted with DCM (30 mL×3). The combined organic layer was washed with brine (30 mL), dried over anhydrous Na$_2$SO$_4$, filtered and concentrated in vacuo. The residue was purified by silica gel column chromatography (EtOAc/PE (v/v)=1/3) to afford the title compound as a yellow solid (0.17 g, yield 44%).

MS (ESI, pos. ion) m/z: 392.1 [M+H]⁺;

¹H NMR (400 MHz, CDCl₃) δ (ppm): 8.02 (s, 1H), 5.70 (d, J=7.7 Hz, 1H), 4.51-4.38 (m, 1H), 3.85 (s, 1H), 3.35-3.22 (m, 4H), 2.84-2.71 (m, 2H), 2.63-2.57 (m, 1H), 2.53-2.44 (m, 2H), 1.50-1.37 (m, 2H), 0.75-0.70 (m, 4H).

Step 2) 5-((5-chloro-2-((1-(2-hydroxy-2-methylpropyl)-1H-pyrazol-4-yl)amino)pyrimidin-4-yl)amino)-N-cyclopropylhexahydrocyclopenta[c]pyrrole-2(1H)-sulfonamide To a suspension of N-cyclopropyl-5-((2,5-dichloropyrimidin-4-yl)amino)hexahydrocyclopenta[c]pyrrole-2(1H)-sulfonamide (0.11 g, 0.28 mmol) in anhydrous 1,4-dioxane (10.0 mL) was added 1-(4-amino-1H-pyrazol-1-yl)-2-methylpropan-2-ol (54 mg, 0.35 mmol), Pd(OAc)₂ (14 mg, 0.06 mmol), BINAP (37 mg, 0.06 mmol) and cesium carbonate (0.20 g, 0.61 mmol). The mixture was degassed for 2 min and refilled with N₂ and heated to 105° C. and stirred for 3 h. The mixture was concentrated in vacuo. The residue was purified by silica gel column chromatography (DCM/MeOH (v/v)=50/1 to 30/1) to get the crude product. The crude product was purified once again by preparative TLC (DCM/MeOH (v/v)=20/1) to afford the title compound as a brown solid (55 mg, yield 38%).

MS (ESI, pos. ion) m/z: 511.2 [M+H]⁺;

HRMS (ESI, pos. ion) m/z: 511.1974 [M+H]⁺, calculated value for C₂₁H₃₂ClN₈O₃S [M+H]⁺ is 511.2001;

¹H NMR (600 MHz, DMSO-d₆) δ (ppm): 9.06 (s, 1H), 7.87 (s, 1H), 7.84 (s, 1H), 7.54 (d, J=1.9 Hz, 1H), 7.43 (s, 1H), 6.97 (s, 1H), 4.67 (s, 1H), 4.44-4.32 (m, 1H), 3.94 (s, 2H), 3.25-3.21 (m, 2H), 3.11-3.03 (m, 2H), 2.75-2.65 (m, 2H), 2.46-2.44 (m, 1H), 2.30-2.20 (m, 2H), 1.56-1.46 (m, 2H), 1.05 (s, 6H), 0.63-0.56 (m, 2H), 0.56-0.49 (m, 2H).

Example 44 1-(4-((5-chloro-4-((2-(cyclopropylsulfonyl)octahydrocyclopenta[c]pyrrol-5-yl)amino)pyrimidin-2-yl)amino)-1H-pyrazol-1-yl)propan-2-ol

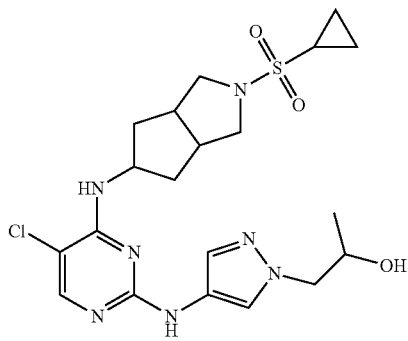 [SMILES: CC(O)Cn1cc(Nc2ncc(Cl)c(NC3CC4CN(S(=O)(=O)C5CC5)CC4C3)n2)cn1]

Step 1) 2-(cyclopropylsulfonyl)-N-(2, 5-dichloropyrimidin-4-yl)octahydrocyclopenta[c]pyrrol-1-amine To a solution of triethylamine (120 mg, 1.17402 mmol) and N-(2,5-dichloropyrimidin-4-yl)octahydrocyclopenta[c]pyrrol-5-amine (100 mg, 0.3661 mmol) in DCM (20 mL, 311 mmol) was dropwise added cyclopropanesulfonyl chloride (77 mg, 0.5477 mmol) at 0° C. After the addition, the reaction mixture was stirred at rt for 6 h and concentrated in vacuo. The residue was purified by silica gel column chromatography (DCM/MeOH (v/v)=40/1) to give the title compound as a light yellow solid (102 mg, yield 73.9%).

MS (ESI, pos. ion) m/z: 377.3 [M+H]⁺.

Step 2) 1-(4-((5-chloro-4-((2-(cyclopropylsulfonyl)octahydrocyclopenta[c]pyrrol-5-yl)amino)pyrimidin-2-yl)amino)-1H-pyrazol-1-yl)propan-2-ol To a solution of 2-(cyclopropylsulfonyl)-N-(2,5-dichloropyrimidin-4-yl) octahydrocyclopenta[c]pyrrol-5-amine (101.2 mg, 0.2682 mmol), 1-(4-aminopyrazol-1-yl)propan-2-ol (58.8 mg, 0.417 mmol), BINAP (15.2 mg, 0.0237 mmol and Pd(OAc)₂ (6.3 mg, 0.028 mmol) in 1,4-dioxane (15 mL) was added cesium carbonate (261.0 mg, 0.800 mmol). The reaction was stirred at 100° C. under N₂ atmosphere overnight and then concentrated in vacuo. The residue was purified by silica gel column chromatography (DCM/MeOH (v/v)=40/1) to give the crude compound as a light yellow solid. The crude product was then purified by preparative TLC (DCM/MeOH (v/v)=30/1) to give the title compound as a white solid (30 mg, yield 23.2%).

MS (ESI, pos. ion) m/z: 482.1 [M+H];

¹H NMR (600 MHz, CDCl₃) δ (ppm): 7.86 (s, 1H), 7.73 (s, 1H), 7.57 (s, 1H), 6.63 (s, 1H), 5.38 (d, J=7.4 Hz, 1H), 4.33 (m, 1H), 4.21 (m, 1H), 4.11 (dd, J=13.8, 2.5 Hz, 1H), 3.94 (dd, J=13.8, 8.0 Hz, 1H), 3.36 (m, 2H), 3.31 (m, 2H), 2.77 (m, 2H), 2.47 (m, 2H), 2.35 (m, 1H), 1.49 (m, 2H), 1.23 (d, J=6.3 Hz, 3H), 1.21 (m, 2H), 1.01 (m, 2H);

¹³C NMR (150 MHz, CDCl₃) δ (ppm): 157.9, 157.6, 152.9, 131.5, 129.9, 123.0, 121.2, 67.3, 58.8, 54.2, 52.5, 40.5, 39.3, 29.7, 25.1, 20.1, 4.5.

Example 45 5-((5-chloro-2-((1-(2-hydroxypropyl)-1H-pyrazol-4-yl)amino)pyrimidin-4-yl)amino)-N-ethylhexahydrocyclopenta[c]pyrrole-2(1H)-sulfonamide

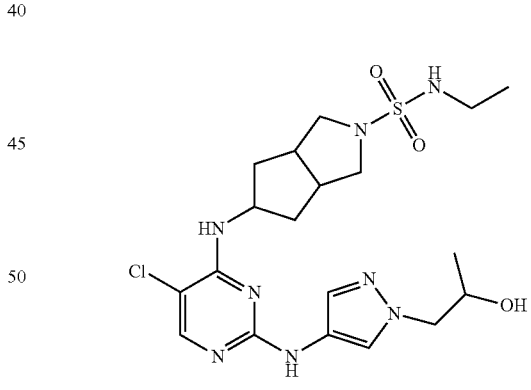

Step 1) 5-((2,5-dichloropyrimidin-4-yl)amino)-N-ethylhexahydrocyclopenta[c]pyrrole-2(1)-sulfonamide To a solution of N-(2,5-dichloropyrimidin-4-yl)octahydrocyclopenta[c]pyrrol-5-amine (303.4 mg, 1.111 mmol) in DCM (5 mL) was added TEA (354.7 mg, 3.505 mmol). The mixture was cooled to 0° C., then the solution of N-ethylsulfamoyl chloride (100 mg, 0.6964 mmol) in DCM (4 mL) was added. The reaction mixture was warmed to rt and stirred overnight, then concentrated in vacuo. The residue was purified by silica gel column chromatography (DCM/MeOH (v/v)=70/1) to give the title compound as a white solid (95 mg, yield 22.49%).
MS (ESI, pos. ion) m/z: 380.4 [M+H]+.

Step 2) 5-((5-chloro-2-((1-(2-hydroxypropyl)-1H-pyrazol-4-yl)amino)pyrimidin-4-yl)amino)-N-ethyl-hexahydrocyclopenta[c]pyrrole-2(1H)-sulfonamide To a mixture of 5-((2,5-dichloropyrimidin-4-yl)amino)-N-ethylhexahydrocyclopenta[c]pyrrole-2(1H)-sulfonamide (95 mg, 0.2498 mmol) and 1-(4-aminopyrazol-1-yl) propan-2-ol (44.6 mg, 0.316 mmol) were added $Cs_2CO_3$ (168.4 mg, 0.5168 mmol), BINAP (17.2 mg, 0.0276 mmol), $Pd(OAc)_2$ (6.8 mg, 0.030 mmol) and 1,4-dioxane (10 mL). The reaction mixture was heated to reflux and stirred for 4 h under $N_2$ atmosphere and concentrated in vacuo. The residue was purified by silica gel column chromatography (DCM/MeOH (v/v)=20/1) to give the title compound as a light yellow solid (35.4 mg, yield 29.2%).
MS (ESI, pos. ion) m/z: 485.1 [M+H]+;
HRMS (ESI, pos. ion) m/z: 485.1853 [M+H]+, calculated value for $C_{19}H_{30}ClN_8O_3S$ [M+H]+ is 485.1850;
$^1H$ NMR (600 MHz, $CDCl_3$) δ (ppm): 7.84 (s, 1H), 7.72 (s, 1H), 7.57 (s, 1H), 6.96-6.78 (m, 1H), 5.44 (d, J=6.9 Hz, 1H), 4.35-4.29 (m, 1H), 4.27 (t, J=5.7 Hz, 1H), 4.23-4.16 (m, 1H), 4.11 (dd, J=13.8, 2.4 Hz, 1H), 3.94 (dd, J=13.8, 8.0 Hz, 1H), 3.27-3.15 (m, 6H), 2.79-2.72 (m, 2H), 2.51-2.40 (m, 2H), 1.49-1.40 (m, 2H), 1.22 (t, J=7.1 Hz, 6H);
$^{13}C$ NMR (150 MHz, $CDCl_3$) δ (ppm): 157.9, 157.7, 152.7, 131.6, 122.9, 121.4, 67.2, 58.9, 54.4, 52.7, 40.4, 39.5, 39.1, 20.1, 15.7.

Example 46 1-(4-((5-chloro-4-((2-((cyclopropylmethyl)sulfonyl)octahydrocyclopenta[c]pyrrol-5-yl)amino)pyrimidin-2-yl)amino)-1H-pyrazol-1-yl)propan-2-ol

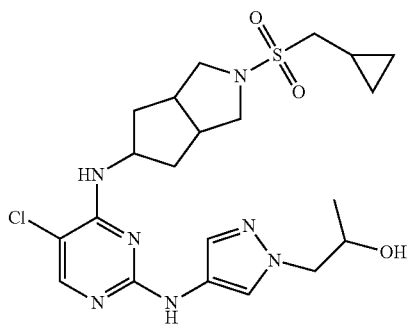 [SMILES: CC(O)Cn1cc(Nc2ncc(Cl)c(NC3CC4CN(S(=O)(=O)CC5CC5)CC4C3)n2)cn1]

Step 1) sodium cyclopropylmethanesulfonate

To a saturated $Na_2SO_3$ aqueous solution (10 mL) was added 1-bromo-1-methylcyclopropane (1.00 g, 7.4074 mmol). After the addition, the reaction mixture was stirred at 100° C. overnight and then concentrated in vacuo. The residue was suspended in EtOH (20 mL) and the suspension system was stirred at 50° C. for 5 h. Filtered and collected the filter cake to give the title compound as a white solid (1.12 g, yield 95.6%).

Step 2) cyclopropylmethanesulfonyl chloride

To a solution of sodium cyclopropylmethanesulfonate (1.12 g, 7.08 mmol) in THF (10 mL, 123 mmol) was dropwise added thionyl chloride (2.1 mL, 29 mmol). After the addition, the reaction was stirred at 100° C. for 5 h and concentrated in vacuo to give the product as brown oil (1.00 g, yield 91.3%).

Step 3) 2-((cyclopropylmethyl)sulfonyl)-N-(2,5-dichloropyrimidin-4-yl)octahydro-cyclopenta[c]pyrrol-5-amine To a solution of N-(2,5-dichloropyrimidin-4-yl)octahydrocyclopenta[c]pyrrol-5-amine (200.2 mg, 0.7329 mmol) and triethylamine (120 mg, 1.1740 mmol) in DCM (30 mL, 467 mmol) was dropwise added a solution of cyclopropylmethanesulfonyl chloride (200 mg, 1.2935 mmol) in DCM (5 mL) at 0° C. After the addition, the reaction was stirred at rt for 5 h and then concentrated in vacuo. The residue was purified by silica gel column chromatography (DCM/MeOH (v/v)=50/1) to give the target compound as a light yellow solid (180.1 mg, yield 62.8%).
MS (ESI, pos. ion) m/z: 391.2 [M+H].

Step 4) 1-(4-((5-chloro-4-((2-((cyclopropylmethyl)sulfonyl)octahydrocyclopenta[c]pyrrol-5-yl)amino)pyrimidin-2-yl)amino)-1H-pyrazol-1-yl)propan-2-ol

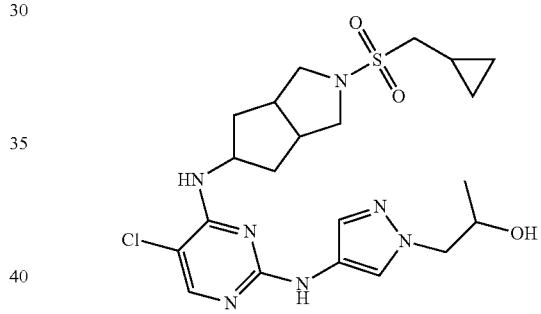

To a solution of 2-((cyclopropylmethyl)sulfonyl)-N-(2,5-dichloropyrimidin-4-yl) octahydro-cyclopenta[c]pyrrol-5-amine (180.5 mg, 0.46 mmol), 1-(4-aminopyrazol-1-yl)propan-2-ol (97.3 mg, 0.69 mmol), BINAP (29.3 mg, 0.046 mmol) and $Pd(OAc)_2$ (10.2 mg, 0.044 mmol) in 1,4-dioxane (15 mL), was added cesium carbonate (451.2 mg, 1.38 mmol). The reaction was stirred at 100° C. under $N_2$ atmosphere overnight and then concentrated in vacuo. The residue was purified by silica gel column chromatography (DCM/MeOH (v/v)=40/1) to give the crude compound as a light yellow solid. The crude product was then purified by preparative TLC (DCM/MeOH (v/v)=30/1) to give the title compound as a light yellow solid (125.6 mg, yield 55%).
MS (ESI, pos. ion) m/z: 496.1 [M+H];
$^1H$ NMR (400 MHz, DMSO-$d_6$) δ (ppm): 9.05 (s, 1H), 7.84 (d, J=13.4 Hz, 2H), 7.43 (s, 1H), 6.98 (d, J=5.3 Hz, 1H), 4.98 (s, 1H), 4.39 (d, J=4.9 Hz, 1H), 3.93 (s, 3H), 3.34 (s, 2H), 3.16 (d, J=8.7 Hz, 2H), 3.05 (d, J=6.3 Hz, 2H), 2.68 (s, 2H), 2.24 (s, 2H), 1.51 (s, 2H), 1.23 (s, 1H), 1.01 (s, 3H), 0.60 (d, J=6.0 Hz, 2H), 0.35 (s, 2H);
$^{13}C$ NMR (100 MHz, DMSO-$d_6$) δ (ppm): 158.1, 157.8, 153.8, 130.0, 123.8, 120.4, 110.0, 66.1, 59.3, 53.6, 52.8, 37.8, 21.3, 5.3, 4.8.

Example 47 5-((5-chloro-2-((1-(2-hydroxypropyl)-1H-pyrazol-4-yl)amino)pyrimidin-4-yl)amino)-N-cyclopropylhexahydrocyclopenta[c]pyrrole-2(1H)-sulfonamide

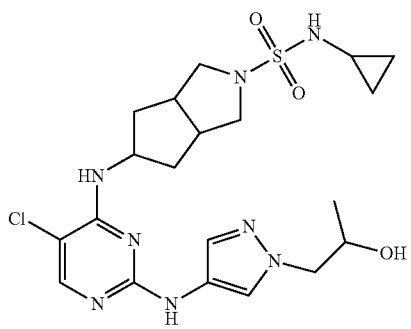 [SMILES: CC(O)Cn1cc(Nc2ncc(Cl)c(NC3CC4CN(S(=O)(=O)NC5CC5)CC4C3)n2)cn1]

Step 1) N-cyclopropyl-5-((2, 5-dichloropyrimidin-4-yl)amino)hexahydrocyclopenta[c]pyrrole-2(1H)-sulfonamide To a solution of N-(2,5-dichloropyrimidin-4-yl)octahydrocyclo-penta[c]pyrrol-5-amine (200 mg, 0.7322 mmol) and TEA (225 mg, 2.2013 mmol) in DCM (40 mL, 622 mmol) was dropwise added a solution of N-cyclopropylsulfamoyl chloride (228 mg, 1.4653 mmol) in DCM (4 mL, 62 mmol) at 0° C. After the addition, the reaction was stirred at rt for 6 h and then concentrated in vacuo. The residue was purified by silica gel column chromatography (DCM/MeOH (v/v)=40/1) to give the compound as a light yellow solid (120 mg, yield 41.8%).

MS (ESI, pos. ion) m/z: 392.0 [M+H]$^+$;

$^1$H NMR (400 MHz, CDCl$_3$): δ (ppm) 7.98 (s, 1H), 5.81 (d, J=7.6 Hz, 1H), 5.08 (s, 1H), 4.41 (m, 1H), 3.24 (d, J=2.6 Hz, 4H), 2.75 (s, 2H), 2.55 (s, 1H), 2.45 (m, 2H), 1.43 (m, 2H), 0.68 (m, 2H), 0.64 (m, 2H).

Step 2) 5-((5-chloro-2-((1-(2-hydroxypropyl)-1H-pyrazol-4-yl)amino)pyrimidin-4-yl)amino)-N-cyclopropylhexahydrocyclopenta[c]pyrrole-2(1H)-sulfonamide To a solution of Pd(OAc)$_2$ (10 mg, 0.0436512 mmol), BINAP (26 mg, 0.04 mmol), 1-(4-aminopyrazol-1-yl)propan-2-ol (113 mg, 0.80 mmol), N-cyclopropyl-5-((2,5-dichloropyrimidin-4-yl)amino)hexahydrocyclopenta[c]pyrrole-2(1H)-sulfonamide (158 mg, 0.4028 mmol) in 1,4-dioxane (25 mL) was added cesium carbonate (400 mg, 1.23 mmol). The reaction mixture was stirred at 100° C. under N$_2$ atmosphere overnight and then concentrated in vacuo. The residue was purified by silica gel column chromatography (MeOH/DCM (v/v)=1/40) to give the crude compound as a light yellow solid. The crude product was then purified by preparative TLC (MeOH/DCM (v/v)=1/30) to give the title compound as a white solid (48 mg, yield 24.0%).

MS (ESI, pos. ion) m/z: 497.2 [M+H]$^+$;

$^1$H NMR (600 MHz, CDCl$_3$) δ (ppm): 9.02 (s, 1H), 7.84 (s, 1H), 7.79 (s, 1H), 7.51 (s, 1H), 7.41 (s, 1H), 6.94 (d, J=6.3 Hz, 1H), 4.36 (m, 1H), 3.91 (s, 3H), 3.20 (m, 2H), 3.15 (d, J=5.1 Hz, 1H), 3.05 (d, J=9.0 Hz, 2H), 2.67 (s, 2H), 2.43 (m, 1H), 2.24 (s, 2H), 1.49 (m, 2H), 0.99 (d, J=5.2 Hz, 3H), 0.57 (m, 2H), 0.51 (m, 2H);

$^{13}$C NMR (151 MHz, DMSO-d$_6$) δ (ppm): 158.1, 157.8, 153.8, 130.1, 129.9, 123.8, 120.3, 66.8, 66.2, 59.4, 54.0, 49.1, 38.1, 24.9, 21.3, 6.6.

Example 48 2-(2-acetyl-5-((5-chloro-2-((1-methyl-1H-pyrazol-4-yl)amino)pyrimidin-4-yl)amino)octahydrocyclopenta[c]pyrrol-5-yl)acetonitrile

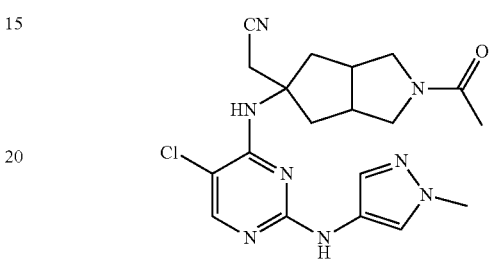

To a mixture of 2-(5-((5-chloro-2-((1-methyl-1H-pyrazol-4-yl)amino)pyrimidin-4-yl)amino)octahydrocyclopenta[c]pyrrol-5-yl)acetonitrile (92.8 mg, 0.25 mmol) and Et$_3$N (60.4 mg, 0.60 mmol) in DCM (10 mL) were added a solution of acetyl acetate (40.8 mg, 0.40 mmol) in DCM (2 mL). The reaction mixture was stirred at rt for 15 min, quenched with H$_2$O (30 mL) and extracted with DCM (100 mL×3). The combined organic phases were washed with brine (100 mL), dried over anhydrous Na$_2$SO$_4$, and concentrated in vacuo. The residue was purified by a silica gel column chromatography (MeOH/DCM (v/v)=1/20) to give the title compound as a beige solid (85.9 mg, yield 83.2%).

MS (ESI, pos. ion) m/z: 415.2 [M+H]$^+$;

HRMS (ESI, pos. ion) m/z: 415.1763 [M+H]$^+$, calculated value for C$_{19}$H$_{24}$ClN$_8$O [M+H]$^+$ is 415.1762;

$^1$H NMR (400 MHz, CDCl$_3$) δ (ppm): 7.94 (s, 1H), 7.64 (s, 1H), 7.47 (d, J=9.1 Hz, 1H), 6.86 (s, 1H), 5.45 and 5.14 (s, 1H), 3.90 and 3.89 (s, 3H), 3.66 and 3.38 (m, 2H), 3.63 and 3.61 (s, 2H), 3.57 and 3.12 (d, J=5.6 Hz, 2H), 2.92 (m, 2H), 2.74 (m, 1H), 2.48 (m, 1H), 2.08 and 2.05 (s, 3H), 2.00 and 1.71 (m, 2H);

$^{13}$C NMR (150 MHz, CDCl$_3$) δ (ppm): 169.6, 157.0 (s), 156.89, 153.8, 122.4, 117.6, 117.5, 64.6, 63.3, 53.0, 52.6, 51.4, 50.4, 44.2, 43.2, 43.1, 42.1, 42.0, 40.5, 40.2, 39.4, 39.3, 29.7, 25.8, 22.5.

Example 49

The compound 49 was prepared using the same synthetic methodology as describe in the example 32. The requisite starting materials were commercially available, described in the literature or readily synthesized by one skilled in the art of organic synthesis without undue experimentation.

TABLE 2

| Example # | Structure | Name | MS (ESI, pos. ion) m/z |
|---|---|---|---|
| Ex. 49 | (chemical structure) | 2-(5-((5-chloro-2-((1-methyl-1H-pyrazol-4-yl)amino)pyrimidin-4-yl)amino)octahydrocyclopenta[c]pyrrol-3a-yl)acetonitrile | 373.1 |

Biological Testing

The LC/MS/MS system used in the analysis consists of an Agilent 1200 Series vacuum degasser, binary pump, well-plate autosampler, thermostatted column compartment, the Agilent G6430 Triple Quadrupole Mass Spectrometer with an electrosprayionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 0.28 MPa |
| Drying Gas Flow | 10 L/min |

An Agilent XDB-C18, 2.1×30 mm, 3.5 μM column was used for the analysis. 5 μL of the samples were injected. Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 μM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 μL of the samples were injected.

Example A: Compound Stability in Human and Rat Liver Microsomes

Human or rat liver microsomes incubations were conducted in duplicate in polypropylene tubes. The typical incubation mixtures consisted of human or rat liver microsomes (0.5 mg protein/mL), compounds of interest (5 μM) and NADPH (1.0 mM) in a total volume of 200 μL potassium phosphate buffer (PBS, 100 mM, pH 7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human or rat liver microsomes were determined by a LC/MS/MS method. The ranges of the linearity in the concentration range were determined for each tested compounds.

A parallel incubation was performed using denatured microsomes as the negative control, and reactions were terminated at various time points (0, 15, 60 min) after incubation at 37° C.

Dextromethorphan (70 μM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Data Analysis

The concentrations of compounds in human or rat liver microsome incubations were plotted as a percentage of the relevant zero time point control for each reaction. The in vivo $CL_{int}$ were extrapolated (ref.: Naritomi, Y.; Terashita, S.; Kimura, S.; Suzuki, A.; Kagayama, A.; and Sugiyama, Y.; Prediction of human hepatic clearance from in vivo animal experiments and in vitro metabolic studies with liver microsomes from animals and humans. *Drug Metab. Dispos.*, 2001, 29: 1316-1324).

Exemplary results from selected compounds of the invention are listed in Table 3. The compounds disclosed herein exhibited desirable stability when the compounds were incubated in human and rat liver microsomes.

TABLE 3

Stability of selected compounds of the invention in human and rat liver microsomes

| Example # | Human $T_{1/2}$ (min) | Human $CL_{int}$ (mL/min/kg) | Rat $T_{1/2}$ (min) | Rat $CL_{int}$ (mL/min/kg) |
|---|---|---|---|---|
| Ex. 1 | 148.5 | 11.71 | 112.0 | 22.18 |
| Ex. 2 | 106.0 | 16.40 | 106.6 | 23.30 |
| Ex. 3 | 554.6 | 3.13 | 3.88 | 639.47 |
| Ex. 4 | 951.3 | 1.83 | 68.73 | 36.14 |
| Ex. 5 | 1045 | 1.66 | NT | NT |
| Ex. 6 | 660.1 | 2.63 | 2641 | 0.94 |
| Ex. 8 | 31.45 | 55.27 | 16.19 | 153.41 |
| Ex. 13 | 33.14 | 52.45 | 5.48 | 453.56 |
| Ex. 14 | 44.17 | 39.36 | 3.33 | 745.19 |
| Ex. 16 | 210.1 | 8.27 | 6.28 | 395.37 |
| Ex. 17 | 35.74 | 48.64 | 7.15 | 347.32 |
| Ex. 18 | 145.0 | 11.99 | 9.46 | 262.60 |
| Ex. 19 | 177.7 | 9.78 | 96.88 | 25.64 |
| Ex. 21 | 404.0 | 4.30 | 62.94 | 39.46 |
| Ex. 22 | 65.67 | 26.47 | 3.33 | 745.19 |
| Ex. 23 | 61.03 | 28.48 | 30.03 | 82.71 |
| Ex. 24 | 33.97 | 51.17 | 9.30 | 266.98 |
| Ex. 28 | 24.2 | 72.0 | 3.6 | 689.5 |
| Ex. 29 | 43.20 | 40.24 | 19.77 | 125.63 |
| Ex. 30 | 24.92 | 69.76 | 8.07 | 307.77 |
| Ex. 33 | 275.0 | 6.32 | 321.4 | 7.73 |
| Ex. 34 | 35.73 | 48.65 | 17.80 | 139.53 |
| Ex. 36 | 69.16 | 25.13 | 30.66 | 81.01 |
| Ex. 37 | 54.33 | 32.00 | 70.45 | 35.25 |
| Ex. 38 | 67.14 | 25.89 | 45.45 | 54.65 |
| Ex. 39 | 49.60 | 35.05 | 39.23 | 63.31 |
| Ex. 41 | 73.49 | 23.7 | 43.72 | 56.8 |
| Ex. 42 | 153.3 | 11.3 | 374.6 | 6.6 |
| Ex. 48 | 310.4 | 5.60 | 100.2 | 24.79 |

NT: Not Test

TABLE 4

Pharmacokinetic profiles of selected compounds of the invention in rats

| | iv dosing | | | | | |
|---|---|---|---|---|---|---|
| Example # | dose (mg/kg) | $T_{1/2}$ (h) | $AUC_{last}$ (ng · h/mL) | Cl/F (L/h/kg) | Vss (L/kg) | F (%) |
| Ex. 1 | 1 | 0.64 | 360 | 2.77 | 1.53 | 61.7 |
| Ex. 8 | 1 | 0.56 | 558 | 1.86 | 1.55 | 36.9 |
| Ex. 11 | 1 | 0.30 | 235 | 4.52 | 1.22 | 19.5 |
| Ex. 12 | 1 | 0.24 | 278 | 3.61 | 0.99 | 30.5 |
| Ex. 17 | 1 | 0.29 | 308 | 3.25 | 1.44 | 37.3 |
| Ex. 19 | 1 | 0.35 | 263 | 3.82 | 0.95 | 24.0 |
| Ex. 20 | 0.5 | 0.70 | 348 | 1.48 | 1.07 | 91.2 |
| Ex. 21 | 1 | 1.46 | 147 | 6.54 | 11.9 | 118.2 |
| Ex. 22 | 1 | 0.56 | 746 | 1.34 | 1.21 | 84.6 |
| Ex. 23 | 1 | 0.62 | 363 | 2.78 | 2.07 | 64.4 |
| Ex. 24 | 1 | 0.40 | 231 | 4.55 | 2.02 | 31.9 |
| Ex. 27 | 1 | 0.22 | 218 | 4.66 | 0.93 | 22.5 |
| Ex. 28 | 1 | 0.38 | 168 | 5.95 | 1.99 | 42.0 |
| Ex. 29 | 1 | 0.35 | 413 | 2.42 | 1.19 | 102.8 |
| Ex. 30 | 1 | 0.61 | 1140 | 0.93 | 0.71 | 268.4 |
| Ex. 34 | 1 | 0.29 | 348 | 2.93 | 1.18 | 54.0 |
| Ex. 37 | 1 | 1.25 | 604 | 1.76 | 2.61 | 53.6 |
| Ex. 38 | 1 | 0.42 | 270 | 3.77 | 1.65 | 35.3 |
| Ex. 39 | 1 | 0.64 | 295 | 5.76 | 1.88 | 40.5 |
| Ex. 44 | 1 | 0.86 | 276 | 3.65 | 1.75 | 31.4 |
| Ex. 45 | 1 | 0.66 | 267 | 3.74 | 1.97 | 27.1 |
| Ex. 46 | 1 | 0.26 | 277 | 3.64 | 1.13 | 24.9 |
| Ex. 47 | 1 | 0.71 | 239 | 4.16 | 2.37 | 22.4 |
| Ex. 48 | 1 | 0.72 | 485 | 2.08 | 0.81 | 40.7 |

NT: Not Test

Example B: Evaluation of Pharmacokinetics after Intravenous and Oral Administration of the Compounds Disclosed Herein in Mice, Rats, Dogs and Monkeys The compounds disclosed herein are assessed in pharmacokinetic studies in mice, rats, dogs or monkeys. The compounds are administered as a water solution, 2% HPMC+1% TWEEN®80 in water solution, 5% DMSO+5% solutol in saline, 4% MC suspension or capsule. For the intravenous administration, the animals are generally given at 0.5, 1 or 2 mg/kg dose. For the oral (p.o.) dosing, mice and rats are generally given 0.5, 1, 5 or 10 mg/kg dose, and dogs and monkeys are generally given 10 mg/kg dose. The blood samples (0.3 mL) are drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected, and stored at −20° C. or −70° C. until analyzed by LC/MS/MS as described above.

Exemplary study results from examples disclosed herein are listed in Table 4. The compounds disclosed herein exhibited optimized pharmacokinetic properties with good absorption and desirable oral bioavailability (F) when the compounds were administered orally or intravenously.

Example C: Kinase Activity Assay

The efficacy of the compounds disclosed herein as inhibitors of protein kinases can be evaluated as follows.

General Description for Kinase Assays

Kinase assays can be performed by measurement of incorporation of γ-$^{33}$P ATP into immobilized myelin basic protein (MBP). High binding white 384 well plates (Greiner) are coated with MBP (Sigma #M-1891) by incubation of 60 μL/well of 20 μg/mL MBP in Tris-buffered saline (TBS; 50 mM Tris pH 8.0, 138 mM NaCl, 2.7 mM KCl) for 24 h at 4° C. Plates are washed 3× with 100 μL TBS. Kinase reactions are carried out in a total volume of 34 μL in kinase buffer (according to the need to make, for example, 5 mM Hepes pH 7.6, 15 mM NaCl, 0.01% bovine gamma globulin (Sigma #1-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and γ-$^{33}$P ATP is added to start the reaction (2×10$^6$ cpm of γ-$^{33}$P ATP per well (3000 Ci/mmole) and 10 μM unlabeled ATP, typically. The reactions are carried out for 1 h at room temperature with shaking. Plates are washed 7× with TBS, followed by the addition of 50 μL/well scintillation fluid (Wallac). Plates are read using a Wallac Trilux counter. This is only one format of such assays; various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the condition of the assay. The IC$_{50}$ value is estimated by preparing a 10 point curve using a ½ log dilution series (for example, a typical curve may be prepared using the following compound concentrations: 3 µM, 1 µM, 0.3 µM, 0.1 µM, 0.03 µM, 0.01 µM, 0.003 µM, 0.001 µM, 0.0003 µM and 0 µM).
Kinase General Assay Protocol
JAK1 (h)

JAK1 (h) is incubated with 20 mM Tris/HCl pH 7.5, 0.2 mM EDTA, 500 µM GEEPLYWSFPAKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.
JAK2 (h)

JAK2 (h) is incubated with 8 mM MOPS pH 7.0, 0.2 mM EDTA, 100 µM KTFCGTPEYLAPEVRREPRILSEE-EQEMFRDFDYIADWC, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.
JAK3 (h)

JAK3 (h) is incubated with 8 mM MOPS pH 7.0, 0.2 mM EDTA, 500 µM GGEEEEYFELVKKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.
TYK2 (h)

TYK2 (h) is incubated with 8 mM MOPS pH 7.0, 0.2 mM EDTA, 250 µLM GGMEDIYFEFMGGKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.
FLT3 (h)

FLT3 (h) is incubated with 8 mM MOPS pH 7.0, 0.2 mM EDTA, 50 µLM EAIYAAPFAKKK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.
Aurora-A (h)

Aurora-A (h) is incubated with 8 mM MOPS pH 7.0, 0.2 mM EDTA, 200 µM LRRASLG (Kemptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.
Aurora-B (h)

Aurora-B (h) is incubated with 8 mM MOPS pH 7.0, 0.2 mM EDTA, 30 µM AKRRRLSSLRA, 10 mM MgAcetate and [γ-$^{33}$PATP] (specific activity approx. 500 cpm/pmol, concentration as required). The reaction is initiated by the addition of the MgATP mix. After incubation for 40 minutes at room temperature, the reaction is stopped by the addition of a 3% phosphoric acid solution. 10 µL of the reaction is then spotted onto a P30 filtermat and washed three times for 5 minutes in 75 mM phosphoric acid and once in methanol prior to drying and scintillation counting.

The kinase assays described herein were performed at Millipore UK Ltd, Dundee Technology Park, Dundee DD2 1SW, UK.

Alternatively, the kinase activities of the compounds can be measured using KINOMEscan™, which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag.

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEA-BLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% TWEEN®20). The beads were then re-suspended in elution buffer (1×PBS, 0.05% TWEEN®20, 0.5 µM non-biotinylated affinity ligand) and incubated at room temperature with shaking for 30 minutes. The kinase concentration in the eluates was measured by qPCR.

The kinase activity assays described herein can be performed using KINOMEscan™ Profiling Service at DiscoveRx Corporation, 42501 Albrae St. Fremont, Calif. 94538, USA.

The compounds disclosed herein displayed inhibitory activities against JAK1, JAK2, JAK3, TYK2, Aurora-A, Aurora-B and/or FLT3 kinases in the corresponding kinase assays. Especially those compounds shown potent inhibitory activities against JAK1, Aurora-A and Aurora-B. Exemplary assay results from compounds disclosed herein are listed in Table 5 and Table 6.

Table 5 lised the IC$_{50}$ of some compounds described herein in the JAK1 and Aurora-A kinase assays. Table 6 lised the IC$_{50}$ of some compounds described herein in the JAK2, Aurora-B and FLT3 kinases assays.

TABLE 5

JAK1 and Aurora-A Kinase inhibition data

| Example # | IC$_{50}$ (nM) | |
|---|---|---|
| | JAK1 (h) | Aurora-A (h) |
| Ex. 1 | 10 | 58 |
| Ex. 2 | 2 | 28 |
| Ex. 7 | 0.6 | 8 |
| Ex. 10 | <0.3 | 4 |
| Ex. 12 | 12 | 17 |
| Ex. 13 | NT | 5 |
| Ex. 14 | 6 | 21 |
| Ex. 15 | 8 | 10 |
| Ex. 16 | 32 | NT |
| Ex. 17 | NT | 6 |
| Ex. 18 | 12 | 11 |
| Ex. 19 | 23 | 8 |
| Ex. 24 | 2 | 3 |
| Ex. 31 | NT | 50 |
| Ex. 34 | 3 | 1 |
| Ex. 37 | 2 | 71 |
| Ex. 38 | 1 | 0.8 |
| Ex. 39 | 2 | 2 |
| Ex. 40 | NT | 12 |
| Ex. 41 | NT | 19 |
| Ex. 43 | NT | 9 |
| Ex. 44 | NT | 5 |
| Ex. 45 | NT | 5 |
| Ex. 46 | NT | 10 |
| Ex. 47 | NT | 7 |

NT: Not Test

TABLE 6

JAK2, Aurora-B and FLT3 Kinase inhibition data

| Example # | IC$_{50}$ (nM) | | |
|---|---|---|---|
| | JAK2 (h) | Aurora-B (h) | FLT3 (h) |
| Ex. 7 | 20 | NT | NT |
| Ex. 10 | 16 | NT | NT |
| Ex. 15 | 136 | 2 | 503 |
| Ex. 18 | 142 | 2 | 1025 |
| Ex. 19 | NT | 1 | NT |
| Ex. 24 | NT | 0.7 | NT |
| Ex. 34 | NT | 0.8 | NT |
| Ex. 37 | 131 | NT | NT |
| Ex. 38 | NT | 1 | NT |
| Ex. 39 | NT | 1 | NT |
| Ex. 44 | NT | 1 | NT |
| Ex. 45 | NT | 0.8 | NT |
| Ex. 46 | NT | 1 | NT |
| Ex. 47 | NT | 0.6 | NT |

NT: Not Test

Finally, it should be noted that there are alternative ways of implementing the present invention. Accordingly, the present embodiments are to be considered as illustrative and not restrictive and the invention is not be limited to the details given herein, but may be modified within the scope and equivalents of the appended claims. All publications and patents cited herein are incorporated by reference.

What is claimed is:

1. A compound having Formula (I):

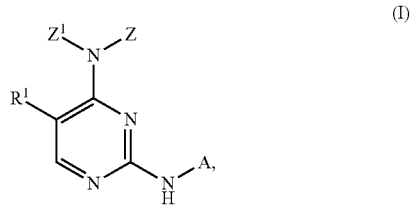

or a stereoisomer, a tautomer, an N-oxide, a solvate, a pharmaceutically acceptable salt or a prodrug thereof, wherein:

Z is $C_7$-$C_{12}$ spiro bicycloalkyl, $C_7$-$C_{12}$ fused bicycloalkyl, 7-12 membered spiro heterobicyclyl or 7-12 membered fused heterobicycloalkyl, wherein Z is substituted by 1, 2, 3, 4 or 5 $R^2$ groups;

$Z^1$ is H, $C_1$-$C_{12}$ alkyl, $C_3$-$C_{12}$ cycloalkyl or 3-12 membered heterocyclyl, wherein each of the $C_1$-$C_{12}$ alkyl, $C_3$-$C_{12}$ cycloalkyl and 3-12 membered heterocyclyl is optionally independently substituted by 1, 2, 3, 4 or 5 $R^{2a}$ groups;

A is

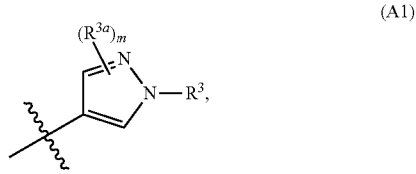

(A1)

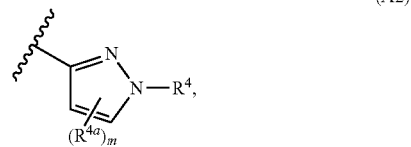

(A2)

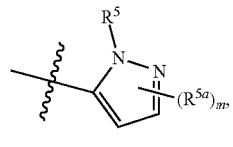

(A3)

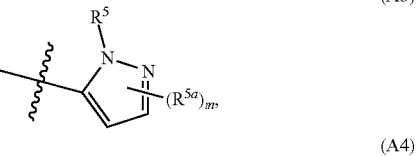

(A4)

(A5)

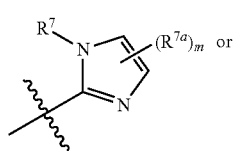

(A6)

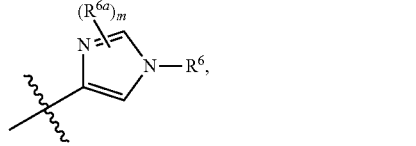

$R^1$ is H, F, Cl, Br, I, $N_3$, CN, —$NO_2$, $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl, 5-12 membered heteroaryl, —$NR^{9a}R^{9b}$, —$OR^{9c}$, —C(=O)$OR^{9c}$, —C(=O)$NR^{9a}R^{9b}$ or —S(=O)$_2$ $NR^{9a}R^{9b}$, wherein each of the $C_1$-$C_{12}$ alkyl, $C_1$-$C_{12}$ alkoxyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl and 5-12 membered heteroaryl is optionally independently substituted by 1, 2, 3, 4 or 5 $R^{11}$ groups;

each $R^2$ is independently F, Cl, Br, I, —$NO_2$, $N_3$, CN, —OH, —$NH_2$, —C(=O)$CH_2CN$, —NHC(=O)$CH_2CN$, —N($CH_3$)C(=O)$CH_2CN$, $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, —$NR^{10a}R^{10b}$, —O—($C_0$-$C_4$ alkylene)-$R^{10c}$, —O—($C_1$-$C_4$ alkylene)-$OR^{10c}$, —C(=O)$R^{10d}$, —OC(=O)$R^{10d}$, —N($R^{10e}$)C(=O)$R^{10d}$, —C(=O)$NR^{10a}R^{10b}$, —N($R^{10e}$)C(=O)$NR^{10a}R^{10b}$, —C(=O)N($R^{10e}$)C(=O)$R^{10d}$, —S(=O)$_2R^{10f}$, —N($R^{10e}$)S(=O)$_2R^{10f}$ or —S(=O)$_2NR^{10a}R^{10b}$, or two adjacent $R^2$ taken together with the atoms to which they are attached form a $C_3$-$C_{12}$ cycloalkyl or 3-12 membered heterocycloalkyl group, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, and 3-12 membered heterocycloalkyl group is optionally independently substituted by 1, 2, 3, 4 or 5 $R^{11}$ groups;

each $R^{2a}$ is independently H, F, Cl, Br, I, —$NO_2$, $N_3$, CN, —OH, —$NH_2$, $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl or 5-12 membered heteroaryl, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, and 5-12 membered heteroaryl is optionally independently substituted by 1, 2, 3, 4 or 5 $R^{11}$ groups;

$R^3$ is H, $C_3$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl or 5-12 membered heteroaryl, wherein each of the $C_3$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, $C_6$-$C_{12}$ aryl, 3-12 membered heterocyclyl and 5-12 membered heteroaryl is optionally independently substituted by 1, 2, 3, 4 or 5 $R^{11}$ groups;

$R^4$ is $C_1$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, Cu alkynyl, $C_3$-$C_{12}$ cycloalkyl, $C_6$-$C_{12}$ aryl, 3-12 membered heterocyclyl or 5-12 membered heteroaryl, wherein $R^4$ is optionally substituted by 1, 2, 3, 4 or 5 $R^{11}$ groups;

each of $R^5$, $R^6$, $R^7$ and $R^8$ is independently H, $C_1$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl or 5-12 membered heteroaryl, wherein each of the $C_1$-$C_{12}$ hydroxyalkyl, $C_3$-$C_{12}$ alkyl, $C_1$-$C_{12}$ haloalkyl, $C_1$-$C_{12}$ aminoalkyl, $C_2$-$C_{12}$ alkenyl, $C_2$-$C_{12}$ alkynyl, $C_3$-$C_{12}$ cycloalkyl, 3-12 membered heterocyclyl, $C_6$-$C_{12}$ aryl and 5-12 membered heteroaryl is optionally independently substituted by 1, 2, 3, 4 or 5 $R^{11}$ groups;

each $R^{3a}$, $R^{4a}$, $R^{5a}$, $R^{6a}$, $R^{7a}$ and $R^{8a}$ is independently H, F, Cl, CN, $C_1$-$C_{12}$ alkyl, $C_2$-$C_{12}$ alkenyl, $C_2$-$C_{12}$ alkynyl, $C_1$-$C_{12}$ alkoxyl, $C_1$-$C_{12}$ alkylamino, —($C_0$-$C_4$ alkylene)-($C_3$-$C_{12}$ cycloalkyl), —($C_0$-$C_4$ alkylene)-(3-12 membered heterocyclyl), $C_6$-$C_{12}$ aryl or 5-12 membered heteroaryl, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_1$-$C_{12}$ alkylamino, —($C_0$-$C_4$ alkylene)-($C_3$-$C_{12}$ cycloalkyl), —($C_0$-$C_4$ alkylene)-(3-12 membered heterocyclyl), $C_6$-$C_{12}$ aryl and 5-12 membered heteroaryl is optionally independently substituted by 1, 2, 3, 4 or 5 $R^{11}$ groups;

each $R^{9a}$, $R^{9b}$, $R^{9c}$, $R^{10a}$, $R^{10b}$, $R^{10c}$ and $R^{10e}$ is independently H, $C_1$-$C_{12}$ alkyl, $C_2$-$C_{12}$ alkenyl, $C_{12}$ alkynyl, $C_1$-$C_{12}$ alkoxyl, $C_3$-$C_{12}$ cycloalkyl, —($C_0$-$C_4$ alkylene)-($C_3$-$C_{12}$ cycloalkyl), —($C_0$-$C_4$ alkylene)-(3-12 membered heterocyclyl), —($C_0$-$C_4$ alkylene)-($C_6$-$C_{10}$ aryl) or —($C_0$-$C_4$ alkylene)-(5-12 membered heteroaryl), or $R^{9a}$ and $R^{9b}$, $R^{10a}$ and $R^{10b}$ taken together with the nitrogen atom to which they are attached form a 3-12 membered heterocyclyl group, wherein each of the $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, —($C_0$-$C_4$ alkylene)-($C_3$-$C_{12}$ cycloalkyl), —($C_0$-$C_4$ alkylene)-(3-12 membered heterocyclyl), —($C_0$-$C_4$ alkylene)-($C_6$-$C_{10}$ aryl), —($C_0$-$C_4$ alkylene)-(5-12 membered heteroaryl) and 3-12 membered heterocyclyl group is optionally substituted by 1, 2, 3 or 4 substituents independently selected from F, Cl, Br, CN, $N_3$, —$NO_2$, —OH, —$NH_2$, $C_1$-$C_6$ alkyl, $C_1$-$C_6$ haloalkyl, $C_1$-$C_6$ alkoxy, $C_1$-$C_6$ hydroxyalkyl, $C_1$-$C_6$ aminoalkyl and $C_1$-$C_6$ alkylamino;

each $R^{10d}$ and $R^{10f}$ is independently $C_1$-$C_{12}$ alkyl, $C_2$-$C_{12}$ alkenyl, $C_2$-$C_{12}$ alkynyl, $C_1$-$C_{12}$ alkoxyl, $C_3$-$C_{12}$ cycloalkyl, 3-12 membered heterocyclyl, $C_6$-$C_{12}$ aryl, 5-12 membered heteroaryl, —($C_1$-$C_4$ alkylene)-($C_3$-$C_{12}$ cycloalkyl), —($C_1$-$C_4$ alkylene)-(3-12 membered heterocyclyl), —($C_1$-$C_4$ alkylene)-($C_6$-$C_{12}$ aryl) or —($C_1$-$C_4$ alkylene)-(5-12 membered heteroaryl), wherein each of the above substituents is optionally substituted by 1, 2, 3 or 4 substituents independently selected from F, Cl, Br, CN, $N_3$, —OH, —$NH_2$, $C_1$-$C_6$ alkyl, $C_1$-$C_6$ haloalkyl, $C_1$-$C_6$ alkoxy, $C_1$-$C_6$ hydroxyalkyl, $C_1$-$C_6$ aminoalkyl and $C_1$-$C_6$ alkylamino;

each $R^{11}$ is independently F, Cl, Br, I, CN, —$NO_2$, $N_3$, —OH, —$NH_2$, $C_1$-$C_{12}$ alkyl, $C_2$-$C_{12}$ alkenyl, $C_2$-$C_{12}$ alkynyl, $C_1$-$C_{12}$ haloalkyl, $C_3$-$C_{12}$ cycloalkyl, $C_6$-$C_{12}$ aryl, 3-12 membered heterocyclyl, 5-12 membered heteroaryl, $C_1$-$C_{12}$ aminoalkyl, $C_1$-$C_{12}$ alkylamino, $C_1$-$C_{12}$ alkoxyl, $C_1$-$C_{12}$ hydroxyalkyl, —NH($C_0$-$C_4$ alkylene)-($C_3$-$C_{12}$ cycloalkyl), —NH($C_0$-$C_4$ alkylene)-($C_6$-$C_{12}$ aryl), —NH($C_0$-$C_4$ alkylene)-(3-12 membered heterocyclyl), —NH($C_0$-$C_4$ alkylene)-(5-12 membered heteroaryl), —N[($C_0$-$C_4$ alkylene)-($C_3$-$C_{12}$ cycloalkyl)]$_2$, —N[($C_0$-$C_4$ alkylene)-($C_6$-$C_{12}$ aryl)]$_2$, —N[($C_0$-$C_4$ alkylene)-(3-12 membered heterocyclyl)]$_2$, —N[($C_0$-$C_4$ alkylene)-(5-12 membered heteroaryl)]$_2$, —O—($C_0$-$C_4$ alkylene)-($C_3$-$C_{12}$ cycloalkyl), —O—($C_0$-$C_4$ alkylene)-($C_6$-$C_{12}$ aryl), —O—($C_0$-$C_4$ alkylene)-(3-12 membered heterocyclyl) or —O—($C_0$-$C_4$ alkylene)-(5-12 membered heteroaryl); and each m is independently 0, 1 or 2.

2. The compound of claim 1, wherein Z is 8-11 membered spiro heterobicyclyl or 8-10 membered fused heterobicycloalkyl, wherein Z is substituted by 1, 2, 3 or 4 $R^2$ groups.

3. The compound of claim 1, wherein Z is:
(Z-1) 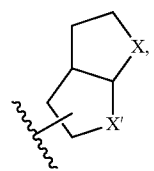
(Z-2) 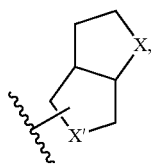
(Z-3) 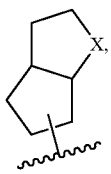
(Z-4) 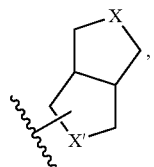
(Z-5) 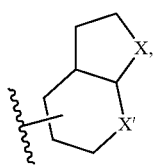
(Z-6) 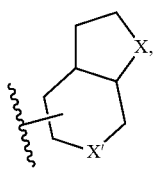
(Z-7) 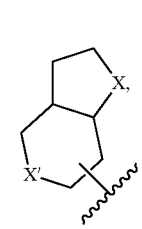
(Z-8) 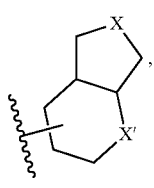
-continued
(Z-9) 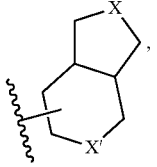
(Z-10) 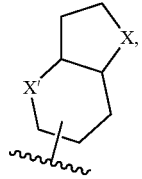
(Z-11) 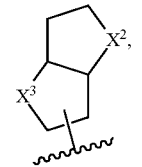
(Z-12) 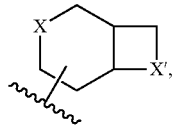
(Z-13) 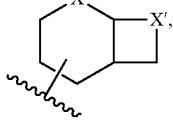
(Z-14) 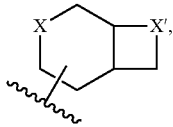
(Z-15) 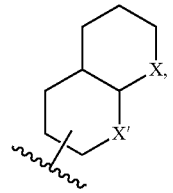
(Z-16) 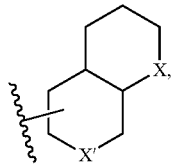
(Z-17) 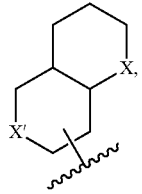

-continued
(Z-18)
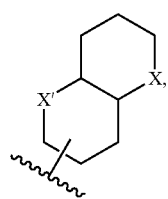
(Z-19)
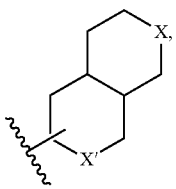
(Z-20)
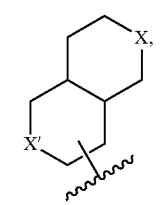
(Z-21)
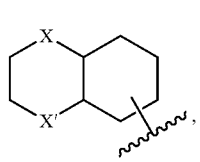
(Z-22)
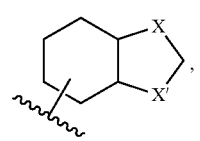
(Z-23)
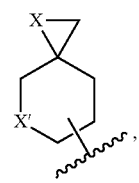
(Z-24)
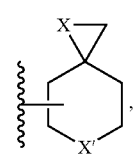
(Z-25)
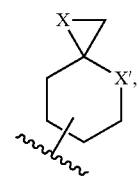
(Z-26)
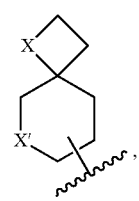
-continued
(Z-27)
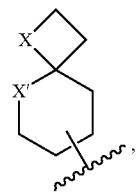
(Z-28)
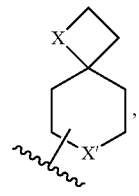
(Z-29)
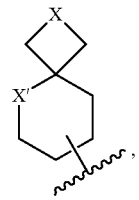
(Z-30)
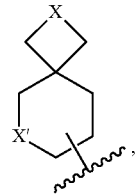
(Z-31)
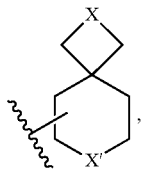
(Z-32)
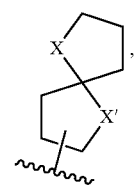
(Z-33)
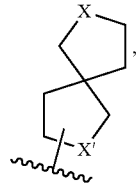
(Z-34)
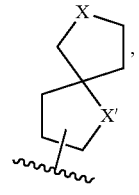

(Z-35), (Z-36), (Z-37), (Z-38), (Z-39), (Z-40), (Z-41), (Z-42), (Z-43), (Z-44), (Z-45), (Z-46), (Z-47), (Z-48), (Z-49)

-continued
(Z-50)
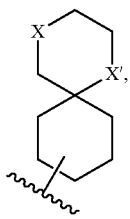
(Z-51)
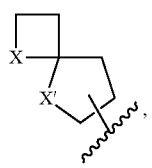
(Z-52)
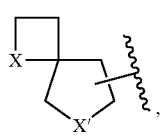
(Z-53)
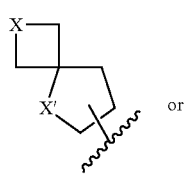 or
(Z-54)
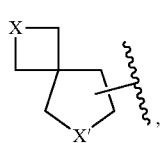
or a stereoisomer thereof, wherein each X, X', $X^2$, and $X^3$ is independently —CH$_2$—, —NH— or —O—, with the proviso that $X^2$ and $X^3$ are not —O— simultaneously; and wherein Z is substituted by 1, 2 or 3 $R^2$ groups.
4. The compound of claim 1, wherein Z is:
(Z-55)
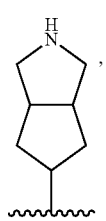
(Z-56)
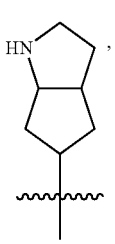
-continued
(Z-57)
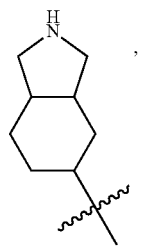
(Z-58)
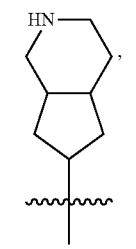
(Z-59)
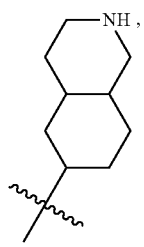
(Z-60)
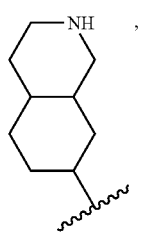
(Z-61)
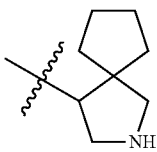
(Z-62)
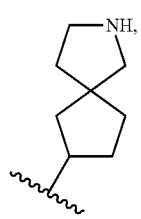
(Z-63)
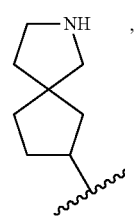

-continued (Z-64) 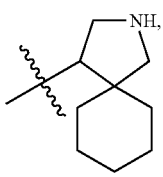

(Z-65) 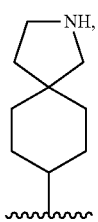

(Z-66) 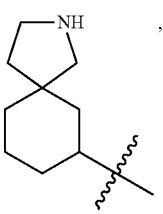

(Z-67) 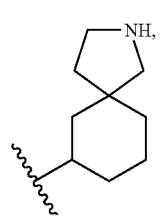

(Z-68) 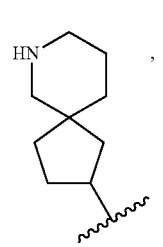

(Z-69) 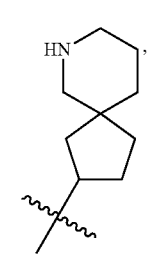

(Z-70) 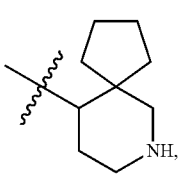

-continued (Z-71) 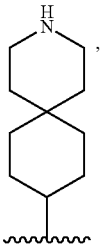

(Z-72) 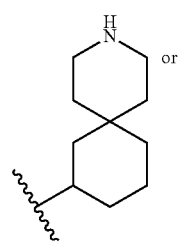

or (Z-73) 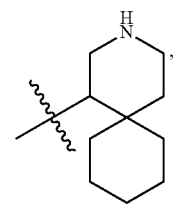

or a stereoisomer thereof, and wherein Z is substituted by 1, 2 or 3 $R^2$ groups.

5. The compound of claim 1, wherein $Z^1$ is H, $C_1$-$C_6$ alkyl, $C_3$-$C_6$ cycloalkyl or 4-7 membered heterocyclyl, wherein each of the $C_1$-$C_6$ alkyl, $C_3$-$C_6$ cycloalkyl and 4-7 membered heterocyclyl is optionally independently substituted by 1, 2 or 3 $R^{2a}$ groups.

6. The compound of claim 1, wherein $R^1$ is H, F, Cl, Br, I, $N_3$, CN, —$NO_2$, $C_1$-$C_6$ alkyl, $C_1$-$C_6$ alkoxyl, $C_2$-$C_6$ alkenyl, $C_2$-$C_6$ alkynyl, $C_3$-$C_6$ cycloalkyl, 4-7 membered heterocyclyl, —$NR^{9a}R^{9b}$, —$OR^{9c}$, —C(=O)$OR^{9c}$, —C(=O)$NR^{9a}R^{9b}$ or —S(=O)$_2NR^{9a}R^{9b}$, wherein each of the $C_1$-$C_6$ alkyl, $C_1$-$C_6$ alkoxyl, $C_2$-$C_6$ alkenyl, $C_2$-$C_6$ alkynyl, $C_3$-$C_6$ cycloalkyl and 4-7 membered heterocyclyl is optionally independently substituted by 1, 2 or 3 $R^{11}$ groups.

7. The compound of claim 1, wherein each $R^2$ is independently F, Cl, Br, I, —$NO_2$, $N_3$, CN, —OH, —$NH_2$, —C(=O)$CH_2CN$, —NHC(=O)$CH_2CN$, —N($CH_3$)C(=O)$CH_2CN$, $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl, —$NR^{10a}R^{10b}$, —O—($C_0$-$C_3$ alkylene)-$R^{10c}$, —O—($C_1$-$C_3$ alkylene)-$OR^{10c}$, —C(=O)$R^{10d}$, —OC(=O)$R^{10d}$, —N($R^{10e}$)C(=O)$R^{10d}$, —C(=O)$NR^{10a}R^{10b}$, —N($R^{10e}$)C(=O)$NR^{10a}R^{10b}$, —C(=O)N($R^{10e}$)C(=O)$R^{10d}$, —S(=O)$_2R^{10f}$, —N($R^{10e}$)S(=O)$_2R^{10f}$ or —S(=O)$_2NR^{10a}R^{10b}$, or two adjacent $R^2$ taken together with the atoms to which they are attached form a $C_3$-$C_6$ cycloalkyl or 4-7 membered heterocycloalkyl group, wherein each of the $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl, 5-6 membered heteroaryl and 4-7 membered heterocloalkyl group is optionally independently substituted by 1, 2 or 3 $R^{11}$ groups;

each $R^{2a}$ is independently H, F, Cl, Br, I, —$NO_2$, $N_3$, CN, —OH, —$NH_2$, $C_1$-$C_6$ alkyl, $C_2$-$C_6$ alkenyl, $C_1$-$C_6$ alkoxyl, $C_3$-$C_6$ cycloalkyl, 4-7 membered heterocyclyl, phenyl or 5-6 membered heteroaryl.

8. The compound of claim 1, wherein $R^3$ is H, $C_3$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_3$-$C_6$ cycloalkyl, phenyl, 4-7 membered heterocyclyl or 5-6 membered heteroaryl, wherein each of the $C_3$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_3$-$C_6$ cycloalkyl, phenyl, 4-7 membered heterocyclyl and 5-6 membered heteroaryl is optionally independently substituted by 1, 2 or 3 $R^{11}$ groups.

9. The compound of claim 1, wherein $R^3$ is H, —CH$_2$C(CH$_3$)$_2$OH, —(CH$_2$)$_2$CH$_2$OH, —CH$_2$CH(OH)CH$_3$, piperidinyl, pyrrolidinyl, morpholinyl, piperazinyl, pyridyl, pyrimidinyl, pyridazinyl, pyrazinyl, thiazolyl, pyrrolyl or oxazolyl, wherein each of the piperidinyl, pyrrolidinyl, morpholinyl, piperazinyl, pyridyl, pyrimidinyl, pyridazinyl, thiazolyl, pyrrolyl or oxazolyl is optionally independently substituted by 1, 2 or 3 $R^{11}$ groups.

10. The compound of claim 1, wherein $R^4$ is $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, phenyl, 4-7 membered heterocyclyl or 5-6 membered heteroaryl, wherein $R^4$ is optionally substituted by 1, 2, or 3 $R^{11}$ groups.

11. The compound of claim 1, wherein each of $R^5$, $R^6$, $R^7$ and $R^8$ is independently H, $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, 4-7 membered heterocyclyl, phenyl or 5-6 membered heteroaryl, wherein each of the $C_1$-$C_6$ hydroxyalkyl, $C_3$-$C_6$ alkyl, $C_1$-$C_6$ haloalkyl, $C_1$-$C_6$ aminoalkyl, $C_2$-$C_6$ alkenyl, $C_2$-$C_6$ alkynyl, $C_3$-$C_6$ cycloalkyl, 4-7 membered heterocyclyl, phenyl and 5-6 membered heteroaryl is optionally independently substituted by 1, 2 or 3 $R^{11}$ groups.

12. The compound of claim 1, wherein each $R^{3a}$, $R^{4a}$, $R^{5a}$, $R^{6a}$, $R^{7a}$ and $R^{8a}$ is independently H, F, Cl, CN, $C_1$-$C_6$ alkyl, $C_2$-$C_6$ alkenyl, $C_1$-$C_6$ alkoxyl, $C_1$-$C_6$ alkylamino, —(C$_0$-$C_3$ alkylene)-(C$_3$-$C_6$ cycloalkyl), —(C$_0$-$C_3$ alkylene)-(4-7 membered heterocyclyl), phenyl or 5-6 membered heteroaryl, wherein each of the $C_1$-$C_6$ alkyl, $C_2$-$C_6$ alkenyl, $C_1$-$C_6$ alkoxyl, $C_1$-$C_6$ alkylamino, —(C$_0$-$C_3$ alkylene)-(C$_3$-$C_6$ cycloalkyl), —(C$_0$-$C_3$ alkylene)-(4-7 membered heterocyclyl), phenyl and 5-6 membered heteroaryl is optionally independently substituted by 1, 2 or 3 $R^{11}$ groups.

13. The compound of claim 1, wherein each $R^{9a}$, $R^{9b}$, $R^{9c}$, $R^{10a}$, $R^{10b}$, $R^{10c}$ and $R^{10e}$ is independently H, $C_1$-$C_6$ alkyl, $C_2$-$C_6$ alkenyl, $C_2$-$C_6$ alkynyl, $C_1$-$C_6$ alkoxyl, $C_3$-$C_6$ cycloalkyl, —(C$_0$-$C_3$ alkylene)-(C$_3$-$C_6$ cycloalkyl), —(C$_0$-$C_3$ alkylene)-(4-7 membered heterocyclyl), —(C$_0$-$C_3$ alkylene)-phenyl, —(C$_0$-$C_3$ alkylene)-(5-6 membered heteroaryl), or $R^{9a}$ and $R^{9b}$, $R^{10a}$ and $R^{10b}$ taken together with the nitrogen atom to which they are attached form a 4-7 membered heterocyclyl group, wherein each of the $C_1$-$C_6$ alkyl, $C_2$-$C_6$ alkenyl, $C_2$-$C_6$ alkynyl, $C_1$-$C_6$ alkoxyl, $C_3$-$C_6$ cycloalkyl, —(C$_0$-$C_3$ alkylene)-(C$_3$-$C_6$ cycloalkyl), —(C$_0$-$C_3$ alkylene)-(4-7 membered heterocyclyl), —(C$_0$-$C_3$ alkylene)-phenyl, —(C$_0$-$C_3$ alkylene)-(5-6 membered heteroaryl), and 4-7 membered heterocyclyl group is optionally substituted by 1, 2 or 3 substitutents independently selected from F, Cl, Br, CN, N$_3$, —NO$_2$, —OH, —NH$_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

14. The compound of claim 1, wherein each $R^{9a}$, $R^{9b}$, $R^{9c}$, $R^{10a}$, $R^{10b}$, $R^{10c}$ and $R^{10e}$ is independently H, methyl, ethyl, n-propyl, isopropyl, n-butyl, isobutyl, sec-butyl, tert-butyl, allyl, vinyl, propenyl, $C_1$-$C_4$ alkoxyl, cyclopropyl, cyclobutyl, cyclopentyl, cyclohexyl, piperidinyl, pyrrolidinyl, morpholinyl, piperazinyl, -methylene-cyclopropyl, -ethylidene-cyclopropyl, -methylene-cyclobutyl, -ethylidene-cyclobutyl, -methylene-cyclopentyl, -ethylidene-cyclopentyl, -methylene-cyclohexyl, -ethylidene-cyclohexyl, alkylene)-(4-7 membered heterocyclyl), phenyl, pyridyl, pyridazinyl, pyrimidinyl, —(C$_1$-$C_3$ alkylene)-phenyl or —(C$_1$-$C_3$ alkylene)-(5-6 membered heteroaryl), wherein each of the methyl, ethyl, n-propyl, isopropyl, n-butyl, isobutyl, sec-butyl, tert-butyl, allyl, vinyl, propenyl, $C_1$-$C_4$ alkoxyl, cyclopropyl, cyclobutyl, cyclopentyl, cyclohexyl, piperidinyl, pyrrolidinyl, morpholinyl, piperazinyl, -methylene-cyclopropyl, -ethylidene-cyclopropyl, -methylene-cyclobutyl, -ethylidene-cyclobutyl, -methylene-cyclopentyl, -ethylidene-cyclopentyl, -methylene-cyclohexyl, -ethylidene-cyclohexyl, alkylene)-(4-7 membered heterocyclyl), phenyl, pyridyl, pyridazinyl, pyrimidinyl, —(C$_1$-$C_3$ alkylene)-phenyl and —(C$_1$-$C_3$ alkylene)-(5-6 membered heteroaryl) is optionally substituted by 1, 2 or 3 substitutents independently selected from F, Cl, Br, CN, N$_3$, —NO$_2$, —OH, —NH$_2$, —CF$_3$, —OCH$_3$, —CH$_2$OH, —CH$_2$CH$_2$OH, —NHCH$_3$, —N(CH$_3$)$_2$ and —CH$_2$NH$_2$.

15. The compound of claim 1, wherein each $R^{10d}$ and $R^{10f}$ is independently $C_1$-$C_4$ alkyl, $C_2$-$C_4$ alkenyl, $C_2$-$C_4$ alkynyl, $C_1$-$C_4$ alkoxyl, $C_3$-$C_6$ cycloalkyl, 4-7 membered heterocyclyl, phenyl, 5-6 membered heteroaryl, —(C$_1$-$C_3$ alkylene)-(C$_3$-$C_6$ cycloalkyl), —(C$_1$-$C_3$ alkylene)-(4-7 membered heterocyclyl), —(C$_1$-$C_3$ alkylene)-phenyl or —(C$_1$-$C_3$ alkylene)-(5-6 membered heteroaryl), wherein each of the above substituents is optionally substituted by 1, 2 or 3 substitutents independently selected from F, Cl, Br, CN, N$_3$, —OH, —NH$_2$, $C_1$-$C_3$ alkyl, $C_1$-$C_3$ haloalkyl, $C_1$-$C_3$ alkoxy, $C_1$-$C_3$ hydroxyalkyl, $C_1$-$C_3$ aminoalkyl and $C_1$-$C_3$ alkylamino.

16. The compound of claim 1, wherein each $R^{10d}$ and $R^{10f}$ is independently methyl, ethyl, n-propyl, isopropyl, n-butyl, isobutyl, sec-butyl, tert-butyl, cyclopropyl, cyclobutyl, cyclopentyl, cyclohexyl, allyl, vinyl, propenyl, phenyl, piperidinyl, pyrrolidinyl, morpholinyl, piperazinyl, $C_1$-$C_4$ alkoxyl, methylene-cyclopropyl, -ethylidene-cyclopropyl, -methylene-cyclobutyl, -ethylidene-cyclobutyl, -methylene-cyclopentyl, -ethylidene-cyclopentyl, -methylene-cyclohexyl or -ethylidene-cyclohexyl, wherein each of the above substituents is optionally substituted by 1, 2 or 3 substitutents independently selected from F, Cl, Br, CN, N$_3$, —OH, —NH$_2$, —CF$_3$, —OCH$_3$, —CH$_2$OH, —CH$_2$CH$_2$OH, —NHCH$_3$, —N(CH$_3$)$_2$ and —CH$_2$NH$_2$.

17. The compound of claim 1, wherein each $R^{11}$ is independently F, Cl, Br, I, CN, —NO$_2$, N$_3$, —OH, —NH$_2$, methyl, ethyl, n-propyl, isopropyl, cyclopropyl, methoxy, ethyoxyl, n-propoxy, isopropoxy, hydroxymethyl, hydroxyethyl, methylamino, dimethylamino or aminomethyl.

18. The compound of claim 1 having one of the following structures:

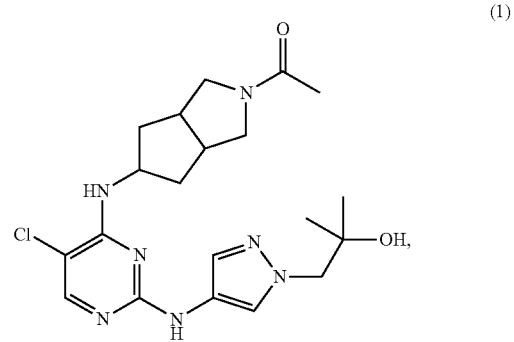

(1)

-continued
(2)
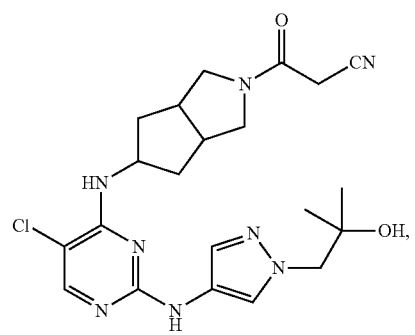
(3)
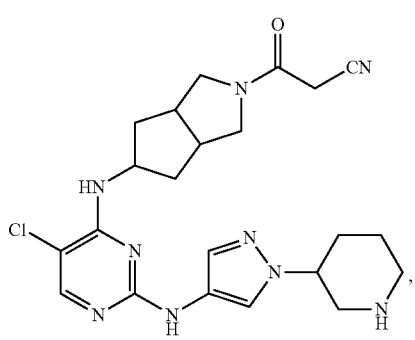
(4)
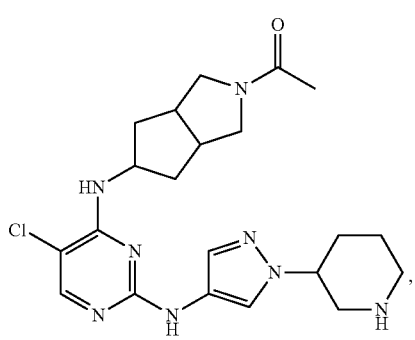
(5)
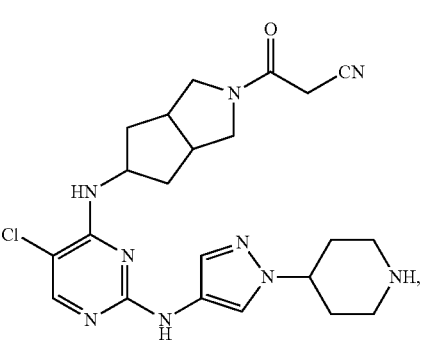
-continued
(6)
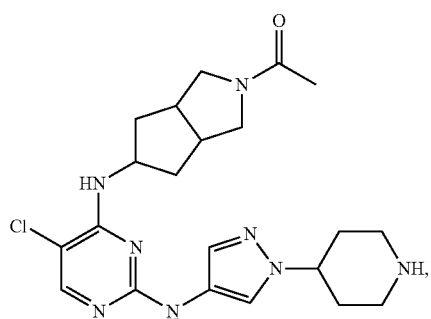
(7)
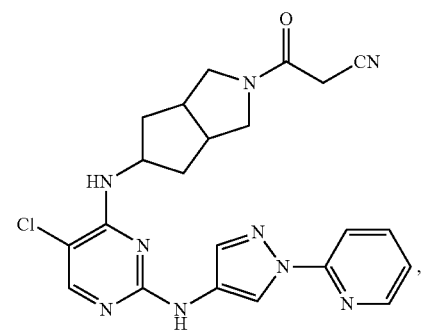
(8)
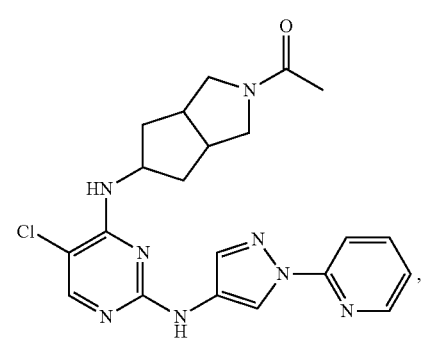
(9)
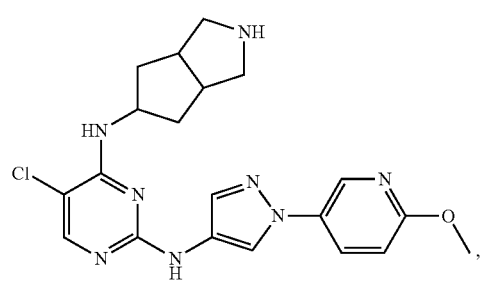
(10)
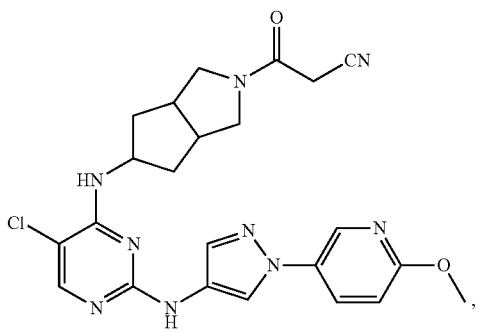

(11)
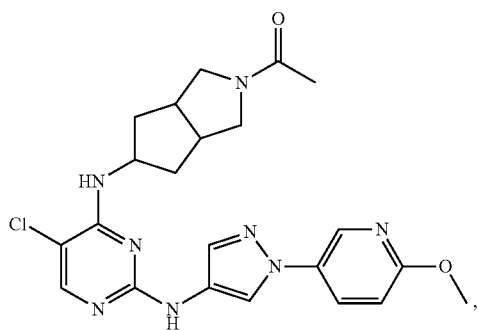
(33)
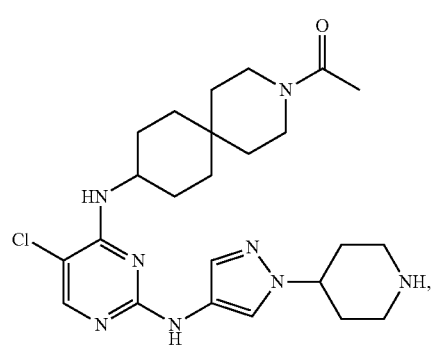
(35)
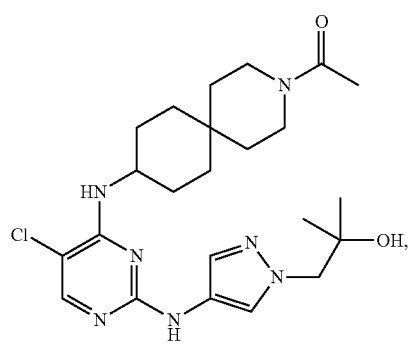
(36)
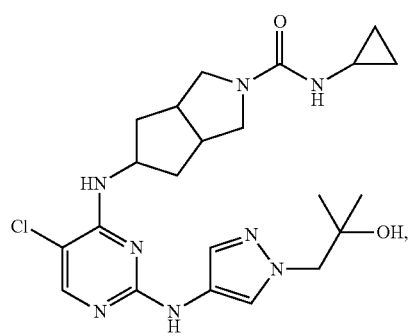
(37)
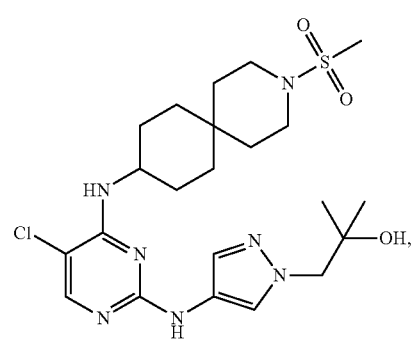
(38)
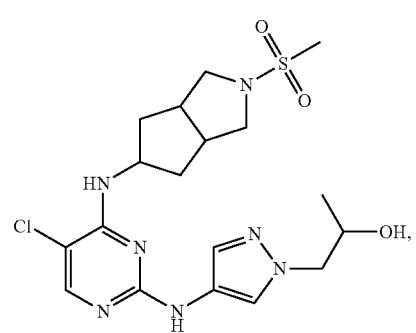
(39)
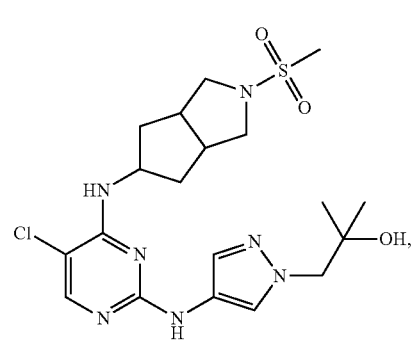
(40)
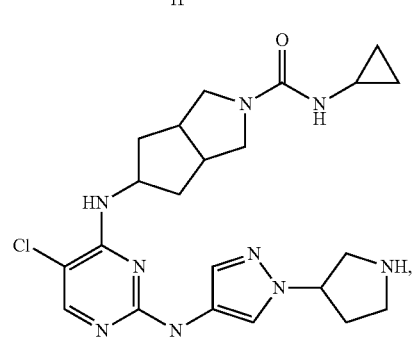
(41)
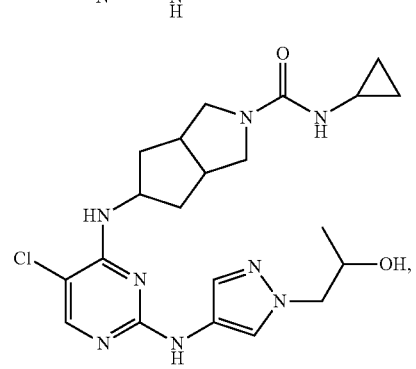

(42)

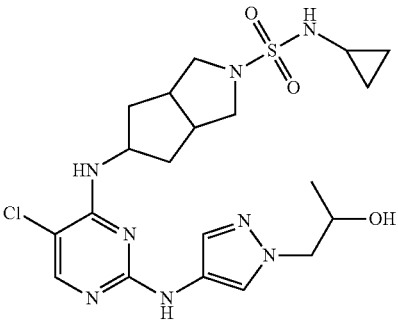

(43)

(44)

(45)

(46)

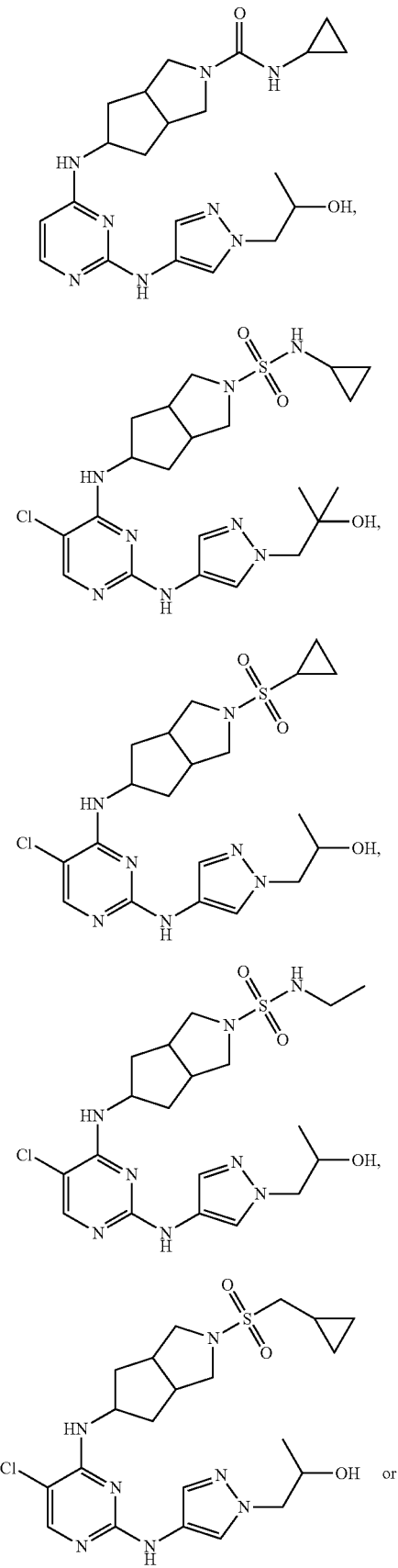

-continued (47)

or a stereoisomer, a tautomer, an N-oxide, a solvate, or a pharmaceutically acceptable salt thereof.

19. A pharmaceutical composition comprising the compound of claim 1, and a pharmaceutically acceptable excipient, carrier, adjuvant, vehicle or a combination thereof.

20. The pharmaceutical composition of claim 19 further comprising a therapeutic agent selected from the group consisting of chemotherapeutic agents, anti-proliferative agents, phosphodiesterase 4 (PDE4) inhibitors, $\beta_2$-adrenoreceptor agonists, corticosteroids, non-steroidal GR agonists, anticholinergic agents, antihistamines, anti-inflammatory agents, immunosuppressants, immunomodulators, agents for treating atherosclerosis, agents for treating pulmonary fibrosis and combinations thereof.

21. A method of treating or lessening the severity of a disease by inhibiting a protein kinase selected from JAK1, JAK2, Aurora A, Aurora B and FLT3, the method comprising administering to a patient the compound of claim 1, wherein the disease is a cancer selected from head and neck cancer, prostate cancer, breast cancer, ovarian cancer, melanoma, lung cancer, brain tumor, pancreatic cancer and renal carcinoma, or a disease selected from polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic lupus erythematosis, cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Chron's disease, rheumatoid arthritis, juvenile arthritis and psoriatic arthritis, or a graft-versus-host disease selected from organ transplant rejection, tissue transplant rejection and cell transplant rejection.

22. A method of treating or lessening the severity of a disease by inhibiting a protein kinase selected from JAK1, JAK2, Aurora A, Aurora B and FLT3, the method comprising administering to a patient the pharmaceutical composition of claim 19, wherein the disease is a cancer selected from head and neck cancer, prostate cancer, breast cancer, ovarian cancer, melanoma, lung cancer, brain tumor, pancreatic cancer and renal carcinoma, or a disease selected from polycythemia vera, essential thrombocytosis, myelofibrosis, chronic myelogenous leukemia (CML), acute myeloid leukemia (AML), acute lymphocytic leukemia (ALL), chronic obstruction pulmonary disease (COPD), asthma, systemic lupus erythematosis, cutaneous lupus erythematosis, lupus nephritis, dermatomyositis, Sjogren's syndrome, psoriasis, type I diabetes mellitus, allergic airway disease, sinusitis, eczema, hives, food allergies, allergies to insect venom, inflammatory bowel syndrome, Chron's disease, rheumatoid arthritis, juvenile arthritis and psoriatic arthritis, or a graft-versus-host disease selected from organ transplant rejection, tissue transplant rejection and cell transplant rejection.

23. A method of inhibiting the activity of a protein kinase by contacting the protein kinase with the compound of claim 1, wherein the protein kinase is selected from JAK1, JAK2, Aurora A, Aurora B and FLT3.

24. A method of inhibiting the activity of a protein kinase by contacting the protein kinase with the pharmaceutical composition of claim 19, wherein the protein kinase is selected from JAK1, JAK2, Aurora A, Aurora B and FLT3.

* * * * *